(12) United States Patent
Singh et al.

(10) Patent No.: US 11,858,889 B2
(45) Date of Patent: *Jan. 2, 2024

(54) COMPOUND FOR MODULATING DDAH AND ADMA LEVELS, AS WELL AS METHODS OF USING THEREOF TO TREAT DISEASE

(71) Applicant: THE TRUSTEES OF INDIANA UNIVERSITY, Bloomington, IN (US)

(72) Inventors: Jaipal Singh, Carmel, IN (US); Kerry Fowler, Seattle, WA (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/565,981

(22) Filed: Dec. 30, 2021

(65) Prior Publication Data

US 2022/0144795 A1    May 12, 2022

Related U.S. Application Data

(63) Continuation of application No. 17/040,832, filed as application No. PCT/US2019/030020 on Apr. 30, 2019, now Pat. No. 11,267,780.

(60) Provisional application No. 62/664,580, filed on Apr. 30, 2018.

(51) Int. Cl.

| | | |
|---|---|---|
| C07D 333/24 | (2006.01) | |
| C07D 263/32 | (2006.01) | |
| C07D 213/55 | (2006.01) | |
| C07D 277/30 | (2006.01) | |
| C07C 63/49 | (2006.01) | |
| C07C 65/17 | (2006.01) | |
| C07D 295/088 | (2006.01) | |
| C07C 65/19 | (2006.01) | |
| C07C 49/513 | (2006.01) | |
| C07C 63/64 | (2006.01) | |
| C07C 65/10 | (2006.01) | |
| C07C 65/24 | (2006.01) | |
| C07C 65/40 | (2006.01) | |
| C07C 211/55 | (2006.01) | |
| C07C 215/74 | (2006.01) | |
| C07C 233/65 | (2006.01) | |
| C07C 233/81 | (2006.01) | |
| C07C 317/32 | (2006.01) | |
| C07C 323/62 | (2006.01) | |
| C07D 209/18 | (2006.01) | |
| C07D 257/04 | (2006.01) | |
| C07D 295/16 | (2006.01) | |

(52) U.S. Cl.
CPC ............ *C07C 65/19* (2013.01); *C07C 49/513* (2013.01); *C07C 63/49* (2013.01); *C07C 63/64* (2013.01); *C07C 65/10* (2013.01); *C07C 65/17* (2013.01); *C07C 65/24* (2013.01); *C07C 65/40* (2013.01); *C07C 211/55* (2013.01); *C07C 215/74* (2013.01); *C07C 233/65* (2013.01); *C07C 233/81* (2013.01); *C07C 317/32* (2013.01); *C07C 323/62* (2013.01); *C07D 209/18* (2013.01); *C07D 213/55* (2013.01); *C07D 257/04* (2013.01); *C07D 263/32* (2013.01); *C07D 277/30* (2013.01); *C07D 295/088* (2013.01); *C07D 295/16* (2013.01); *C07D 333/24* (2013.01); C07C 2601/16 (2017.05); C07C 2602/08 (2017.05)

(58) Field of Classification Search
CPC ....... C07C 65/19; C07C 49/513; C07C 63/49; C07C 63/64; C07C 65/10; C07C 65/17; C07C 65/24; C07C 65/40; C07C 211/55; C07C 215/74; C07C 233/65; C07C 233/81; C07C 317/32; C07C 323/62; C07C 2601/16; C07C 2602/08; C07D 209/18; C07D 213/55; C07D 257/04; C07D 263/32; C07D 277/30; C07D 295/088; C07D 295/16; C07D 333/24

USPC .......................................................... 544/172
See application file for complete search history.

(56) References Cited

U.S. PATENT DOCUMENTS

| | | |
|---|---|---|
| 5,504,244 A | 4/1996 | Hargrave |
| 8,242,144 B2 | 8/2012 | Wong et al. |
| 8,952,042 B2 | 2/2015 | Kremoser et al. |
| 11,267,780 B2 * | 3/2022 | Singh .................. A61K 31/421 |
| 2005/0059733 A1 | 3/2005 | Chen et al. |
| 2008/0255245 A1 * | 10/2008 | Chen ..................... A61K 47/10 |
| | | 568/744 |

FOREIGN PATENT DOCUMENTS

| | | |
|---|---|---|
| WO | 2005/032549 | 4/2005 |
| WO | 2015/073864 | 5/2005 |
| WO | 2017/170859 | 10/2017 |

OTHER PUBLICATIONS

Connelly et al., Semi-quantitative models for identifying potent and selective transthyretin amyloidogenesis inhibitors, 2017, Bioorganic & Medicinal Chemistry Letters, 27, 3441-3449 (Year: 2017).*

(Continued)

*Primary Examiner* — Kristin A Vajda
(74) *Attorney, Agent, or Firm* — Barnes & Thornburg LLP

(57) ABSTRACT

Disclosed are compounds that can modulate DDAH and the amount of asymmetric dimethylarginine (ADMA) in a subject. Also provided are pharmaceutical compositions comprising these compounds, as well as methods of using these compositions to treat and/or prevent diseases associated with elevated or low levels of DDAH and ADMA.

4 Claims, 5 Drawing Sheets

(56) References Cited

OTHER PUBLICATIONS

Choi et al., A Substructure Combination Strategy to Create Potent and Selective Transthyretin Kinetic Stabilizers That Prevent Amyloidogenesis and Cytotoxicity, 2010, J. Am. Chem. Soc., 132, 1359-1370 (Year: 2010).
Smith et al., Stilbene Boronic Acids Form a Covalent Bond with Human Transthyretin and Inhibit Its Aggregation, 2017, J. Med. Chem., 60, 7820-7834 (Year: 2017).
PCT International Search Report and Written Opinion completed by the ISA/US dated Jun. 26, 2019 and issued in connection with PCT/US2019/030020.
"Pubchem CID 131633021" Create Date: Oct. 17, 2017 (Oct. 17, 2017) Date Accessed: Jun. 26, 2019 (Jun. 26, 2019); p. 2.
"Pubchem CID 12092234" Create Date: Feb. 7, 2007 (Feb. 7, 2007) Date Accessed: Jun. 26, 2019 (Jun. 26, 2019); p. 2.
Bonnefont-Rousselot "Resveratrol and Cardiovascular Diseases" Nutrients. May 2, 2016 (May 2, 2016) vol. 8, p. 1-24.
Supplemental EP Search Report for EP application No. 19795946.3, dated Feb. 24, 2022.
Shrestha S et al: Bioorganic & Medicinal Chemistry, vol. 16, No. 18, Sep. 15, 2008 (Sep. 15, 2008), pp. 8643-8652.
Hu Tonghuan et al: Journal of Biological Chemistry, vol. 281, No. 52, Dec. 1, 2006 (Dec. 1, 2006), pp. 39831-39838.
Nees D et al: Colloid Pol Ym Sci, vol. 274, No. 9, Jan. 1, 1996 (Jan. 1, 1996), pp. 904-907.

\* cited by examiner

COMPOUND FOR MODULATING DDAH AND ADMA LEVELS, AS WELL AS METHODS OF USING THEREOF TO TREAT DISEASE

CROSS-REFERENCE TO RELATED APPLICATIONS

This application is a continuation application of U.S. Ser. No. 17/040,832, filed Sep. 23, 2020, which is a national stage entry of PCT/US2019/030020 filed Apr. 30, 2019, which claims benefit of U.S. Provisional Application No. 62/664,580, filed Apr. 30, 2018, the disclosures of which are hereby incorporated herein by reference in their entirety.

BACKGROUND

Asymmetric dimethyl arginine (ADMA) produced in the body as a result of degradation of arginine methylated proteins is an inhibitor of nitric oxide (NO) synthesis [Franceschelli et al., *Int. J. Mol. Sci.* 14: 24412 (2013)]. During the disease states where protein degradation rates are high or the mechanisms of ADMA clearance are impaired, high levels of ADMA accumulate in the tissues and blood [Leiper and Nandi. *Nat. Rev. Drug Discov.*, 10:277 (2011)].

In some conditions such as kidney disease, there may be 3- to 9-fold increase in plasma levels of ADMA. ADMA in high concentrations is known to contribute to disease states by inhibiting nitric oxide synthase (NOS) and the cationic amino acid transporter for arginine. ADMA also inhibits phosphorylation of endothelial NOS, thereby reducing its activity. High ADMA can uncouple nitric oxide synthase leading to production of damaging oxygen free radicals. Deficiency of NO production which may be caused by ADMA is associated with a wide range of vascular diseases including hypertension, heart failure, pulmonary arterial hypertension, erectile dysfunction, coronary and peripheral arterial disease, renal, disease, insulin resistance, diabetes, atrial fibrillation, sickle cell disease, organ damage, sepsis, and tissue regeneration.

By reducing NO bioavailability, high levels of ADMA can promote endothelial dysfunction, vasoconstriction, pro-inflammatory, fibrotic and pro-thrombogenic state. A persistent dysfunction of vascular endothelium can lead to a variety of disease states and death. An association of high ADMA levels has been documented with vascular diseases such as retinal venous occlusive disease, early autosomal dominant polycystic kidney disease, proteinuria, secondary amyloidosis, focal segmental glomerulosclerosis, pre-eclampsia, chronic thromboembolic pulmonary hypertension, diabetes, insulin resistance, obesity, pulmonary arterial hypertension, lung injury, COPD, sickle cell disease, encephlopathy, depression, congestive heart failure, Alzheimer's disease, cardio-renal syndrome, hyperhomocysteinaemia, hypertension, atherosclerosis and stroke [reviewed in Leiper and Nandi. *Nat. Rev. Drug Discov.*, 10:277 (2011)]

A major pathway for reducing ADMA is through metabolism by the enzyme dimethylarginine dimethylaminohydrolase (DDAH) which eliminates more than 80% of ADMA. [Achan, V. et al. *Arterioscler. Thromb. Vasc. Biol.* 23:1455 (2003)]. Two isoforms of DDAH are encoded by separate genes located on human chromosome 1 (DDAH-1) and 6 (DDAH-2). Both enzymes metabolize ADMA. DDAH can hydrolase both the $N^G$-monomethyl-L-arginine (L-NMMA) and ADMA, therefore it can reduce the inhibitory concentrations of the methylamines and allow more NO generation.

DDAH gene deletion and transgenic animal studies have shown that DDAH levels and activity regulate ADMA levels. Heterologous deletion of gene DDAH−/+ increased ADMA level and impaired vascular responses. Conversely, transgenic expression of DDAH-1 reduced plasma ADMA, increased NO production, and decreased arterial blood pressure and systemic vascular resistance [Hu, X. et al. *Arterioscler. Thromb. Vasc. Biol.* 31:1540 (2011); Jacobi, J. at al. *Am. J. Pathol.* 176:2559 (2010)]. Thus, ADMA levels in plasma can be modulated by the level of DDAH-1 gene expression.

In disease states where DDAH expression or activity is impaired, ADMA clearance is reduced leading to its accumulation in tissues and blood. For example, in pathological conditions such as diabetes, atherosclerosis or inflammation, DDAH-1 gene expression is reduced and ADMA is increased. In lung diseases such as pulmonary arterial hypertension (PAH), DDAH mRNA and protein expression are reduced and ADMA levels are increased [Dimitroulas, T. et al. *Rheumatology*, 47:682 (2008)]. High levels of ADMA are observed in patients with COPD. Therefore, methods that can modulate enzyme levels in the body would modulate ADMA and produce therapeutic benefit in prevention or treatment of disease.

In some disease state the DDAH levels may be high leading to low ADMA. Low ADMA in specific tissues is associated with disease such in pain and migraine [D'Mello, R. et. at. *Pain*, 156, 2052 (2015)], sepsis [Wang, Z. et al *Biochem J.* 460:309 (2014)], angiogenic eye disease such as diabetic retinopathy and macular degeneration [Lange, C. et al. *Exp. Eye Res.* 147:148 (2016)] and kidney disease [Tomlinson, et al. *J. Am. Soc. Nephrol.*, 26: 3045, (2015)]. Decreasing DDAH by modulation may be efficacious in these diseases.

Similarly, in certain cancers, high expression of DDAH may increase metastatic potential of tumors and therefore lowering of DDAH may prevent cancer spread [Ye, J. et al. *Mol. Oncol.*, 1:1208 (2017), Hulin, J. A. et al. *Biomed. Pharmacother.*, 111:602 (2019), Boult, J. K. et al. *J. Pathol.*, 225:344 (2011)].

Modulation of DDAH in tissue and organ selective manner has been documented [Dayal, S. et al. *Am. J. Physiol. Heart Circ. Physiol.* 295: H816 (2008); Sydow, K. el al. *PLOS ONE*, 7:e48150 (2012)]. Therefore, a DDAH modulator may enhance or reduce DDAH levels depending upon its expression in the disease state for the organ.

Accordingly, compounds and methods for modulating DDAH and ADMA levels are needed to prevent or treat these diseases.

SUMMARY

The compounds described herein can modulate (e.g., elevate or reduce) DDAH in a cell and treatment selective manner.

For example, provided herein are methods for modulating (e.g., elevating or reducing) DDAH and asymmetric dimethylarginine (ADMA) in a subject, the method comprising administering to the subject a composition comprising a therapeutically effective amount of a compound defined by Formula I:

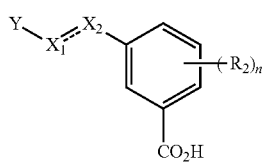

Formula I or a pharmaceutically acceptable salt or prodrug thereof, wherein ----- represents a single, double, or triple bond; $X_1$ and $X_2$, as valence permits, are independently absent or selected from C, CH, $CH_2$, O, CO, S, $SO_2$, and NR'; wherein R is independently selected from hydrogen or $C_1$-$C_6$ alkyl; or $X_1$ and $X_2$ together with the bond to which they are attached form a 3 or 4 membered carbocyclic ring; $R_2$ is, independently for each occurrence, selected from halogen, cyano, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl; n is an integer from 0 to 4; Y is selected from aryl, heteroaryl, cycloalkyl, and heterocycloalkyl, each optionally substituted with one or more substituents individually selected from R"; and R" is, independently for each occurrence, selected from halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the method comprising administering to the subject a composition comprising a therapeutically effective amount of a compound defined by Formula IA:

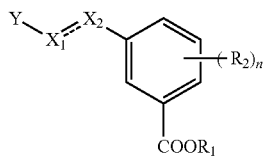

Formula IA wherein -----, $X_1$, $X_2$, $R_2$, n, Y, R', and R" are as defined above with respect to Formula I; and $R_1$ is selected from hydrogen, alkyl, haloalkyl, alkenyl, haloalkenyl, alkynyl, haloalkynyl, aryl, and alkylaryl.

In some embodiments of Formula I and Formula IA, Y can be a substituted or unsubstituted aryl ring (e.g., a substituted or unsubstituted phenyl ring). In other embodiments of Formula I and Formula IA, Y can be a substituted or unsubstituted 5- to 7-membered heteroaryl ring. For example, Y can be an oxazole ring, a pyridinyl ring, a thiazole ring, and a thiophene ring.

In some embodiments of Formula I and Formula IA, $X_1$ and $X_2$ are both CH. In other embodiments of Formula I and Formula IA, $X_1$ and $X_2$ are independently O or $CH_2$. In other embodiments of Formula I and Formula IA, $X_1$ and $X_2$ together with the bond to which they are attached forms a 3-membered carbocyclic ring.

In these methods, administering the composition to the subject modulates levels of ADMA and nitric oxide synthase (NOS) in the subject.

Also provided are methods of reducing one or more risk factors associated with inhibition of nitric oxide synthase in a subject. These methods can comprise administering to the subject a therapeutically effective amount of a compound defined by Formula I or Formula IA. In some cases, the risk factors can include renal failure, endothelial dysfunction, vascular disease, fibrosis, heart failure or a combination thereof.

Also provided are methods of treating or preventing a disease or condition associated with elevated levels of asymmetric dimethylarginine (ADMA) in a subject. These methods can comprise administering a therapeutically effective amount of a compound defined by Formula I or Formula IA. In some cases, the disease or condition can include renal failure, endothelial dysfunction, vascular disease, or a combination thereof.

Also provided herein are compounds that can modulate (e.g., increase or reduce) DDAH levels in a subject. In some examples, the compound can be represented by a structure having the Formula II:

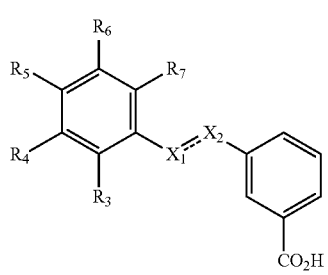

Formula II or a pharmaceutically acceptable salt or prodrug thereof, wherein ----- is a single, double, or triple bond; $X_1$ and $X_2$ as valence permits, are independently absent or selected from C, CH, $CH_2$, O, CO, S, $SO_2$, and NR'; wherein R' is independently selected from hydrogen or $C_1$-$C_6$ alkyl; or $X_1$ and $X_2$ together with the bond to which they are attached form a 3 or 4 membered carbocyclic ring; and $R_3$ $R_4$, $R_5$, $R_6$, and $R_7$ are independently selected from hydrogen, halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound can be a compound defined by Formula IIA:

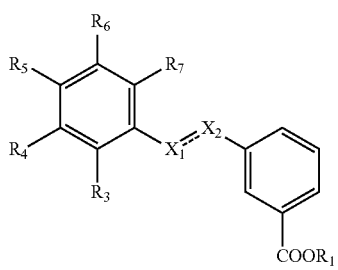

Formula IIA wherein $\rule{1cm}{0.4pt}$, $X_1$, $X_2$, R', $R_3$, $R_4$, $R_5$, $R_6$, and $R_7$ are as defined above with respect to Formula II; and $R_1$ is selected from hydrogen, alkyl, haloalkyl, alkenyl, haloalkenyl, alkynyl, haloalkynyl, aryl, and alkylaryl.

In some embodiments of Formula II and Formula IIA, $X_1$ and $X_2$ are both CH. In other embodiments of Formula II and Formula IIA, $X_1$ and $X_2$ are independently O or $CH_2$. In other embodiments of Formula I and Formula IIA, $X_1$ and $X_2$ together with the bond to which they are attached forms a 3-membered carbocyclic ring.

In some embodiments of Formula II and Formula IIA, $R_4$, $R_6$, and $R_7$ are hydrogen. In some embodiments of Formula II and Formula IIA, $R_3$ can be a $C_1$-$C_4$ alkyl group (e.g., a methyl group). In some embodiments of Formula II and Formula IIA, $R_5$ can be selected from hydroxyl and $C_1$-$C_4$ alkoxy (e.g., a methoxy group). In some embodiments of Formula II and Formula IIA, $R_5$ can hydroxyl. In some embodiments of Formula II and Formula IIA, $R_5$ can be $C_1$-$C_4$ alkoxy (e.g., a methoxy group).

In other examples, the compound can be defined by Formula III:

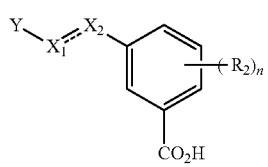

Formula III or a pharmaceutically acceptable salt or prodrug thereof, wherein $\rule{1cm}{0.4pt}$ is a single, double, or triple bond; $X_1$ and $X_2$ as valence permits, are independently absent or selected from C, CH, $CH_2$, O, CO, S, $SO_2$, and NR; wherein R is independently selected from hydrogen or $C_1$-$C_6$ alkyl; or $X_1$ and $X_2$ together with the bond to which they are attached form a 3 or 4 membered carbocyclic ring; $R_2$ is, independently for each occurrence, selected from halogen, cyano, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl; n is an integer from 0 to 4; Y is a 5- to 7-membered heteroaryl ring selected from an oxazole ring, a pyridinyl ring, a thiazole ring, and a thiophene ring, each optionally substituted with one or more substituents individually selected from R"; and R" is, independently for each occurrence, selected from halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound can be a compound defined by Formula IIIA:

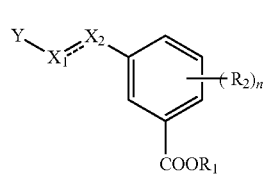

Formula IIIA wherein $\rule{1cm}{0.4pt}$, $X_1$, $X_2$, R', $R_2$, and R" are as defined above with respect to Formula III; and $R_1$ is selected from hydrogen, alkyl, haloalkyl, alkenyl, haloalkenyl, alkynyl, haloalkynyl, aryl, and alkylaryl.

In some embodiments of Formula III and Formula IIIA, Y can be a substituted or unsubstituted oxazole ring, pyridinyl ring, thiazole ring, or thiophene ring.

In some embodiments of Formula III and Formula IIIA, $X_1$ and $X_2$ are both CH. In other embodiments of Formula III and Formula IIIA, $X_1$ and $X_2$ are independently O or $CH_2$. In other embodiments of Formula III and Formula IIIA, $X_1$ and $X_2$ together with the bond to which they are attached forms a 3-membered carbocyclic ring.

Also provided herein are pharmaceutical compositions. The compositions can include a compound defined by Formula I, Formula IA, Formula II, Formula IIA, Formula III, or Formula IIIA and a pharmaceutically acceptable carrier. The compound can be present in a therapeutically effective amount to modulate DDAH and asymmetric dimethylarginine (ADMA) in a subject.

In some embodiments, the compounds described herein can reduce profibrotic gene and protein expression. Accordingly, the compounds described herein can also be administered to a subject in need thereof to treat or prevent fibrosis/fibrotic conditions. By way of example, the compounds described herein can be administered to a subject in need thereof, for example, to reduce fibrosis associated with diseases such as liver and renal fibrosis, cirrhosis, pulmonary fibrosis, scleroderma, graft vs host disease, keloids, intestinal fibrosis, Crohn's disease, idiopathic pulmonary fibrosis, and non-alcoholic hepatic steatosis.

DETAILED DESCRIPTION

Figure 1A:
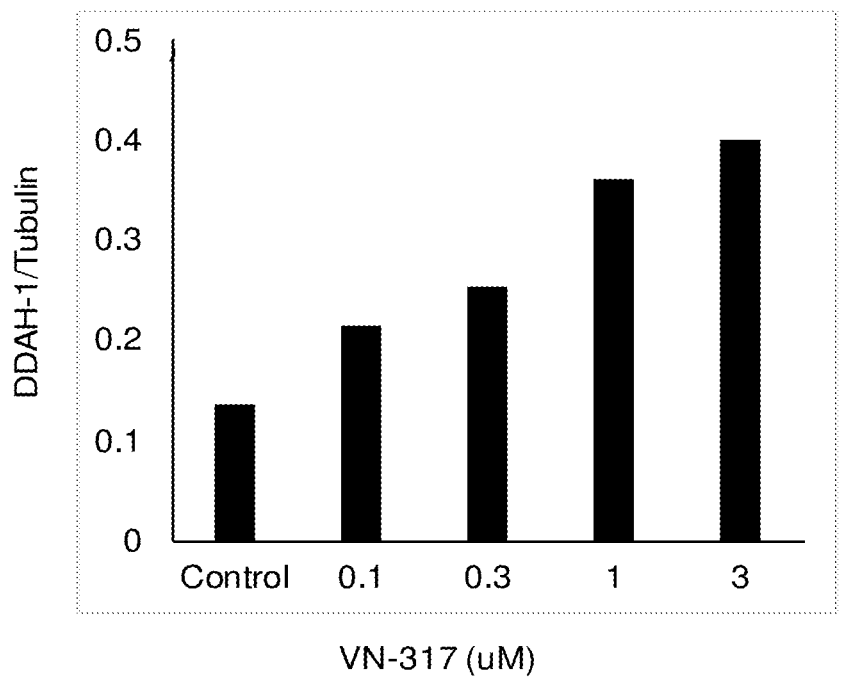
FIGS. 1A and 1B show modulation of DDAH in human pulmonary artery smooth muscle cells and human retinal endothelial cells. VN-317 produced differential modulation of DDAH, enhancing DDAH in lung smooth muscle cells whereas reducing in retinal endothelial cells.

The compounds, compositions, and methods described herein may be understood more readily by reference to the following detailed description of specific aspects of the disclosed subject matter and the Examples included therein.

Before the present compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., DDAH or ADMA). It is understood that this is typically in relation to some standard or expected value, in other words it is relative, but that it is not always necessary for the standard or relative value to be referred to. For example, "reduces AMDA" means reducing the circulating levels of ADMA in a subject relative to a standard or a control.

A modulator is a compound that can reduce or increase DDAH in different cells, tissues or in response to different stimulator or inhibitor. A modulator may produce efficacy in certain disease by increasing DDAH such as heart disease or PAH whereas in other disease, it may produce efficacy by reducing DDAH such as pain, eye disease and cancer.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "fibrotic condition" refers to a disease or condition involving the formation and/or deposition of fibrous tissue, e.g., excessive connective tissue builds up in a tissue and/or spreads over or replaces normal organ tissue (reviewed in, e.g., Wynn, *Nature Reviews* 4:583-594 (2004) and Abdel-Wahab, O. et al. (2009) *Annu. Rev. Med.* 60:233-45, incorporated herein by reference). In certain embodiments, the fibrotic condition involves excessive collagen mRNA production and deposition. In certain embodiments, the fibrotic condition is caused, at least in part, by injury, e.g., chronic injury (e.g., an insult, a wound, a toxin, a disease). In certain embodiments, the fibrotic condition is associated with an inflammatory, an autoimmune or a connective tissue disorder. For example, chronic inflammation in a tissue can lead to fibrosis in that tissue. Exemplary fibrotic tissues include, but are not limited to, biliary tissue, liver tissue, lung tissue, heart tissue, vascular tissue, kidney tissue, skin tissue, gut tissue, peritoneal tissue, bone marrow, and the like. In certain embodiments, the tissue is epithelial tissue.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "prodrug" refers to a compound that, when metabolized in vivo, undergo conversion to a compound having the desired pharmacological activity. Prodrugs can be prepared by replacing appropriate functionalities present in compound of Formula I with "pro-moieties" as described, for example, in H. Bundgaar, Design of Prodrugs (1985). Examples of prodrugs include ester (e.g., alkyl esters, glycyl esters, amino acid esters such as valine esters, PEG esters, glycerol esters, N-methylpiperazino esters, aminocarboxylic acid esters, etc.), ether, amide (e.g., benzamides, carboxamides, amides derived from amino acids residues, etc.), carbonate, carbamate, imine, and phosphate derivatives of the compounds herein, and their pharmaceutically acceptable salts. For further discussions of prodrugs, see, for example, T. Higuchi and V. Stella "Pro-drugs as Novel Delivery Systems," ACS Symposium Series 14 (1975) and E. B. Roche ed., Bioreversible Carriers in Drug Design (1987); and D. H. Jornada, G. S. dos Santos Fernandes, D. E. Chiba, T. R. F. de Melo, J. L. dos Santos, and M. C. Chung. *Molecules,* 2016, 21, 42.

The term "pharmaceutically acceptable salt" refers generally to compounds prepared by reaction of a free acid or base form of a compound described herein with a stoichiometric amount of an appropriate base or acid in water or in an organic solvent, or in a mixture of the two; generally, non-aqueous media like ether, ethyl acetate, ethanol, isopropanol, or acetonitrile are preferred. Lists of suitable salts are found, for example, in Remington's Pharmaceutical Sciences, 20th ed., Lippincott Williams & Wilkins, Baltimore, M D, 2000, p. 704. In some cases, it may be desirable to prepare a salt of a compound described herein due to one or more of the salt's advantageous physical properties, such as enhanced stability or a desirable solubility or dissolution profile.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, aralphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt may include alkali metal salts, including but not limited to sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, heteroatoms present in a compound or moiety, such as nitrogen, can have hydrogen substituents and/or any permissible substituents of organic compounds described herein which satisfy the valency of the heteroatom. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound (e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "alkyl" refers to saturated, straight-chained or branched saturated hydrocarbon moieties. Unless otherwise specified, $C_1$-$C_{24}$ (e.g., $C_1$-$C_{22}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. The alkyl group can be substituted with one or more groups including, but not limited to, hydroxy, halogen, acyl, alkyl, alkoxy, alkenyl, alkynyl, aryl, heteroaryl, acyl, aldehyde, amino, carboxylic acid, ester, ether, ketone, nitro, silyl, sulfo-oxo, sulfonyl, sulfone, sulfoxide, or thiol, as described below, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides (halogens; e.g., fluorine, chlorine, bromine, or iodine). The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "alkenyl" refers to unsaturated, straight-chained, or branched hydrocarbon moieties containing a double bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure-CH=CH—CH$_3$; and 2-propenyl refers to a group with the structure —CH$_2$—CH=CH$_2$. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. Alkenyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol, as described below, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol, as described below.

As used herein, the term "aryl," as well as derivative terms such as aryloxy, refers to groups that include a monovalent aromatic carbocyclic group of from 3 to 20 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, cycloalkyl, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "acyl" as used herein is represented by the formula —C(O)$Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. As used herein, the term "acyl" can be used interchangeably with "carbonyl." Throughout this specification "C(O)" or "CO" is a short hand notation for C=O.

As used herein, the term "alkoxy" refers to a group of the formula $Z^1$—O—, where $Z^1$ is unsubstituted or substituted alkyl as defined above. Unless otherwise specified, alkoxy groups wherein $Z^1$ is a $C_1$-$C_{24}$ (e.g., $C_1$-$C_{22}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-pentoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

The term "aldehyde" as used herein is represented by the formula —C(O)H.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)NZ$^1$Z$^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" or "halo" as used herein refers to fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

As used herein, Me refers to a methyl group; OMe refers to a methoxy group; and i-Pr refers to an isopropyl group.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible stereoisomer or mixture of stereoisomer (e.g., each enantiomer, each diastereomer, each meso compound, a racemic mixture, or scalemic mixture).

Reference will now be made in detail to specific aspects of the disclosed materials, compounds, compositions, and methods, examples of which are illustrated in the accompanying Examples.

Compounds

Provided herein are compounds that can reduce ADMA levels in a subject. In some embodiments, the compound can be defined by Formula I:

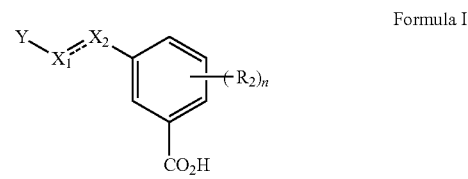

Formula I or a pharmaceutically acceptable salt or prodrug thereof, wherein
  ====== represents a single, double, or triple bond;
  X$_1$ and X$_2$, as valence permits, are independently absent or selected from C, CH, CH$_2$, O, CO, S, SO$_2$, and NR';
    wherein R is independently selected from hydrogen or C$_1$-C$_6$ alkyl; or X$_1$ and X$_2$ together with the bond to which they are attached form a 3 or 4 membered carbocyclic ring;
  R$_2$ is, independently for each occurrence, selected from halogen, cyano, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl; n is an integer from 0 to 4; Y is selected from aryl, heteroaryl, cycloalkyl, and heterocycloalkyl, each optionally substituted with one or more substituents individually selected from R"; and R" is, independently for each occurrence, selected from halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound can be defined by Formula IA:

Formula IA wherein ======, X$_1$, X$_2$, R$_2$, n, Y, R', and R" are as defined above with respect to Formula I; and R$_1$ is selected from hydrogen, alkyl, haloalkyl, alkenyl, haloalkenyl, alkynyl, haloalkynyl, aryl, and alkylaryl.

In some embodiments of Formula I and Formula IA, Y can be a substituted or unsubstituted aryl ring (e.g., a substituted or unsubstituted phenyl ring). In certain embodiments, Y can be a substituted phenyl ring. In certain embodiments, Y can be a di-substituted phenyl ring.

In other embodiments of Formula I and Formula IA, Y can be a substituted or unsubstituted 5- to 7-membered heteroaryl ring. For example, Y can be an oxazole ring, a pyridinyl ring, a thiazole ring, or a thiophene ring.

In some embodiments, the compound of Formula I and Formula IA can be defined by the formula below

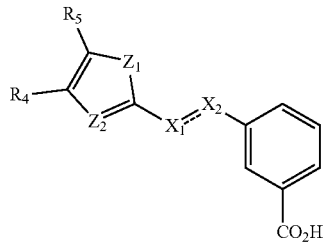

or a pharmaceutically acceptable salt or prodrug thereof, wherein ⸺, $X_1$, $X_2$, $R_2$, n, Y, R', and R" are as defined above with respect to Formula I; $Z_1$ is S or O; $Z_2$ is N or C—$R_3$; and $R_3$ $R_4$, and $R_5$, are independently selected from hydrogen, halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound of Formula I and Formula IA can be defined by the formula below

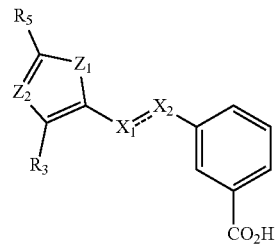

or a pharmaceutically acceptable salt or prodrug thereof, wherein ⸺, $X_1$, $X_2$, $R_2$, n, Y, R', and R" are as defined above with respect to Formula I; $Z_1$ is S or O; $Z_2$ is N or C—$R_4$; and $R_3$ $R_4$, and $R_5$, are independently selected from hydrogen, halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound of Formula I and Formula IA can be defined by the formula below

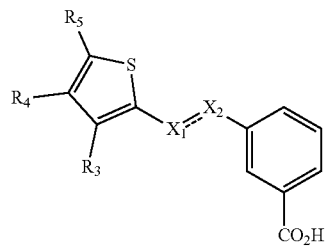

or a pharmaceutically acceptable salt or prodrug thereof, wherein ⸺, $X_1$, $X_2$, $R_2$, n, Y, R', and R" are as defined above with respect to Formula I; and $R_3$ $R_4$, and $R_5$, are independently selected from hydrogen, halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments of Formula I and Formula IA, $X_1$ and $X_2$ are both CH. In some of these embodiments, the stereochemistry of the double bond can be cis. In other cases, the stereochemistry of the double bond can be trans.

In other embodiments of Formula I and Formula IA, $X_1$ and $X_2$ are independently O or $CH_2$. For example, in some embodiments, $X_1$ can be $CH_2$ and $X_2$ can be O. In other embodiments, $X_2$ can be $CH_2$ and $X_1$ can be O.

In other embodiments of Formula I and Formula IA, $X_1$ and $X_2$ together with the bond to which they are attached forms a 3-membered carbocyclic ring.

In some embodiments, the compound can be defined by Formula II:

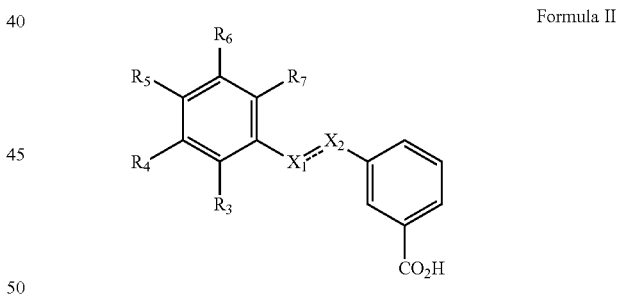

Formula II or a pharmaceutically acceptable salt or prodrug thereof, wherein ⸺ is a single, double, or triple bond; $X_1$ and $X_2$ as valence permits, are independently absent or selected from C, CH, $CH_2$, O, CO, S, $SO_2$, and NR'; wherein R is independently selected from hydrogen or $C_1$-$C_6$ alkyl; or $X_1$ and $X_2$ together with the bond to which they are attached form a 3 or 4 membered carbocyclic ring; and $R_3$ $R_4$, $R_5$, $R_6$, and $R_7$ are independently selected from hydrogen, halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound can be a compound defined by Formula IIA:

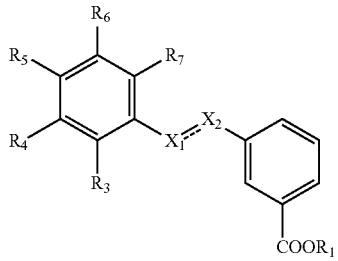

Formula IIA wherein -----, $X_1$, $X_2$, R', $R_3$, $R_4$, $R_5$, $R_6$, and $R_7$ are as defined above with respect to Formula II; and $R_1$ is selected from hydrogen, alkyl, haloalkyl, alkenyl, haloalkenyl, alkynyl, haloalkynyl, aryl, and alkylaryl.

In some embodiments of Formula II and Formula IIA, $X_1$ and $X_2$ are both CH. In some of these embodiments, the stereochemistry of the double bond can be cis. In other cases, the stereochemistry of the double bond can be trans.

In other embodiments of Formula II and Formula IIA, $X_1$ and $X_2$ are independently O or $CH_2$. For example, in some embodiments, $X_1$ can be $CH_2$ and $X_2$ can be O. In other embodiments, $X_2$ can be $CH_2$ and $X_1$ can be O.

In other embodiments of Formula II and Formula IIA, $X_1$ and $X_2$ together with the bond to which they are attached forms a 3-membered carbocyclic ring.

In some embodiments of Formula II and Formula IIA, $R_4$, $R_6$, and $R_7$ are hydrogen. In some embodiments of Formula II and Formula IIA, $R_3$ can be a $C_1$-$C_4$ alkyl group (e.g., a methyl group). In some embodiments of Formula II and Formula IIA, $R_5$ can be selected from hydroxyl and $C_1$-$C_4$ alkoxy (e.g., a methoxy group). In some embodiments of Formula II and Formula IIA, $R_5$ can hydroxyl. In some embodiments of Formula II and Formula IIA, $R_5$ can be $C_1$-$C_4$ alkoxy (e.g., a methoxy group).

In other examples, the compound can be defined by Formula III:

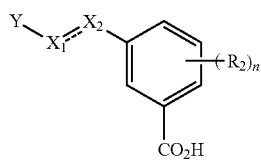

Formula III or a pharmaceutically acceptable salt or prodrug thereof, wherein ----- is a single, double, or triple bond; $X_1$ and $X_2$ as valence permits, are independently absent or selected from C, CH, $CH_2$, O, CO, S, $SO_2$, and NR'; wherein R' is independently selected from hydrogen or $C_1$-$C_6$ alkyl; or $X_1$ and $X_2$ together with the bond to which they are attached form a 3 or 4 membered carbocyclic ring; $R_2$ is, independently for each occurrence, selected from halogen, cyano, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl; n is an integer from 0 to 4; Y is a 5- to 7-membered heteroaryl ring selected from an oxazole ring, a pyridinyl ring, a thiazole ring, and a thiophene ring, each optionally substituted with one or more substituents individually selected from R"; and R" is, independently for each occurrence, selected from halogen, cyano, nitro, hydroxyl, amino, alkylamino, dialkylamino, alkyl, haloalkyl; alkylthio; haloalkylthio; alkoxy, haloalkoxy, alkenyl, haloalkenyl, alkynyl, haloalkynyl, alkylsulfinyl, haloalkylsulfinyl, alkylsulfonyl, haloalkylsulfonyl, alkylcarbonyl, haloalkylcarbonyl, alkoxycarbonyl, haloalkoxycarbonyl, alkylaminocarbonyl, heteroalkylaminocarbonyl, dialkylaminocarbonyl, and heterodialkylaminocarbonyl.

In some embodiments, the compound can be a compound defined by Formula IIIA:

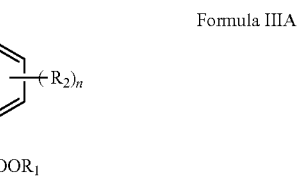

Formula IIIA wherein -----, $X_1$, $X_2$, R, $R_2$, and R" are as defined above with respect to Formula III; and $R_1$ is selected from hydrogen, alkyl, haloalkyl, alkenyl, haloalkenyl, alkynyl, haloalkynyl, aryl, and alkylaryl.

In some embodiments of Formula III and Formula IIIA, Y can be a substituted or unsubstituted oxazole ring. In some embodiments of Formula III and Formula IIIA, Y can be a substituted or unsubstituted pyridinyl ring. In some embodiments of Formula III and Formula IIIA, Y can be a substituted or unsubstituted thiazole ring. In some embodiments of Formula III and Formula IIIA, Y can be a substituted or unsubstituted thiophene ring.

In some embodiments of Formula III and Formula IIIA, $X_1$ and $X_2$ are both CH. In some of these embodiments, the stereochemistry of the double bond can be cis. In other cases, the stereochemistry of the double bond can be trans.

In other embodiments of Formula III and Formula IIIA, $X_1$ and $X_2$ are independently O or $CH_2$. For example, in some embodiments, $X_1$ can be $CH_2$ and $X_2$ can be O. In other embodiments, $X_2$ can be $CH_2$ and $X_1$ can be O.

In other embodiments of Formula III and Formula IIIA, $X_1$ and $X_2$ together with the bond to which they are attached forms a 3-membered carbocyclic ring.

Pharmaceutical Compositions

Also provided are compositions that include one or more of the compounds described herein. In some embodiments, ADMA-modulating (e.g., increasing or reducing) compositions are provided, comprising a carrier and an effective amount of a compound described herein.

In some embodiments, the carrier can be a pharmaceutically acceptable carrier. A "pharmaceutically acceptable carrier" as used herein refers to a carrier that, when combined with a compound described herein, facilitates the application or administration of that compound described herein for its intended purpose (e.g., to modulate DDAH and ADMA levels in a subject, to treat or prevent a disease or condition associated with elevated levels of asymmetric dimethylarginine (ADMA) in a subject, to increase DDAH levels in a subject, to reduce one or more risk factors associated with inhibition of nitric oxide synthase in a subject, or a combination thereof). In other embodiments, the modulator may decrease the levels of DDAH. The compound described herein may be formulated for administration in a pharmaceutically acceptable carrier in accordance with known techniques. See, e.g., Remington, The Science and Practice of Pharmacy (9th Ed. 1995). The pharmaceutically acceptable carrier can, of course, also be acceptable in the sense of being compatible with any other ingredients in the composition.

The carrier may be a solid or a liquid, or both, and is preferably formulated with the a compound described herein as a unit-dose composition, for example, a tablet, which may contain from 0.01 or 0.5% to 95% or 99% by weight of the a compound described herein. One or more a compounds described herein can be included in the compositions, which may be prepared by any of the well-known techniques of pharmacy comprising admixing the components, optionally including one or more accessory ingredients.

In general, compositions may be prepared by uniformly and intimately admixing a compound described herein with a liquid or finely divided solid carrier, or both, and then, if necessary, shaping the resulting mixture. For example, a tablet may be prepared by compressing or molding a powder or granules containing the a compound described herein, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Compositions can be formulated to be suitable for oral, nasal, rectal, topical, buccal (e.g., sub-lingual), vaginal, parenteral (e.g., subcutaneous, intramuscular, intradermal, or intravenous), topical (i.e., both skin and mucosal surfaces, including airway surfaces) or transdermal administration, although the most suitable route in any given case will depend on the nature and severity of the condition being treated and on the nature of the particular compound that is being used.

Compositions suitable for oral administration may be presented in discrete units, such as capsules, cachets, lozenges, or tablets, each containing a predetermined amount of the compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the compound and a suitable carrier (which may contain one or more accessory ingredients as noted above).

Compositions suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Compositions suitable for parenteral administration comprise sterile aqueous and non-aqueous injection solutions of the compound, which preparations are preferably isotonic with the blood of the intended recipient. These preparations may contain antioxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, the composition can be an injectable, stable, sterile composition comprising a compound described herein in a unit dosage form in a sealed container. The composition can be provided in the form of a lyophilizate that can be reconstituted with a suitable pharmaceutically acceptable carrier to form a liquid composition suitable for injection thereof into a subject. The unit dosage form can comprise from about 10 mg to about 10 grams of the compound. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration can be presented as unit dose suppositories. These may be prepared by mixing the active compound with one or more conventional solid carriers, for example, cocoa butter, and then shaping the resulting mixture.

Compositions suitable for topical application to the skin can take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration can be presented as discrete patches adapted to remain in intimate contact with the epidermis of the recipient for a prolonged period of time. Compositions suitable for transdermal administration may also be delivered by iontophoresis and typically take the form of an optionally buffered aqueous solution of the active compound.

In some embodiments, the compositions described herein can further include one or more additional active agents. Examples of suitable additional active agents include antidiabetics, hypotensive agents, perfusion-enhancing agents, lipid metabolism modulators, antithrombotic agents, antioxidants, chemokine receptor antagonists, p38-kinase inhibitors, NPY agonists, orexin agonists, anorectics, PAF-AH inhibitors, antiphlogistics, COX inhibitors, LTB4-receptor antagonists, analgesics, prostacyclin analogs, guanylate cyclase stimulators, endothelin receptor antagonists, PDE5 inhibitors, ACE inhibitors, angiotensin receptor antagonists, diuretics, analgesics (e.g., NSAIDs such as aspirin), antidepressants, and other psychopharmaceuticals.

Examples of lipid metabolism modulators include HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists, cannabinoid receptor 1 antagonists, and antioxidants/radical scavengers.

In some embodiments, the lipid metabolism modulator can comprise a statins, such as, by way of example, lovastatin, simvastatin, pravastatin, fluvastatin, atorvastatin, rosuvastatin, cerivastatin, or pitavastatin.

In some embodiments, the lipid metabolism modulator can comprise a squalene synthesis inhibitor, such as, by way of example, BMS-188494 or TAK-475.

In some embodiments, the lipid metabolism modulator can comprise an ACAT inhibitor, such as, by way of example, avasimibe, melinamide, pactimibe, eflucimibe or SMP-797.

In some embodiments, the lipid metabolism modulator can comprise a cholesterol absorption inhibitor, such as, by way of example, ezetimibe, tiqueside or pamaqueside.

In some embodiments, the lipid metabolism modulator can comprise an MTP inhibitor, such as, by way of example, implitapide, BMS-201038, R-103757 or JTT-130.

In some embodiments, the lipid metabolism modulator can comprise a lipase inhibitor, such as, by way of example, orlistat.

In some embodiments, the lipid metabolism modulator can comprise a thyroid hormone and/or thyroid mimetic, such as, by way of example, D-thyroxine or 3,5,3'-triiodothyronine (T3).

In some embodiments, the lipid metabolism modulator can comprise an agonist of the niacin receptor, such as, by way of example, niacin, acipimox, acifran or radecol.

In some embodiments, the lipid metabolism modulator can comprise a CETP inhibitor, such as, by way of example, dalcetrapib, BAY 60-5521, anacetrapib or CETP vaccine (CETi-1).

In some embodiments, the lipid metabolism modulator can comprise a PPAR-γ agonist, for example from the class of the thiazolidinediones, such as, by way of example, pioglitazone or rosiglitazone.

In some embodiments, the lipid metabolism modulator can comprise a PPAR-δ agonist, such as, by way of example, GW-501516 or BAY 68-5042.

In some embodiments, the lipid metabolism modulator can comprise a polymeric bile acid adsorber, such as, by way of example, cholestyramine, colestipol, colesolvam, CholestaGel or colestimide.

In some embodiments, the lipid metabolism modulator can comprise a bile acid reabsorption inhibitor, such as, by way of example, ASBT (=IBAT) inhibitors, such as, for example, AZD-7806, S-8921, AK-105, BARI-1741, SC-435 or SC-635.

In some embodiments, the lipid metabolism modulator can comprise an antioxidant/radical scavenger, such as, by way of example, probucol, AGI-1067, BO-653 or AEOL-10150.

In some embodiments, the lipid metabolism modulator can comprise a cannabinoid receptor 1 antagonist, such as, by way of example, rimonabant or SR-147778.

Examples of suitable antidiabetics since insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients for example may include sulfonylureas, biguanides, meglitinide derivatives, glucosidase inhibitors and PPAR-gamma agonists.

In some embodiments, the antidiabetics can comprise insulin and modified insulins.

In some embodiments, the antidiabetics can comprise a sulfonylurea, such as, by way of example, tolbutamide, glibenclamide, glimepiride, glipizide or gliclazide.

In some embodiments, the antidiabetics can comprise a biguanide, such as, by way of example, metformin.

In some embodiments, the antidiabetics can comprise a meglitinide derivative, such as, by way of example, repaglinide or nateglinide.

In some embodiments, the antidiabetics can comprise a glucosidase inhibitor, such as, by way of example, miglitol or acarbose.

In some embodiments, the antidiabetics can comprise a DPP-IV inhibitor, such as, by way of example, sitagliptin and vildagliptin.

In some embodiments, the antidiabetics can comprise a PPAR-gamma agonist, for example from the class of the thiazolinediones, such as, by way of example, pioglitazone or rosiglitazone.

Examples of suitable hypotensive agents include calcium antagonists, angiotensin AII antagonists, ACE inhibitors, beta-receptor blockers, alpha-receptor blockers and diuretics.

In some embodiments, the hypotensive agent can comprise a calcium antagonist, such as, by way of example, nifedipine, amlodipine, verapamil or diltiazem.

In some embodiments, the hypotensive agent can comprise an angiotensin AII antagonist, such as, by way of example, losartan, valsartan, candesartan, embusartan, olmesartan or telmisartan.

In some embodiments, the hypotensive agent can comprise an ACE inhibitor, such as, by way of example, enalapril, captopril, lisinopril, ramipril, delapril, fosinopril, quinopril, perindopril or trandopril.

In some embodiments, the hypotensive agent can comprise a beta-receptor blocker, such as, by way of example, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In some embodiments, the hypotensive agent can comprise an alpha-receptor blocker, such as, by way of example, prazosin.

In some embodiments, the hypotensive agent can comprise a diuretic, such as, by way of example, furosemide, bumetanide, torsemide, bendroflumethiazide, chlorothiazide, hydrochlorothiazide, hydroflumethiazide, methyclothiazide, polythiazide, trichloromethiazide, chlorthalidone, indapamide, metolazone, quinethazone, acetazolamide, dichlorophenamide, methazolamide, glycerol, isosorbide, mannitol, amiloride or triamteren.

In some embodiments, the one or more additional active agents can comprise an aldosterone or mineralocorticoid receptor antagonist, such as, by way of example, spironolactone or eplerenone.

In some embodiments, the one or more additional active agents can comprise a vasopressin receptor antagonist, such as, by way of example, conivaptan, tolvaptan, lixivaptan or SR-121463.

In some embodiments, the one or more additional active agents can comprise an organic nitrate or NO donor, such as, by way of example, sodium nitroprusside, nitroglycerol, isosorbide mononitrate, isosorbide dinitrate, molsidomin or SIN-1, or in combination with inhalative NO.

In some embodiments, the one or more additional active agents can comprise a positive-inotropic compound, such as, by way of example, cardiac glycosides (digoxin), beta-adrenergic and dopaminergic agonists, such as isoproterenol, adrenaline, noradrenaline, dopamine or dobutamine.

In some embodiments, the one or more additional active agents can comprise an antisympathotonic, such as reserpine, clonidine or alpha-methyldopa, or a potassium channel agonist, such as minoxidil, diazoxide, dihydralazine or hydralazine, or a substance which releases nitrogen oxide, such as glycerol nitrate or sodium nitroprusside.

Examples of antithrombotics include platelet aggregation inhibitors and anticoagulants.

In some embodiments, the antithrombotic can comprise a platelet aggregation inhibitor, such as, by way of example, aspirin, clopidogrel, ticlopidine or dipyridamol.

In some embodiments, the antithrombotic can comprise a thrombin inhibitor, such as, by way of example, ximelagatran, melagatran, dabigatran, bivalirudin or clexane.

In some embodiments, the one or more additional active agents can comprise a GPIIb/IIIa antagonist, such as, by way of example, tirofiban or abciximab.

In some embodiments, the one or more additional active agents can comprise a factor Xa inhibitor, such as, by way of example, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In some embodiments, the one or more additional active agents can comprise heparin or a low molecular weight (LMW) heparin derivative.

In some embodiments, the one or more additional active agents can comprise a vitamin K antagonist, such as, by way of example, coumarin.

In some embodiments, the one or more additional active agents can comprise an endothelin receptor antagonist, such as, by way of example, bosentan or ambrisentan.

In some embodiments, the one or more additional active agents can comprise a phosphodiesterase type 5 inhibitor, such as, by way of example, sildenafil or tadalafil.

In some embodiments, the one or more additional active agents can comprise a prostacyclin analogue, such as, by way of example, epoprostenol, treprostinil or iloprost.

Coating compositions are also provided. A "coating" as used herein is generally known. Any of a variety of organic and aqueous coating compositions, with or without pigments, may be modified to contain one or more compounds described herein. Examples of suitable coating compositions include, for example, the coating compositions described in U.S. Pat. Nos. 7,109,262, 6,964,989, 6,835,459, 6,677,035, 6,528,580, and 6,235,812, each incorporated by reference herein in their entirety.

In some examples, coating compositions can comprise (in addition to one or more compounds described herein) a film-forming resin, an aqueous or organic solvent that disperses the resin; and, optionally, at least one pigment. Other ingredients such as colorants, secondary pigments, stabilizers and the like can be included if desired. The one or more compounds described herein may be dissolved or dispersed in the solvent and/or resin, so that the compound(s) are dispersed or distributed on an article or substrate coated by the coating composition. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with the coating compositions described herein. Suitable articles include, but are not limited to, the surface of implantable medical devices such as stents. Coating of the article with the composition can be carried out by any suitable means, such as by brushing, spraying, electrostatic deposition, dip coating, doctor blading, etc.

The compositions described herein can include an effective amount of a compound described herein to achieve the intended purpose, e.g. to modulating DDAH and ADMA levels in a subject. The determination of an effective dose is well within the capability of those skilled in the art in view of the present disclosure.

For any compound, the therapeutically effective dose can be estimated initially either in in vitro assays, e.g. those described in the Examples herein, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of a compound described herein that ameliorates the symptoms or condition. Therapeutic efficacy and toxicity of such compounds can be determined by standard pharmaceutical procedures in vitro or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Exemplary pharmaceutical compositions exhibit large therapeutic indices. The data obtained from in vitro assays and animal studies are used in formulating a range of dosage for human use. The dosage of such compounds lies for example within a range of circulating concentrations what include the ED50 with little or no toxicity. The dosage varies within this range depending upon the dosage form employed, sensitivity of the patient, and the route of administration.

Normal dosage amounts may vary from 0.1 to 1000 milligrams total dose, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc.

Methods of Use

The compounds described herein can modulate the enzyme dimethylarginine diaminohydrolase (DDAH), modulate ADMA, and/or treat diseases characterized by elevated or low levels of ADMA. The compounds described herein can be administered to a subject in order to modulate tissue or plasma levels of ADMA.

ADMA is eliminated from the body through a combination of renal clearance and the enzymatic action of DDAH. It has been shown that there is a direct correlation between renal failure and increased levels of ADMA in patient's blood along with decreased levels of NO. Elevated levels of ADMA have been found in patients with a wide variety of diseases and conditions such as renal disease, coronary artery disease, ischemic heart disease, congestive heart failure, hypertension, lung injury, pulmonary hypertension, hypercholesterolemia, diabetes, atherosclerosis, sepsis, organ failure, surgical trauma, and in particular end stage renal failure. ADMA levels are also increased in patients with acute kidney injury and contrast induced renal injury. In addition, it has been reported that increased ADMA level is an indicator of risk for cardiovascular-related death.

Thus, there is an urgent need to develop a means to modulate ADMA or at least reduce ADMA concentration in the blood of patients, in particular patients with chronic kidney disease, organ failure and those who are receiving hemodialysis treatment for kidney related diseases. The ability to reduce ADMA from the blood of end stage renal disease patients in conjunction with hemodialysis treatment by administering the compounds may reduce ADMA-mediated morbidity and extend life. In exemplary embodiments, the DDAH and ADMA-modulating compounds described herein can exhibit activity that is indicative of clinical efficacy, including hydrolyzing ADMA, in vitro or in vivo activity, and efficacy for treatment of cardiac diseases, heart failure, kidney diseases, lung disease, sepsis or in a model thereof.

Accordingly, provided herein are methods for modulating DDAH and asymmetric dimethylarginine (ADMA) in a subject, the method comprising administering to the subject a composition comprising a therapeutically effective amount of a compound described herein.

Also provided are methods of reducing one or more risk factors associated with inhibition of nitric oxide synthase in a subject. These methods can comprise administering to the subject a therapeutically effective amount of a compound described herein. In some cases, the risk factors can include renal failure, endothelial dysfunction, vascular disease, or a combination thereof.

Also provided are methods of treating or preventing a disease or condition associated with elevated levels of asymmetric dimethylarginine (ADMA) in a subject. These methods can comprise administering a therapeutically effective amount of a compound described herein. Administration of the compounds described herein may reduce the concentration of ADMA, and/or increase the levels of citrulline, and/or increase the levels of NO in the subject.

The disease can any diseases or conditions associated with elevated ADMA levels, including but not limited to cardiac diseases such as heart failure, or renal diseases. For example, the compounds described herein can be used for the prophylaxis and/or treatment of renal disease, sepsis, sickle cell crisis, severe malaria, Mediterranean fever, trauma, ICU patients, acute kidney injury contrast induced kidney injury, decompensated heart failure, diuretic resistant heart failure, cardiac failure and cardiac insufficiency thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (coronary artery bypass graft, CABG), primary percutaneous transluminal coronary angioplasties (PTCAs), PTCAs after thrombolysis, rescue PTCA, heart transplants and open-heart operations, and for organ protection in connection with transplants, bypass operations, catheter examinations and other surgical procedures.

The compounds described herein can be used for the prophylaxis and/or treatment of respiratory disorders, such as, for example, chronic obstructive pulmonary disease (chronic bronchitis, COPD), asthma, pulmonary emphysema, bronchiectases, lung injury, cystic fibrosis (mucoviscidosis) and pulmonary hypertension, in particular pulmonary arterial hypertension.

The compounds described herein can be used for the prophylaxis and/or treatment of kidney diseases, especially of acute and chronic kidney diseases and acute and chronic renal insufficiencies, as well as acute and chronic renal failure, including acute and chronic stages of renal failure with or without the requirement of dialysis, as well as the underlying or related kidney diseases such as renal hypoperfusion, dialysis induced hypotension, glomerulopathies, glomerular and tubular proteinuria, renal edema, hematuria, primary, secondary, as well as acute and chronic glomerulonephritis, membranous and membranoproliferative glomerulonephritis, Alport-Syndrome, glomerulosclerosis, interstistial tubular diseases, nephropathic diseases, such as primary and inborn kidney diseases, renal inflammation, immunological renal diseases like renal transplant rejection, immune complex induced renal diseases, as well as intoxication induced nephropathic diseases, diabetic and non-diabetic renal diseases, pyelonephritis, cystic kidneys, nephrosclerosis, hypertensive nephrosclerosis, nephrotic syndrome, that are characterized and diagnostically associated with an abnormal reduction in creatinine clearance and/or water excretion, abnormal increased blood concentrations of urea, nitrogen, potassium and/or creatinine, alteration in the activity of renal enzymes, such as glutamyl synthetase, urine osmolarity and urine volume, increased microalbuminuria, macroalbuminuria, glomerular and arteriolar lesions, tubular dilation, hyperphosphatemia and/or the requirement of dialysis.

The compounds described herein can be used for the prophylaxis and/or treatment of renal carcinomas, after incomplete resection of the kidney, suppression of gastric cancer, dehydration after overuse of diuretics, uncontrolled blood pressure increase with malignant hypertension, urinary tract obstruction and infection, amyloidosis, as well as systemic diseases associated with glomerular damage, such as Lupus erythematosus, and rheumatic immunological systemic diseases, as well as renal artery stenosis, renal artery thrombosis, renal vein thrombosis, analgetics induced nephropathy and renal tubular acidosis.

The compounds described herein can be used for the prophylaxis and/or treatment of contrast medium induced and drug induced acute and chronic interstitial kidney diseases, metabolic syndrome and insulin resistance.

The compounds described herein can be used for the prophylaxis and/or treatment of aftereffects associated with acute and/or chronic kidney diseases, such as pulmonary edema, heart failure, uremia, anemia, electrolyte disturbances (e.g. hyperkalemia, hyponatremia), as well as bone and carbohydrate metabolism.

The compounds described herein can be used for the prophylaxis and/or treatment of coronary heart disease, acute coronary syndrome, heart failure, and myocardial infarction.

In therapeutic applications, the compounds described herein are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

In prophylactic applications, the compounds described herein are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The compounds described herein can be used to modulate the concentration of ADMA in a patient. In one embodiment, a subject in need thereof receives a therapeutic amount of a compound described herein that would decrease the subject's ADMA concentration over the baseline of their seeking treatment by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%. In another embodiment, provided are methods of treatment of a subject in need thereof to increase the subject's NO production by administering a therapeutically effective amount of a compound described herein to increase NO production by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%.

The compound described here can reduce DDAH in disease state in certain cells and therefore used for the treatment of pain, eye disease and cancer.

The compounds described herein can also be used to treat or prevent fibrotic conditions. Example fibrotic conditions that can be treated or prevented using the compounds described herein include, but are not limited to, a fibrotic condition of the lung, liver, heart, vasculature, kidney, skin, gastrointestinal tract, bone marrow, or a combination thereof. Each of these conditions is described in more detail herein.

Fibrosis of the lung (also referred to herein as "pulmonary fibrosis") is characterized by the formation of scar tissue within the lungs, which results in a decreased function. Pulmonary fibrosis is associated with shortness of breath, which progresses to discomfort in the chest weakness and fatigue, and ultimately to loss of appetite and rapid weight-loss. Approximately 500,000 people in the U.S. and 5 million worldwide suffer from pulmonary fibrosis, and 40,000 people in the U.S. die annually from the disease. Pulmonary fibrosis has a number of causes, including radiation therapy, but can also be due to smoking or hereditary factors (Meltzer, E B et al. (2008) *Orphanet J. Rare Dis.* 3:8).

Pulmonary fibrosis can occur as a secondary effect in disease processes such as asbestosis and silicosis, and is known to be more prevalent in certain occupations such as coal miner, ship workers and sand blasters where exposure to environmental pollutants is an occupational hazard (Green, F H et al. (2007) *Toxicol Pathol.* 35:136-47). Other factors that contribute to pulmonary fibrosis include cigarette smoking, and autoimmune connective tissue disorders, like rheumatoid arthritis, scleroderma and systemic lupus erythematosus (SLE) (Leslie, K O et al. (2007) *Semin Respir Crit. Care Med.* 28:369-78; Swigris, J J et al. (2008) Chest. 133:271-80; and Antoniou, K M et al. (2008) *Curr Opin Rheumatol.* 20:686-91). Other connective tissue disorders such as sarcoidosis can include pulmonary fibrosis as part of the disease (Paramothayan, S et al. (2008) *Respir Med.* 102:1-9), and infectious diseases of the lung can cause fibrosis as a long term consequence of infection, particularly chronic infections. Pulmonary fibrosis can also be a side effect of certain medical treatments, particularly radiation therapy to the chest and certain medicines like bleomycin, methotrexate, amiodarone, busulfan, and nitrofurantoin (Catane, R et al. (1979) *Int J Radiat Oncol Biol Phys.* 5:1513-8; Zisman, D A et al. (2001) *Sarcoidosis Vasc Diffuse Lung Dis.* 18:243-52; Rakita, L et al. (1983) *Am Heart J.* 106:906-16; Twohig, K J et al. (1990) *Clin Chest Med.* 11:31-54; and Witten C M. (1989) *Arch Phys Med. Rehabil.* 70:55-7). In other embodiments, idiopathic pulmonary fibrosis can occur where no clear causal agent or disease can be identified. Increasingly, it appears that genetic factors can play a significant role in these cases of pulmonary fibrosis (Steele, M P et al. (2007) Respiration 74:601-8; Brass, D M et al. (2007) *Proc Am Thorac Soc.* 4:92-100 and du Bois R M. (2006) *Semin Respir Crit. Care Med.* 27:581-8).

In some examples, the fibrotic condition of the lung can be chosen from one or more of: pulmonary fibrosis, idiopathic pulmonary fibrosis (IPF), usual interstitial pneumonitis (UIP), interstitial lung disease, cryptogenic fibrosing alveolitis (CFA), or bronchiectasis.

In other examples, the pulmonary fibrosis can include, but is not limited to, pulmonary fibrosis associated with chronic obstructive pulmonary disease (COPD), scleroderma, pleural fibrosis, chronic asthma, acute lung syndrome, amyloidosis, bronchopulmonary dysplasia, Caplan's disease, Dressler's syndrome, histiocytosis X, idiopathic pulmonary haemosiderosis, lymphangiomyomatosis, mitral valve stenosis, polymyositis, pulmonary edema, pulmonary hypertension (e.g., idiopathic pulmonary hypertension (IPH)), pneumoconiosis, radiotherapy (e.g., radiation induced fibrosis), rheumatoid disease, Shaver's disease, systemic lupus erythematosus, systemic sclerosis, tropical pulmonary eosinophilia, tuberous sclerosis, Weber-Christian disease, Wegener's granulomatosis, Whipple's disease, or exposure to toxins or irritants (e.g., pharmaceutical drugs such as amiodarone, bleomycin, busulphan, carmustine, chloramphenicol, hexamethonium, methotrexate, methysergide, mitomycin C, nitrofurantoin, penicillamine, peplomycin, and practolol; inhalation of talc or dust, e.g., coal dust, silica). In certain embodiments, the pulmonary fibrosis is associated with an inflammatory disorder of the lung, e.g., asthma, COPD.

In some embodiments, the fibrotic condition can be a fibrotic condition of the liver (also referred to herein as "hepatic fibrosis"), such as fatty liver disease e.g., steatosis such as nonalcoholic steatohepatitis (NASH), biliary fibrosis, cholestatic liver disease (e.g., primary biliary cirrhosis (PBC), and cholangiopathies (e.g., chronic cholangiopathies)).

In certain embodiments, the fibrotic of the liver or hepatic fibrosis can be chosen from one or more of: fatty liver disease, steatosis (e.g., nonalcoholic steatohepatitis (NASH), cholestatic liver disease, primary biliary cirrhosis (PBC), biliary fibrosis, cirrhosis, alcohol induced liver fibrosis, biliary duct injury, infection or viral induced liver fibrosis, congenital hepatic fibrosis, autoimmune hepatitis, or cholangiopathies (e.g., chronic cholangiopathies).

In certain embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins such as arsenic), alpha-1 antitrypsin deficiency, hemochromatosis, Wilson's disease, galactosemia, or glycogen storage disease. In certain embodiments, the hepatic fibrosis is associated with an inflammatory disorder of the liver.

In some embodiments, the fibrotic condition can be a fibrotic condition of the heart or vasculature, such as myocardial fibrosis. Fibrotic conditions of the heart or vasculature can include, but are not limited to, myocardial fibrosis (e.g., myocardial fibrosis associated with radiation myocarditis, a surgical procedure complication (e.g., myocardial post-operative fibrosis), vascular restenosis, atherosclerosis, cerebral disease, peripheral vascular disease, infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis).

In some embodiments, the fibrotic condition can be a fibrotic condition of the kidney, such as renal fibrosis (e.g., chronic kidney fibrosis). Renal fibrosis can include, but is not limited to, nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic kidney fibrosis, nephrogenic systemic fibrosis, chronic progressive nephropathy (CPN), tubulointerstitial fibrosis, ureteral obstruction (e.g., fetal partial urethral obstruction), chronic uremia, chronic interstitial nephritis, radiation nephropathy, glomerulosclerosis (e.g., focal segmental glomerulosclerosis (FSGS)), progressive glomerulonephrosis (PGN), endothelial/thrombotic microangiopathy injury, scleroderma of the kidney, HIV-associated nephropathy (HIVVAN), or exposure to toxins, irritants, chemotherapeutic agents. In one embodiment, the kidney fibrosis is mediated by a bone morphogeneic protein (BMP). In certain embodiments, the renal fibrosis is a result of an inflammatory disorder of the kidney.

In some embodiments, the fibrotic condition can be a fibrotic condition of the bone marrow. In certain embodiments, the fibrotic condition of the bone marrow is myelofibrosis (e.g., primary myelofibrosis (PMF)), myeloid metaplasia, chronic idiopathic myelofibrosis, or primary myelofibrosis. In other embodiments, bone marrow fibrosis is associated with a hematologic disorder chosen from one or more of hairy cell leukemia, lymphoma, or multiple myeloma.

In other embodiments, the bone marrow fibrosis can be associated with one or more myeloproliferative neoplasms (MPN) chosen from: essential thrombocythemia (ET), polycythemia vera (PV), mastocytosis, chronic eosinophilic leukemia, chronic neutrophilic leukemia, or other MPN.

In some examples, the fibrotic condition can be primary myelofibrosis. Primary myelofibrosis (PMF) (also referred to in the literature as idiopathic myeloid metaplasia, and Agnogenic myeloid metaplasia) is a clonal disorder of multipotent hematopoietic progenitor cells (reviewed in Abdel-Wahab, O. et al. (2009) *Annu. Rev. Med.* 60:233-45; Varicchio, L. et al. (2009) *Expert Rev. Hematol.* 2(3):315-334; Agrawal, M. et al. (2010) *Cancer* 1-15). The disease is characterized by anemia, splenomegaly and extramedullary hematopoiesis, and is marked by progressive marrow fibrosis and atypical megakaryocytic hyperplasia. CD34+ stem/progenitor cells abnormally traffic in the peripheral blood and multi organ extramedullary erythropoiesis is a hallmark of the disease, especially in the spleen and liver. The bone marrow structure is altered due to progressive fibrosis, neoangiogenesis, and increased bone deposits. A significant percentage of patients with PMF have gain-of-function mutations in genes that regulate hematopoiesis, including Janus kinase 2 (JAK2) (~50%) (e.g., JAK2$^{V617F}$) or the thrombopoietin receptor (MPL) (5-10%), resulting in abnormal megakaryocyte growth and differentiation. Studies have suggested that the clonal hematopoietic disorder leads to secondary proliferation of fibroblasts and excessive collagen deposition. Decreased bone marrow fibrosis can improve clinical signs and symptoms, including anemia, abnormal leukocyte counts, and splenomegaly.

Bone marrow fibrosis can be observed in several other hematologic disorders including, but not limited to hairy cell leukemia, lymphoma, and multiple myeloma. However, each of these conditions is characterized by a constellation of clinical, pathologic, and molecular findings not characteristic of PMF (see Abdel-Wahab, O. et al. (2009) supra at page 235).

In other embodiments, the bone marrow fibrosis can be secondary to non-hematologic disorders, including but not limited to, solid tumor metastases to bone marrow, autoimmune disorders (systemic lupus erythematosus, scleroderma, mixed connective tissue disorder, polymyositis), and secondary hyperparathyroidism associated with vitamin D deficiency (see Abdel-Wahab, O. et al. (2009) supra at page 235). In most cases, it is possible to distinguish between these disorders and PMF, although in rare cases the presence of the JAK2V617F or MPLW515L/K mutation can be used to demonstrate the presence of a clonal MPN and to exclude the possibility of reactive fibrosis.

Optionally, monitoring a clinical improvement in a subject with bone marrow fibrosis can be evaluated by one or more of: monitoring peripheral blood counts (e.g., red blood cells, white blood cells, platelets), wherein an increase in peripheral blood counts is indicative of an improved outcome. In other embodiments, clinical improvement in a subject with bone marrow fibrosis can be evaluated by monitoring one or more of: spleen size, liver size, and size of extramedullary hematopoiesis, wherein a decrease in one or more of these parameters is indicative of an improved outcome.

In other embodiments, the fibrotic condition can be a fibrotic condition of the skin. In certain embodiments, the fibrotic condition is chosen from one or more of: skin fibrosis and/or scarring, post-surgical adhesions, scleroderma (e.g., systemic scleroderma), or skin lesions such as keloids.

In certain embodiments, the fibrotic condition can be a fibrotic condition of the gastrointestinal tract. Such fibrotic conditions can be associated with an inflammatory disorder of the gastrointestinal tract, e.g., fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In certain embodiments, the fibrotic condition can be diffuse scleroderma.

Fibrotic conditions can further include diseases that have as a manifestation fibrotic disease of the penis, including Peyronie's disease (fibrosis of the cavernous sheaths leading to contracture of the investing fascia of the corpora, resulting in a deviated and painful erection).

In certain embodiments, the fibrotic condition can be selected from pulmonary fibrosis, bronchiectasis, interstitial lung disease; fatty liver disease; cholestatic liver disease, biliary fibrosis, hepatic fibrosis; myocardial fibrosis; and renal fibrosis.

In certain embodiments, the fibrotic condition can be selected from biliary fibrosis, hepatic fibrosis, pulmonary fibrosis, myocardial fibrosis and renal fibrosis In certain embodiments, the fibrotic condition can be selected from nonalcoholic fatty liver disease (NAFLD) and nonalcoholic steatohepatitis (NASH).

Other fibrotic conditions that can be treated with the methods and compositions of the invention include cystic fibrosis, endomyocardial fibrosis, mediastinal fibrosis, sarcoidosis, scleroderma, spinal cord injury/fibrosis.

A number of models in which fibrosis is induced are available in the art. Administration of ERβ agonists can be readily used to evaluate whether fibrosis is ameliorated in such models. Examples of such models, include but are not limited to, the unilateral ureteral obstruction model of renal fibrosis (see Chevalier et al., "Ureteral Obstruction as a Model of Renal Interstitial Fibrosis and Obstructive Nephropathy" *Kidney International* (2009) 75:1145-1152), the bleomycin induced model of pulmonary fibrosis (see Moore and Hogaboam "Murine Models of Pulmonary Fibrosis" *Am. J. Physiol. Lung. Cell. Mol. Physiol.* (2008) 294:L152-L160), a variety of liver/biliary fibrosis models (see Chuang et al., "Animal Models of Primary Biliary Cirrhosis" *Clin Liver Dis* (2008) 12:333-347; Omenetti, A. et al. (2007) *Laboratory Investigation* 87:499-514 (biliary duct-ligated model); or a number of myelofibrosis mouse models as described in Varicchio, L. (2009) supra. Regardless of the model, ERβ agonists can be evaluated in essentially three paradigms: 1) test whether ERβ agonists can inhibit the fibrotic state; 2) test whether ERβ agonists can stop fibrotic progression once initiated; and/or 3) test whether ERβ agonists can reverse the fibrotic state once initiated.

In certain embodiments, the fibrotic condition is provided in a tissue (e.g., biliary tissue, liver tissue, lung tissue, heart tissue, kidney tissue, skin tissue, gut tissue, or neural tissue). In certain embodiments, the tissue is biliary tissue. In certain embodiments, the tissue is liver tissue. In certain embodiments the tissue is lung tissue. In certain embodiments, the tissue is heart tissue. In certain embodiments, the tissue is kidney tissue. In certain embodiments, the tissue is skin tissue. In certain embodiments, the tissue is gut tissue. In certain embodiments, the tissue is bone marrow tissue. In certain embodiments, the tissue is epithelial tissue. In certain embodiments, the tissue is neural tissue.

Also provided are composition for use, and use of, an compound described herein, alone or in combination with another agent, for preparation of one or more medicaments for use in reducing fibrosis, or treatment of a fibrotic condition.

By way of non-limiting illustration, examples of certain embodiments of the present disclosure are given below.

EXAMPLES

Materials and Methods

DDAH Assay. DDAH activity is determined by modification of method published in the art (M. Knipp and M. Vasak Analytical Biochemistry 286, 257-264 (2000). The enzyme activity in cell or tissue extracts generated by homogenization in 0.1 M sodium phosphate buffer pH 6.2 will be determined by L-citrulline generation from ADMA. A 100 µl of sample will be transferred to a tube and 400 µl of 1 mM ADMA in sodium phosphate buffer will be added and incubated at 37° C. for 45 min. The reaction will be terminated by addition of 500 µl of 4% sulfosalicyclic acid. The mixture will be centrifuged at 3000 g for 10 minutes. A 60 µl of supernatant will be transferred to NUNC 96 well plate in triplicates. A 200 µl of COLDER (color development regent) will be added. COLDER is prepared by mixing 1 volume of solution A [80 mM DAMO (diacetyl monoxime) and 2.0 mM TSC (thiosemicarbazide)] and 3 volume of solution B [3 M $H_3PO_4$, 6 M $H_2SO_4$, and 2 mM $NH_4Fe(SO_4)_2$]. The plates will be sealed and heated at 95° C. for 20 minutes. After cooling, they will be read at 530 nM. DDAH activity will be expressed as µM citrulline produced per gram protein per minute at 37° C.

DDAH promoter activation assay. Activation of DDAH promoter was determined using a DDAH promoter-Luciferase reporter assay. DDAH promoter DNA sequence was cloned in pGL4.10 luciferase reporter plasmid. For transfection of HEK-293 cells, the cells were seeded in six well plates at a density of $2.0 \times 10^5$ cells/well. After 24 hours, the cells were transfected with the DDAH promoter plasmid by adding 200 ng DNA/well and incubated for 24 hours. Transfected cells were then transferred to 96 well plates at 50,000 cells/well and incubated overnight with various concentrations of the test compounds. The medium was removed from the wells and 20 µL of lysis reagent was added. After 5 min, 100 µL Luciferase assay reagent was added, and luminescence was measured.

DDAH and Collagen western blot analysis. Human umbilical vein endothelial cells (HUVEC), retinal endothelial cells and vascular smooth muscle cells from Lonza were transferred to 6 well plates at a density of $4.0 \times 10^5$/well and incubated overnight. Various concentrations of test compounds were then added. After 24 hours, medium was removed, the cells were scraped and collected in 50 µL of lysis buffer containing 50 mM Tris-HCl, 0.25% deoxycholic acid, 1% NP-40, 1 mM EDTA and protease inhibitor cocktails. Cell extract was subjected to SDS polyacrylamide gel electrophoresis. Proteins from the 12% polyacrylamide gels were transferred to PVDF membranes for westerns and blotted with DDAH or collagen 1 antibodies from Abcam.

Determination of Pharmacokinetic Properties. PK of compounds will be determined following both i.v. (1 mg/kg) and s.c. (1 mg/kg) administration. Three rats are bled at each time point and serum samples are analyzed by compound level using LC or LC-MS. Two monkeys will be bled at each time point and serum samples will be analyzed compound level using LC or LC-MS. In beagle dogs, the PK of the compound will be determined following both i.v. (1 mg/kg) and s.c. (1 mg/kg) administration. Two dogs will be bled at each time point after i.v. dosing and one dog per dose group will be bled after s.c. dosing. Serum samples will be analyzed compound level using LC or LC-MS.

Following collection, blood samples will be centrifuged at 10,000 rpm for 10 min at 4° C. to obtain serum and serum samples are stored at −20° C. until analysis. Pharmacokinetic parameters will be estimated using non-compartmental analysis by Kinetica software (Thermo Fisher Scientific Corporation, version 5.0). The peak concentration ($C_{max}$) and time for $C_{max}$ ($T_{max}$) are recorded directly from experimental observations. The area under the curve from time zero to the last sampling time [$AUC_{last}$] and the area under the curve from time zero to infinity [$AUC_{total}$] will be calculated using a combination of linear and log trapezoidal summations. The total plasma clearance, steady-state volume of distribution (Vss), apparent elimination half-life ($t_{half}$), and mean residence time (MRT) will be estimated after i.v. administration. Estimations of AUC and $t_{half}$ will be made using a minimum of 3 time points with quantifiable concentrations. The absolute s.c. bioavailability (F) will be estimated as the ratio of dose-normalized AUC values following s.c. and i.v. doses. The PK parameters will be calculated when applicable.

Synthesis of DDAH-ADMA-Modulating Compounds

Preparation of VN-317. The synthetic strategy for preparing VN-317 is detailed in the scheme below.

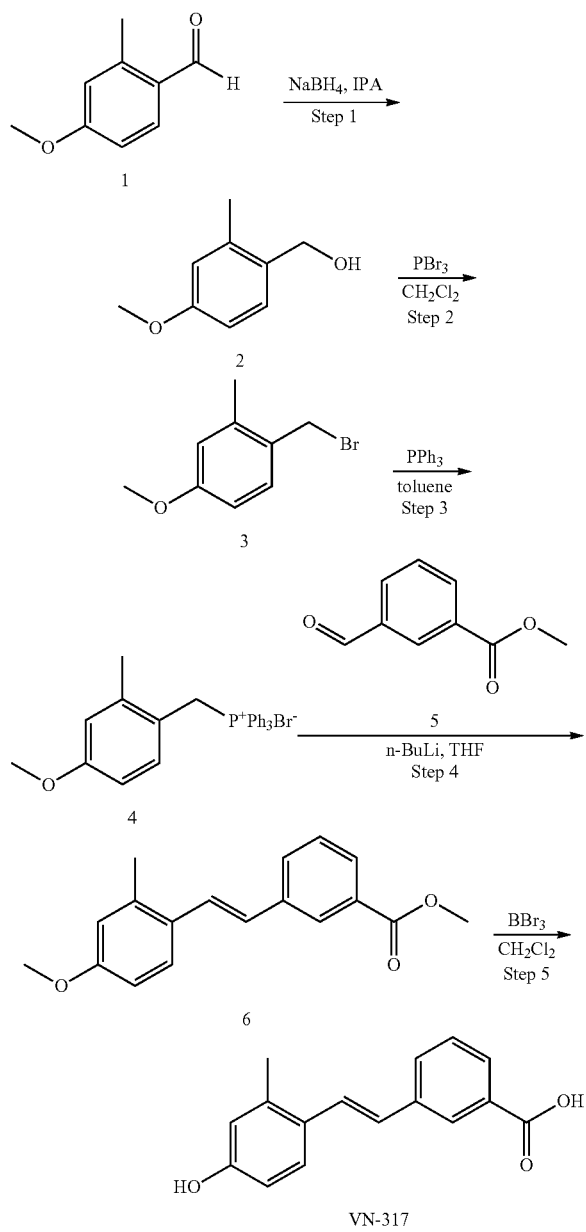

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous Na$_2$SO$_4$, filtered and concentrated under reduced pressure to afford compound 2 (10 g, 65.71 mmol) as colorless syrup. The crude material was taken to next step without further purification. $^1$H NMR (500 MHz, CDCl$_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in CH$_2$Cl$_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with CH$_2$Cl$_2$ (100 mL), washed with water (100 mL) and saturated NaHCO$_3$ solution (100 mL). The combined organic extracts were washed with brine (50 mL), dried over anhydrous Na$_2$SO$_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-d$_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-3-(4-methoxy-2-methylstyryl)benzoate (6). To a stirred solution of compound 4 (4.6 g, 9.64 mmol) in THF (46 mL) was added n-BuLi (2.5 M in hexanes, 4.63 mL, 11.57 mmol) at −78° C. under inert atmosphere. The reaction mixture was gradually warmed to RT and stirred for 30 min. Then a solution of methyl 3-formylbenzoate 5 (1.9 g, 11.57 mmol) in THF (13.8 mL) was added at −78° C. The reaction mixture was gradually warmed to RT and stirred for 2 h. The progress of the reaction was monitored by TLC; after the completion, the reaction mixture was quenched with saturated NH$_4$Cl solution (50 mL) and extracted with EtOAc (2×70 mL). The combined organic extracts were washed with brine (30 mL), dried over anhydrous Na$_2$SO$_4$, filtered and concentrated under reduced pressure. The crude material was purified by silica gel column chromatography (eluent: 10% EtOAc/n-hexanes) to afford compound 6 (1.8 g, 6.37 mmol, 66%) as a mixture of cis and trans-isomers as colorless syrup. $^1$H NMR (500 MHz, CDCl$_3$): δ 8.18 (s, 1H), 7.92 (d, J=7.8 Hz, 1H), 7.87 (s, 1H), 7.82 (d, J=7.7 Hz, 1H), 7.69 (d, J=7.8 Hz, 1H), 7.56 (d, J=8.5 Hz, 1H), 7.44 (t, J=7.7 Hz, 1H), 7.36 (d, J=16.1 Hz, 1H), 7.30 (s, 1H), 7.23-7.17 (m, 1H), 7.02 (d, J=8.4 Hz, 1H), 6.94 (d, J=16.1 Hz, 1H), 6.82-6.75 (m, 3H), 6.71-6.66 (m, 1H), 6.63-6.57 (m, 2H), 3.96 (s, 3H), 3.89 (s, 3H), 3.84 (s, 3H), 3.80 (s, 3H), 2.45 (s, 3H), 2.27 (s, 3H).

Step-5: Synthesis of (E)-3-(4-hydroxy-2-methylstyryl)benzoic acid (VN-317). To a stirred solution of compound 6 (1 g, 3.55 mmol) in CH$_2$Cl$_2$ (20 mL) was added boron tribromide (1M in CH$_2$Cl$_2$, 10.64 mL, 10.64 mmol) at −78° C. under inert atmosphere. The reaction mixture was gradually warmed to RT and stirred for 16 h. The progress of the reaction was monitored by TLC; after the completion, the reaction mixture was quenched with ice cold water (30 mL) and extracted with EtOAc (2×30 mL). The combined organic extracts were washed with brine (20 mL), dried over anhydrous Na$_2$SO$_4$, filtered and concentrated under reduced pressure. The crude material was purified by reverse phase preparative HPLC followed by normal phase prep-HPLC (Methods N & J) to afford VN-317 (25 mg, 0.1 mmol, 3%) as white solid. $^1$H NMR (400 MHz, DMSO-d$_6$): δ 12.99 (br s, 1H), 9.45 (br s, 1H), 8.07 (s, 1H), 7.88-7.76 (m, 2H), 7.55-7.45 (m, 2H), 7.36 (d, J=16.3 Hz, 1H), 7.01 (d, J=16.2 Hz, 1H), 6.66-6.60 (m, 2H), 2.34 (s, 3H); $^1$H NMR (400

MHz, DMSO-$d_6$, $D_2O$ Exc.): δ 8.04 (s, 1H), 7.83-7.76 (m, 2H), 7.54-7.45 (m, 2H), 7.33 (d, J=16.3 Hz, 1H), 6.98 (d, J=16.2 Hz, 1H), 6.65-6.60 (m, 2H), 2.31 (s, 3H). LC-MS: m/z 252.8 [M−H]⁻ at 2.57 RT (98.77% purity). HPLC: 97.35%.

Preparation of VN-318. The synthetic strategy for preparing VN-318 is detailed in the scheme below.

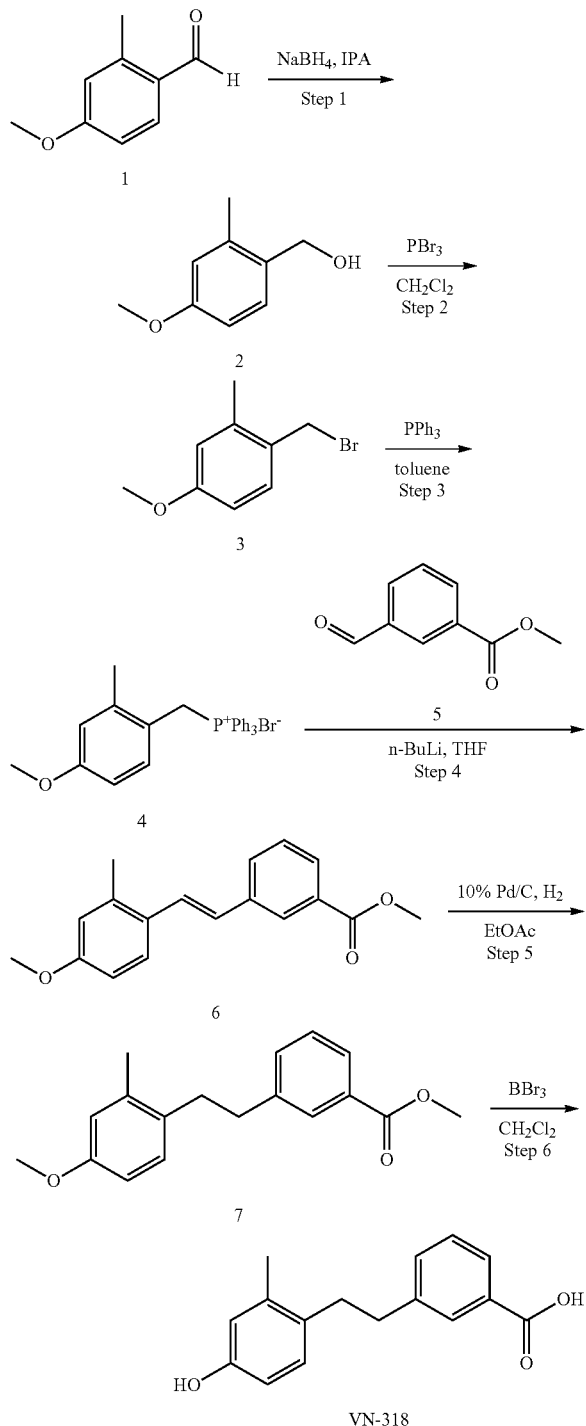

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. ¹H NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. ¹H NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-3-(4-methoxy-2-methylstyryl)benzoate (6). To a stirred solution of compound 4 (4.6 g, 9.64 mmol) in THF (46 mL) was added n-BuLi (2.5 M in hexanes, 4.63 mL, 11.57 mmol) at −78° C. under inert atmosphere. The reaction mixture was gradually warmed to RT and stirred for 30 min. Then a solution of methyl 3-formylbenzoate 5 (1.9 g, 11.57 mmol) in THF (13.8 mL) was added at −78° C. The reaction mixture was gradually warmed to RT and stirred for 2 h. The progress of the reaction was monitored by TLC; after the completion, the reaction mixture was quenched with saturated $NH_4Cl$ solution (50 mL) and extracted with EtOAc (2×70 mL). The combined organic extracts were washed with brine (30 mL), dried over anhydrous $Na_2SO_4$, filtered and concentrated under reduced pressure. The crude material was purified by silica gel column chromatography (eluent: 10% EtOAc/n-hexanes) to afford compound 6 (1.8 g, 6.37 mmol, 66%) as a mixture of cis and trans-isomers as colorless syrup. ¹H NMR (500 MHz, $CDCl_3$): δ 8.18 (s, 1H), 7.92 (d, J=7.8 Hz, 1H), 7.87 (s, 1H), 7.82 (d, J=7.7 Hz, 1H), 7.69 (d, J=7.8 Hz, 1H), 7.56 (d, J=8.5 Hz, 1H), 7.44 (t, J=7.7 Hz, 1H), 7.36 (d, J=16.1 Hz, 1H), 7.30 (s, 1H), 7.23-7.17 (m, 1H), 7.02 (d, J=8.4 Hz, 1H), 6.94 (d, J=16.1 Hz, 1H), 6.82-6.75 (m, 3H), 6.71-6.66 (m, 1H), 6.63-6.57 (m, 2H), 3.96 (s, 3H), 3.89 (s, 3H), 3.84 (s, 3H), 3.80 (s, 3H), 2.45 (s, 3H), 2.27 (s, 3H).

Step-5: Synthesis of Methyl 3-(4-methoxy-2-methylphenethyl)benzoate (7). To a stirred solution of compound 6 (400 mg, mixture) in ethylacetate (10 mL) was added 10% Pd/C (160 mg) at RT under inert atmosphere. The reaction mixture was evacuated and stirred at RT under hydrogen atmosphere (balloon pressure) for 6 h. The progress of the reaction was monitored by TLC; after the completion, the reaction mixture was filtered through a pad of celite and the celite bed was washed with EtOAc (15 mL). The filtrate was concentrated under reduced pressure. The combined organic extracts were washed with brine (10 mL), dried over anhydrous $Na_2SO_4$, filtered and concentrated under reduced pressure. The crude material was purified by silica gel column chromatography (eluent: 15% EtOAc/n-hexanes) to afford compound 7 (230 mg, 0.81 mmol, 57%) as colorless syrup. $^1$H NMR (400 MHz, $CDCl_3$): δ 7.91-7.86 (m, 2H), 7.36-7.32 (m, 2H), 7.02 (d, J=8.3 Hz, 1H), 6.74-6.65 (m, 2H), 3.92 (s, 3H), 3.78 (s, 3H), 2.92-2.81 (m, 4H), 2.28 (s, 3H). LC-MS: m/z 285.2 [M+H]$^+$ at 3.02 RT (91.48% purity).

Step-6: Synthesis of 3-(4-hydroxy-2-methylphenethyl) benzoic acid (VN-318). To a stirred solution of compound 7 (230 mg, 0.81 mmol) in $CH_2Cl_2$ (6 mL) was added boron tribromide (1 M in $CH_2Cl_2$, 2.83 mL, 2.83 mmol) at −78° C. under inert atmosphere. The reaction mixture was gradually warmed to RT and stirred for 16 h. The progress of the reaction was monitored by TLC; after the completion, the reaction mixture was quenched with ice cold water (15 mL) and extracted with EtOAc (2×20 mL). The combined organic extracts were washed with brine (15 mL), dried over anhydrous $Na_2SO_4$, filtered and concentrated under reduced pressure. The crude material was purified by preparative HPLC (Method J) to afford VN-319 (40 mg, 0.16 mmol, 20%) as an off white solid. $^1$H NMR (400 MHz, DMSO-$d_6$): δ 12.86 (br s, 1H), 9.00 (s, 1H), 7.83-7.73 (m, 2H), 7.49-7.35 (m, 2H), 6.92 (d, J=8.2 Hz, 1H), 6.57-6.46 (m, 2H), 2.86-2.69 (m, 4H), 2.17 (s, 3H); $^1$H NMR (400 MHz, DMSO-$d_6$, $D_2O$ Exc.): δ 7.77-7.71 (m, 2H), 7.45-7.35 (m, 2H), 6.88 (d, J=8.2 Hz, 1H), 6.55-6.43 (m, 2H), 2.83-2.67 (m, 4H), 2.12 (s, 3H). LC-MS: m/z 254.9 [M−H]$^-$ at 2.31 RT (98.01% purity). HPLC: 99.50%.

Preparation of VN-319. The synthetic strategy for preparing VN-319 is detailed in the scheme below.

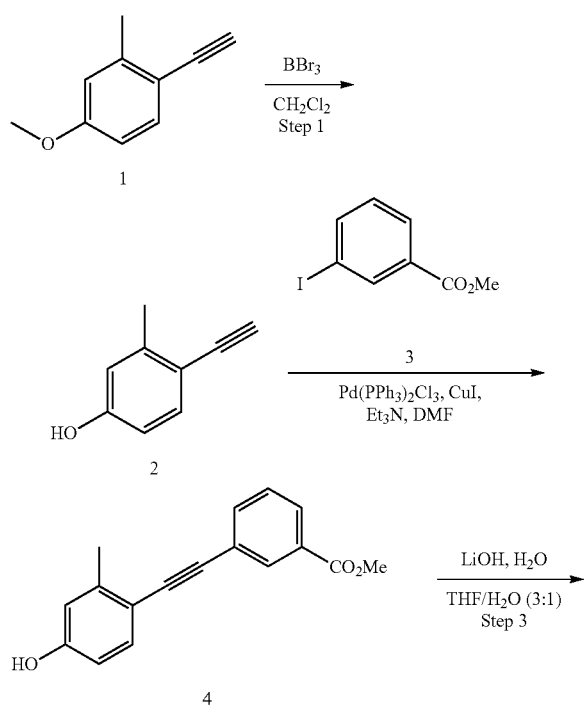

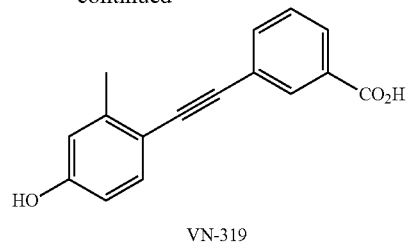

VN-319

Step-1: Synthesis of 4-ethynyl-3-methylphenol (2). To a stirred solution of 1-ethynyl-4-methoxy-2-methylbenzene 1 (1 g, 6.85 mmol) in $CH_2Cl_2$ (40 mL) was added boron tribromide (1 M in $CH_2Cl_2$, 20.55 mL, 20.55 mmol) at −78° C. under inert atmosphere. The reaction mixture was gradually warmed to RT and stirred for 2 h. The progress of the reaction was monitored by TLC; after the completion, the reaction mixture was quenched with ice cold water (50 mL) and extracted with EtOAc (2×50 mL). The combined organic extracts were washed with brine (20 mL), dried over anhydrous $Na_2SO_4$, filtered and concentrated under reduced pressure to afford compound 2 (1 g) as brown syrup. The crude material was taken to next step without further purification. LC-MS: m/z 130.9 [M−H]$^-$ at 2.96 RT (10.01% purity).

Step-2: Synthesis of Methyl 3-((4-hydroxy-2-methylphenyl)ethynyl)benzoate (4). To a stirred solution of compound 2 (500 mg, crude) in DMF (10 mL) were added methyl 3-iodobenzoate 3 (1.09 g, 4.17 mmol), copper(l) iodide (72 mg, 0.38 mmol) followed by triethylamine (2.64 mL, 18.94 mmol) in a sealed tube at RT under inert atmosphere and purged under argon for 15 min. To this reaction mixture was added Pd(PPh$_3$)$_2$Cl$_2$ (266 mg, 0.38 mmol) at RT. The vessel was sealed and heated to 80° C. and stirred for 16 h. The progress of the reaction was monitored by TLC, after the completion, the reaction mixture was diluted with water (20 mL) and extracted with EtOAc (2×20 mL). The combined organic extracts were washed with brine (15 mL), dried over anhydrous $Na_2SO_4$, filtered and concentrated under reduced pressure. The crude material was purified by silica gel column chromatography (eluent: 15% EtOAc/n-hexanes) to afford compound 4 (300 mg, 1.13 mmol, 30%) as an off white solid. $^1$H NMR (500 MHz, $CDCl_3$): δ 8.17 (s, 1H), 7.97 (d, J=7.8 Hz, 1H), 7.68 (br d, J=7.5 Hz, 1H), 7.45-7.37 (m, 2H), 6.73 (d, J=2.0 Hz, 1H), 6.66 (dd, J=8.3, 2.5 Hz, 1H), 5.10 (br s, 1H), 3.94 (s, 3H), 2.48 (s, 3H). LC-MS: m/z 265.1 [M−H]$^-$ at 3.26 RT (93.70% purity).

Step-3: Synthesis of Methyl 3-((4-hydroxy-2-methylphenyl)ethynyl)benzoate VN-319. To a stirred solution of compound 4 (150 mg, 0.56 mmol) in a mixture of THF/water (3:1, 4 mL) was added lithium hydroxide monohydride (71 mg, 1.69 mmol) at RT and stirred for 16 h. The progress of the reaction was monitored by TLC; after the completion, the reaction mixture was acidified with 1N HCl solution to pH ~2-3. The precipitated solid was filtered, washed with 30% Et$_2$O/n-pentane (10 mL) and dried under vacuum to afford VN-320 (70 mg, 0.28 mmol, 49%) as an off white solid. $^1$H NMR (400 MHz, DMSO-$d_6$): δ 9.84 (br s, 1H), 7.99 (br s, 1H), 7.92 (br d, J=7.5 Hz, 1H), 7.74 (d, J=7.7 Hz, 1H), 7.60-7.50 (m, 1H), 7.35 (d, J=8.4 Hz, 1H), 6.72 (d, J=2.1 Hz, 1H), 6.64 (dd, J=8.3, 2.4 Hz, 1H), 2.40 (s, 3H); $^1$H NMR (400 MHz, DMSO-$d_6$, $D_2O$ Exc.): δ 7.97 (br s, 1H), 7.90 (br d, J=7.4 Hz, 1H), 7.72 (d, J=7.7 Hz, 1H), 7.58-7.51 (m, 1H), 7.34 (d, J=8.4 Hz, 1H), 6.71 (d, J=2.1 Hz, 1H), 6.63

(dd, J=8.3, 2.4 Hz, 1H), 2.37 (s, 3H). LC-MS: m/z 250.8 [M–H]⁻ at 2.34 RT (96.53% purity). HPLC: 99.66%.

Preparation of VN-321. The synthetic strategy for preparing VN-321 is detailed in the scheme below.

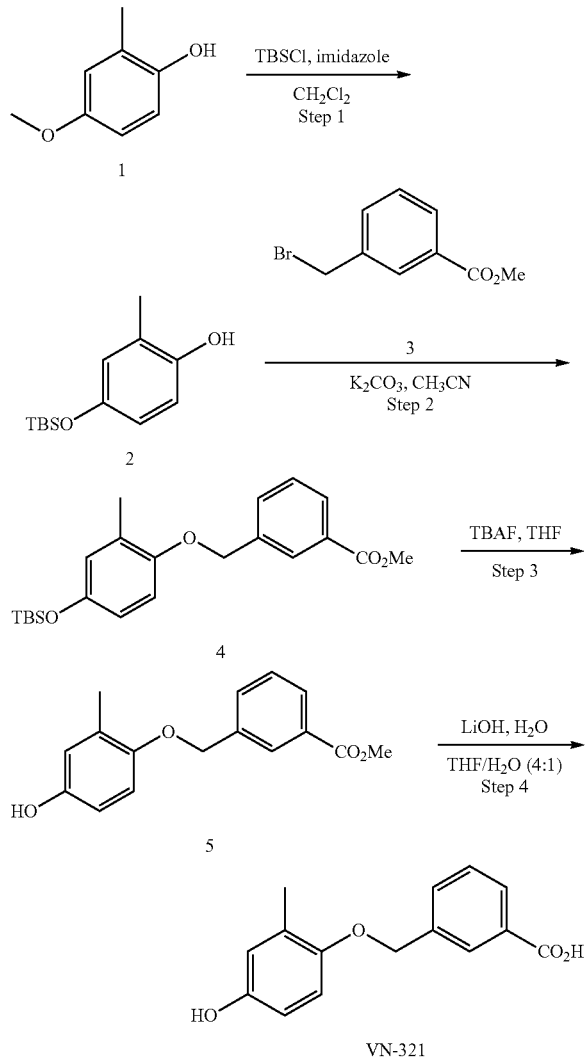

Step-1: Synthesis of 4-((tert-butyldimethylsilyl)oxy)-2-methylphenol (2). To a stirred solution of 2-methylbenzene-1,4-diol 1 (1 g, 8.06 mmol) in CH₂Cl₂ (20 mL) were added imidazole (822 mg, 12.1 mmol) and tert-butyldimethylchlorosilane (1.21 g, 8.06 mmol) at 0° C. under inert atmosphere. The reaction mixture was gradually warmed to RT and stirred for 16 h. The progress of the reaction was monitored by TLC; after the completion, the reaction mixture was diluted with water (30 mL) and extracted with CH₂Cl₂ (2×50 mL). The combined organic extracts were washed with brine (20 mL), dried over anhydrous Na₂SO₄, filtered and concentrated under reduced pressure. The crude material was purified by silica gel column chromatography (eluent: 5% EtOAc/n-hexanes) to afford compound 2 (500 mg, 2.1 mmol, 26%) as pale yellow liquid. ¹H NMR (400 MHz, CDCl₃): δ 6.65-6.60 (m, 2H), 6.56-6.50 (m, 1H), 4.43-4.38 (m, 1H), 2.20-2.15 (m, 3H), 1.02-0.95 (m, 9H), 0.19-0.15 (m, 6H) (NMR not clean because of close running impurity like positional isomers).

Step-2: Synthesis of Methyl 3-((4-((tert-butyldimethylsilyl)oxy)-2-methylphenoxy)methyl)benzoate (4). To a stirred solution of compound 2 (400 mg, 1.68 mmol) in acetonitrile (10 mL) were added methyl 3-(bromomethyl)benzoate 3 (381 mg, 1.68 mmol) and potassium carbonate (464 mg, 3.36 mmol) at RT under inert atmosphere. The reaction mixture was heated to 60° C. and stirred for 6 h. The progress of the reaction was monitored by TLC; after the completion, the reaction mixture was quenched with water (20 mL) and extracted with EtOAc (2×25 mL). The combined organic extracts were washed with brine (15 mL), dried over anhydrous Na₂SO₄, filtered and concentrated under reduced pressure. The crude material was purified by silica gel column chromatography (eluent: 5-10% EtOAc/n-hexanes) to afford compound 4 (450 mg, 1.16 mmol, 69%) as colorless liquid. ¹H NMR (400 MHz, CDCl₃): δ 8.11-8.10 (m, 1H), 7.99 (dt, J=7.8, 1.4 Hz, 1H), 7.69-7.62 (m, 1H), 7.49-7.41 (m, 1H), 6.72 (d, J=8.7 Hz, 1H), 6.68-6.66 (m, 1H), 6.62-6.56 (m, 1H), 5.06-5.00 (m, 2H), 3.93-3.92 (m, 3H), 2.25-2.13 (m, 3H), 1.02-0.96 (m, 9H), 0.20-0.15 (m, 6H). NMR not clean Step-3: Synthesis of Methyl 3-((4-hydroxy-2-methylphenoxy)methyl)benzoate (5). To a stirred solution of compound 4 (400 mg, 1.04 mmol) in THF (8 mL) was added tetra-n-butylammonium fluoride (1M in THF, 1.24 mL, 1.24 mmol) at RT under inert atmosphere and stirred for 1 h. The progress of the reaction was monitored by TLC; after the completion, the reaction mixture was quenched with water (20 mL) and extracted with EtOAc (2×25 mL). The combined organic extracts were washed with brine (15 mL), dried over anhydrous Na₂SO₄, filtered and concentrated under reduced pressure. The crude material was purified by silica gel column chromatography (eluent: 30% EtOAc/n-hexanes) to afford compound 5 (210 mg, 0.77 mmol, 75%) as pale yellow liquid. ¹H NMR (400 MHz, CDCl₃): δ 8.10 (s, 1H), 7.99 (d, J=7.8 Hz, 1H), 7.66-7.61 (m, 1H), 7.49-7.41 (m, 1H), 6.74 (d, J=8.7 Hz, 1H), 6.70-6.66 (m, 1H), 6.59 (dd, J=8.7, 3.1 Hz, 1H), 5.04 (s, 2H), 4.52 (br s, 1H), 3.93 (s, 3H), 2.25 (s, 3H). LC-MS: m/z 273.4 [M+H]⁺ at 3.64 RT (85.23% purity).

Step-4: Synthesis of 3-((4-hydroxy-2-methylphenoxy)methyl)benzoic acid (VN-321). To a stirred solution of compound 5 (200 mg, 0.73 mmol) in a mixture of THF/water (4:1, 5 mL) was added lithium hydroxide monohydride (93 mg, 2.2 mmol) at RT under inert atmosphere and stirred for 2 h. The progress of the reaction was monitored by TLC; after the completion, the reaction mixture was acidified with 6N HCl to pH ~2-3 and extracted with EtOAc (2×25 mL). The combined organic extracts were washed with brine (10 mL), dried over anhydrous Na₂SO₄, filtered and concentrated under reduced pressure. The crude material was purified by normal phase preparative HPLC (Method G) to afford VN-322 (50 mg, 0.19 mmol, 26%) as brown solid. The structure was confirmed by 2 D NMR (NOESY, gDQFCOSY) studies. ¹H NMR (500 MHz, DMSO-d₆): δ 12.96 (br s, 1H), 8.80 (s, 1H), 8.00 (s, 1H), 7.87 (d, J=7.5 Hz, 1H), 7.66 (d, J=8.1 Hz, 1H), 7.50 (t, J=7.8 Hz, 1H), 6.79 (d, J=8.7 Hz, 1H), 6.56 (d, J=2.9 Hz, 1H), 6.49 (dd, J=8.7, 2.9 Hz, 1H), 5.05 (s, 2H), 2.12 (s, 3H); ¹H NMR (500 MHz, DMSO-d₆, D₂O Exc.): δ 7.98 (s, 1H), 7.86 (d, J=7.5 Hz, 1H), 7.65 (d, J=8.1 Hz, 1H), 7.50 (t, J=7.5 Hz, 1H), 6.79 (d, J=8.7 Hz, 1H), 6.57 (d, J=2.3 Hz, 1H), 6.49 (dd, J=8.7, 2.9 Hz, 1H), 5.04 (s, 2H), 2.10 (s, 3H). LC-MS: m/z 256.8 [M–H]⁻ at 1.83 RT (92.45% purity). HPLC: 96.21%.

Preparation of VN-378. The synthetic strategy for preparing VN-378 is detailed in the scheme below.

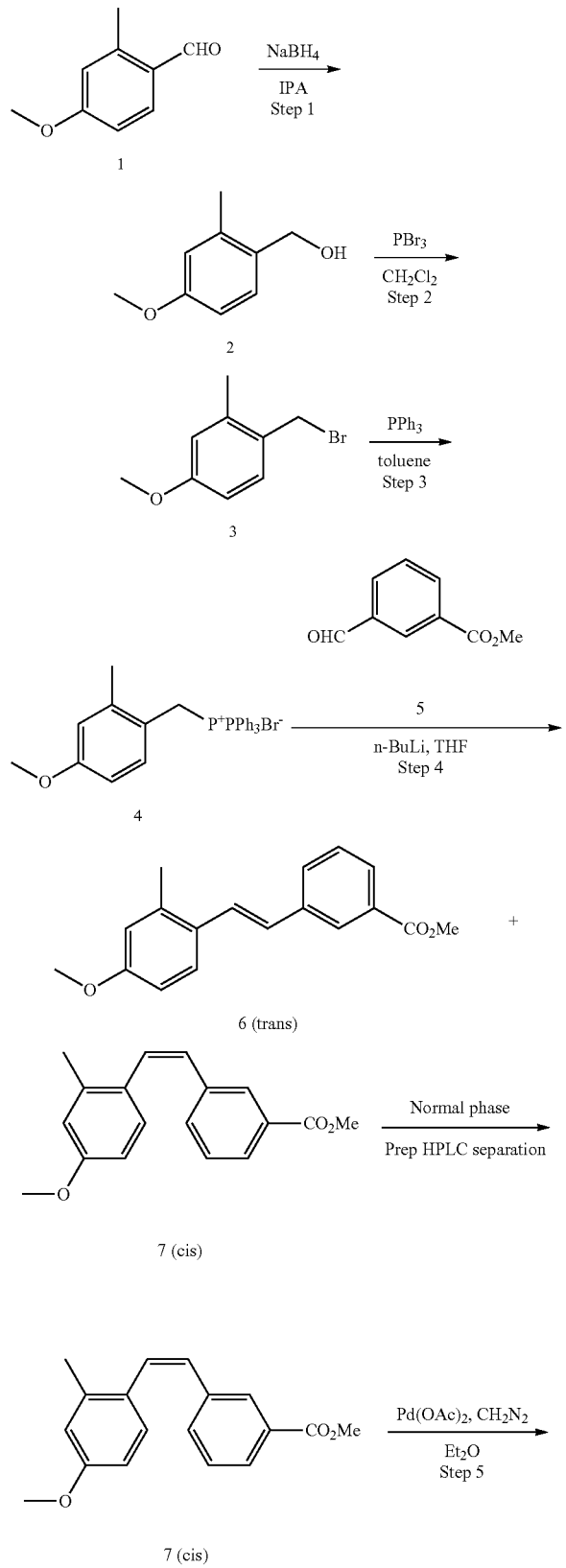

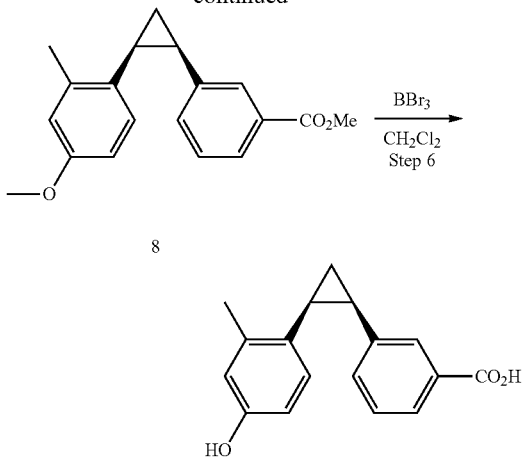

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. $^1$H NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-3-(4-methoxy-2-methylstyryl)benzoate (6) & Methyl (Z)-3-(4-methoxy-2-methylstyryl)benzoate (7). To a stirred solution of compound 4 (4 g, 8.38 mmol) in THF (30 mL) was added n-BuLi (2.5 M in hexanes, 4.02 mL, 10.06 mmol) at −78° C. under inert atmosphere. The reaction mixture was gradually warmed to RT and stirred for 1 h. Then a solution of methyl 3-formylbenzoate 5 (2.06 g, 12.58 mmol) in THF (10 mL) was added at −78° C. The reaction mixture was gradually warmed to RT and stirred for 16 h. The progress of the reaction was monitored by TLC, after the completion, the reaction mixture was quenched with saturated $NH_4Cl$ solution (50 mL) and extracted with EtOAc (2×70 mL). The combined organic extracts were washed with brine (30 mL), dried over anhydrous $Na_2SO_4$, filtered and concentrated under reduced pressure. The crude material was purified by silica gel column chromatography (eluent: 10% EtOAc/n-hexanes) followed by normal phase preparative HPLC (Method H) to afford trans compound 6 (300 mg, 1.06 mmol, 13%) & cis compound 7 (500 mg, 1.77 mmol, 21%) as colorless liquids respectively.

Analytical data of compound 6 (trans): $^1$H NMR (500 MHz, $CDCl_3$): δ 8.17 (s, 1H), 7.90 (d, J=7.5 Hz, 1H), 7.67 (d, J=7.5 Hz, 1H), 7.54 (d, J=8.7 Hz, 1H), 7.42 (t, J=7.5 Hz, 1H), 7.34 (d, J=16.2 Hz, 1H), 6.92 (d, J=16.2 Hz, 1H), 6.78 (dd, J=8.4, 2.6 Hz, 1H), 6.74 (d, J=2.3 Hz, 1H), 3.95 (s, 3H), 3.82 (s, 3H), 2.44 (s, 3H). LC-MS: m/z 283.2 $[M+H]^+$ at 4.58 RT (98.78% purity).

Analytical data of compound 7 (cis): $^1$H NMR (500 MHz, $CDCl_3$): δ 7.85 (s, 1H), 7.80 (br d, J=7.5 Hz, 1H), 7.29-7.25 (m, 2H), 7.21-7.16 (m, 1H), 7.01 (d, J=8.7 Hz, 1H), 6.75 (d, J=1.7 Hz, 1H), 6.69-6.65 (m, 1H), 6.61-6.56 (m, 2H), 3.87 (s, 3H), 3.79 (s, 3H), 2.25 (s, 3H). LC-MS: m/z 283.2 $[M+H]^+$ at 4.67 RT (98.13% purity).

Step-5: Synthesis of Methyl 3-((1R,2S)-2-(4-methoxy-2-methylphenyl)cyclopropyl)benzoate (8). To a stirred solution of compound 7 (cis) (400 mg, 1.42 mmol) in diethylether (20 mL) was added palladium(II) acetate (127 mg, 0.57 mmol) at RT under inert atmosphere. Then a solution of freshly prepared diazomethane (15 mL) was added at −50° C. The reaction mixture was gradually warmed to RT and stirred for 16 h. The progress of the reaction was monitored by TLC; after the completion, the reaction mixture was quenched with water (20 mL) and extracted with EtOAc (2×25 mL). The combined organic extracts were washed with brine (15 mL), dried over anhydrous $Na_2SO_4$, filtered and concentrated under reduced pressure to afford compound 8 (400 mg, 1.35 mmol) as brown syrup. The crude material was taken to next step without further purification. LC-MS: m/z 297.3 $[M+H]^+$ at 4.37 RT (75.19% purity).

Step-6: Synthesis of 3-((1R,2S)-2-(4-hydroxy-2-methylphenyl)cyclopropyl)benzoic acid (VN-378). To a stirred solution of compound 8 (300 mg, 1.01 mmol) in $CH_2Cl_2$ (15 mL) was added boron tribromide (1 M in $CH_2Cl_2$, 4.05 mL, 4.05 mmol) at −78° C. under inert atmosphere. The reaction mixture was gradually warmed to RT and stirred for 3 h. The progress of the reaction was monitored by TLC; after the completion, the reaction mixture was quenched with ice cold water (20 mL) and extracted with $CH_2Cl_2$ (2×20 mL). The combined organic extracts were washed with brine (15 mL), dried over anhydrous $Na_2SO_4$, filtered and concentrated under reduced pressure. The crude material was purified by preparative HPLC (Method I) to afford VN-378 (30 mg, 0.11 mmol) as an off white solid. The compound was highly hygroscopic. $^1$H NMR (400 MHz, DMSO-$d_6$): δ 7.57-7.48 (m, 2H), 7.04-6.94 (m, 2H), 6.80 (br d, J=7.8 Hz, 1H), 6.42 (dd, J=8.2, 2.4 Hz, 1H), 6.33 (d, J=2.3 Hz, 1H), 2.48-2.43 (m, 1H), 2.35-2.27 (m, 1H), 1.98 (s, 3H), 1.49-1.34 (m, 2H); $^1$H NMR (400 MHz, DMSO-$d_6$, $D_2O$ Exc.): δ 7.54-7.45 (m, 2H), 7.03-6.92 (m, 2H), 6.79 (br d, J=7.7 Hz, 1H), 6.41 (dd, J=8.2, 2.5 Hz, 1H), 6.33 (d, J=2.4 Hz, 1H), 2.48-2.40 (m, 1H), 2.36-2.24 (m, 1H), 1.97 (s, 3H), 1.46-1.32 (m, 2H). LC-MS: m/z 266.9 $[M-H]^-$ at 2.38 RT (96.39% purity). HPLC: 86.80%.

HPLC: 87.75%.

Preparation of VN-323. The synthetic strategy for preparing VN-323 is detailed in the scheme below.

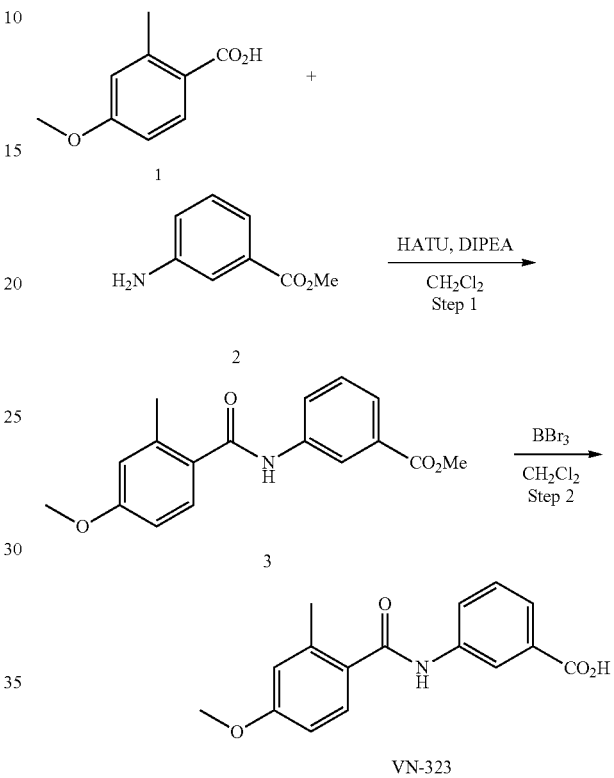

Step-1: Synthesis of Methyl 3-(4-methoxy-2-methylbenzamido)benzoate (3). To a stirred solution of 4-methoxy-2-methylbenzoic acid 1 (1 g, 6.02 mVN-324 mol) in $CH_2Cl_2$ (15 mL) were added methyl 3-aminobenzoate 2 (909 mg, 6.01 mmol), HATU (2.74 g, 7.22 mmol) and ethyldiisopropylamine (2.62 mL, 15.04 mmol) at 0° C. under inert atmosphere. The reaction mixture was gradually warmed to RT and stirred for 16 h. The progress of the reaction was monitored by TLC; after the completion, the reaction mixture was diluted with water (30 mL) and extracted with $CH_2Cl_2$ (2×40 mL). The combined organic extracts were washed with brine (15 mL), dried over anhydrous $Na_2SO_4$, filtered and concentrated under reduced pressure. The crude material was purified by silica gel column chromatography (eluent: 40% EtOAc/n-hexanes) to afford compound 3 (500 mg, 1.67 mmol, 28%) as an off white solid. $^1$H NMR (400 MHz, $CDCl_3$): δ 8.09 (s, 1H), 8.01 (br d, J=7.7 Hz, 1H), 7.81 (d, J=7.8 Hz, 1H), 7.58 (br s, 1H), 7.47 (t, J=8.0 Hz, 2H), 6.82-6.74 (m, 2H), 3.91 (s, 3H), 3.84 (s, 3H), 2.53 (s, 3H). LC-MS: m/z 299.9 $[M+H]^+$ at 2.90 RT (88.64% purity); m/z 300.0 $[M+H]^+$ at 3.03 RT (11.35% purity).

Step-2: Synthesis of 3-(4-hydroxy-2-methylbenzamido) benzoic acid (VN-323). To a stirred solution of compound 3 (300 mg, 1.0 mmol) in $CH_2Cl_2$ (15 mL) was added boron tribromide (1 M in $CH_2Cl_2$, 6.02 mL, 6.02 mmol) at −78° C. under inert atmosphere. The reaction mixture was gradually warmed to RT and stirred for 16 h. The progress of the reaction was monitored by TLC; after the completion, the reaction mixture was quenched with ice cold water (20 mL) and extracted with $CH_2Cl_2$ (2×20 mL). The combined organic extracts were washed with brine (10 mL), dried over anhydrous $Na_2SO_4$, filtered and concentrated under reduced pressure. The crude material was purified by silica gel column chromatography (eluent: 100% EtOAc) followed by preparative HPLC (Method P) to afford VN-324 (40 mg, 0.15 mmol, 15%) as an off white solid. $^1$H NMR (400 MHz, DMSO-$d_6$): δ 12.92 (br s, 1H), 10.23 (s, 1H), 9.77 (s, 1H), 8.40 (t, J=1.8 Hz, 1H), 7.94-7.89 (m, 1H), 7.64 (dt, J=7.8, 1.3 Hz, 1H), 7.47-7.36 (m, 2H), 6.70-6.65 (m, 2H), 2.35 (s, 3H); $^1$H NMR (400 MHz, DMSO-$d_6$, $D_2O$ Exc.): δ 8.37 (t, J=1.8 Hz, 1H), 7.89-7.85 (m, 1H), 7.64 (dt, J=7.8, 1.3 Hz, 1H), 7.44 (t, J=7.9 Hz, 1H), 7.35 (d, J=8.2 Hz, 1H), 6.69-6.63 (m, 2H), 2.32 (s, 3H). LC-MS: m/z 270.0 [M−H]$^+$ at 6.14 RT (99.89% purity). HPLC: 99.83%.

Preparation of VN-324. The synthetic strategy for preparing VN-324 is detailed in the scheme below.

afford compound 3 (1.5 g, 5.01 mmol, 90%) as an off white solid. $^1$H NMR (500 MHz, CDCl$_3$): δ 8.50 (br s, 1H), 8.21 (br d, J=7.8 Hz, 1H), 8.13 (br d, J=7.3 Hz, 1H), 7.66 (br s, 1H), 7.61-7.55 (m, 2H), 6.82-6.76 (m, 2H), 3.96 (s, 3H), 3.81 (s, 3H), 2.31 (s, 3H).

Step-2: Synthesis of 3-((4-hydroxy-2-methylphenyl)carbamoyl)benzoic acid (VN-325). To a stirred solution of compound 3 (200 mg, 0.67 mmol) in $CH_2Cl_2$ (15 mL) was added boron tribromide (1 M in $CH_2Cl_2$, 4.01 mL, 4.01 mmol) at −78° C. under inert atmosphere. The reaction mixture was gradually warmed to RT and stirred for 16 h. The progress of the reaction was monitored by TLC; after the completion, the reaction mixture was quenched with ice cold water (20 mL) and extracted with $CH_2Cl_2$ (2×20 mL). The combined organic extracts were washed with brine (10 mL), dried over anhydrous $Na_2SO_4$, filtered and concentrated under reduced pressure. The crude material was purified by silica gel column chromatography (eluent: 100% EtOAc) to afford VN-324 (40 mg, 0.15 mmol, 22%) as an off white solid. $^1$H NMR (400 MHz, DMSO-$d_6$): δ 13.25 (br s, 1H), 9.88 (s, 1H), 9.31 (br s, 1H), 8.52 (s, 1H), 8.22-8.07 (m, 2H), 7.64 (t, J=7.7 Hz, 1H), 7.05 (d, J=8.4 Hz, 1H), 6.66 (d, J=2.5 Hz, 1H), 6.60 (dd, J=8.4, 2.5 Hz, 1H), 2.13 (s, 3H); $^1$H NMR (400 MHz, DMSO-$d_6$, $D_2O$ Exc.): δ 8.47 (s, 1H), 8.13 (br t, J=9.2 Hz, 2H), 7.64 (t, J=7.7 Hz, 1H), 7.04 (d, J=8.4 Hz, 1H), 6.67 (d, J=2.5 Hz, 1H), 6.61 (dd, J=8.4, 2.6 Hz, 1H), 2.11 (s, 3H). LC-MS: m/z 270.1 [M−H]$^+$ at 5.89 RT (97.19% purity). HPLC: 96.95%.

Preparation of VN-325. The synthetic strategy for preparing VN-325 is detailed in the scheme below.

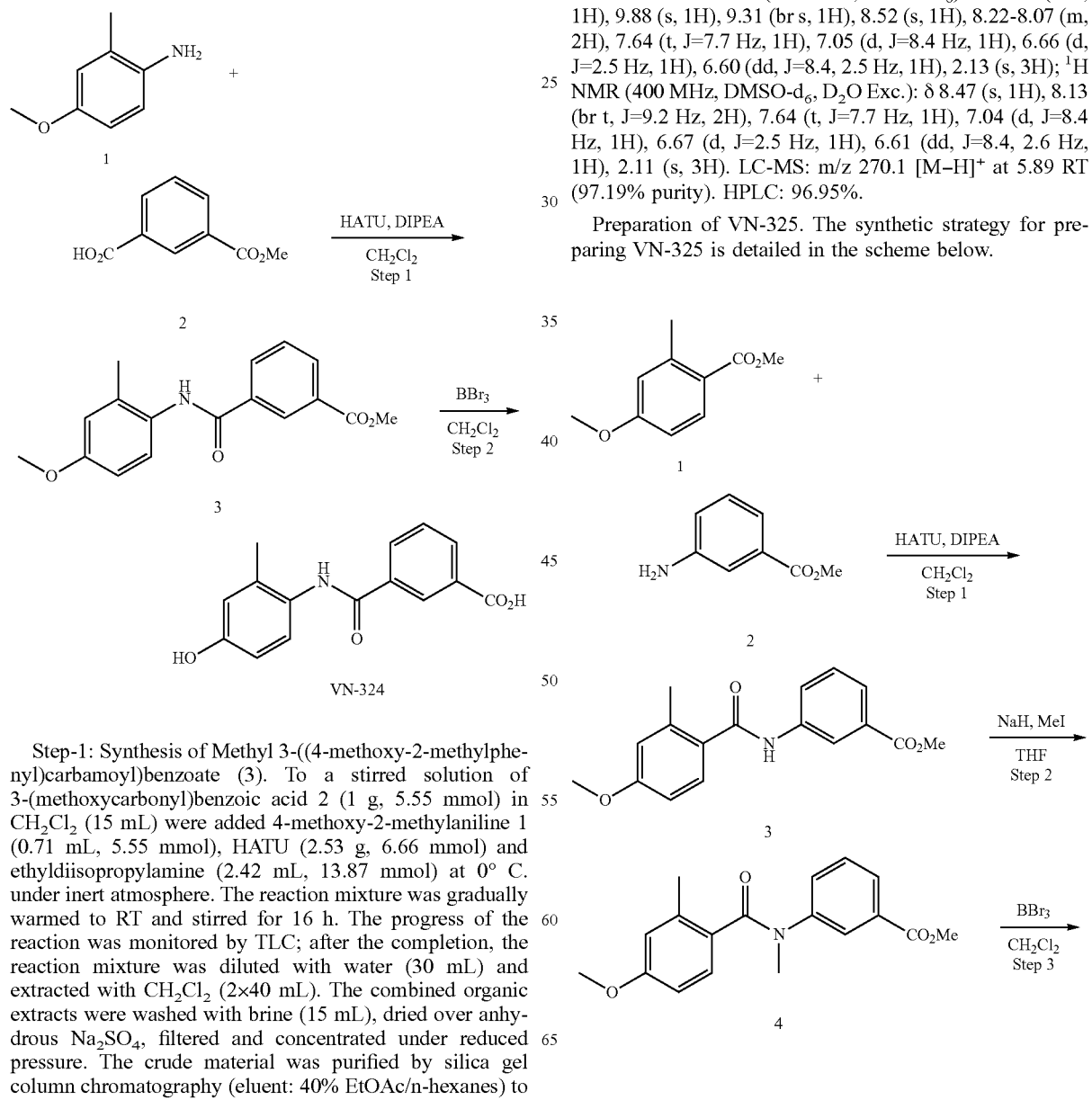

Step-1: Synthesis of Methyl 3-((4-methoxy-2-methylphenyl)carbamoyl)benzoate (3). To a stirred solution of 3-(methoxycarbonyl)benzoic acid 2 (1 g, 5.55 mmol) in $CH_2Cl_2$ (15 mL) were added 4-methoxy-2-methylaniline 1 (0.71 mL, 5.55 mmol), HATU (2.53 g, 6.66 mmol) and ethyldiisopropylamine (2.42 mL, 13.87 mmol) at 0° C. under inert atmosphere. The reaction mixture was gradually warmed to RT and stirred for 16 h. The progress of the reaction was monitored by TLC; after the completion, the reaction mixture was diluted with water (30 mL) and extracted with $CH_2Cl_2$ (2×40 mL). The combined organic extracts were washed with brine (15 mL), dried over anhydrous $Na_2SO_4$, filtered and concentrated under reduced pressure. The crude material was purified by silica gel column chromatography (eluent: 40% EtOAc/n-hexanes) to

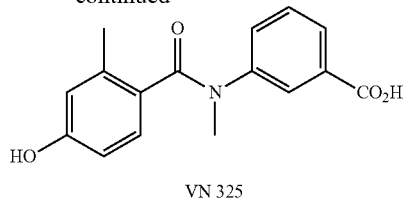

VN 325

Step-1: Synthesis of Methyl 3-(4-methoxy-2-methylbenzamido)benzoate (3). To a stirred solution of 4-methoxy-2-methylbenzoic acid 1 (1 g, 6.02 mmol) in CH$_2$Cl$_2$ (15 mL) were added methyl 3-aminobenzoate 2 (909 mg, 6.02 mmol), HATU (2.74 g, 7.22 mmol) and ethyldiisopropylamine (2.62 mL, 15.04 mmol) at 0° C. under inert atmosphere. The reaction mixture was gradually warmed to RT and stirred for 16 h. The progress of the reaction was monitored by TLC; after the completion, the reaction mixture was diluted with water (30 mL) and extracted with CH$_2$Cl$_2$ (2×40 mL). The combined organic extracts were washed with brine (15 mL), dried over anhydrous Na$_2$SO$_4$, filtered and concentrated under reduced pressure. The crude material was purified by silica gel column chromatography (eluent: 40% EtOAc/n-hexanes) to afford compound 3 (500 mg, 1.67 mmol, 28%) as an off white solid. $^1$H NMR (400 MHz, CDCl$_3$): δ 8.09 (s, 1H), 8.01 (br d, J=7.7 Hz, 1H), 7.81 (d, J=7.8 Hz, 1H), 7.58 (br s, 1H), 7.47 (t, J=8.0 Hz, 2H), 6.82-6.74 (m, 2H), 3.91 (s, 3H), 3.84 (s, 3H), 2.53 (s, 3H). LC-MS: m/z 299.9 [M+H]$^+$ at 2.90 RT (88.64% purity); m/z 300.0 [M+H]$^+$ at 3.03 RT (11.35% purity).

Step-2: Synthesis of Methyl 3-(4-methoxy-N,2-dimethylbenzamido)benzoate (4). To a stirred solution of compound 3 (300 mg, 1.0 mmol) in THF (6 mL) was added sodium hydride (60% in mineral oil, 52 mg, 1.3 mmol) at 0° C. under inert atmosphere and stirred for 10 min. Then iodomethane (0.09 mL, 1.5 mmol) was added at 0° C.; warmed to RT and stirred for 3 h. The progress of the reaction was monitored by TLC & LCMS; after the completion, the reaction mixture was quenched with ice cold water (20 mL) and extracted with EtOAc (2×30 mL). The combined organic extracts were washed with brine (15 mL), dried over anhydrous Na$_2$SO$_4$, filtered and concentrated under reduced pressure. The crude material was purified by silica gel column chromatography (eluent: 20% EtOAc/n-hexanes) to afford compound 4 (200 mg, 0.64 mmol, 64%) as brown syrup. $^1$H NMR (400 MHz, DMSO-d$_6$): δ 7.78-7.69 (m, 2H), 7.44-7.36 (m, 2H), 7.02 (br d, J=8.3 Hz, 1H), 6.69 (d, J=1.9 Hz, 1H), 6.59 (br d, J=8.2 Hz, 1H), 3.83 (s, 3H), 3.67 (s, 3H), 3.34 (s, 3H), 2.24 (s, 3H). LC-MS: m/z 313.9 [M+H]$^+$ at 2.77 RT (92.87% purity).

Step-3: Synthesis of 3-(4-hydroxy-N,2-dimethylbenzamido)benzoic acid (VN-325). To a stirred solution of compound 4 (200 mg, 0.64 mmol) in CH$_2$Cl$_2$ (15 mL) was added boron tribromide (1 M in CH$_2$Cl$_2$, 3.83 mL, 3.83 mmol) at −78° C. under inert atmosphere. The reaction mixture was gradually warmed to RT and stirred for 16 h. The progress of the reaction was monitored by TLC; after the completion, the reaction mixture was quenched with ice cold water (15 mL) and extracted with EtOAc (2×20 mL). The combined organic extracts were washed with brine (15 mL), dried over anhydrous Na$_2$SO$_4$, filtered and concentrated under reduced pressure. The crude material was purified by silica gel column chromatography (eluent: 2% MeOH/CH$_2$Cl$_2$) to afford VN-326 (40 mg, 0.14 mmol, 22%) as an off white solid. $^1$H NMR (400 MHz, DMSO-d$_6$): δ 13.08 (br s, 1H), 9.47 (br s, 1H), 7.71-7.67 (m, 2H), 7.40-7.34 (m, 2H), 6.87 (d, J=8.3 Hz, 1H), 6.48 (d, J=1.9 Hz, 1H), 6.39 (dd, J=8.3, 1.8 Hz, 1H), 3.33 (s, 3H), 2.17 (s, 3H); $^1$H NMR (400 MHz, DMSO-d$_6$, D$_2$O Exc.): δ 7.70-7.65 (m, 1H), 7.61 (s, 1H), 7.39-7.33 (m, 2H), 6.85 (br d, J=8.0 Hz, 1H), 6.46 (d, J=1.6 Hz, 1H), 6.37 (br d, J=8.2 Hz, 1H), 3.30 (s, 3H), 2.13 (s, 3H). LC-MS: m/z 286.1 [M+H]$^+$ at 2.72 RT (98.64% purity). HPLC: 98.76%.

Preparation of VN-326. The synthetic strategy for preparing VN-326 is detailed in the scheme below.

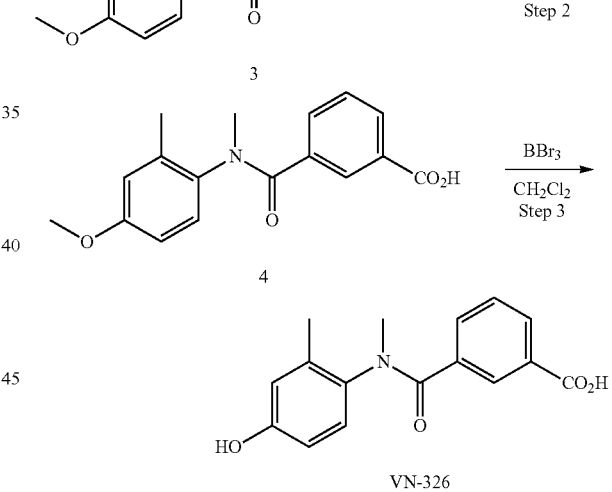

Step-1: Synthesis of Methyl 3-((4-methoxy-2-methylphenyl)carbamoyl)benzoate (3). To a stirred solution of 3-(methoxycarbonyl)benzoic acid 2 (1 g, 5.55 mmol) in CH$_2$Cl$_2$ (15 mL) were added 4-methoxy-2-methylaniline 1 (0.71 mL, 5.55 mmol), HATU (2.53 g, 6.66 mmol) and ethyldiisopropylamine (2.42 mL, 13.87 mmol) at 0° C. under inert atmosphere. The reaction mixture was gradually warmed to RT and stirred for 16 h. The progress of the reaction was monitored by TLC, after the completion, the reaction mixture was diluted with water (30 mL) and extracted with CH$_2$Cl$_2$ (2×40 mL). The combined organic extracts were washed with brine (15 mL), dried over anhydrous Na$_2$SO$_4$, filtered and concentrated under reduced pressure. The crude material was purified by silica gel column chromatography (eluent: 40% EtOAc/n-hexanes) to afford compound 3 (1.5 g, 5.01 mmol, 90%) as an off white solid. $^1$H NMR (500 MHz, CDCl$_3$): δ 8.50 (br s, 1H), 8.21 (br d, J=7.8 Hz, 1H), 8.13 (br d, J=7.3 Hz, 1H), 7.66 (br s, 1H), 7.61-7.55 (m, 2H), 6.82-6.76 (m, 2H), 3.96 (s, 3H), 3.81 (s, 3H), 2.31 (s, 3H).

Step-2: Synthesis of 3-((4-methoxy-2-methylphenyl)(methyl)carbamoyl)benzoic acid (4). To a stirred solution of compound 3 (300 mg, 1.0 mmol) in THF (12 mL) was added sodium hydride (60% in mineral oil, 52 mg, 1.3 mmol) at 0° C. under inert atmosphere. The reaction mixture was gradually warmed to RT and stirred for 20 min. Then iodomethane (0.09 mL, 1.5 mmol) was added at 0° C.; warmed to RT and stirred for 3 h. The progress of the reaction was monitored by TLC; after the completion, the reaction mixture was diluted with ice cold water (20 mL) and extracted with EtOAc (2×50 mL). The combined organic extracts were washed with brine (15 mL), dried over anhydrous Na$_2$SO$_4$, filtered and concentrated under reduced pressure. The crude material was purified by silica gel column chromatography (eluent: 5% MeOH/CH$_2$Cl$_2$) to afford compound 4 (300 mg, impure) as pale yellow sticky liquid. $^1$H NMR (400 MHz, DMSO-d$_6$): δ 13.15 (br s, 1H), 7.86-7.76 (m, 2H), 7.39 (d, J=7.8 Hz, 1H), 7.32-7.25 (m, 1H), 7.13 (d, J=8.5 Hz, 1H), 6.73-6.64 (m, 2H), 3.66 (s, 3H), 3.17 (s, 3H), 2.12 (s, 3H). LC-MS: m/z 299.9 [M+H]$^+$ at 1.57 RT (80.28% purity).

Step-3: Synthesis of 3-((4-hydroxy-2-methylphenyl)(methyl)carbamoyl)benzoic acid (VN-326). To a stirred solution of compound 4 (300 mg, 1.0 mmol) in CH$_2$Cl$_2$ (6 mL) was added boron tribromide (1 M in CH$_2$Cl$_2$, 6.02 mL, 6.02 mmol) at −78° C. under inert atmosphere. The reaction mixture was gradually warmed to RT and stirred for 16 h. The progress of the reaction was monitored by TLC; after the completion, the reaction mixture was quenched with ice cold water (20 mL) and the organic layer was separated. The aqueous layer was extracted with EtOAc (2×50 mL). The combined organic extracts (DCM & EtOAc layers) were dried over anhydrous Na$_2$SO$_4$, filtered and concentrated under reduced pressure. The crude material was triturated with EtOAc/MeOH (20 mL/1 mL) followed by washings with Et$_2$O (2×10 mL), n-pentane (2×10 mL) and dried under vacuum to afford VN-337 (80 mg, 0.28 mmol, 28%) as an off white solid. $^1$H NMR (500 MHz, DMSO-d$_6$): δ 12.99 (br s, 1H), 9.39 (s, 1H), 7.83-7.76 (m, 2H), 7.40 (d, J=7.5 Hz, 1H), 7.32-7.27 (m, 1H), 6.98 (d, J=8.4 Hz, 1H), 6.51-6.44 (m, 2H), 3.20 (s, 3H), 2.04 (s, 3H); $^1$H NMR (500 MHz, DMSO-d$_6$, D$_2$O Exc.): δ 7.82-7.74 (m, 2H), 7.41 (d, J=7.8 Hz, 1H), 7.34-7.27 (m, 1H), 6.97 (d, J=8.4 Hz, 1H), 6.50-6.42 (m, 2H), 3.18 (s, 3H), 2.00 (s, 3H). LC-MS: m/z 286.2 [M+H]$^+$ at 1.80 RT (99.16% purity). HPLC: 98.82%.

Preparation of VN-327. The synthetic strategy for preparing VN-327 is detailed in the scheme below.

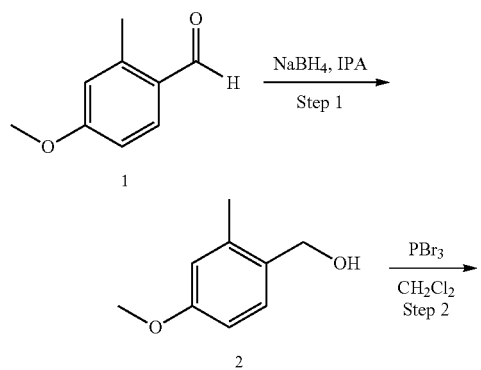

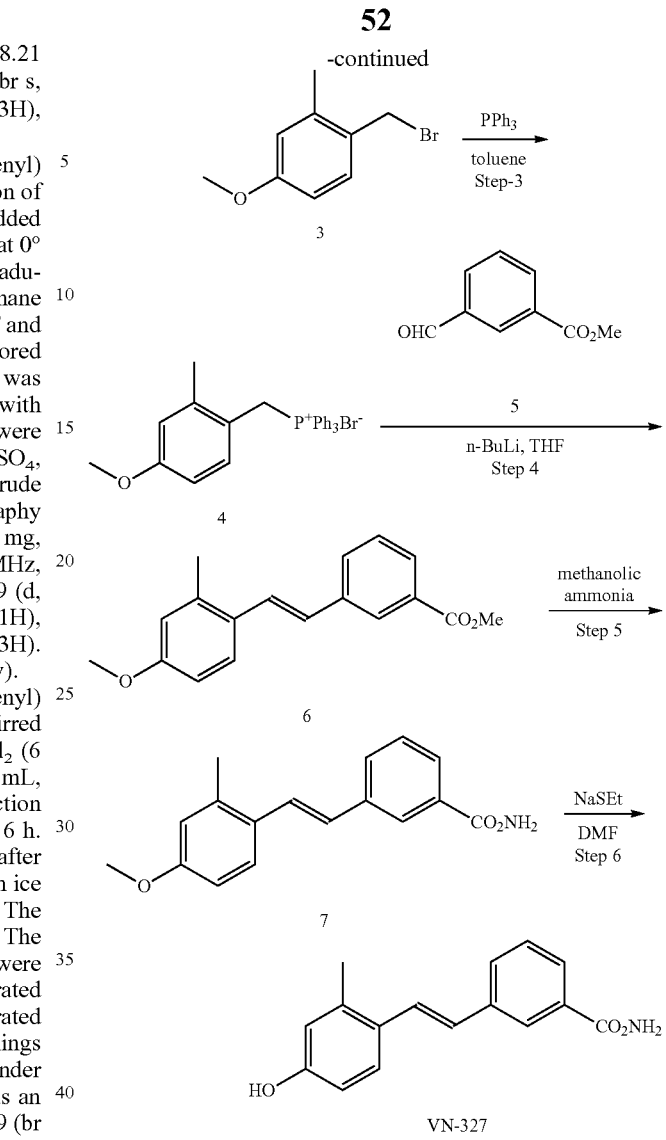

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous Na$_2$SO$_4$, filtered and concentrated under reduced pressure to afford compound 2 (10 g, 65.71 mmol) as colorless syrup. The crude material was taken to next step without further purification. $^1$H NMR (500 MHz, CDCl$_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in CH$_2$Cl$_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with CH$_2$Cl$_2$ (100 mL), washed with water (100 mL) and saturated NaHCO₃ solution (100 mL). The combined organic extracts were washed with brine (50 mL), dried over anhydrous Na₂SO₄, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. ¹H NMR (400 MHz, DMSO-d₆): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-3-(4-methoxy-2-methylstyryl)benzoate (6). To a stirred solution of compound 4 (4.6 g, 9.64 mmol) in THF (46 mL) was added n-BuLi (2.5 M in hexanes, 4.63 mL, 11.57 mmol) at −78° C. under inert atmosphere. The reaction mixture was gradually warmed to RT and stirred for 30 min. Then a solution of methyl 3-formylbenzoate 5 (1.9 g, 11.57 mmol) in THF (13.8 mL) was added at −78° C. The reaction mixture was gradually warmed to RT and stirred for 2 h. The progress of the reaction was monitored by TLC; after the completion, the reaction mixture was cooled to 0° C.; quenched with saturated NH₄Cl solution (50 mL) and extracted with EtOAc (2×70 mL). The combined organic extracts were washed with brine (30 mL), dried over anhydrous Na₂SO₄, filtered and concentrated under reduced pressure. The crude material was purified by silica gel column chromatography (eluent: 10% EtOAc/n-hexanes) to afford compound 6 (1.8 g, 6.37 mmol, 66%) as a mixture of cis and trans-isomers as colorless syrup. ¹H NMR (500 MHz, CDCl₃): δ 8.18 (s, 1H), 7.92 (d, J=7.8 Hz, 1H), 7.87 (s, 1H), 7.82 (d, J=7.7 Hz, 1H), 7.69 (d, J=7.8 Hz, 1H), 7.56 (d, J=8.5 Hz, 1H), 7.44 (t, J=7.7 Hz, 1H), 7.36 (d, J=16.1 Hz, 1H), 7.30 (s, 1H), 7.23-7.17 (m, 1H), 7.02 (d, J=8.4 Hz, 1H), 6.94 (d, J=16.1 Hz, 1H), 6.82-6.75 (m, 3H), 6.71-6.66 (m, 1H), 6.63-6.57 (m, 2H), 3.96 (s, 3H), 3.89 (s, 3H), 3.84 (s, 3H), 3.80 (s, 3H), 2.45 (s, 3H), 2.27 (s, 3H).

Step-5: Synthesis of (E)-3-(4-methoxy-2-methylstyryl)benzamide (7). To compound 6 (600 mg, 2.13 mmol) was added methanolic ammonia (10 mL) in a sealed tube at RT under inert atmosphere. The sealed tube was sealed and the reaction mixture was heated to 90° C. and stirred for 24 h. The progress of the reaction was monitored by TLC & LCMS, after the completion, the reaction mixture was concentrated under reduced pressure to obtain the crude. The crude material was purified by silica gel column chromatography (eluent: 30% EtOAc/n-hexanes) to afford compound 7 (200 mg, 0.75 mmol, 35%) as a mixture of cis and trans-isomers as an off white solid. ¹H NMR (400 MHz, DMSO-d₆): δ 8.11-8.02 (m, 2H), 7.88 (br s, 1H), 7.77-7.69 (m, 3H), 7.66-7.59 (m, 2H), 7.47-7.39 (m, 3H), 7.31 (br s, 1H), 7.26-7.18 (m, 1H), 7.17-7.13 (m, 1H), 7.04 (d, J=16.3 Hz, 1H), 6.93 (d, J=8.4 Hz, 1H), 6.84-6.78 (m, 3H), 6.70-6.58 (m, 3H), 3.76 (s, 3H), 3.72 (s, 3H), 2.41 (s, 3H), 2.21 (s, 3H). LC-MS: m/z 308.9 [M+ACN]⁺ at 2.80 RT (93.84% purity).

Step-6: Synthesis of (E)-3-(4-hydroxy-2-methylstyryl)benzamide (VN-327). To a stirred solution of compound 7 (200 mg, 0.75 mmol) in DMF (2 mL) was added sodium thioethoxide (503 mg, 6.0 mmol) in a microwave vessel at RT. The vessel was sealed and the reaction mixture was irradiated to 120° C. and stirred for 3 h. The progress of the reaction was monitored by TLC & LC-MS; after the completion, the reaction mixture was diluted with water (20 mL) and extracted with EtOAc (2×20 mL). The combined organic extracts were washed with brine (10 mL), dried over anhydrous Na₂SO₄, filtered and concentrated under reduced pressure. The crude material was purified by silica gel column chromatography (eluent: 2% MeOH/CH₂Cl₂) to afford VN-327 (25 mg, 0.1 mmol, 13%) as an off white solid. ¹H NMR (400 MHz, DMSO-d₆): δ 9.45 (s, 1H), 8.08-8.00 (m, 2H), 7.74-7.66 (m, 2H), 7.51 (d, J=8.2 Hz, 1H), 7.45-7.35 (m, 3H), 6.97 (d, J=16.3 Hz, 1H), 6.66-6.61 (m, 2H), 2.35 (s, 3H); ¹H NMR (400 MHz, DMSO-d₆, D₂O Exc.): δ 8.02 (s, 1H), 7.73-7.66 (m, 2H), 7.51 (d, J=8.2 Hz, 1H), 7.45-7.33 (m, 2H), 6.96 (d, J=16.2 Hz, 1H), 6.66-6.60 (m, 2H), 2.33 (s, 3H). LC-MS: m/z 254.0 [M+H]⁺ at 2.96 RT (94.04% purity). HPLC: 99.42%.

Preparation of VN-328. The synthetic strategy for preparing VN-328 is detailed in the scheme below.

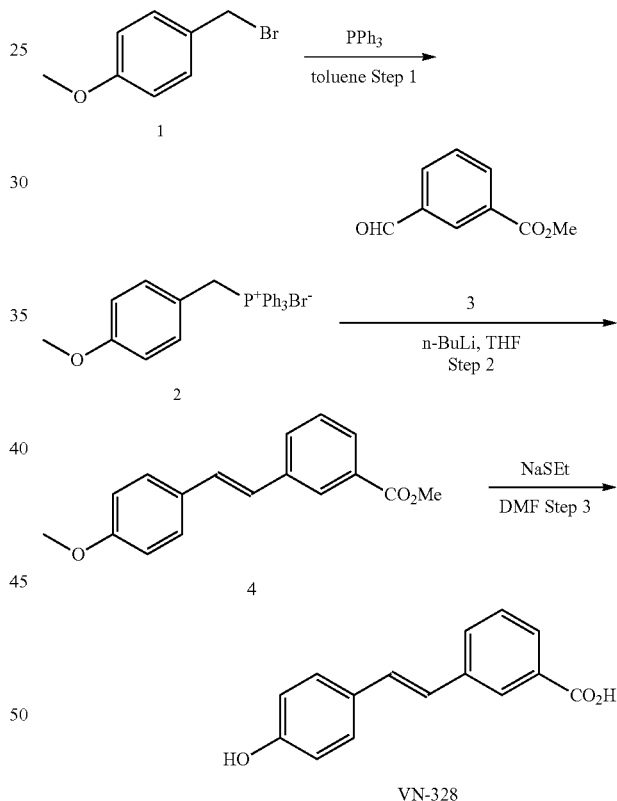

Step-1: Synthesis of (4-methoxybenzyl)triphenylphosphonium bromide (2). To a stirred solution of 1-(bromomethyl)-4-methoxybenzene 1 (500 mg, 2.49 mmol) in toluene (5 mL) was added triphenylphosphine (652 mg, 2.49 mmol) at RT under inert atmosphere. The reaction mixture was heated to reflux temperature and stirred for 12 h. Then the solid was filtered, washed with toluene (2×10 mL), n-hexanes (2×10 mL) and dried under vacuum to afford compound 2 (950 mg, 2.05 mmol, 83%) as white solid. ¹H NMR (400 MHz, DMSO-d₆): δ 7.95-7.87 (m, 3H), 7.78-7.71 (m, 6H), 7.69-7.61 (m, 6H), 6.91-6.85 (m, 2H), 6.83-6.77 (m, 2H), 5.07 (d, J=14.9 Hz, 2H), 3.69 (s, 3H).

Step-2: Synthesis of Methyl (E)-3-(4-methoxystyryl)benzoate (4). To a stirred solution of compound 2 (1 g, 2.16 mmol) in THF (10 mL) was added n-BuLi (2.5 M in hexanes, 0.95 mL, 2.37 mmol) at −78° C. under inert atmosphere. The reaction mixture was gradually warmed to RT and stirred for 30 min. Then a solution of methyl 3-formylbenzoate 3 (354 mg, 2.16 mmol) in THF (2 mL) was added at −78° C. The reaction mixture was gradually warmed to RT and stirred for 16 h. The progress of the reaction was monitored by TLC; after the completion, the reaction mixture was quenched with saturated NH$_4$Cl solution (30 mL) and extracted with EtOAc (2×30 mL). The combined organic extracts were washed with brine (10 mL), dried over anhydrous Na$_2$SO$_4$, filtered and concentrated under reduced pressure. The crude material was purified by silica gel column chromatography (eluent: 10% EtOAc/n-hexanes) to afford compound 4 (400 mg, 1.49 mmol, 70%) as a mixture of cis and trans-isomers as an off white semi solid. $^1$H NMR (500 MHz, DMSO-d$_6$): δ 8.12 (s, 1H), 7.90-7.77 (m, 3H), 7.59 (d, J=8.5 Hz, 1H), 7.54-7.46 (m, 2H), 7.45-7.39 (m, 1H), 7.33-7.18 (m, 2H), 7.13 (d, J=8.7 Hz, 2H), 6.96 (d, J=8.7 Hz, 1H), 6.82 (d, J=8.7 Hz, 2H), 6.67-6.56 (m, 2H), 3.88 (s, 2H), 3.81 (s, 3H), 3.78 (s, 2H), 3.73 (s, 3H). LC-MS: m/z 269.1 [M+H]$^+$ at 4.51 RT (96.39% purity).

Step-3: Synthesis of (E)-3-(4-hydroxystyryl)benzoic acid (VN-328). To a stirred solution of compound 4 (100 mg, 0.37 mmol) in DMF (2 mL) was added sodium thioethoxide (188 mg, 2.24 mmol) in a microwave vessel at RT. The vessel was sealed and the reaction mixture was irradiated to 120° C. and stirred for 2 h. The progress of the reaction was monitored by TLC; after the completion, the reaction mixture was quenched with 2N HCl (20 mL) and extracted with EtOAc (2×20 mL). The combined organic extracts were washed with brine (10 mL), dried over anhydrous Na$_2$SO$_4$, filtered and concentrated under reduced pressure to obtain the crude.

The above lot was combined with two other lots (200 mg) and was purified by reverse phase preparative HPLC (Method K) to afford VN-329 (43 mg, 0.18 mmol, 16% for three batches) as an off white solid. $^1$H NMR (400 MHz, DMSO-d$_6$): δ 12.97 (br s, 1H), 9.60 (s, 1H), 8.08 (s, 1H), 7.83-7.75 (m, 2H), 7.51-7.43 (m, 3H), 7.23 (d, J=16.1 Hz, 1H), 7.10 (d, J=16.2 Hz, 1H), 6.78 (d, J=8.7 Hz, 2H); $^1$H NMR (400 MHz, DMSO-d$_6$, D$_2$O Exc.): δ 8.04 (s, 1H), 7.80-7.74 (m, 2H), 7.50-7.42 (m, 3H), 7.18 (d, J=16.4 Hz, 1H), 7.06 (d, J=16.3 Hz, 1H), 6.77 (d, J=8.7 Hz, 2H). LC-MS: m/z 238.8 [M−H]$^-$ at 2.14 RT (98.79% purity). HPLC: 97.92%.

Preparation of VN-329 & VN-338. The synthetic strategy for preparing VN-329 and VN-338 is detailed in the scheme below.

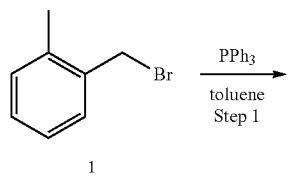

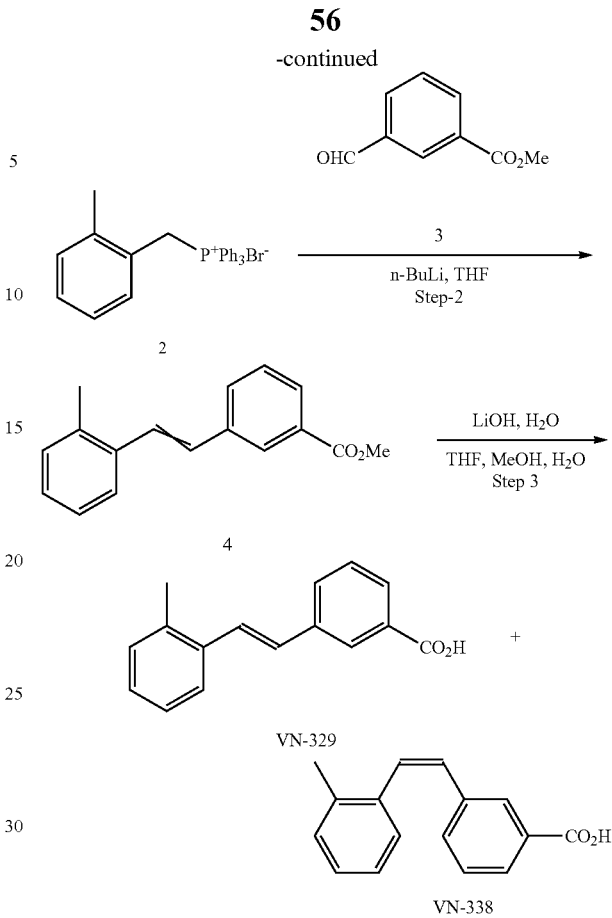

Step-1: Synthesis of (2-methylbenzyl)triphenylphosphonium bromide (2). To a stirred solution of 1-(bromomethyl)-2-methylbenzene 1 (2 g, 10.81 mmol) in toluene (20 mL) was added triphenylphosphine (2.83 g, 10.81 mmol) at RT under inert atmosphere. The reaction mixture was heated to reflux temperature and stirred for 12 h. Then the solid was filtered, washed with toluene (2×20 mL), n-hexanes (2×15 mL) and dried under vacuum to afford compound 2 (3.5 g, 7.82 mmol, 73%) as white solid. $^1$H NMR (400 MHz, DMSO-d$_6$): δ 7.96-7.89 (m, 3H), 7.78-7.69 (m, 6H), 7.67-7.58 (m, 6H), 7.27-7.19 (m, 1H), 7.11 (d, J=7.4 Hz, 1H), 7.04 (t, J=7.5 Hz, 1H), 6.96-6.92 (m, 1H), 5.06-5.02 (m, 2H), 3.32 (s, 3H).

Step-2: Synthesis of Methyl (E)-3-(2-methylstyryl)benzoate (4). To a stirred solution of compound 2 (1 g, 2.24 mmol) in THF (3.5 mL) was added n-BuLi (2.5M in hexanes, 0.98 mL, 2.46 mmol) at −78° C. under inert atmosphere. The reaction mixture was gradually warmed to RT and stirred for 30 min. Then methyl 3-formylbenzoate 3 (367 mg, 2.24 mmol) in THF (1 mL) was added at −78° C. The reaction mixture was gradually warmed to RT and stirred for 1 h. The progress of the reaction was monitored by TLC; after the completion, the reaction mixture was quenched with saturated NH$_4$Cl solution (30 mL) at 0° C. and extracted with EtOAc (2×30 mL). The combined organic extracts were washed with brine (10 mL), dried over anhydrous Na$_2$SO$_4$, filtered and concentrated under reduced pressure. The crude material was purified by silica gel column chromatography (eluent: 10% EtOAc/n-hexanes) to afford compound 4 (330 mg, 1.31 mmol, 57%) as a mixture of cis and trans-isomers as colorless liquid. $^1$H NMR (400 MHz, DMSO-d$_6$): δ 8.15 (s, 1H), 7.98-7.94 (m, 1H), 7.90-

7.84 (m, 1H), 7.77-7.66 (m, 3H), 7.59-7.46 (m, 2H), 7.36-7.29 (m, 2H), 7.28-7.15 (m, 5H), 7.10-6.99 (m, 2H), 6.83-6.72 (m, 2H), 3.88 (s, 3H), 3.77 (s, 3H), 2.43 (s, 3H), 2.22 (s, 3H). LC-MS: m/z 253.8 [M+H]+ at 4.73 RT (98.87% purity).

Step-3: Synthesis of (E)-3-(2-methylstyryl)benzoic acid (VN-329) & (Z)-3-(2-methylstyryl)benzoic acid (VN-338). To a stirred solution of compound 4 (320 mg, mixture) in a mixture of methanol (0.7 mL), THF (1 mL) and water (0.7 mL) was added lithium hydroxide monohydride (80 mg, 1.9 mmol) at 0-5° C. The reaction mixture was gradually warmed to RT and stirred for 6 h. The progress of the reaction was monitored by TLC; after the completion, the volatiles were removed under reduced pressure. The residue was acidified with 2N HCl to pH ~2-3 and extracted with EtOAc (2×25 mL). The combined organic extracts were washed with brine (10 mL), dried over anhydrous $Na_2SO_4$, filtered and concentrated under reduced pressure. The crude material was purified by normal phase preparative HPLC (Method N) to afford VN-329 (35 mg, 0.15 mmol, 11%) & VN-338 (35 mg, 0.15 mmol, 11%) as off white solids respectively.

Analytical data of VN-329: $^1$H NMR (400 MHz, DMSO-$d_6$): δ 13.06 (br s, 1H), 8.13 (t, J=1.6 Hz, 1H), 7.94-7.92 (m, 1H), 7.84 (dt, J=7.7, 1.3 Hz, 1H), 7.72-7.67 (m, 1H), 7.54-7.45 (m, 2H), 7.26-7.19 (m, 4H), 2.42 (s, 3H); $^1$H NMR (500 MHz, DMSO-$d_6$, $D_2O$ Exc.): δ 8.09 (s, 1H), 7.91-7.79 (m, 2H), 7.66 (br d, J=7.1 Hz, 1H), 7.51 (t, J=7.7 Hz, 1H), 7.44 (d, J=16.2 Hz, 1H), 7.24-7.15 (m, 4H), 2.38 (s, 3H). LC-MS: m/z 236.9 [M−H]+ at 2.89 RT (99.97% purity). HPLC: 99.20%.

Analytical data of VN-3338: $^1$H NMR (400 MHz, DMSO-$d_6$): δ 12.88 (br s, 1H), 7.76-7.69 (m, 2H), 7.32-7.23 (m, 3H), 7.18 (td, J=7.3, 1.6 Hz, 1H), 7.09-7.00 (m, 2H), 6.81-6.72 (m, 2H), 2.23 (s, 3H); $^1$H NMR (400 MHz, DMSO-$d_6$, $D_2O$ Exc.): δ 7.75-7.65 (m, 2H), 7.32-7.26 (m, 2H), 7.26-7.21 (m, 1H), 7.16 (td, J=7.3, 1.5 Hz, 1H), 7.06-6.97 (m, 2H), 6.80-6.69 (m, 2H), 2.19 (s, 3H). LC-MS: m/z 236.9 [M−H]+ at 2.90 RT (99.93% purity). HPLC: 98.29%.

Preparation of VN-330 & VN-339. The synthetic strategy for preparing VN-330 and VN-339 are detailed in the scheme below.

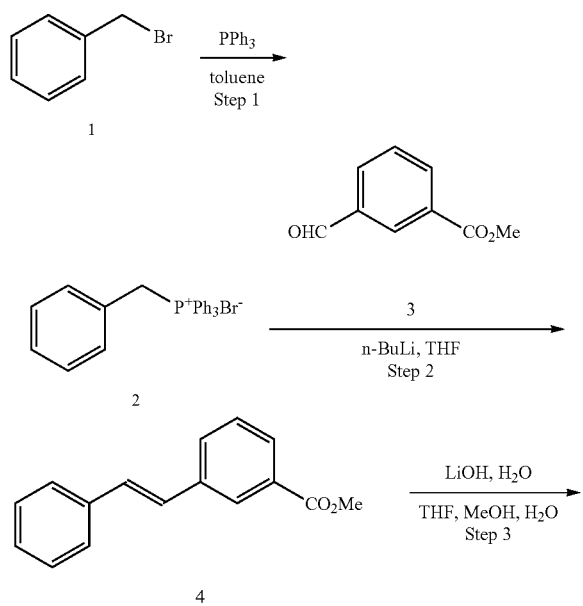

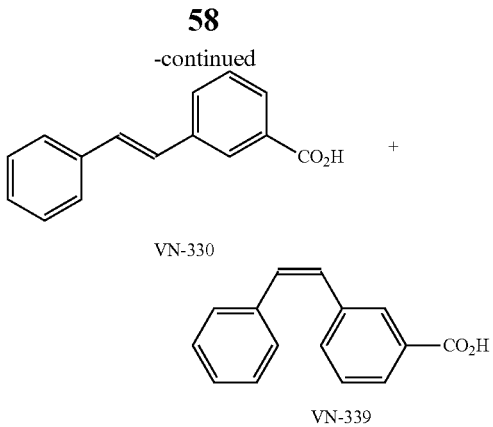

Step-1: Synthesis of Benzyltriphenylphosphonium bromide (2). To a stirred solution of (bromomethyl)benzene 1 (1.39 mL, 11.69 mmol) in toluene (20 mL) was added triphenylphosphine (3.06 g, 11.69 mmol) at RT under inert atmosphere. The reaction mixture was heated to reflux temperature and stirred for 16 h. Then the solid was filtered, washed with toluene (2×20 mL), n-hexanes (2×15 mL) and dried under vacuum to afford compound 2 (4.7 g, 10.85 mmol, 97%) as white solid. $^1$H NMR (400 MHz, DMSO-$d_6$): δ 7.95-7.86 (m, 3H), 7.79-7.63 (m, 12H), 7.33-7.26 (m, 1H), 7.26-7.20 (m, 2H), 7.00-6.96 (m, 2H), 5.22-5.16 (m, 2H).

Step-2: Synthesis of Methyl (E)-3-styrylbenzoate (4). To a stirred solution of compound 2 (500 mg, 1.21 mmol) in THF (3.5 mL) was added n-BuLi (2.5 M in hexanes, 0.53 mL, 1.33 mmol) at −78° C. under inert atmosphere. The reaction mixture was gradually warmed to RT and stirred for 20 min. Then methyl 3-formylbenzoate 3 (198 mg, 1.21 mmol) in THF (0.7 mL) was added at −78° C. The reaction mixture was gradually warmed to RT and stirred for 30 min. The progress of the reaction was monitored by TLC; after the completion, the reaction mixture was quenched with saturated $NH_4Cl$ solution (30 mL) at 0° C. and extracted with EtOAc (2×30 mL). The combined organic extracts were washed with brine (10 mL), dried over anhydrous $Na_2SO_4$, filtered and concentrated under reduced pressure. The crude material was purified by combi flash column chromatography (eluent: 10% EtOAc/n-hexanes) to afford compound 4 (250 mg, 1.05 mmol, 97%) as a mixture of cis and trans-isomers as colorless liquid. $^1$H NMR (400 MHz, $CDCl_3$): δ 8.20 (t, J=1.8 Hz, 1H), 7.94-7.91 (m, 2H), 7.86 (dt, J=7.7, 1.3 Hz, 1H), 7.68 (dt, J=7.7, 1.3 Hz, 1H), 7.55-7.51 (m, 2H), 7.45-7.35 (m, 4H), 7.31-7.27 (m, 1H), 7.25-7.19 (m, 6H), 7.16 (d, J=11.4 Hz, 2H), 6.70-6.65 (m, 1H), 6.64-6.58 (m, 1H), 3.95 (s, 3H), 3.87 (s, 3H). LC-MS: m/z 239.2 [M+H]+ at 4.52 RT (98.96% purity).

Step-3: Synthesis of (E)-3-styrylbenzoic acid (VN-330) & (Z)-3-styrylbenzoic acid (VN-339). To a stirred solution of compound 4 (200 mg, mixture) in methanol/THF/water (1:1:1, 1.5 mL) was added lithium hydroxide monohydride (53 mg, 1.26 mmol) at 0° C. The reaction mixture was gradually warmed to RT and stirred for 5 h. The progress of the reaction was monitored by TLC; after the completion, the volatiles were removed under reduced pressure. The residue was acidified with 5N HCl to pH ~2-3 and extracted with EtOAc (2×20 mL). The combined organic extracts were washed with brine (10 mL), dried over anhydrous $Na_2SO_4$, filtered and concentrated under reduced pressure. The crude material was purified by preparative HPLC (Method F & M) to afford VN-330 (20 mg, 0.09 mmol, 11%) & VN-339 (60 mg, 0.27 mmol, 32%) as off white solids respectively.

Analytical data of VN-330: $^1$H NMR (500 MHz, DMSO-$d_6$): δ 13.03 (br s, 1H), 8.15 (s, 1H), 7.85 (br dd, J=12.9, 7.7 Hz, 2H), 7.65 (d, J=7.2 Hz, 2H), 7.51 (t, J=7.7 Hz, 1H), 7.39 (t, J=7.7 Hz, 2H), 7.36-7.34 (m, 2H), 7.32-7.27 (m, 1H); $^1$H NMR (500 MHz, DMSO-$d_6$, $D_2O$ Exc.): δ 8.10 (s, 1H), 7.83 (br dd, J=14.6, 7.7 Hz, 2H), 7.61 (d, J=7.2 Hz, 2H), 7.50 (t, J=7.5 Hz, 1H), 7.37 (t, J=7.5 Hz, 2H), 7.31-7.24 (m, 3H). LC-MS: m/z 222.8 [M–H]$^+$ at 2.78 RT (99.73% purity). HPLC: 100.00%.

Analytical data of VN-339: $^1$H NMR (500 MHz, DMSO-$d_6$): δ 12.88 (s, 1H), 7.84-7.76 (m, 2H), 7.45-7.35 (m, 2H), 7.29-7.19 (m, 5H), 6.74-6.68 (m, 2H); $^1$H NMR (500 MHz, DMSO-$d_6$, $D_2O$ Exc.): δ 7.79-7.74 (m, 2H), 7.45-7.35 (m, 2H), 7.26-7.14 (m, 5H), 6.73-6.63 (m, 2H). LC-MS: m/z 222.8 [M–H]$^+$ at 2.72 RT (99.60% purity). HPLC: 98.31%.

Preparation of VN-331. The synthetic strategy for preparing VN-381 is detailed in the scheme below.

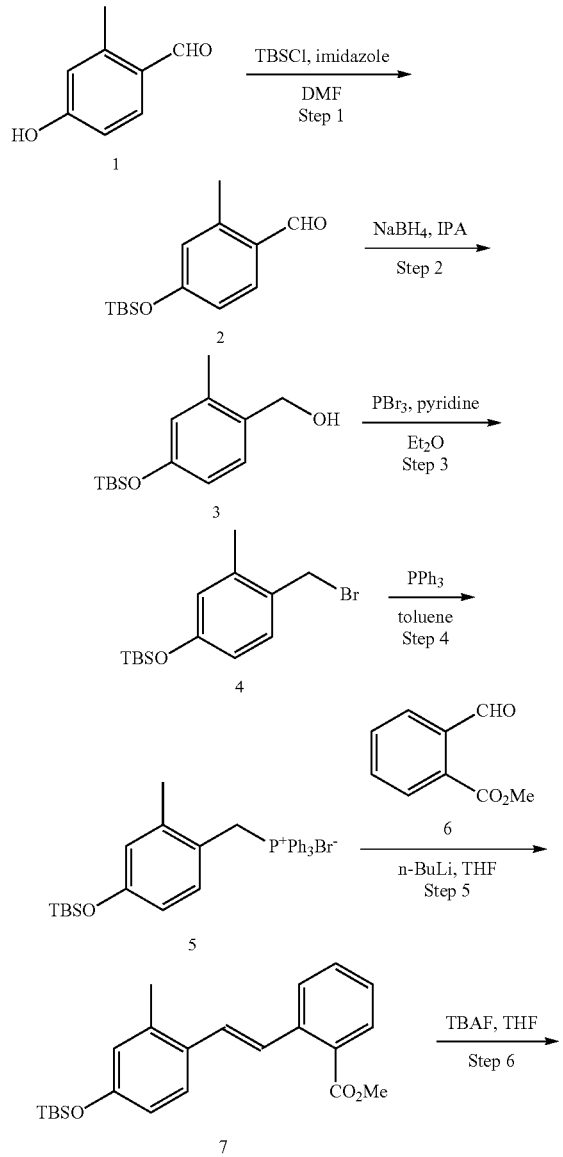

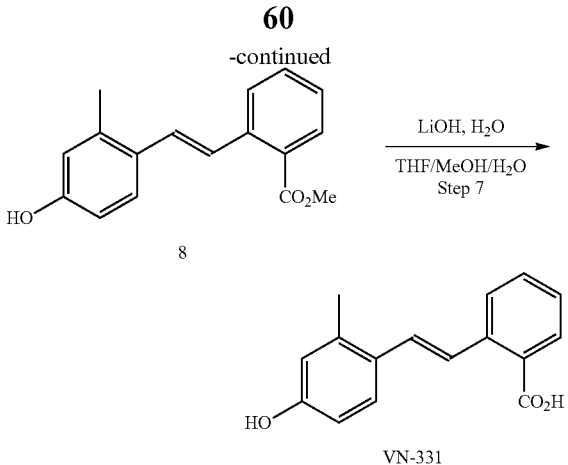

Step-1: Synthesis of 4-((tert-butyldimethylsilyl)oxy)-2-methylbenzaldehyde (2). To a stirred solution of 4-hydroxy-2-methylbenzaldehyde 1 (2 g, 14.7 mmol) in DMF (14 mL) were added imidazole (2.5 g, 36.76 mmol) and tert-butyldimethylchlorosilane (3.32 g, 22.06 mmol) at 0° C. under inert atmosphere. The reaction mixture was gradually warmed to RT and stirred for 6 h. The progress of the reaction was monitored by TLC; after the completion, the reaction mixture was diluted with water (50 mL) and extracted with EtOAc (2×50 mL). The combined organic extracts were washed with brine (20 mL), dried over anhydrous $Na_2SO_4$, filtered and concentrated under reduced pressure. The crude material was purified by silica gel column chromatography (eluent: 5% EtOAc/n-hexanes) to afford compound 2 (2.1 g, 8.39 mmol, 57%) as colorless liquid. $^1$H NMR (400 MHz, CDCl$_3$): δ 10.12 (s, 1H), 7.70 (d, J=8.4 Hz, 1H), 6.78 (dd, J=8.4, 2.4 Hz, 1H), 6.69 (d, J=2.3 Hz, 1H), 2.62 (s, 3H), 0.99 (s, 9H), 0.24 (s, 6H). LC-MS: m/z 251.2 [M+H]$^+$ at 3.31 RT (98.30% purity).

Step-2: Synthesis of (4-((tert-butyldimethylsilyl)oxy)-2-methylphenyl)methanol (3). To a stirred solution of compound 2 (1 g, 4.0 mmol) in isopropanol (10 mL) was added sodium borohydride (91 mg, 2.4 mmol) at 0° C. under inert atmosphere. The reaction mixture was gradually warmed to RT and stirred for 2 h. The progress of the reaction was monitored by TLC; after the completion, the reaction mixture was quenched with ice pieces and extracted with EtOAc (2×40 mL). The combined organic extracts were dried over anhydrous $Na_2SO_4$, filtered and concentrated under reduced pressure to afford compound 3 (1 g) as colorless syrup. The crude material was taken to next step without further purification. $^1$H NMR (500 MHz, CDCl$_3$): δ 7.16 (d, J=8.1 Hz, 1H), 6.70-6.63 (m, 2H), 4.62 (s, 2H), 2.33 (s, 3H), 0.98 (s, 9H), 0.19 (s, 6H). LC-MS: m/z 235.2 [M-17]$^+$ at 3.02 RT (82.70% purity).

Step-3: Synthesis of (4-(bromomethyl)-3-methylphenoxy)(tert-butyl)dimethylsilane (4). To a stirred solution of compound 3 (500 mg, crude) in diethylether (10 mL) were added pyridine (0.03 mL, 0.4 mmol) followed by phosphorus tribromide (0.21 mL, 2.18 mmol) drop wise at 0° C. under inert atmosphere. The reaction mixture was gradually warmed to RT and stirred for 6 h. The progress of the reaction was monitored by TLC; after the completion, the reaction mixture was quenched with water (20 mL) and extracted with EtOAc (2×20 mL). The combined organic extracts were washed with brine (10 mL), dried over anhydrous $Na_2SO_4$, filtered and concentrated under reduced pressure to afford compound 4 (440 mg) as pale yellow syrup. The crude material was taken to next step without further purification.

Step-4: Synthesis of (4-((tert-butyldimethylsilyl)oxy)-2-methylbenzyl)triphenylphosphonium bromide (5). To a stirred solution of compound 4 (480 mg, crude) in toluene (20 mL) was added triphenylphosphine (399 mg, 1.52 mmol) at RT under inert atmosphere. The reaction mixture was heated to reflux temperature and stirred for 6 h. Then the precipitated solid was filtered, washed with toluene (2×10 mL), n-hexanes (2×10 mL) and dried under vacuum to afford compound 5 (680 mg, 1.18 mmol, 77%) as white solid. LC-MS: m/z 497.4 [(M-Br)+H]$^+$ at 2.74 RT (57.03% purity).

Step-5: Synthesis of Methyl (E)-2-(4-((tert-butyldimethylsilyl)oxy)-2-methylstyryl)benzoate (7). To a stirred solution of compound 5 (1 g, 1.73 mmol) in THF (8 mL) was added n-BuLi (2.5 M in hexanes, 0.83 mL, 2.08 mmol) at −78° C. under inert atmosphere. The reaction mixture was gradually warmed to RT and stirred for 30 min. Then a solution of methyl 2-formylbenzoate 6 (313 mg, 1.91 mmol) in THF (2 mL) was added at −78° C. The reaction mixture was gradually warmed to RT and stirred for 16 h. The progress of the reaction was monitored by TLC, after the completion, the reaction mixture was quenched with saturated NH$_4$Cl solution (30 mL) and extracted with EtOAc (2×30 mL). The combined organic extracts were washed with brine (15 mL), dried over anhydrous Na$_2$SO$_4$, filtered and concentrated under reduced pressure. The crude material was purified by silica gel column chromatography (eluent: 3-5% EtOAc/n-hexanes) to afford compound 7 (400 mg, 1.04 mmol, 60%) as a mixture of cis and trans-isomers as colorless semi solid. LC-MS: m/z 383.3 [M+H]$^+$ at 6.01 RT (49.99% purity) & m/z 383.3 [M+H]$^+$ at 6.14 RT (44.12% purity).

Step-6: Synthesis of Methyl (E)-2-(4-hydroxy-2-methylstyryl)benzoate (8). To a stirred solution of compound 7 (430 mg, 1.12 mmol) in THF (5 mL) was added tetra-n-butylammonium fluoride (1 M in THF, 1.35 mL, 1.35 mmol) at 0° C. under inert atmosphere. The reaction mixture was gradually warmed to RT and stirred for 6 h. The progress of the reaction was monitored by TLC; after the completion, the reaction mixture was quenched with water (20 mL) and extracted with EtOAc (2×20 mL). The combined organic extracts were washed with brine (15 mL), dried over anhydrous Na$_2$SO$_4$, filtered and concentrated under reduced pressure. The crude material was purified by combi flash column chromatography (eluent: 30% EtOAc/n-hexanes) followed by preparative HPLC (Method D) to afford compound 8 (100 mg, 0.37 mmol, 33%) as colorless semi solid. $^1$H NMR (400 MHz, CDCl$_3$): δ 7.92 (dd, J=7.8, 1.2 Hz, 1H), 7.77-7.68 (m, 2H), 7.56-7.48 (m, 2H), 7.30 (td, J=7.6, 1.1 Hz, 1H), 7.15 (d, J=15.9 Hz, 1H), 6.72-6.66 (m, 2H), 3.92 (s, 3H), 2.38 (s, 3H).

Step-7: Synthesis of (E)-2-(4-hydroxy-2-methylstyryl) benzoic acid (VN-331). To a stirred solution of compound 8 (100 mg, 0.37 mmol) in a mixture of THF/methanol/water (1:1:1, 6 mL) was added lithium hydroxide monohydride (23 mg, 0.56 mmol) at 0° C. The reaction mixture was gradually warmed to RT and stirred for 16 h. The progress of the reaction was monitored by TLC; after the completion, the volatiles were removed under reduced pressure. The residue was diluted with water (5 mL) and extracted with EtOAc (2×5 mL). The organic layer was separated; the aqueous layer was acidified with 6N HCl to pH ~2 and extracted with EtOAc (2×20 mL). The combined organic extracts were dried over anhydrous Na$_2$SO$_4$, filtered and concentrated under reduced pressure to afford VN-331 (50 mg, 0.2 mmol, 52%) as white solid. $^1$H NMR (400 MHz, DMSO-d$_6$): δ 12.94 (br s, 1H), 9.46 (s, 1H), 7.81 (d, J=7.9 Hz, 2H), 7.62 (d, J=16.2 Hz, 1H), 7.54 (td, J=7.7, 1.0 Hz, 1H), 7.40 (d, J=8.3 Hz, 1H), 7.37-7.31 (m, 1H), 7.20 (d, J=16.2 Hz, 1H), 6.67-6.60 (m, 2H), 2.32 (s, 3H); $^1$H NMR (400 MHz, DMSO-d$_6$, D$_2$O Exc.): δ 7.82-7.76 (m, 2H), 7.60-7.51 (m, 2H), 7.41-7.31 (m, 2H), 7.18 (d, J=16.2 Hz, 1H), 6.68-6.61 (m, 2H), 2.30 (s, 3H). LC-MS: m/z 255.2 [M+H]$^+$ at 2.11 RT (96.10% purity). HPLC: 99.11%.

Preparation of VN-322. The synthetic strategy for preparing VN-322 is detailed in the scheme below.

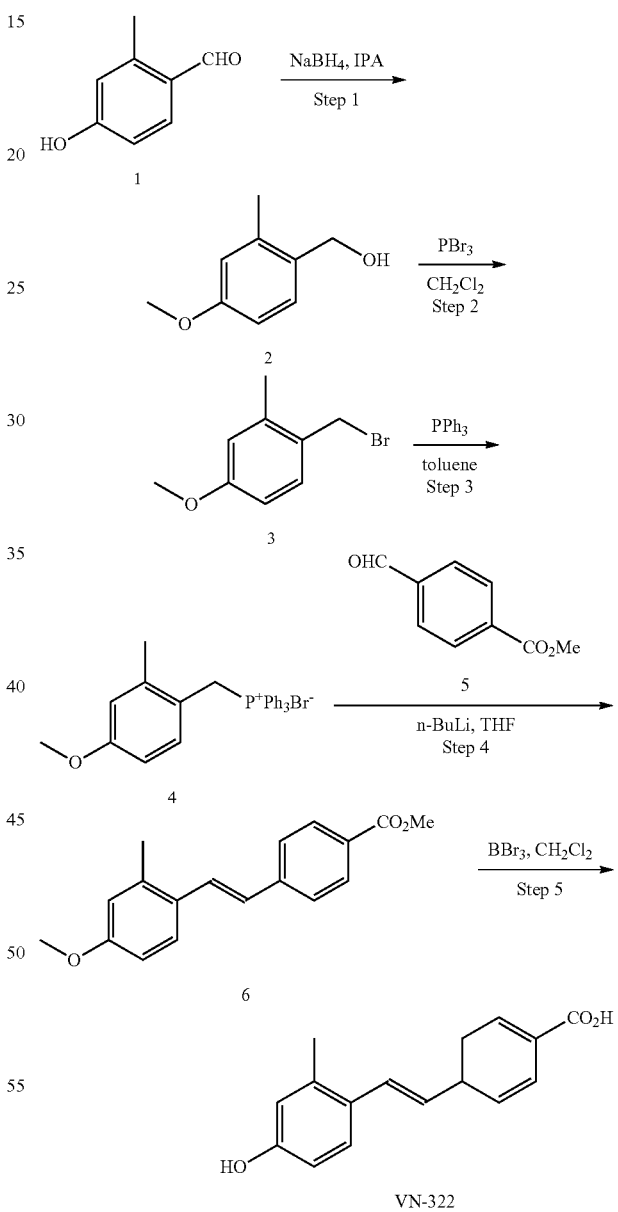

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. $^1$H NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-4-(4-methoxy-2-methylstyryl)benzoate (6). To a stirred solution of compound 4 (800 mg, 1.68 mmol) in THF (10 mL) was added n-BuLi (2.5 M in hexanes, 0.8 mL, 2.01 mmol) at −78° C. under inert atmosphere. The reaction mixture was stirred at the same temperature for 20 min. and at RT for 30 min. Then a solution of methyl 4-formylbenzoate 5 (275 mg, 1.68 mmol) in THF (5 mL) was added at −78° C. The reaction mixture was gradually warmed to RT and stirred for 16 h. The progress of the reaction was monitored by TLC, after the completion, the reaction mixture was quenched with saturated $NH_4Cl$ solution (20 mL) and extracted with EtOAc (2×30 mL). The combined organic extracts were washed with brine (20 mL), dried over anhydrous $Na_2SO_4$, filtered and concentrated under reduced pressure. The crude material was purified by silica gel column chromatography (eluent: 20% EtOAc/n-hexanes) to afford compound 6 (400 mg, 1.42 mmol, 84%) as a mixture of cis and trans-isomers as pale yellow liquid. $^1$H NMR (500 MHz, DMSO-$d_6$): δ 7.94 (d, J=8.4 Hz, 2H), 7.80-7.71 (m, 4H), 7.68-7.64 (m, 1H), 7.50 (d, J=16.5 Hz, 1H), 7.24 (d, J=8.1 Hz, 2H), 7.09 (d, J=16.2 Hz, 1H), 6.92 (d, J=8.4 Hz, 1H), 6.85-6.74 (m, 4H), 6.69-6.60 (m, 2H), 3.85 (s, 3H), 3.81 (s, 3H), 3.77 (s, 3H), 3.73 (s, 3H), 2.41 (s, 3H), 2.21 (s, 3H). LC-MS: m/z 283.2 [M+H]$^+$ at 4.74 RT (91.09% purity).

Step-5: Synthesis of (E)-4-(4-hydroxy-2-methylstyryl) benzoic acid (VN-322). To a stirred solution of compound 6 (400 mg, 1.42 mmol) in $CH_2Cl_2$ (8 mL) was added boron tribromide (1 M in $CH_2Cl_2$, 8.51 mL, 8.51 mmol) at −78° C. under inert atmosphere. The reaction mixture was gradually warmed to RT and stirred for 16 h. The progress of the reaction was monitored by TLC; after the completion, the reaction mixture was quenched with ice cold water (20 mL) and extracted with EtOAc (2×20 mL). The combined organic extracts were washed with brine (15 mL), dried over anhydrous $Na_2SO_4$, filtered and concentrated under reduced pressure. The crude material was purified by preparative HPLC (reverse phase followed by normal phase) (Methods J & N) to afford VN-322 (26 mg, 0.1 mmol, 7%) as an off white solid. $^1$H NMR (400 MHz, DMSO-$d_6$): δ 12.85 (br s, 1H), 9.52 (br s, 1H), 7.90 (d, J=8.4 Hz, 2H), 7.67 (d, J=8.4 Hz, 2H), 7.54 (d, J=8.2 Hz, 1H), 7.45 (d, J=16.3 Hz, 1H), 7.01 (d, J=16.2 Hz, 1H), 6.66-6.61 (m, 2H), 2.35 (s, 3H); $^1$H NMR (400 MHz, DMSO-$d_6$, $D_2O$ Exc.): δ 7.89 (d, J=8.4 Hz, 2H), 7.65 (d, J=8.5 Hz, 2H), 7.53 (d, J=8.2 Hz, 1H), 7.42 (d, J=16.2 Hz, 1H), 6.98 (d, J=16.3 Hz, 1H), 6.66-6.59 (m, 2H), 2.31 (s, 3H). LC-MS: m/z 252.8 [M−H]$^−$ at 2.11 RT (96.79% purity). HPLC: 98.11%.

Preparation of VN-333 & VN-342. The synthetic strategy for preparing VN-334 and VN-343 is detailed in the scheme below.

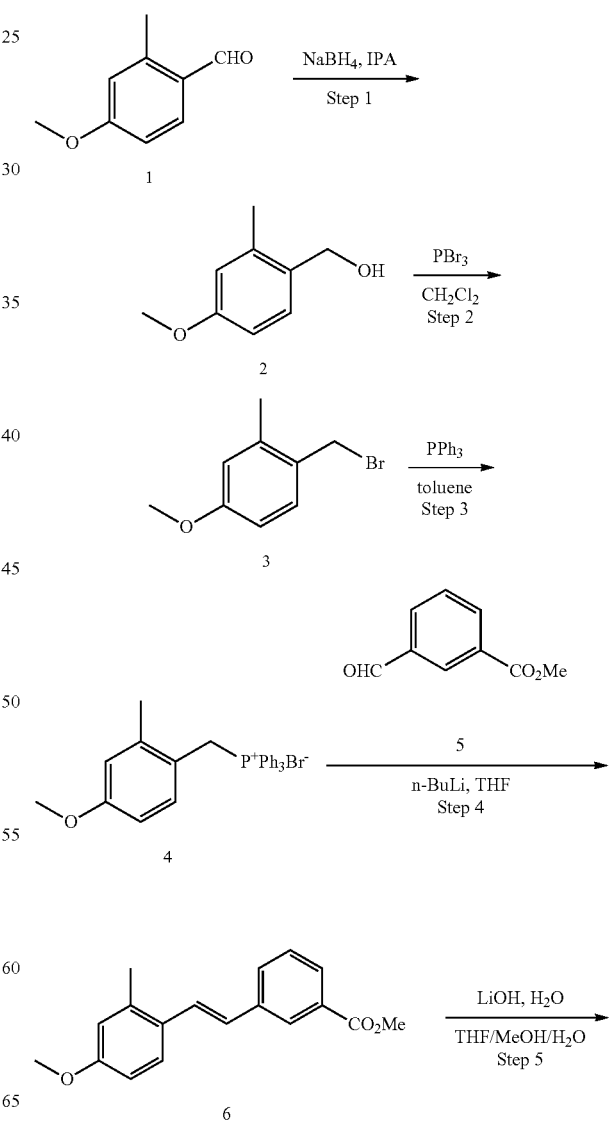

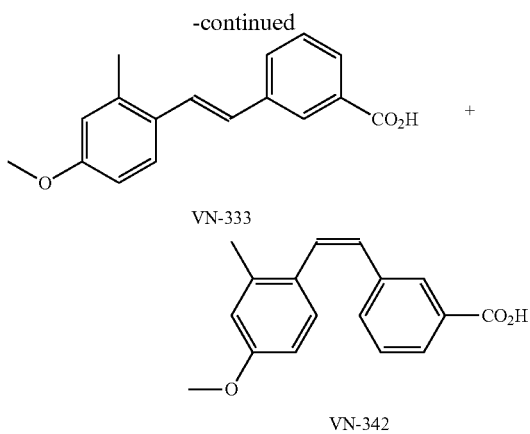

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. $^1$H NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-3-(4-methoxy-2-methylstyryl)benzoate (6). To a stirred solution of compound 4 (4.6 g, 9.64 mmol) in THF (46 mL) was added n-BuLi (2.5 M in hexanes, 4.63 mL, 11.57 mmol) at −78° C. under inert atmosphere. The reaction mixture was gradually warmed to RT and stirred for 30 min. Then a solution of methyl 3-formylbenzoate 5 (1.9 g, 11.57 mmol) in THF (13.8 mL) was added at −78° C. The reaction mixture was gradually warmed to RT and stirred for 2 h. The progress of the reaction was monitored by TLC; after the completion, the reaction mixture was quenched with saturated $NH_4Cl$ solution (50 mL) and extracted with EtOAc (2×70 mL). The combined organic extracts were washed with brine (30 mL), dried over anhydrous $Na_2SO_4$, filtered and concentrated under reduced pressure. The crude material was purified by silica gel column chromatography (eluent: 10% EtOAc/n-hexanes) to afford compound 6 (1.8 g, 6.37 mmol, 66%) as a mixture of cis and trans-isomers as colorless syrup. $^1$H NMR (500 MHz, $CDCl_3$): δ 8.18 (s, 1H), 7.92 (d, J=7.8 Hz, 1H), 7.87 (s, 1H), 7.82 (d, J=7.7 Hz, 1H), 7.69 (d, J=7.8 Hz, 1H), 7.56 (d, J=8.5 Hz, 1H), 7.44 (t, J=7.7 Hz, 1H), 7.36 (d, J=16.1 Hz, 1H), 7.30 (s, 1H), 7.23-7.17 (m, 1H), 7.02 (d, J=8.4 Hz, 1H), 6.94 (d, J=16.1 Hz, 1H), 6.82-6.75 (m, 3H), 6.71-6.66 (m, 1H), 6.63-6.57 (m, 2H), 3.96 (s, 3H), 3.89 (s, 3H), 3.84 (s, 3H), 3.80 (s, 3H), 2.45 (s, 3H), 2.27 (s, 3H).

Step-5: Synthesis of (E)-3-(4-methoxy-2-methylstyryl)benzoic acid (VN-333) & (Z)-3-(4-methoxy-2-methylstyryl)benzoic acid (VN-342). To a stirred solution of compound 6 (250 mg, mixture) in a mixture of methanol (0.5 mL), THF (1 mL) and water (0.5 mL) was added lithium hydroxide monohydride (56 mg, 1.33 mmol) at 0-5° C. The reaction mixture was gradually warmed to RT and stirred for 5 h. The progress of the reaction was monitored by TLC; after the completion, the volatiles were removed under reduced pressure. The residue was diluted with water (10 mL), acidified with 1N HCl to pH ~2-3 and extracted with EtOAc (2×25 mL). The combined organic extracts were washed with brine (10 mL), dried over anhydrous $Na_2SO_4$, filtered and concentrated under reduced pressure. The crude material was purified by normal phase preparative HPLC (Method F) to afford VN-333 (40 mg, 0.15 mmol, 17%) & VN-342 (40 mg, 0.15 mmol, 17%) as white solids respectively.

Analytical data of VN-333: $^1$H NMR (400 MHz, DMSO-$d_6$): δ 13.00 (br s, 1H), 8.09 (s, 1H), 7.89-7.85 (m, 1H), 7.81 (dt, J=7.7, 1.3 Hz, 1H), 7.65-7.62 (m, 1H), 7.49 (t, J=7.7 Hz, 1H), 7.40 (d, J=16.3 Hz, 1H), 7.09 (d, J=16.2 Hz, 11H), 6.83-6.79 (m, 2H), 3.76 (s, 3H), 2.41 (s, 3H); $^1$H NMR (400 MHz, DMSO-$d_6$, $D_2O$ Exc.): δ 8.06 (s, 1H), 7.87-7.82 (m, 1H), 7.79 (dt, J=7.7, 1.3 Hz, 1H), 7.64-7.60 (m, 1H), 7.48 (t, J=7.7 Hz, 1H), 7.36 (d, J=16.3 Hz, 1H), 7.05 (d, J=16.3 Hz, 1H), 6.81-6.77 (m, 2H), 3.73 (s, 3H), 2.37 (s, 3H). LC-MS: m/z 266.9 [M−H] at 2.82 RT (97.22% purity). HPLC: 98.77%.

Analytical data of VN-342: $^1$H NMR (400 MHz, DMSO-$d_6$): δ 12.84 (br s, 1H), 7.78-7.70 (m, 2H), 7.35-7.28 (m, 2H), 6.94 (d, J=8.4 Hz, 1H), 6.83 (d, J=2.6 Hz, 1H), 6.73-6.61 (m, 3H), 3.73 (s, 3H), 2.21 (s, 3H); $^1$H NMR (400 MHz, DMSO-$d_6$, $D_2O$ Exc.): δ 7.72-7.62 (m, 2H), 7.30 (d, J=4.9 Hz, 2H), 6.89 (d, J=8.5 Hz, 1H), 6.78 (d, J=2.5 Hz, 1H), 6.69-6.54 (m, 3H), 3.67 (s, 3H), 2.15 (s, 3H). LC-MS: m/z 266.9 [M−H]$^-$ at 2.88 RT (99.43% purity). HPLC: 99.35%.

Preparation of VN-314. The synthetic strategy for preparing VN-314 is detailed in the scheme below.

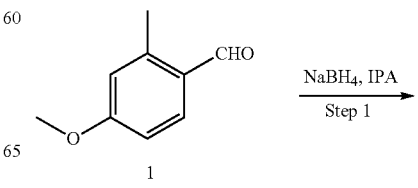

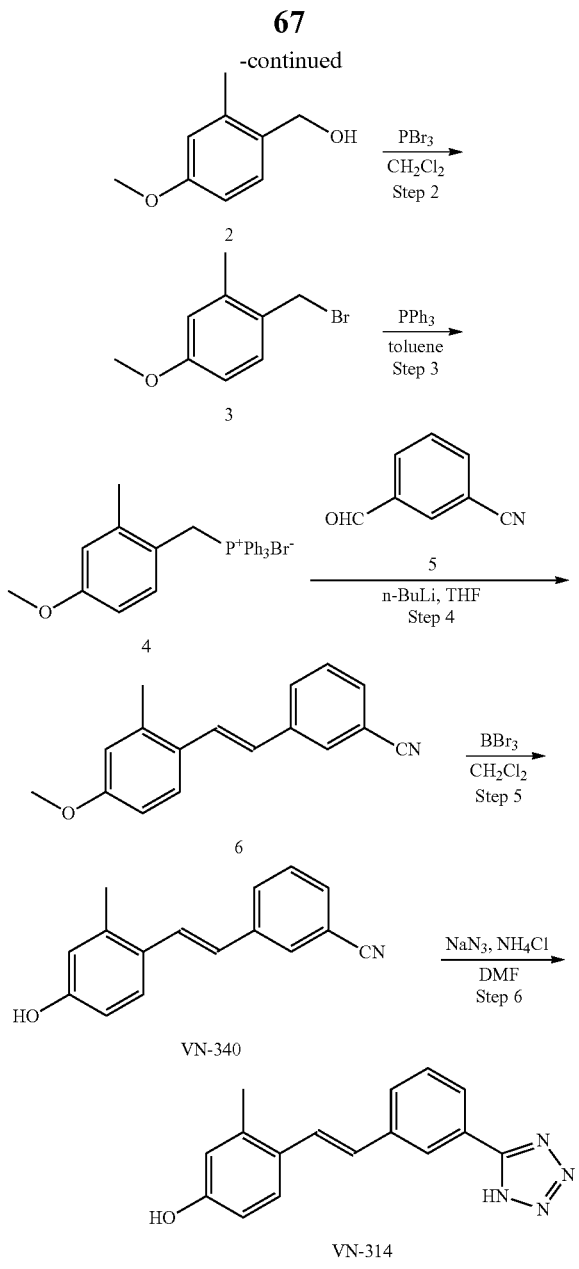

tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. This material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1H$ NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of (E)-3-(4-methoxy-2-methylstyryl) benzonitrile (6). To a stirred solution of compound 4 (1 g, 2.1 mmol) in THF (8 mL) was added n-BuLi (2.5 M in hexanes, 1.57 mL, 2.51 mmol) at −78° C. under inert atmosphere. The reaction mixture was gradually warmed to RT and stirred for 30 min. Then a solution of 3-formylbenzonitrile 5 (412 mg, 3.14 mmol) in THF (2 mL) was added at −78° C. The reaction mixture was gradually warmed to RT and stirred for 16 h. The progress of the reaction was monitored by TLC, after the completion, the reaction mixture was quenched with saturated $NH_4Cl$ solution (30 mL) and extracted with EtOAc (2×50 mL). The combined organic extracts were washed with brine (20 mL), dried over anhydrous $Na_2SO_4$, filtered and concentrated under reduced pressure. The crude material was purified by silica gel column chromatography (eluent: 10% EtOAc/n-hexanes) to afford compound 6 (500 mg, 2.0 mmol, 96%) as a mixture of cis and trans-isomers as an off white solid. $^1H$ NMR (500 MHz, $CDCl_3$): δ 7.76 (s, 1H), 7.69 (d, J=7.8 Hz, 1H), 7.56-7.48 (m, 2H), 7.47-7.39 (m, 2H), 7.36-7.30 (m, 2H), 7.25-7.23 (m, 1H), 6.96 (d, J=8.7 Hz, 1H), 6.85 (d, J=16.2 Hz, 1H), 6.81-6.70 (m, 4H), 6.58 (dd, J=8.4, 2.6 Hz, 1H), 6.51 (d, J=11.9 Hz, 1H), 3.83 (s, 3H), 3.79 (s, 3H), 2.43 (s, 3H), 2.25 (s, 3H).

Step-5: Synthesis of (E)-3-(4-hydroxy-2-methylstyryl) benzonitrile (VN-340). To a stirred solution of compound 6 (500 mg, 2.01 mmol) in $CH_2Cl_2$ (20 mL) was added boron tribromide (1 M in $CH_2Cl_2$, 6.02 mL, 6.02 mmol) at −78° C. under inert atmosphere. The reaction mixture was gradually warmed to RT and stirred for 16 h. The progress of the reaction was monitored by TLC; after the completion, the reaction mixture was quenched with ice cold water (20 mL) and extracted with EtOAc (2×20 mL). The combined organic extracts were washed with brine (15 mL), dried over anhydrous $Na_2SO_4$, filtered and concentrated under reduced pressure. The crude material was purified by silica gel column chromatography (eluent: 30% EtOAc/n-hexanes) to afford VN-340 (200 mg, 0.85 mmol, 42%) as a brown solid. $^1H$ NMR (500 MHz, $CDCl_3$): δ 7.77 (s, 1H), 7.70 (d, J=7.8 Hz, 1H), 7.54-7.44 (m, 3H), 7.32 (d, J=16.2 Hz, 1H), 6.86 (d, J=16.2 Hz, 1H), 6.75-6.69 (m, 2H), 2.42 (s, 3H). LC-MS: m/z 234.0 [M−H]⁻ at 3.06 RT (98.54% purity).

Step-6: Synthesis of (E)-4-(3-(2H-tetrazol-5-yl)styryl)-3-methylphenol (VN-314). To a stirred solution of VN-340

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. $^1H$ NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous (200 mg, 0.85 mmol) in DMF (2 mL) were added sodium azide (166 mg, 2.55 mmol) and ammonium chloride (135 mg, 2.55 mmol) in a microwave vessel at RT under inert atmosphere. The vessel was sealed and the reaction mixture was irradiated to 120° C. and stirred for 2 h. The progress of the reaction was monitored by TLC; after the completion, the reaction mixture was quenched with 1N HCl solution (20 mL) and extracted with EtOAc (2×20 mL). The combined organic extracts were washed with brine (15 mL), dried over anhydrous $Na_2SO_4$, filtered and concentrated under reduced pressure. The crude material was purified by preparative HPLC (Method O) to afford VN-314 (70 mg, 0.25 mmol, 30%) as an off white solid. $^1$H NMR (400 MHz, DMSO-$d_6$): δ 9.49 (s, 1H), 8.21 (s, 1H), 7.88 (d, J=7.9 Hz, 1H), 7.78 (d, J=7.9 Hz, 1H), 7.62-7.53 (m, 2H), 7.44 (d, J=16.2 Hz, 1H), 7.04 (d, J=16.2 Hz, 1H), 6.69-6.61 (m, 2H), 2.37 (s, 3H); $^1$H NMR (400 MHz, DMSO-$d_6$, $D_2O$ Exc.): δ 8.19 (s, 1H), 7.87 (d, J=7.8 Hz, 1H), 7.77 (d, J=7.9 Hz, 1H), 7.60-7.53 (m, 2H), 7.42 (d, J=16.3 Hz, 1H), 7.02 (d, J=16.2 Hz, 1H), 6.68-6.62 (m, 2H), 2.35 (s, 3H). LC-MS: m/z 279.1 [M+H]$^+$ at 2.41 RT (96.98% purity). HPLC: 98.97%.

Preparation of VN-335. The synthetic strategy for preparing VN-335 is detailed in the scheme below.

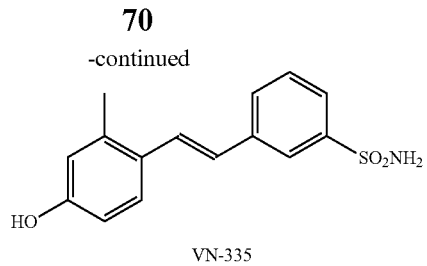

VN-335

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. $^1$H NMR (500 MHz, CDCl$_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated NaHCO$_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of (E)-3-(4-methoxy-2-methylstyryl)benzenesulfonamide (6). To a stirred solution of compound 4 (200 mg, 0.42 mmol) in anhydrous THF (1.5 mL) was added n-BuLi (2.5 M in hexanes, 0.18 mL, 0.46 mmol) at −78° C. under inert atmosphere. The reaction mixture was gradually warmed to RT and stirred for 30 min. Then a solution of 3-formylbenzenesulfonamide 5 (77 mg, 0.42 mmol) in THF (0.5 mL) was added at −78° C. The reaction mixture was gradually warmed to RT and stirred for 16 h. The progress of the reaction was monitored by TLC; after the completion, the reaction mixture was quenched with saturated NH$_4$Cl solution (20 mL) and extracted with EtOAc (2×20 mL). The combined organic extracts were washed with brine (10 mL), dried over anhydrous $Na_2SO_4$, filtered

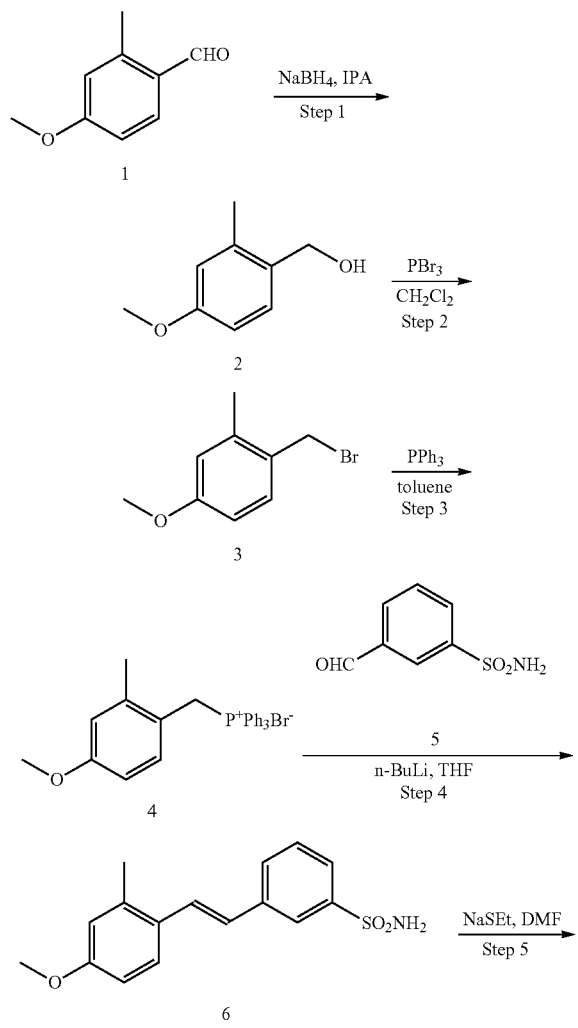

and concentrated under reduced pressure. The crude material was purified by silica gel column chromatography (eluent: 10% EtOAc/n-hexanes) to afford compound 6 (100 mg, 0.33 mmol, 83%) as yellow syrup. $^1$H NMR (500 MHz, DMSO-$d_6$): δ 8.01 (s, 1H), 7.81 (d, J=7.8 Hz, 1H), 7.70-7.52 (m, 4H), 7.45-7.20 (m, 5H), 7.10 (d, J=16.2 Hz, 1H), 6.93 (d, J=8.4 Hz, 1H), 6.85-6.79 (m, 2H), 6.76-6.60 (m, 2H), 3.77 (s, 3H), 3.73 (s, 2H), 2.41 (s, 3H), 2.22 (s, 2H). LC-MS: m/z 301.9 [M−H]$^-$ at 2.98 RT (95.58% purity).

Step-5: Synthesis of (E)-3-(4-hydroxy-2-methylstyryl) benzenesulfonamide (VN-335). To a stirred solution of compound 6 (150 mg, 0.49 mmol) in DMF (1.5 mL) was added sodium thioethoxide (208 mg, 2.47 mmol) in a microwave vessel at RT. The vessel was sealed and the reaction mixture was irradiated to 120° C. and stirred for 1 h. The progress of the reaction was monitored by LC-MS; after the completion, the reaction mixture was combined with another lot (SMB-MA1704-035, 150 mg), diluted with water (30 mL) and extracted with EtOAc (2×30 mL). The combined organic extracts were washed with brine (10 mL), dried over anhydrous Na$_2$SO$_4$, filtered and concentrated under reduced pressure. The crude material was purified by preparative HPLC (Method L) to afford VN-335 (28 mg, 0.1 mmol, 10% for two batches) as an off white solid. $^1$H NMR (400 MHz, DMSO-$d_6$): δ 9.50 (s, 1H), 7.99 (s, 1H), 7.80-7.76 (m, 1H), 7.68-7.64 (m, 1H), 7.57-7.51 (m, 2H), 7.42-7.35 (m, 3H), 7.03 (d, J=16.3 Hz, 1H), 6.67-6.61 (m, 2H), 2.35 (s, 3H); $^1$H NMR (400 MHz, DMSO-$d_6$, D$_2$O Exc.): δ 7.94 (s, 1H), 7.78-7.72 (m, 1H), 7.67-7.61 (m, 1H), 7.55-7.50 (m, 2H), 7.35 (d, J=16.2 Hz, 1H), 6.98 (d, J=16.2 Hz, 1H), 6.65-6.61 (m, 2H), 2.30 (s, 3H). LC-MS: m/z 287.9 [M−H]$^-$ at 3.11 RT (94.06% purity). HPLC: 95.59%.

Preparation of VN-336. The synthetic strategy for preparing VN-336 is detailed in the scheme below.

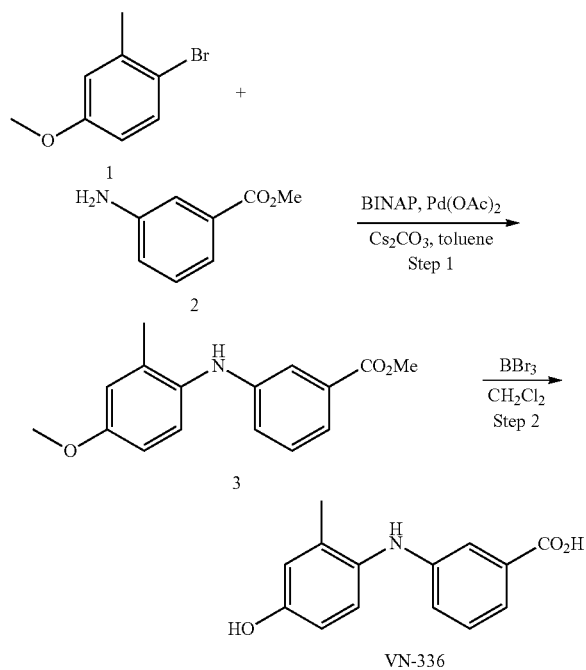

Step-1: Synthesis of Methyl 3-((4-methoxy-2-methylphenyl)amino)benzoate (3). To a stirred solution of 1-bromo-4-methoxy-2-methylbenzene 1 (1 g, 4.97 mmol) and methyl 3-aminobenzoate 2 (901 mg, 5.97 mmol) in toluene (10 mL) were added cesium carbonate (2.43 g, 7.46 mmol) and BINAP (247 mg, 0.4 mmol) in a sealed tube at RT and purged under argon for 10 min. Then Pd(OAc)$_2$ (56 mg, 0.25 mmol) was added and again purged under argon for 5 min. The reaction mixture was heated to 120° C. and stirred for 8 h. The progress of the reaction was monitored by TLC; after the completion, the reaction mixture was filtered through a pad of celite and the celite bed was washed with EtOAc (15 mL). The filtrate was washed with water (20 mL) and extracted with EtOAc (2×40 mL). The combined organic extracts were washed with brine (15 mL), dried over anhydrous Na$_2$SO$_4$, filtered and concentrated under reduced pressure. The crude material was purified by silica gel column chromatography (eluent: 30% EtOAc/n-hexanes) to afford compound 3 (700 mg, 2.58 mmol, 52%) as yellow sticky liquid. $^1$H NMR (400 MHz, DMSO-$d_6$): δ 7.58 (s, 1H), 7.24-7.19 (m, 3H), 7.07 (d, J=8.7 Hz, 1H), 6.88-6.84 (m, 2H), 6.77 (dd, J=8.6, 2.9 Hz, 1H), 3.78 (s, 3H), 3.74 (s, 3H), 2.13 (s, 3H). LC-MS: m/z 271.9 [M+H]$^+$ at 3.35 RT (92.41% purity).

Step-2: Synthesis of 3-((4-hydroxy-2-methylphenyl) amino)benzoic acid (VN-336). To a stirred solution of compound 3 (300 mg, 1.11 mmol) in CH$_2$Cl$_2$ (6 mL) was added boron tribromide (1 M in CH$_2$Cl$_2$, 6.64 mL, 6.64 mmol) at −78° C. under inert atmosphere. The reaction mixture was gradually warmed to RT and stirred for 16 h. The progress of the reaction was monitored by TLC; after the completion, the reaction mixture was quenched with ice cold water (30 mL) and the organic layer was separated. The aqueous layer was extracted with EtOAc (2×30 mL). The combined organic extracts (CH$_2$Cl$_2$ and EtOAc layers) were dried over anhydrous Na$_2$SO$_4$, filtered and concentrated under reduced pressure. The crude material was purified by reverse phase preparative HPLC (Method J) followed by lyophilization to afford VN-336 (30 mg, 0.12 mmol, 11%) as an off white solid. $^1$H NMR (400 MHz, DMSO-$d_6$): δ 12.63 (br s, 1H), 9.15 (br s, 1H), 7.42 (br s, 1H), 7.19-7.12 (m, 3H), 6.94 (d, J=8.4 Hz, 1H), 6.80-6.75 (m, 1H), 6.67 (d, J=2.6 Hz, 1H), 6.59 (dd, J=8.3, 2.8 Hz, 1H), 2.06 (s, 3H); $^1$H NMR (400 MHz, DMSO-$d_6$, D$_2$O Exc.): δ 7.22-7.14 (m, 2H), 7.06-7.04 (m, 1H), 6.93 (d, J=8.5 Hz, 1H), 6.83-6.78 (m, 1H), 6.68 (d, J=2.8 Hz, 1H), 6.59 (dd, J=8.4, 2.9 Hz, 1H), 2.03 (s, 3H). LC-MS: m/z 244.2 [M+H]$^+$ at 2.00 RT (97.06% purity). HPLC: 99.50%.

Preparation of VN-337. The synthetic strategy for preparing VN-337 is detailed in the scheme below.

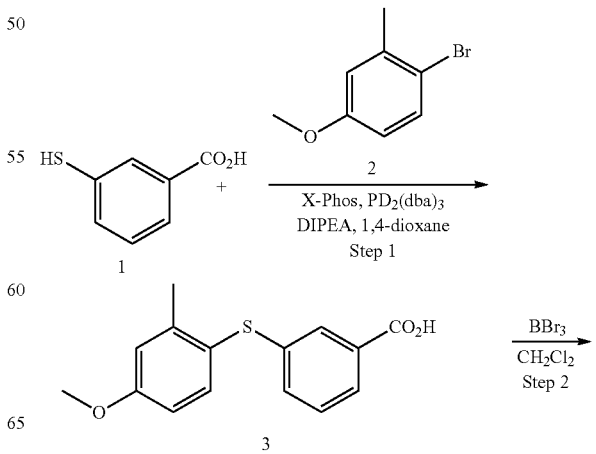

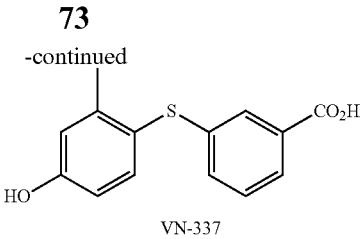

VN-337

Step-1: Synthesis of 3-((4-methoxy-2-methylphenyl)thio) benzoic acid (3). To a stirred solution of 3-mercaptobenzoic acid 1 (200 mg, 1.3 mmol) in 1,4-dioxane (8 mL) were added 1-bromo-4-methoxy-2-methylbenzene 2 (0.21 mL, 1.56 mmol), N,N-diisopropylethylamine (0.68 mL, 3.9 mmol) followed by Xantphos (150 mg, 0.26 mmol) in a sealed tube at RT under inert atmosphere and purged under argon for 15 min. To this reaction mixture was added $Pd_2(dba)_3$ (238 mg, 0.26 mmol) at RT. The vessel was sealed and heated to 90° C. and stirred for 16 h. The progress of the reaction was monitored by TLC; after the completion, the reaction mixture was filtered through a pad of celite and the celite bed was washed with EtOAc (20 mL). The filtrate was concentrated under reduced pressure to obtain the crude. The crude material was purified by silica gel column chromatography (eluent: 2% $MeOH/CH_2Cl_2$) to afford compound 3 (130 mg, impure) as brown syrup. This material was taken to next step without further purification. LC-MS: m/z 272.9 [M−H]⁻ at 2.63 RT (29.28% purity).

Step-2: Synthesis of 3-((4-hydroxy-2-methylphenyl)thio) benzoic acid (VN-337). To a stirred solution of compound 3 (100 mg, 0.36 mmol) in $CH_2Cl_2$ (5 mL) was added boron tribromide (1 M in $CH_2Cl_2$, 1.09 mL, 1.09 mmol) at −78° C. under inert atmosphere.

The reaction mixture was gradually warmed to RT and stirred for 3 h. The progress of the reaction was monitored by TLC; after the completion, the reaction mixture was quenched with ice cold water (15 mL) and extracted with EtOAc (2×15 mL). The combined organic extracts were washed with brine (10 mL), dried over anhydrous $Na_2SO_4$, filtered and concentrated under reduced pressure. The crude material was purified by silica gel column chromatography (eluent: 3-4% $MeOH/CH_2Cl_2$) followed by normal phase preparative HPLC to afford VN-337 (15 mg, 0.06 mmol, 16%) as an off white solid. ¹H NMR (400 MHz, $CD_3OD$): δ 7.72 (dt, J=7.7, 1.4 Hz, 1H), 7.62 (t, J=1.6 Hz, 1H), 7.37 (d, J=8.4 Hz, 1H), 7.30 (t, J=7.8 Hz, 1H), 7.18-7.14 (m, 1H), 6.81 (d, J=2.8 Hz, 1H), 6.70 (dd, J=8.3, 2.8 Hz, 1H), 2.28 (s, 3H). LC-MS: m/z 258.9 [M−H⁻ at 2.31 RT (95.69% purity). HPLC: 99.06%.

Preparation of VN-340. The synthetic strategy for preparing VN-340 is detailed in the scheme below.

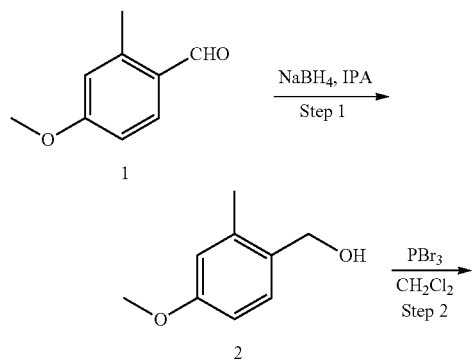

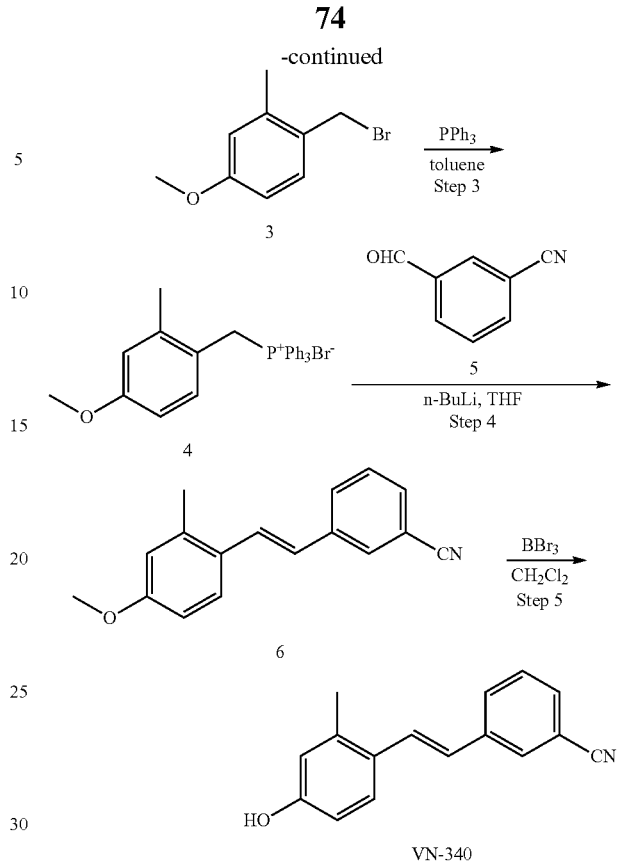

VN-340

Step-1: Synthesis of (4-methoxy-2-methylphenyl)methanol (2). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC; after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. ¹H NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC; after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-d$_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of (E)-3-(4-methoxy-2-methylstyryl)benzonitrile (6). To a stirred solution of compound 4 (1.5 g, 3.14 mmol) in THF (11 mL) was added n-BuLi (2.5 M in hexanes, 1.51 mL, 3.77 mmol) at −78° C. under inert atmosphere. The reaction mixture was gradually warmed to RT and stirred for 30 min. Then a solution of 3-formylbenzonitrile (618 mg, 4.72 mmol) in THF (5 mL) was added at −78° C. and allowed to stir at the same temperature for 1 h. Then the reaction mixture was gradually warmed to RT and stirred for 16 h. The progress of the reaction was monitored by TLC & LCMS, after the completion, the reaction mixture was quenched with saturated NH$_4$Cl solution (30 mL) and extracted with EtOAc (2×50 mL). The combined organic extracts were washed with brine (30 mL), dried over anhydrous Na$_2$SO$_4$, filtered and concentrated under reduced pressure. The crude material was purified by silica gel column chromatography (eluent: 10% EtOAc/n-hexanes) to afford compound 6 (700 mg, 2.81 mmol, 89%) as a mixture of cis and trans-isomers as an off white solid. $^1$H NMR (500 MHz, CDCl$_3$): δ 7.76 (s, 1H), 7.69 (d, J=7.8 Hz, 1H), 7.56-7.49 (m, 2H), 7.47-7.40 (m, 2H), 7.35-7.30 (m, 2H), 7.26-7.23 (m, 0.5H), 6.96 (d, J=8.4 Hz, 0.5H), 6.85 (d, J=16.2 Hz, 1H), 6.80-6.70 (m, 3H), 6.59 (dd, J=8.4, 2.3 Hz, 0.5H), 6.51 (d, J=11.9 Hz, 0.5H), 3.83 (s, 3H), 3.80 (s, 2H), 2.43 (s, 3H), 2.26 (s, 2H). LC-MS: m/z 250.0 [M+H]$^+$ at 4.52 RT (95.06% purity).

Step-5: Synthesis of (E)-3-(4-hydroxy-2-methylstyryl)benzonitrile (VN-340). To a stirred solution of compound 6 (200 mg, 0.8 mmol) in CH$_2$Cl$_2$ (15 mL) was added boron tribromide (1 M in CH$_2$Cl$_2$, 2.41 mL, 2.41 mmol) at −78° C. under inert atmosphere. The reaction mixture was gradually warmed to RT and stirred for 16 h. The progress of the reaction was monitored by TLC & LCMS, after the completion, the reaction mixture was quenched with ice cold water (20 mL) and extracted with EtOAc (2×20 mL). The combined organic extracts were washed with brine (15 mL), dried over anhydrous Na$_2$SO$_4$, filtered and concentrated under reduced pressure. The crude material was purified by silica gel column chromatography (eluent: 25% EtOAc/n-hexanes) to afford VN-340 (100 mg, 0.42 mmol, 53%) as an off white solid. $^1$H NMR (400 MHz, DMSO-d$_6$): δ 9.51 (s, 1H), 8.09 (s, 1H), 7.88 (d, J=7.9 Hz, 1H), 7.66 (d, J=7.7 Hz, 1H), 7.57-7.44 (m, 3H), 6.97 (d, J=16.2 Hz, 1H), 6.67-6.60 (m, 2H), 2.35 (s, 3H); $^1$H NMR (400 MHz, DMSO-d$_6$, D$_2$O Exc.): δ 8.01 (s, 1H), 7.87 (d, J=7.9 Hz, 1H), 7.61 (d, J=7.7 Hz, 1H), 7.55-7.48 (m, 2H), 7.42 (d, J=16.2 Hz, 1H), 6.94 (d, J=16.2 Hz, 1H), 6.65-6.59 (m, 2H), 2.31 (s, 3H). LC-MS: m/z 233.9 [M−H]$^-$ at 3.08 RT (98.90% purity). HPLC: 99.87%.

Preparation of VN-341. The synthetic strategy for preparing VN-341 is detailed in the scheme below.

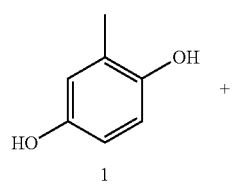

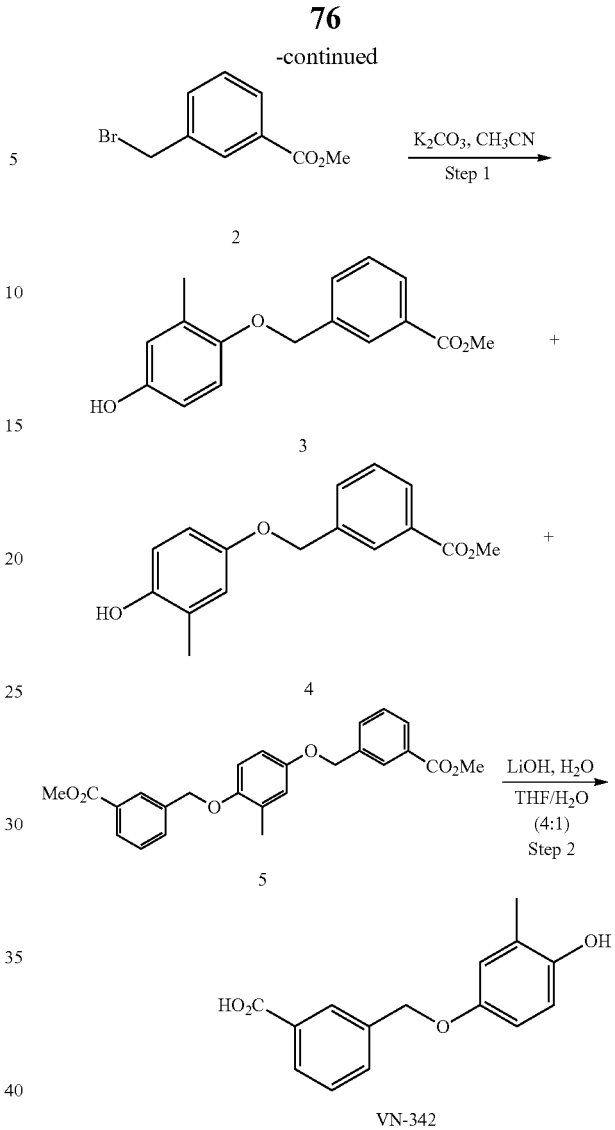

Step-1: Synthesis of Methyl 3-((4-hydroxy-2-methylphenoxy)methyl)benzoate (3). To a stirred solution of 2-methylbenzene-1,4-diol 1 (500 mg, 4.03 mmol) in acetonitrile (10 mL) were added methyl 3-(bromomethyl)benzoate 2 (915 mg, 4.03 mmol) and potassium carbonate (1.11 g, 8.06 mmol) at RT under inert atmosphere and stirred for 16 h. The progress of the reaction was monitored by TLC, after the completion, the reaction mixture was quenched with water (20 mL) and extracted with EtOAc (2×30 mL). The combined organic extracts were washed with brine (15 mL), dried over anhydrous Na$_2$SO$_4$, filtered and concentrated under reduced pressure to afford a mixture of mono and dialkylated compounds 3, 4 & 5 (500 mg) as colorless liquid. The mixture was taken to next step without further purification. LC-MS: m/z 271.2 [M−H]$^-$ at 3.61 RT (28.34% purity).

Step-2: Synthesis of 3-((4-hydroxy-3-methylphenoxy)methyl)benzoic acid (VN-341). To a stirred solution of mixture of mono and dialkylated compounds 3, 4 & 5 (500 mg) in a mixture of THF/water (4:1, 5 mL) was added lithium hydroxide monohydride (300 mg) at RT under inert atmosphere and stirred for 2 h. The progress of the reaction was monitored by TLC, after the completion, the reaction mixture was acidified with 6 N HCl to pH ~2-3 and extracted with EtOAc (2×25 mL). The combined organic extracts were dried over anhydrous Na$_2$SO$_4$, filtered and concentrated under reduced pressure. The crude material was purified by reverse phase followed by normal phase preparative HPLC (Method G) to afford VN-341 (12 mg, 0.05 mmol) as brown solid. The structure was confirmed by 2 D NMR (NOESY, DQFCOSY and HMBC) studies. $^1$H NMR (400 MHz, DMSO-d$_6$): δ 12.99 (br s, 1H), 8.79 (s, 1H), 7.99 (s, 1H), 7.88 (d, J=7.8 Hz, 1H), 7.66 (d, J=7.7 Hz, 1H), 7.54-7.48 (m, 1H), 6.77 (d, J=2.1 Hz, 1H), 6.68-6.64 (m, 2H), 5.05 (s, 2H), 2.09 (s, 3H); $^1$H NMR (400 MHz, DMSO-d$_6$, D$_2$O Exc.): δ 7.94 (s, 1H), 7.85 (br d, J=7.7 Hz, 1H), 7.63 (br d, J=7.7 Hz, 1H), 7.54-7.46 (m, 1H), 6.73 (s, 1H), 6.67-6.58 (m, 2H), 5.02 (s, 2H), 2.05 (s, 3H). $^{13}$C NMR (101 MHz, DMSO-d$_6$): δ 167.17, 150.80, 149.48, 138.26, 131.76, 130.87, 128.65, 128.48, 128.09, 124.74, 118.93, 117.35, 114.95, 112.56, 69.05, 16.17. LC-MS: m/z 256.8 [M−H]$^-$ at 1.79 RT (91.16% purity). HPLC: 96.45%.

Preparation of VN-343. The synthetic strategy for preparing VN-343 is detailed in the scheme below.

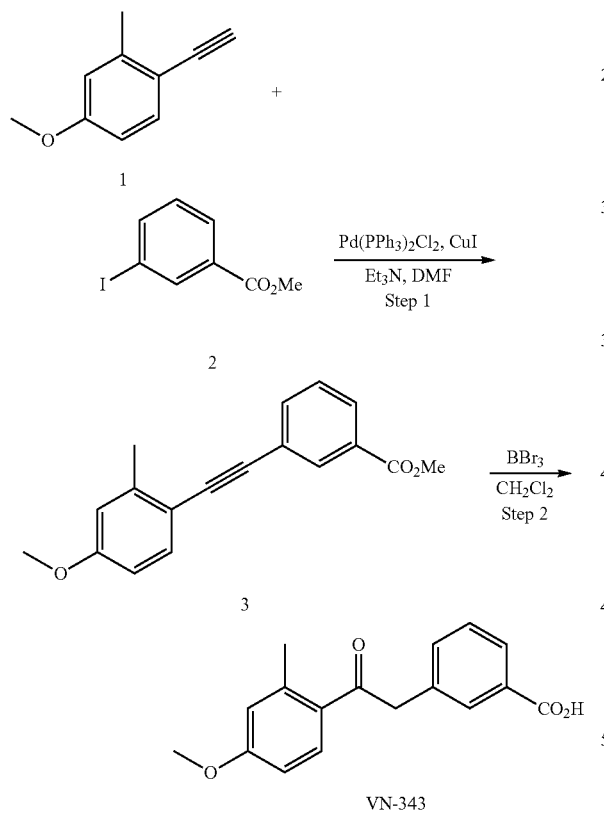

Step-1: Synthesis of Methyl 3-((4-methoxy-2-methylphenyl)ethynyl)benzoate (3). To a stirred solution of 1-ethynyl-4-methoxy-2-methylbenzene 1 (500 mg, 3.42 mmol) in DMF (10 mL) were added methyl 3-iodobenzoate 2 (983 mg, 3.77 mmol), copper(I) iodide (65 mg, 0.34 mmol) followed by triethylamine (2.38 mL, 17.12 mmol) at RT under inert atmosphere and purged under argon for 10 min. Then Pd(PPh$_3$)$_2$Cl$_2$ (240 mg, 0.34 mmol) was added and again purged under argon for 10 min. The reaction mixture was heated to 80° C. and stirred for 8 h. The progress of the reaction was monitored by TLC, after the completion, the reaction mixture was diluted with water (20 mL) and extracted with EtOAc (2×20 mL). The combined organic extracts were washed with brine (15 mL), dried over anhydrous Na$_2$SO$_4$, filtered and concentrated under reduced pressure. The crude material was purified by silica gel column chromatography (eluent: 20% EtOAc/n-hexanes) to afford compound 3 (600 mg, 2.14 mmol, 63%) as pale yellow liquid. $^1$H NMR (400 MHz, CDCl$_3$): δ 8.18-8.16 (m, 1H), 7.99-7.95 (m, 1H), 7.70-7.66 (m, 1H), 7.45-7.41 (m, 2H), 6.80-6.67 (m, 2H), 3.94 (s, 3H), 3.82 (s, 3H), 2.50 (s, 3H).

Step-2: Synthesis of 3-(2-(4-hydroxy-2-methylphenyl)-2-oxoethyl) benzoic acid (VN-343). To a stirred solution of compound 3 (300 mg, 1.07 mmol) in CH$_2$Cl$_2$ (15 mL) was added boron tribromide (1 M in CH$_2$Cl$_2$, 4.28 mL, 4.28 mmol) at −78° C. under inert atmosphere. The reaction mixture was gradually warmed to RT and stirred for 16 h. The progress of the reaction was monitored by TLC, after the completion, the reaction mixture was quenched with ice cold water (20 mL) and extracted with EtOAc (2×20 mL). The combined organic extracts were washed with brine (15 mL), dried over anhydrous Na$_2$SO$_4$, filtered and concentrated under reduced pressure. The crude material was purified by preparative HPLC (Method J) to afford VN-343 (30 mg, 0.11 mmol, 10%) as an off white solid. The structure was confirmed by 2 D NMR (NOESY, COSY and HMBC) studies. $^1$H NMR (400 MHz, DMSO-d$_6$): δ 12.88 (br s, 1H), 10.14 (s, 1H), 7.94 (d, J=8.7 Hz, 1H), 7.83-7.78 (m, 2H), 7.50-7.39 (m, 2H), 6.73-6.64 (m, 2H), 4.33 (s, 2H), 2.37 (s, 3H); $^1$H NMR (400 MHz, DMSO-d$_6$, D$_2$O Exc.): δ 7.88 (d, J=8.5 Hz, 1H), 7.81-7.72 (m, 2H), 7.46-7.39 (m, 2H), 6.70-6.62 (m, 2H), 4.26 (s, 2H), 2.31 (s, 3H). $^{13}$C NMR (101 MHz, DMSO-d$_6$): δ 198.28, 167.29, 160.43, 141.54, 136.37, 134.22, 132.73, 130.63, 130.55, 128.38, 127.64, 127.27, 118.60, 112.41, 46.19, 21.90. LC-MS: m/z 271.2 [M+H]$^+$ at 2.01 RT (98.53% purity). HPLC: 99.31%.

Preparation of VN-344. The synthetic strategy for preparing VN-344 is detailed in the scheme below.

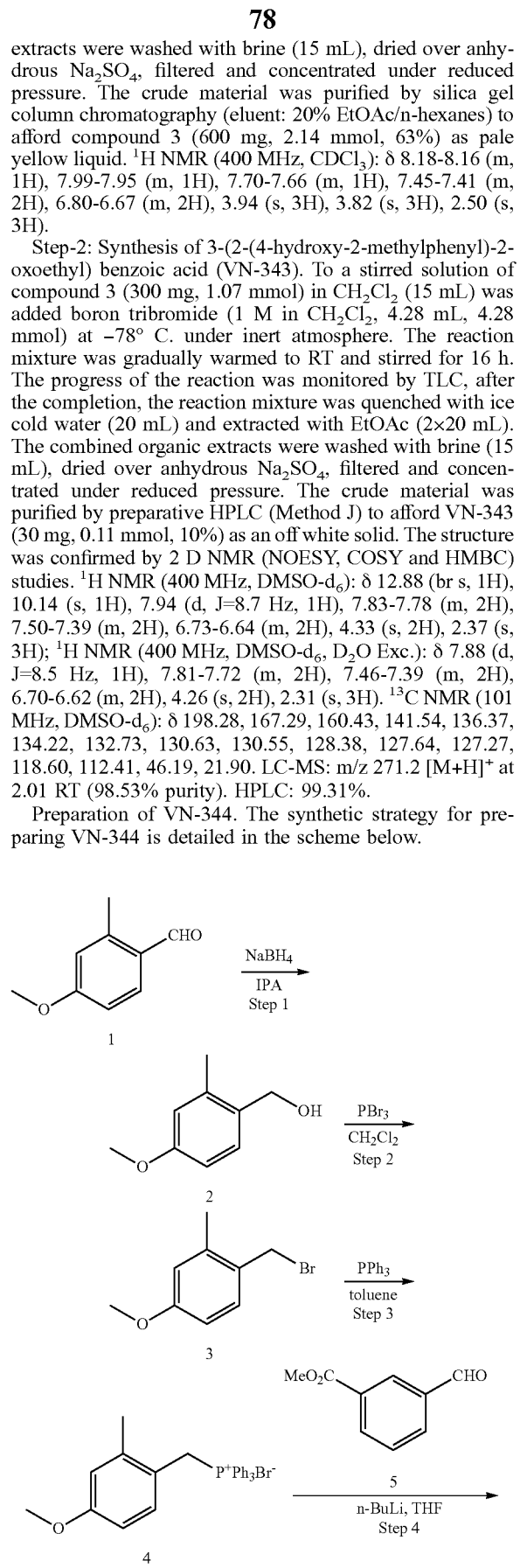

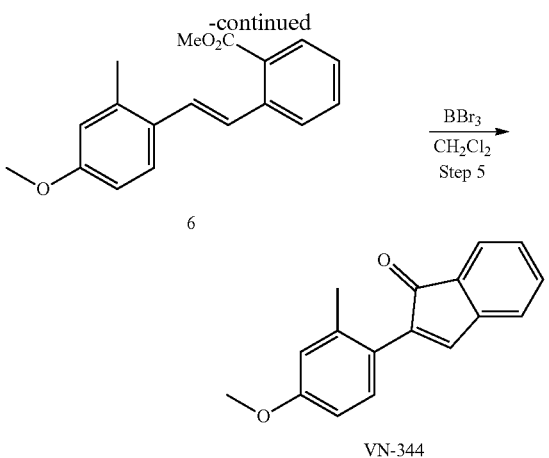

Step-1: Synthesis of (4-methoxy-2-methylphenyl)methanol (2)). To a stirred solution of 4-methoxy-2-methylbenzaldehyde 1 (10 g, 66.67 mmol) in isopropanol (100 mL) was added sodium borohydride (1.52 g, 40.0 mmol) at 0° C. under inert atmosphere. The reaction mixture was gradually warmed to RT and stirred for 3 h. The progress of the reaction was monitored by TLC, after the completion, the reaction mixture was quenched with ice cold water (100 mL) and extracted with EtOAc (2×100 mL). The combined organic extracts were washed with brine (50 mL), dried over anhydrous $Na_2SO_4$, filtered and concentrated under reduced pressure to afford compound 2 (10 g, 65.71 mmol) as colorless syrup. The crude material was taken to next step without further purification. $^1$H NMR (500 MHz, $CDCl_3$): δ 7.23 (d, J=8.1 Hz, 1H), 6.76-6.70 (m, 2H), 4.64 (s, 2H), 3.80 (s, 3H), 2.37 (s, 3H), 1.40 (br s, 1H).

Step-2: Synthesis of 1-(bromomethyl)-4-methoxy-2-methylbenzene (3). To a stirred solution of compound 2 (10 g, crude) in $CH_2Cl_2$ (100 mL) was added phosphorous tribromide (18.7 mL, 197.37 mmol) at 0-5° C. under inert atmosphere. The reaction mixture was gradually warmed to RT and stirred for 16 h. The progress of the reaction was monitored by TLC, after the completion, the reaction mixture was diluted with $CH_2Cl_2$ (100 mL), washed with water (100 mL) and saturated $NaHCO_3$ solution (100 mL). The combined organic extracts were washed with brine (50 mL), dried over anhydrous $Na_2SO_4$, filtered and concentrated under reduced pressure to afford compound 3 (14.2 g, 66.02 mmol) as colorless syrup. The crude material was taken to next step without further purification.

Step-3: Synthesis of (4-methoxy-2-methylbenzyl)triphenylphosphonium bromide (4). To a stirred solution of compound 3 (5 g, crude) in toluene (50 mL) was added triphenylphosphine (6.12 g, 23.36 mmol) at RT under inert atmosphere. The reaction mixture was heated to reflux temperature and stirred for 16 h. Then the solid was filtered, washed with toluene (2×20 mL), n-hexanes (2×20 mL) and dried under vacuum to afford compound 4 (4.2 g, 8.8 mmol, 38%) as white solid. $^1$H NMR (400 MHz, DMSO-$d_6$): δ 7.96-7.89 (m, 3H), 7.77-7.71 (m, 6H), 7.67-7.59 (m, 6H), 6.85 (dd, J=8.5, 2.6 Hz, 1H), 6.70-6.61 (m, 2H), 4.99-4.93 (m, 2H), 3.69 (s, 3H), 1.58 (s, 3H).

Step-4: Synthesis of Methyl (E)-2-(4-methoxy-2-methylstyryl)benzoate (6). To a stirred solution of compound 4 (1.5 g, 3.14 mmol) in THF (10 mL) was added n-BuLi (2.5 M in hexanes, 1.38 mL, 3.46 mmol) at −78° C. under inert atmosphere. The reaction mixture was gradually warmed to RT and stirred for 30 min. Then a solution of methyl 2-formylbenzoate 5 (516 mg, 3.14 mmol) in THF (5 mL) was added at −78° C. The reaction mixture was gradually warmed to RT and stirred for 12 h. The progress of the reaction was monitored by TLC, after the completion, the reaction mixture was quenched with saturated $NH_4Cl$ solution (50 mL) and extracted with EtOAc (2×50 mL). The combined organic extracts were washed with brine (30 mL), dried over anhydrous $Na_2SO_4$, filtered and concentrated under reduced pressure. The crude material was purified by silica gel column chromatography (eluent: 20% EtOAc/n-hexanes) to afford compound 6 (730 mg, 2.58 mmol, 83%) as a mixture of cis and trans-isomers as colorless syrup. LC-MS: m/z 283.2 [M+H]$^+$ at 4.47 RT (43.24% purity) & m/z 283.2 [M+H]$^+$ at 4.58 RT (43.82% purity).

Step-5: Synthesis of 2-(4-hydroxy-2-methylphenyl)-1H-inden-1-one (VN-344). To a stirred solution of compound 6 (600 mg, 2.13 mmol) in $CH_2Cl_2$ (15 mL) was added boron tribromide (1 M in $CH_2Cl_2$, 12.76 mL, 12.76 mmol) at −78° C. under inert atmosphere. The reaction mixture was gradually warmed to RT and stirred for 4 h. The progress of the reaction was monitored by TLC, after the completion, the reaction mixture was quenched with ice cold water (30 mL) and extracted with EtOAc (2×30 mL). The combined organic extracts were washed with brine (15 mL), dried over anhydrous $Na_2SO_4$, filtered and concentrated under reduced pressure. The crude material was purified by preparative HPLC (Method M) to afford VN-344 (40 mg, 0.17 mmol, 8%) as brown solid. The structure was confirmed by 2 D NMR (NOESY, DQFCOSY, HMBC and HSQC) studies. $^1$H NMR (400 MHz, DMSO-$d_6$): δ 9.51 (s, 1H), 7.65 (s, 1H), 7.48-7.42 (m, 1H), 7.39 (d, J=6.9 Hz, 1H), 7.28-7.19 (m, 2H), 7.12 (d, J=8.3 Hz, 1H), 6.68 (d, J=2.4 Hz, 1H), 6.63 (dd, J=8.3, 2.4 Hz, 1H), 2.22 (s, 3H). $^{13}$C NMR (101 MHz, DMSO-$d_6$): δ 197.01, 157.32, 144.85, 144.31, 137.99, 137.04, 134.50, 131.07, 129.54, 128.55, 122.53, 122.23, 121.54, 117.22, 112.54, 20.81. LC-MS: m/z 234.8 [M−H]$^-$ at 3.67 RT (90.90% purity). HPLC: 97.43%.

Preparation of VN-346 & VN-377. The synthetic strategy for preparing VN-346 and VN-377 is detailed in the scheme below.

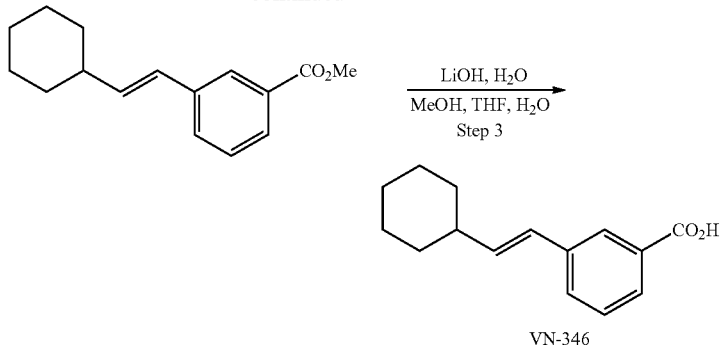

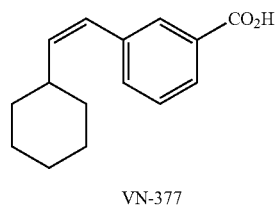

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-d$_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-cyclohexylvinyl) benzoate (4). To a stirred solution of compound 2 (2 g, 4.08 mmol) in THF (25 mL) was added n-BuLi (2.0 M in hexanes, 2.24 mL, 4.49 mmol) at −78° C. under inert atmosphere. The reaction mixture was gradually warmed to RT and stirred for 30 min. Then a solution of cyclohexanecarbaldehyde 3 (457 mg, 4.08 mmol) in THF (5 mL) was added at −78° C. The reaction mixture was gradually warmed to RT and stirred for 16 h. The progress of the reaction was monitored by TLC, after the completion, the reaction mixture was quenched with saturated NH$_4$Cl solution (30 mL) and extracted with EtOAc (2×30 mL). The combined organic extracts were washed with brine (20 mL), dried over anhydrous Na$_2$SO$_4$, filtered and concentrated under reduced pressure. The crude material was purified by silica gel column chromatography (eluent: 5% EtOAc/n-hexanes) to afford compound 4 (800 mg, 3.27 mmol, 80%) as a mixture of cis and trans-isomers as colorless syrup. The mixture was taken to next step without further purification. LC-MS: m/z 245.2 [M+H]$^+$ at 5.37 RT (57.23% purity).

Step-3: Synthesis of (E)-3-(2-cyclohexylvinyl)benzoic acid (VN-346) & (Z)-3-(2-cyclohexylvinyl)benzoic acid (VN-377). To a stirred solution of compound 4 (800 mg, mixture) in a mixture of THF/methanol (1:1, 6 mL) was added a solution of lithium hydroxide monohydride (413 mg, 9.84 mmol) in water (2 mL) at RT and stirred for 5 h. The progress of the reaction was monitored by TLC, after the completion, the reaction mixture was concentrated under reduced pressure. The residue was diluted with water (15 mL) and extracted with ether (2×10 mL). The organic layer was separated and the aqueous layer was acidified with 2 N HCl solutions to pH ~3-4 and extracted with EtOAc (2×30 mL). The combined organic extracts were dried over anhydrous Na$_2$SO$_4$, filtered and concentrated under reduced pressure to obtain the crude. The crude material was purified by normal phase preparative HPLC (Method A) to afford VN-346 (30 mg, 0.13 mmol) & VN-377 (25 mg, 0.11 mmol) as off white solids respectively.

Analytical data of VN-367: $^1$H NMR (400 MHz, DMSO-d$_6$): δ 12.94 (br s, 1H), 7.92 (t, J=1.6 Hz, 1H), 7.76 (dt, J=7.7, 1.3 Hz, 1H), 7.65-7.61 (m, 1H), 7.42 (t, J=7.7 Hz, 1H), 6.47-6.41 (m, 1H), 6.36-6.28 (m, 1H), 2.19-2.09 (m, 1H), 1.82-1.69 (m, 4H), 1.68-1.61 (m, 1H), 1.36-1.11 (m, 5H); $^1$H NMR (400 MHz, DMSO-d$_6$, D$_2$O Exc.): δ 7.87 (s, 1H), 7.77-7.71 (m, 1H), 7.62-7.58 (m, 1H), 7.42 (t, J=7.4 Hz, 1H), 6.42-6.36 (m, 1H), 6.32-6.24 (m, 1H), 2.17-2.05 (m, 1H), 1.76-1.55 (m, 5H), 1.32-1.06 (m, 5H). LC-MS: m/z 228.8 [M−H]$^-$ at 2.72 RT (99.57% purity). HPLC: 99.28%.

Analytical data of VN-377: $^1$H NMR (400 MHz, DMSO-d$_6$): 12.96 (br s, 1H), 7.85-7.79 (m, 2H), 7.49 (d, J=4.9 Hz, 2H), 6.37 (d, J=11.7 Hz, 1H), 5.57 (dd, J=11.7, 10.2 Hz, 1H), 2.48-2.46 (m, 1H), 1.75-1.59 (m, 5H), 1.31-1.13 (m, 5H); $^1$H NMR (400 MHz, DMSO-d$_6$, D$_2$O Exc.): δ 7.84-7.76 (m, 2H), 7.52-7.44 (m, 2H), 6.35 (d, J=11.8 Hz, 1H), 5.57 (dd, J=11.7, 10.2 Hz, 1H), 2.46-2.44 (m, 1H), 1.72-1.54 (m, 5H), 1.25-1.11 (m, 5H). LC-MS: m/z 228.8 [M−H]$^-$ at 2.66 RT (99.48% purity). HPLC: 99.19%.

Preparation of VN-347 & VN-376. The synthetic strategy for preparing VN-347 and VN-376 is detailed in the scheme below.

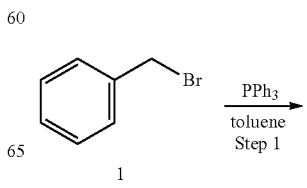

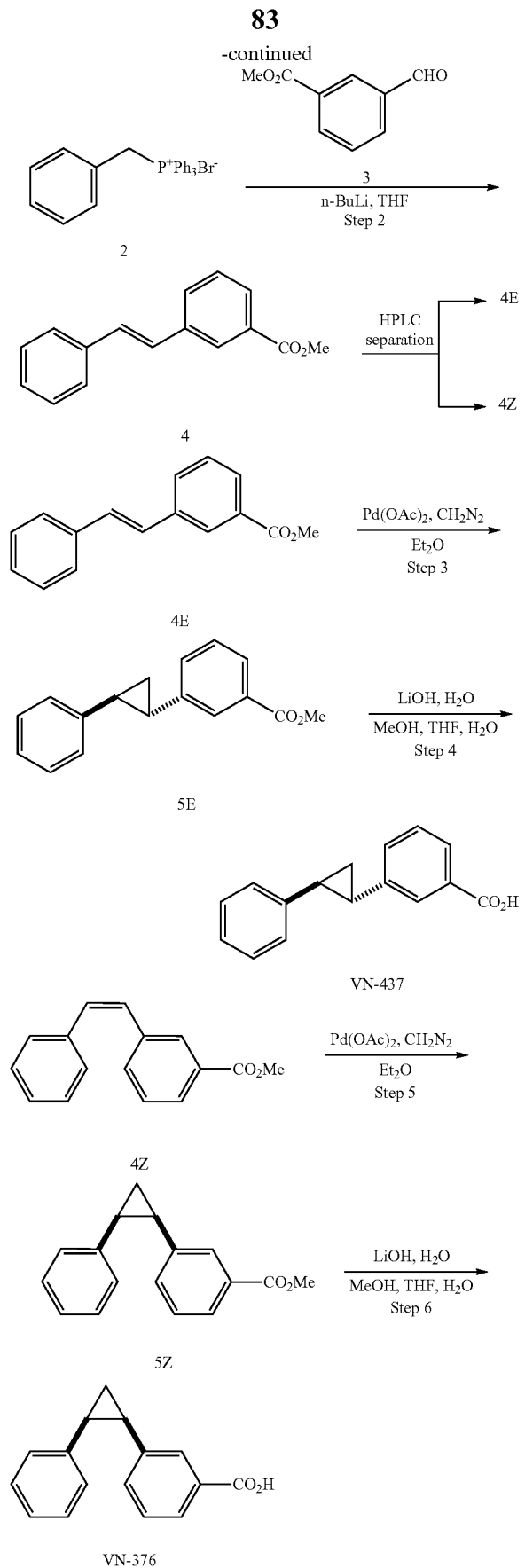

Step-1: Synthesis of Benzyltriphenylphosphonium bromide (2). To a stirred solution of (bromomethyl)benzene 1 (5 g, 29.07 mmol) in toluene (50 mL) was added triphenylphosphine (7.62 g, 29.07 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (11 g, 25.38 mmol, 88%) as white solid. $^1$H NMR (400 MHz, DMSO-$d_6$): δ 7.95-7.86 (m, 3H), 7.79-7.63 (m, 12H), 7.33-7.26 (m, 1H), 7.26-7.20 (m, 2H), 7.00-6.96 (m, 2H), 5.22-5.16 (m, 2H).

Step-2: Synthesis of Methyl 3-styrylbenzoate (4). To a stirred solution of compound 2 (1.5 g, 3.47 mmol) in THF (10 mL) was added n-BuLi (2.5 M in hexanes, 1.53 mL, 3.82 mmol) at −78° C. under inert atmosphere. The reaction mixture was gradually warmed to RT and stirred for 30 min. Then a solution of methyl 3-formylbenzoate 3 (569 mg, 3.47 mmol) in THF (5 mL) was added at −78° C. The reaction mixture was gradually warmed to RT and stirred for 16 h. The progress of the reaction was monitored by TLC, after the completion, the reaction mixture was quenched with saturated NH$_4$Cl solution (30 mL) and extracted with EtOAc (2×30 mL). The combined organic extracts were washed with brine (20 mL), dried over anhydrous Na$_2$SO$_4$, filtered and concentrated under reduced pressure. The crude material was purified by silica gel column chromatography (eluent: 10% EtOAc/n-hexanes) to afford compound 4 (650 mg, 2.73 mmol, 79%) as a mixture of cis and trans-isomers as white solid. This mixture (650 mg) was further purified by normal phase preparative HPLC (Method B) to afford 4E (200 mg) & 4Z (250 mg) as white solids respectively.

Analytical data of 4E: $^1$H NMR (400 MHz, CDCl$_3$): δ 8.20 (t, J=1.8 Hz, 1H), 7.92 (dt, J=7.7, 1.4 Hz, 1H), 7.69 (dt, J=7.7, 1.3 Hz, 1H), 7.55-7.51 (m, 2H), 7.43 (t, J=7.7 Hz, 1H), 7.40-7.35 (m, 2H), 7.31-7.26 (m, 1H), 7.22-7.10 (m, 2H), 3.95 (s, 3H). LC-MS: m/z 239.2 [M+H]$^+$ at 4.63 RT (99.70% purity).

Analytical data of 4Z: $^1$H NMR (400 MHz, DMSO-$d_6$): δ 7.86-7.76 (m, 2H), 7.48-7.38 (m, 2H), 7.30-7.22 (m, 3H), 7.21-7.17 (m, 2H), 6.77-6.66 (m, 2H), 3.80 (s, 3H). LC-MS: m/z 239.1 [M+H]$^+$ at 4.60 RT (97.98% purity).

Step-3: Synthesis of Methyl 3-((1S,2S)-2-phenylcyclopropyl)benzoate (5E). To a stirred solution of compound 4E (150 mg, 0.63 mmol) in diethylether (10 mL) were added Pd(OAc)$_2$ (56 mg, 0.25 mmol) followed by diazomethane (20 mL) drop wise at −50° C. under inert atmosphere. The reaction mixture was gradually warmed to RT and stirred for 16 h. The progress of the reaction was monitored by TLC, after the completion, the reaction mixture was filtered through a pad of celite and the celite bed was washed with EtOAc (20 mL). The filtrate was concentrated under reduced pressure to obtain the crude. The crude material was purified by silica gel column chromatography (eluent: 5% EtOAc/n-hexanes) to afford compound 5E (130 mg, 0.51 mmol, 86%) as colorless syrup. $^1$H NMR (400 MHz, DMSO-$d_6$): δ 7.79-7.73 (m, 2H), 7.50-7.41 (m, 2H), 7.32-7.25 (m, 2H), 7.22-7.14 (m, 3H), 3.85 (s, 3H), 2.38-2.30 (m, 1H), 2.32-2.21 (m, 1H), 1.53-1.47 (m, 2H). LC-MS: m/z 253.3 [M+H]$^+$ at 4.70 RT (91.86% purity).

Step-4: Synthesis of 3-((1S,2S)-2-phenylcyclopropyl)benzoic acid (VN-347). To a stirred solution of compound 5E (160 mg, 0.63 mmol) in a mixture of THF/methanol (1:1, 2 mL) was added a solution of lithium hydroxide monohydride (80 mg, 1.9 mmol) in water (1 mL) at RT and stirred for 6 h. The progress of the reaction was monitored by TLC, after the completion, the reaction mixture was concentrated under reduced pressure. The residue was diluted with water (15 mL) and extracted with ether (2×10 mL). The organic layer was separated and the aqueous layer was acidified with 2 N HCl solutions to pH ~3-4 and extracted with EtOAc (2×20 mL). The combined organic extracts were dried over anhydrous $Na_2SO_4$, filtered and concentrated under reduced pressure to obtain the crude. The crude material was triturated with n-hexanes (2×5 mL) and dried under vacuum to afford VN-347 (40 mg, 0.17 mmol, 26%) as an off white solid. $^1$H NMR (400 MHz, DMSO-$d_6$): δ 12.91 (br s, 1H), 7.78-7.71 (m, 2H), 7.46-7.38 (m, 2H), 7.31-7.25 (m, 2H), 7.22-7.14 (m, 3H), 2.36-2.28 (m, 1H), 2.27-2.20 (m, 1H), 1.49 (t, J=7.4 Hz, 2H); $^1$H NMR (400 MHz, DMSO-$d_6$, $D_2O$ Exc.): δ 7.75-7.67 (m, 2H), 7.43-7.38 (m, 2H), 7.29-7.23 (m, 2H), 7.18-7.11 (m, 3H), 2.28-2.21 (m, 1H), 2.20-2.13 (m, 1H), 1.46 (t, J=7.3 Hz, 2H). LC-MS: m/z 236.8 [M−H]$^-$ at 2.81 RT (98.07% purity). HPLC: 98.27%.

Step-5: Synthesis of Methyl 3-((1R,2S)-2-phenylcyclopropyl)benzoate (5Z). To a stirred solution of compound 4Z (250 mg, 1.05 mmol) in diethylether (10 mL) were added Pd(OAc)$_2$ (93 mg, 0.42 mmol) followed by diazomethane (25 mL) drop wise at −50° C. under inert atmosphere. The reaction mixture was gradually warmed to RT and stirred for 16 h. The progress of the reaction was monitored by TLC, after the completion, the reaction mixture was filtered through a pad of celite and the celite bed was washed with EtOAc (20 mL). The filtrate was concentrated under reduced pressure to obtain the crude. The crude material was purified by silica gel column chromatography (eluent: 5% EtOAc/n-hexanes) followed by normal phase preparative HPLC (Method B) to afford compound 5Z (28 mg, 0.11 mmol, 11%) as colorless syrup. This material was not pure even after preparative HPLC and it is carried forward to the next step without further purification. LC-MS: m/z 253.1 [M+H]$^+$ at 4.52 RT (55.05% purity).

Step-6: Synthesis of 3-((1R,2S)-2-phenylcyclopropyl) benzoic acid (VN-376). To a stirred solution of compound 5Z (25 mg, 0.1 mmol) in a mixture of THF/methanol (1:1, 2 mL) was added a solution of lithium hydroxide monohydride (12 mg, 0.3 mmol) in water (0.5 mL) at RT and stirred for 16 h. The progress of the reaction was monitored by TLC, after the completion, the reaction mixture was concentrated under reduced pressure. The residue was diluted with water (10 mL) and extracted with ether (2×5 mL). The organic layer was separated and the aqueous layer was acidified with 2 N HCl solutions to pH ~3-4 and extracted with EtOAc (2×10 mL). The combined organic extracts were dried over anhydrous $Na_2SO_4$, filtered and concentrated under reduced pressure to afford VN-376 (15 mg, 0.06 mmol, 65%) as an off white solid. $^1$H NMR (400 MHz, DMSO-$d_6$): δ 12.79 (br s, 1H), 7.61-7.56 (m, 2H), 7.21-7.13 (m, 2H), 7.10-7.05 (m, 2H), 7.02-6.96 (m, 3H), 2.60-2.53 (m, 2H), 1.56 (q, J=6.3 Hz, 1H), 1.48-1.40 (m, 1H); $^1$H NMR (400 MHz, DMSO-$d_6$, $D_2O$ Exc.): δ 7.58-7.48 (m, 2H), 7.21-7.13 (m, 2H), 7.07-7.01 (m, 2H), 6.99-6.91 (m, 3H), 2.53-2.51 (m, 2H), 1.52-1.38 (m, 2H). LC-MS: m/z 236.8 [M−H]$^-$ at 2.71 RT (99.62% purity). HPLC: 99.50%.

Preparation of VN-348. The synthetic strategy for preparing VN-348 is detailed in the scheme below.

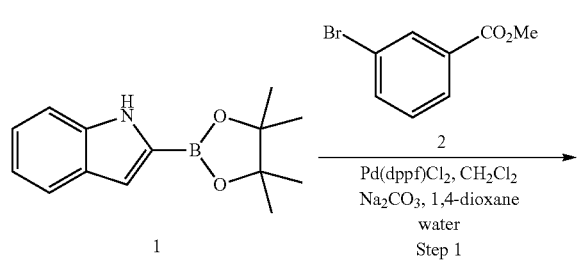

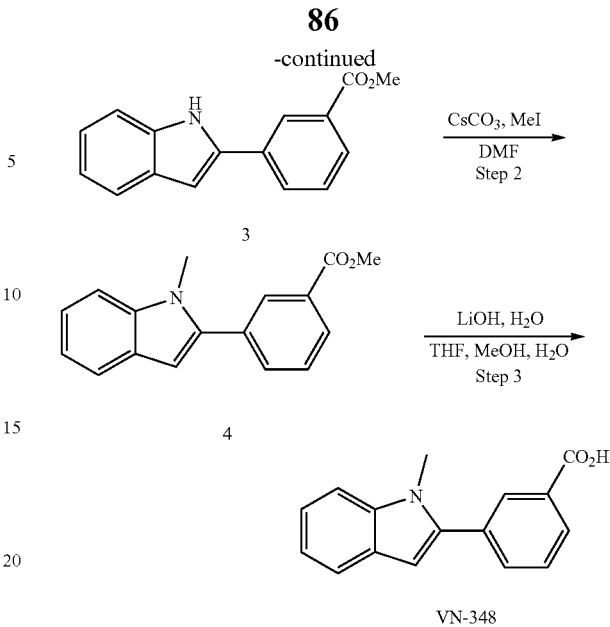

Step-1: Synthesis of Methyl 3-(1H-indol-2-yl)benzoate (3). To a stirred solution of 2-(4,4,5,5-tetramethyl-1,3,2-dioxaborolan-2-yl)-1H-indole 1 (200 mg, 0.93 mmol) and methyl 3-bromobenzoate 2 (271 mg, 1.12 mmol) in 1,4-dioxane (3 mL) was added a solution of sodium carbonate (296 mg, 2.79 mmol) in water (1 mL) at RT and purged with argon for 5 min. Then Pd(dppf)Cl$_2$·CH$_2$Cl$_2$ (76 mg, 0.09 mmol) was added at RT. The reaction mixture was heated to 100° C. and stirred for 16 h. The progress of the reaction was monitored by TLC, after the completion, the reaction mixture was cooled to RT, filtered through a pad of celite and the celite bed was washed with EtOAc (20 mL). The filtrate was concentrated under reduced pressure to obtain the crude. The crude material was purified by silica gel column chromatography (eluent: 10% EtOAc/n-hexanes) to afford compound 3 (185 mg, 0.74 mmol, 79%) as pale yellow liquid. $^1$H NMR (400 MHz, CDCl$_3$): δ 8.47 (br s, 1H), 8.33 (t, J=1.6 Hz, 1H), 7.98 (dt, J=7.7, 1.3 Hz, 1H), 7.89-7.86 (m, 1H), 7.66-7.62 (m, 1H), 7.52 (t, J=7.8 Hz, 1H), 7.44-7.40 (m, 1H), 7.24-7.20 (m, 1H), 7.16-7.11 (m, 1H), 6.91 (dd, J=2.1, 0.9 Hz, 1H), 3.97 (s, 3H). LC-MS: m/z 252.1 [M+H]$^+$ at 4.24 RT (73.82% purity).

Step-2: Synthesis of Methyl 3-(1-methyl-1H-indol-2-yl) benzoate (4). To a stirred solution of compound 3 (100 mg, 0.4 mmol) in DMF (4 mL) was added cesium carbonate (195 mg, 0.6 mmol) at 0° C. under inert atmosphere and stirred at RT for 30 min. Then iodomethane (0.03 mL, 0.52 mmol) was added at 0° C.; warmed to RT and stirred for 16 h. The progress of the reaction was monitored by TLC, after the completion, the reaction mixture was quenched with water (20 mL) and extracted with EtOAc (2×20 mL). The combined organic extracts were washed with brine (15 mL), dried over anhydrous $Na_2SO_4$, filtered and concentrated under reduced pressure. The crude material was purified by silica gel column chromatography (eluent: 2% EtOAc/n-hexanes) to afford compound 4 (75 mg, 0.28 mmol, 71%) as pale brown liquid. $^1$H NMR (500 MHz, CDCl$_3$): δ 8.22-8.19 (m, 1H), 8.10-8.06 (m, 1H), 7.73-7.69 (m, 1H), 7.65 (d, J=8.1 Hz, 1H), 7.58-7.53 (m, 1H), 7.38 (d, J=8.1 Hz, 1H), 7.29-7.25 (m, 1H), 7.16 (t, J=7.5 Hz, 1H), 6.62 (s, 1H), 3.95 (s, 3H), 3.76 (s, 3H).

Step-3: Synthesis of 3-(1-methyl-1H-indol-2-yl)benzoic acid (VN-348). To a stirred solution of compound 4 (75 mg, 0.28 mmol) in a mixture of THF/methanol (1:1, 4 mL) was added a solution of lithium hydroxide monohydride (36 mg, 0.85 mmol) in water (2 mL) at RT and stirred for 12 h. The progress of the reaction was monitored by TLC, after the completion, the volatiles were removed under reduced pressure. The aqueous layer was washed with EtOAc (10 mL) to remove water insoluble organic impurities. The organic layer was separated and the aqueous layer was acidified with 1 N HCl solutions to pH ~3-2.

The precipitated solid was extracted into EtOAc (2×20 mL). The combined organic extracts were dried over anhydrous $Na_2SO_4$, filtered and concentrated under reduced pressure to obtain the crude. The crude material was passed through a pad of silica gel to remove colour impurities and dried under vacuum to afford VN-348 (45 mg, 0.18 mmol, 63%) as an off white solid. $^1$H NMR (400 MHz, DMSO-$d_6$): δ 13.16 (br s, 1H), 8.11 (t, J=1.5 Hz, 1H), 8.01 (dt, J=7.7, 1.4 Hz, 1H), 7.88-7.83 (m, 1H), 7.68-7.63 (m, 1H), 7.61-7.57 (m, 1H), 7.51 (dd, J=8.3, 0.8 Hz, 1H), 7.24-7.18 (m, 1H), 7.12-7.06 (m, 1H), 6.64 (d, J=0.8 Hz, 1H), 3.76 (s, 3H); $^1$H NMR (400 MHz, DMSO-$d_6$, $D_2O$ Exc.): δ 8.05 (s, 1H), 7.99-7.95 (m, 1H), 7.82-7.78 (m, 1H), 7.67-7.61 (m, 1H), 7.56 (d, J=7.8 Hz, 1H), 7.45 (d, J=8.2 Hz, 1H), 7.22-7.16 (m, 1H), 7.09-7.03 (m, 1H), 6.60 (s, 1H), 3.69 (s, 3H). LC-MS: m/z 249.9 [M−H]$^-$ at 2.66 RT (98.80% purity). HPLC: 99.44%.

Preparation of VN-349. The synthetic strategy for preparing VN-349 is detailed in the scheme below.

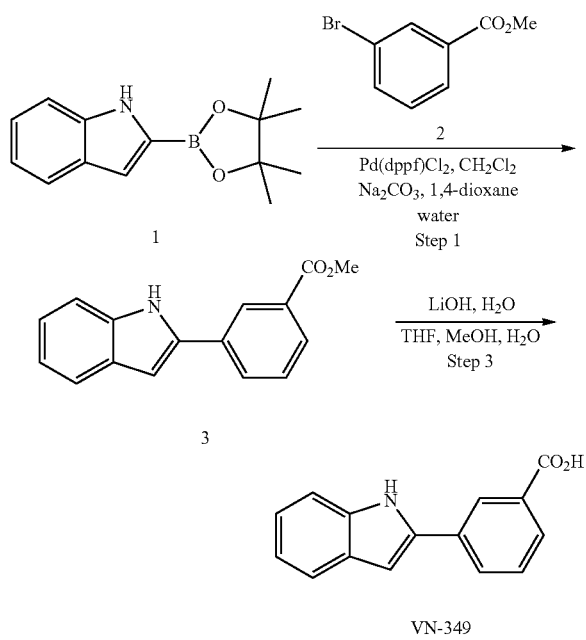

Step-1: Synthesis of Methyl 3-(1H-indol-2-yl)benzoate (3). To a stirred solution of 2-(4,4,5,5-tetramethyl-1,3,2-dioxaborolan-2-yl)-1H-indole 1 (200 mg, 0.93 mmol) and methyl 3-bromobenzoate 2 (271 mg, 1.12 mmol) in 1,4-dioxane (3 mL) was added a solution of sodium carbonate (296 mg, 2.79 mmol) in water (1 mL) at RT and purged with argon for 5 min. Then Pd(dppf)$Cl_2 \cdot CH_2Cl_2$ (76 mg, 0.09 mmol) was added at RT. The reaction mixture was heated to 100° C. and stirred for 16 h. The progress of the reaction was monitored by TLC, after the completion, the reaction mixture was cooled to RT, filtered through a pad of celite and the celite bed was washed with EtOAc (20 mL). The filtrate was concentrated under reduced pressure to obtain the crude. The crude material was purified by silica gel column chromatography (eluent: 10% EtOAc/n-hexanes) to afford compound 3 (185 mg, 0.74 mmol, 79%) as pale yellow liquid. $^1$H NMR (400 MHz, CDCl$_3$): δ 8.47 (br s, 1H), 8.33 (t, J=1.6 Hz, 1H), 7.98 (dt, J=7.7, 1.3 Hz, 1H), 7.89-7.86 (m, 1H), 7.66-7.62 (m, 1H), 7.52 (t, J=7.8 Hz, 1H), 7.44-7.40 (m, 1H), 7.24-7.20 (m, 1H), 7.16-7.11 (m, 1H), 6.91 (dd, J=2.1, 0.9 Hz, 1H), 3.97 (s, 3H). LC-MS: m/z 252.1 [M+H]$^+$ at 4.24 RT (73.82% purity).

Step-2: Synthesis of 3-(1H-indol-2-yl)benzoic acid (VN-349). To a stirred solution of compound 3 (80 mg, 0.32 mmol) in a mixture of THF/methanol (1:1, 4 mL) was added a solution of lithium hydroxide monohydride (27 mg, 0.64 mmol) in water (2 mL) at RT and stirred for 16 h. The progress of the reaction was monitored by TLC, after the completion, the volatiles were removed under reduced pressure. The aqueous layer was washed with EtOAc (10 mL) to remove water insoluble organic impurities. The organic layer was separated and the aqueous layer was acidified with 1 N HCl solutions to pH ~3-2. The precipitated solid was extracted into EtOAc (2×20 mL). The combined organic extracts were dried over anhydrous $Na_2SO_4$, filtered and concentrated under reduced pressure. The crude material was purified by silica gel column chromatography (eluent: 50% EtOAc/n-hexanes) to afford VN-349 (30 mg, 0.13 mmol, 40%) as an off white solid. $^1$H NMR (400 MHz, DMSO-$d_6$): δ 11.70 (s, 1H), 8.43 (t, J=1.6 Hz, 1H), 8.13-8.08 (m, 1H), 7.87 (dt, J=7.8, 1.2 Hz, 1H), 7.61-7.53 (m, 2H), 7.41 (dd, J=8.0, 0.8 Hz, 1H), 7.14-7.08 (m, 1H), 7.03-6.96 (m, 2H); $^1$H NMR (400 MHz, DMSO-$d_6$, $D_2O$ Exc.): δ 8.35 (s, 1H), 8.07-8.00 (m, 1H), 7.85 (d, J=7.9 Hz, 1H), 7.61-7.51 (m, 2H), 7.40 (d, J=8.2 Hz, 1H), 7.14-7.06 (m, 1H), 7.03-6.96 (m, 1H), 6.92 (s, 1H). LC-MS: m/z 235.8 [M−H]$^-$ at 2.42 RT (98.72% purity). HPLC: 99.29%.

Preparation of VN-351 & VN-380. The synthetic strategy for preparing VN-351 and VN-380 is detailed in the scheme below.

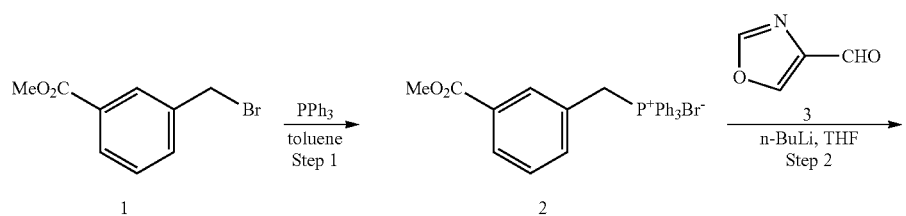

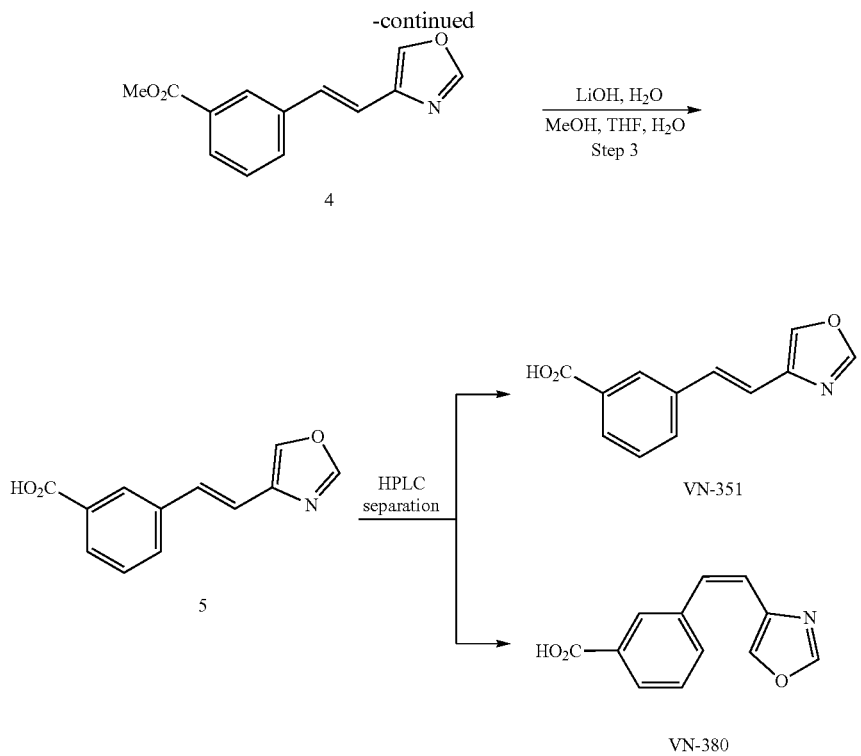

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(oxazol-4-yl)vinyl) benzoate (4). To a stirred solution of compound 2 (1.5 g, 3.06 mmol) in THF (25 mL) was added n-BuLi (2.5 M in hexanes, 3.06 mL, 7.65 mmol) at −78° C. under inert atmosphere. The reaction mixture was gradually warmed to RT and stirred for 30 min. Then a solution of oxazole-4-carbaldehyde 3 (356 mg, 3.67 mmol) in THF (5 mL) was added at −78° C. The reaction mixture was gradually warmed to RT and stirred for 5 h. The progress of the reaction was monitored by TLC; after the completion, the reaction mixture was quenched with saturated NH$_4$Cl solution (30 mL) and extracted with EtOAc (2×40 mL). The combined organic extracts were washed with brine (20 mL), dried over anhydrous Na$_2$SO$_4$, filtered and concentrated under reduced pressure. The crude material was purified by combi-flash column chromatography eluting with 10% EtOAc/n-hexanes to afford compound 4 (265 mg, 1.16 mmol, 38%) as a mixture of cis and trans-isomers as pale yellow semi solid. The mixture was taken to next step without further purification. $^1$H NMR (400 MHz, DMSO-$d_6$): δ 8.43-8.41 (m, 0.3H), 8.37-8.34 (m, 0.6H), 8.22 (d, J=0.8 Hz, 0.3H), 8.13-8.08 (m, 1H), 8.02 (s, 0.6H), 7.88-7.79 (m, 2H), 7.56-7.46 (m, 1H), 7.34-7.22 (m, 0.7H), 6.70 (d, J=12.7 Hz, 0.7H), 6.51 (d, J=12.5 Hz, 0.7H), 3.89-3.84 (m, 3H). LC-MS: m/z 230.0 [M+H]$^+$ at 3.34 RT (59.44% purity); m/z 230.0 [M+H]$^+$ at 3.40 RT (39.50% purity).

Step-3: Synthesis of (E)-3-(2-(oxazol-4-yl)vinyl)benzoic acid (VN-351) & (Z)-3-(2-(oxazol-4-yl)vinyl)benzoic acid (VN-380). To a stirred solution of compound 4 (250 mg, mixture) in a mixture of THF/methanol (1:1, 4 mL) was added a solution of lithium hydroxide monohydride (137 mg, 3.27 mmol) in water (2 mL) at RT and stirred for 16 h. The progress of the reaction was monitored by TLC; after the completion, the reaction mixture was concentrated under reduced pressure. The residue was diluted with water (15 mL) and extracted with ether (2×10 mL). The organic layer was separated; the aqueous layer was acidified with 1 N HCl solutions at 0° C. to pH ~3-4. The obtained solid was filtered and dried under vacuum to afford the desired compound 5 (200 mg). The crude material was purified by preparative HPLC (Method U) to afford VN-351 (20 mg, 0.09 mmol, 8%) & VN-380 (30 mg, 0.14 mmol, 12%) as white solids respectively.

Analytical data of VN-352: $^1$H NMR (400 MHz, DMSO-$d_6$): δ 13.01 (br s, 1H), 8.41 (s, 1H), 8.20 (s, 1H), 8.10 (s, 1H), 7.86-7.79 (m, 2H), 7.50 (t, J=7.7 Hz, 1H), 7.32-7.20 (m, 2H); $^1$H NMR (400 MHz, DMSO-$d_6$, D$_2$O Exc.): δ 8.30 (s, 1H), 8.14 (s, 1H), 8.04 (s, 1H), 7.84-7.77 (m, 2H), 7.50 (t, J=7.7 Hz, 1H), 7.27-7.14 (m, 2H). LC-MS: m/z 216.1 [M+H]$^+$ at 1.97 RT (99.67% purity). HPLC: 98.79%.

Analytical data of VN-380: $^1$H NMR (400 MHz, DMSO-$d_6$): δ 12.92 (br s, 1H), 8.35 (s, 1H), 8.04 (t, J=1.6 Hz, 1H), 7.99 (s, 1H), 7.83 (dt, J=7.8, 1.3 Hz, 1H), 7.79-7.75 (m, 1H), 7.46 (t, J=7.7 Hz, 1H), 6.69 (d, J=12.5 Hz, 1H), 6.48 (d, J=12.5 Hz, 1H); $^1$H NMR (400 MHz, DMSO-$d_6$, D$_2$O Exc.): δ 8.23 (s, 1H), 8.00 (s, 1H), 7.89 (s, 1H), 7.83-7.79 (m, 1H), 7.72-7.68 (m, 1H), 7.45 (t, J=7.7 Hz, 1H), 6.67 (d, J=12.5 Hz, 1H), 6.47 (d, J=12.5 Hz, 1H). LC-MS: m/z 216.1 [M+H]$^+$ at 1.92 RT (99.85% purity). HPLC: 99.78%.

Preparation of VN-353. The synthetic strategy for preparing VN-353 is detailed in the scheme below.

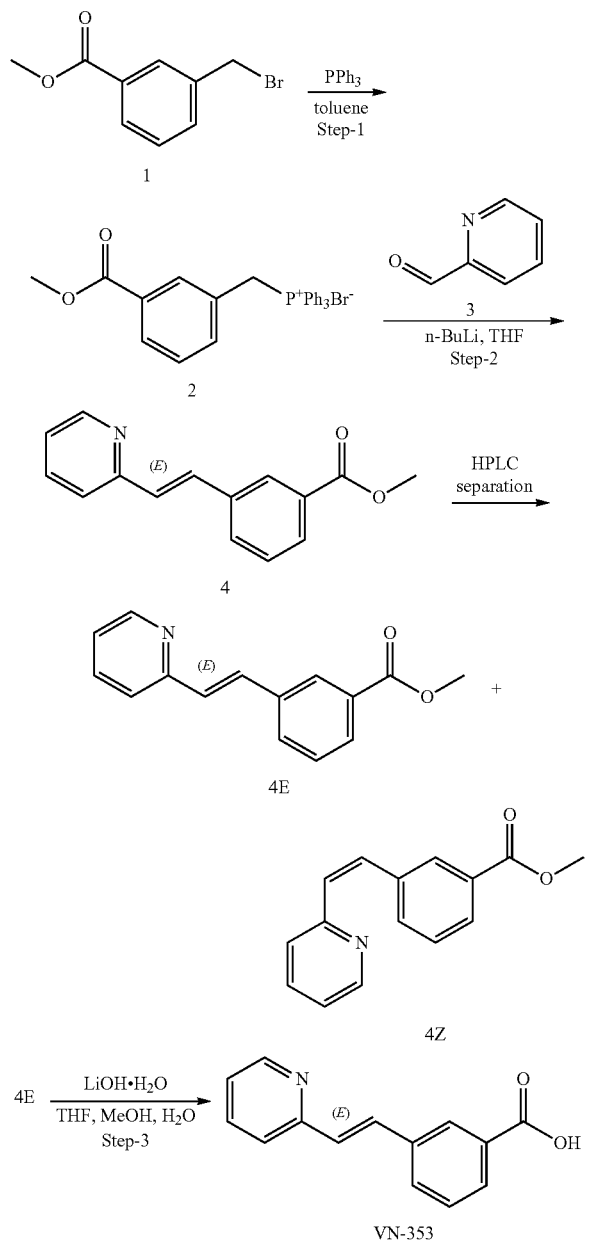

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-d$_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(pyridin-2-yl)vinyl)benzoate (4E). To a stirred solution of compound 2 (1.5 g, 3.06 mmol) in THF (15 mL) was added n-BuLi (2.5 M in hexanes, 1.35 mL, 3.37 mmol) at −78° C. under inert atmosphere. The reaction mixture was gradually warmed to RT and stirred for 30 min. Then a solution of picolinaldehyde 3 (327 mg, 3.06 mmol) in THF (5 mL) was added at −78° C. The reaction mixture was gradually warmed to RT and stirred for 6 h. The progress of the reaction was monitored by TLC; after the completion, the reaction mixture was quenched with saturated NH$_4$Cl solution (30 mL) and extracted with EtOAc (2×40 mL). The combined organic extracts were washed with brine (20 mL), dried over anhydrous Na$_2$SO$_4$, filtered and concentrated under reduced pressure. The crude material was purified by silica gel column chromatography eluting with 30% EtOAc/n-hexanes to afford compound 4 (600 mg). This mixture was purified by normal phase preparative HPLC (Method R) to afford compound 4E (80 mg, 0.33 mmol, 11%) and corresponding cis-isomer 4Z (60 mg, 0.25 mmol, 8%) as colorless syrups respectively. The compound 4E (trans-isomer) was taken to next step.

Analytical data of compound 4E: $^1$H NMR (500 MHz, DMSO-d$_6$): δ 8.70 (d, J=4.6 Hz, 1H), 8.24 (s, 1H), 8.12 (br t, J=7.2 Hz, 1H), 7.99-7.85 (m, 4H), 7.61 (t, J=7.8 Hz, 1H), 7.56-7.51 (m, 1H), 7.47 (d, J=16.2 Hz, 1H), 3.90 (s, 3H). LC-MS: m/z 240.1 [M+H]$^+$ at 1.74 RT (99.55% purity).

Analytical data of compound 4Z: $^1$H NMR (400 MHz, DMSO-d$_6$): δ 8.59 (d, J=4.3 Hz, 1H), 7.94 (s, 1H), 7.87-7.75 (m, 2H), 7.59-7.55 (m, 1H), 7.47-7.40 (m, 1H), 7.40-7.35 (m, 1H), 7.29 (d, J=7.9 Hz, 1H), 6.96 (d, J=12.7 Hz, 1H), 6.77 (d, J=12.5 Hz, 1H), 3.82 (s, 3H). LC-MS: m/z 240.1 [M+H]$^+$ at 3.61 RT (96.41% purity).

Step-3: Synthesis of (E)-3-(2-(pyridin-3-yl)vinyl)benzoic acid (VN-353). To a stirred solution of compound 4E (60 mg, 0.25 mmol) in a mixture of THF/methanol (1:1, 2.4 mL) was added a solution of lithium hydroxide monohydride (32 mg, 0.75 mmol) in water (0.6 mL) at RT and stirred for 6 h. The progress of the reaction was monitored by TLC; after the completion, the reaction mixture was concentrated under reduced pressure. The residue was diluted with water (30 mL) and washed with Et$_2$O (2×5 mL). The organic layer was separated; the aqueous layer was acidified with 1N HCl solutions to pH ~4. The obtained solid was filtered, washed with water (2 mL), n-pentane (2×5 mL) and dried under vacuum to afford VN-353 (15 mg, 0.07 mmol, 25%) as an off white solid. $^1$H NMR (400 MHz, DMSO-d$_6$): δ 13.06 (br s, 1H), 8.61-8.57 (m, 11H), 8.20 (t, J=1.6 Hz, 1H), 7.94-7.86 (m, 2H), 7.81 (td, J=7.7, 1.9 Hz, 1H), 7.74 (d, J=16.2 Hz, 1H), 7.62-7.58 (m, 1H), 7.54 (t, J=7.7 Hz, 1H), 7.40 (d, J=16.1 Hz, 1H), 7.30-7.25 (m, 11H); $^1$H NMR (400 MHz, DMSO-d$_6$, D$_2$O Exc.): δ 8.56-8.53 (m, 1H), 8.16 (t, J=1.4 Hz, 1H), 7.92-7.85 (m, 2H), 7.79 (td, J=7.7, 1.8 Hz, 1H), 7.68 (d, J=16.2 Hz, 1H), 7.62-7.58 (m, 1H), 7.53 (t, J=7.7 Hz, 1H), 7.35 (d, J=16.2 Hz, 1H), 7.30-7.25 (m, 1H). LC-MS: m/z 223.7 [M−H]$^−$ at 1.79 RT (99.70% purity). HPLC: 99.81%.

Preparation of VN-354 & VN-381. The synthetic strategy for preparing VN-354 and VN-381 is detailed in the scheme below.

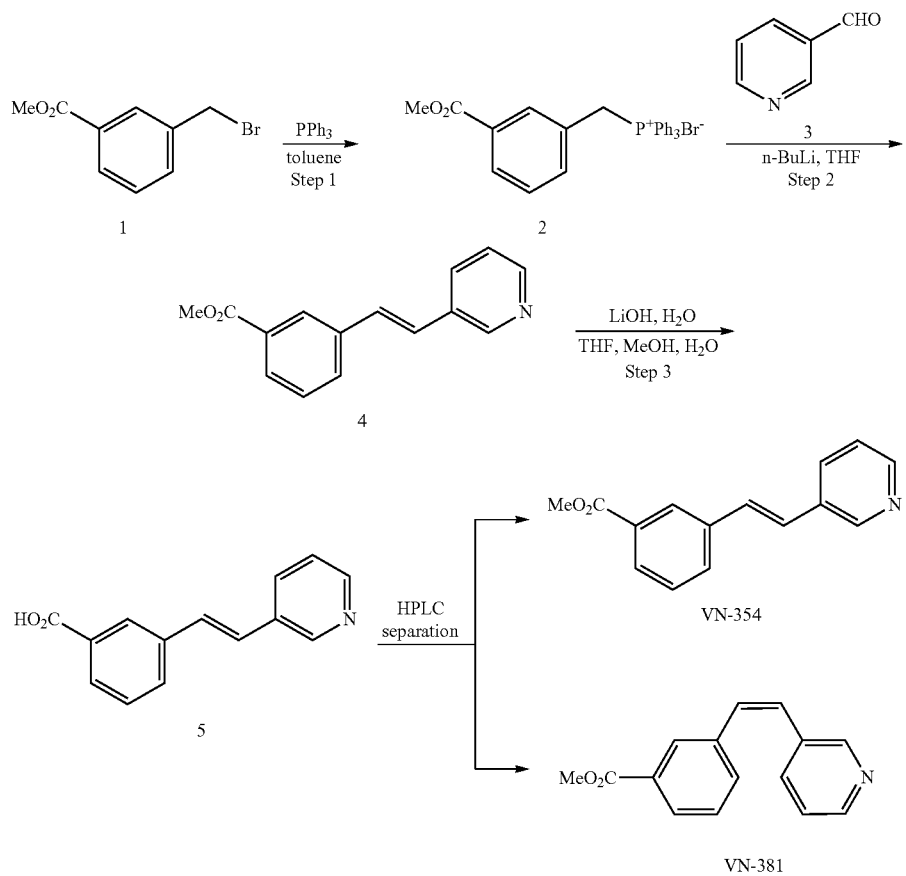

Step-1: Synthesis of (3-(methoxycarbonyl)benzyl)triphenylphosphonium bromide (2). To a stirred solution of methyl 3-(bromomethyl)benzoate 1 (2 g, 8.73 mmol) in toluene (20 mL) was added triphenylphosphine (2.29 g, 8.73 mmol) at RT under inert atmosphere. The reaction mixture was heated to reflux temperature and stirred for 16 h. Then the solid was filtered, washed with toluene (2×10 mL), n-hexanes (2×10 mL) and dried under vacuum to afford compound 2 (3.5 g, 7.13 mmol, 83%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(pyridin-3-yl)vinyl) benzoate (4). To a stirred solution of compound 2 (1 g, 2.04 mmol) in THF (15 mL) was added n-BuLi (2.5 M in hexanes, 0.9 mL, 2.24 mmol) at −78° C. under inert atmosphere. The reaction mixture was gradually warmed to RT and stirred for 30 min. Then a solution of nicotinaldehyde 3 (218 mg, 2.04 mmol) in THF (5 mL) was added at −78° C. The reaction mixture was gradually warmed to RT and stirred for 16 h. The progress of the reaction was monitored by TLC; after the completion, the reaction mixture was quenched with saturated NH$_4$Cl solution (20 mL) and extracted with EtOAc (2×30 mL). The combined organic extracts were washed with brine (20 mL), dried over anhydrous Na$_2$SO$_4$, filtered and concentrated under reduced pressure. The crude material was purified by silica gel column chromatography eluting with 30% EtOAc/n-hexanes to afford compound 4 (350 mg, 1.46 mmol, 73%) as a mixture of cis and trans-isomers as colorless syrup. The mixture was taken to next step without further purification. LC-MS: m/z 240.0 [M+H]$^+$ at 3.49 RT (38.99% purity).

Step-3: Synthesis of (E)-3-(2-(pyridin-3-yl)vinyl)benzoic acid (VN-354) & (Z)-3-(2-(pyridin-3-yl)vinyl)benzoic acid (VN-381). To a stirred solution of compound 4 (340 mg, mixture) in a mixture of THF/methanol (1:1, 4 mL) was added a solution of lithium hydroxide monohydride (179 mg, 4.27 mmol) in water (1.5 mL) at RT and stirred for 16 h. The progress of the reaction was monitored by TLC; after the completion, the reaction mixture was concentrated under reduced pressure. The residue was diluted with water (30 mL) and washed with Et$_2$O (2×10 mL). The organic layer was separated; the aqueous layer was acidified with 1N HCl solutions to pH ~3-4. The aqueous layer was lyophilized to afford the desired compound 5 (270 mg).

This crude material was purified by normal phase preparative HPLC (Method Y) to afford VN-354 (80 mg, 0.35 mmol, 25%) & VN-381 (80 mg, 0.35 mmol, 25%) as off white solids respectively.

Analytical data of VN-354: $^1$H NMR (400 MHz, DMSO-$d_6$): δ 13.06 (br s, 1H), 8.82 (d, J=1.8 Hz, 1H), 8.48 (dd, J=4.7, 1.4 Hz, 1H), 8.18 (s, 1H), 8.10 (dt, J=8.0, 1.8 Hz, 1H), 7.90-7.84 (m, 2H), 7.57-7.47 (m, 2H), 7.46-7.35 (m, 2H); $^1$H NMR (400 MHz, DMSO-$d_6$, D$_2$O Exc.): δ 8.74 (s, 1H), 8.43 (d, J=4.6 Hz, 1H), 8.16-8.05 (m, 2H), 7.91-7.82 (m, 2H), 7.53 (t, J=7.8 Hz, 1H), 7.48-7.39 (m, 2H), 7.36-7.29 (m, 1H). LC-MS: m/z 226.1 [M+H]$^+$ at 1.50 RT (99.67% purity). HPLC: 98.03%.

Analytical data of VN-381: $^1$H NMR (400 MHz, DMSO-$d_6$): δ 12.94 (br s, 1H), 8.44-8.35 (m, 2H), 7.83-7.76 (m, 2H), 7.58 (dt, J=7.9, 1.6 Hz, 1H), 7.45-7.37 (m, 2H), 7.30 (dd, J=7.8, 4.8 Hz, 1H), 6.87 (d, J=12.4 Hz, 1H), 6.73 (d, J=12.4 Hz, 1H); $^1$H NMR (400 MHz, DMSO-d$_6$, D$_2$O Exc.): δ 8.39-8.29 (m, 2H), 7.79 (td, J=4.4, 1.6 Hz, 1H), 7.72 (s, 1H), 7.60-7.55 (m, 1H), 7.41 (d, J=5.1 Hz, 2H), 7.30 (dd, J=7.9, 4.9 Hz, 1H), 6.84 (d, J=12.4 Hz, 1H), 6.71 (d, J=12.2 Hz, 1H). LC-MS: m/z 226.1 [M+H]$^+$ at 1.48 RT (97.24% purity). HPLC: 99.80%.

Preparation of VN-355 & VN-387. The synthetic strategy for preparing VN-355 and VN-387 is detailed in the scheme below.

and extracted with EtOAc (2×40 mL). The combined organic extracts were washed with brine (20 mL), dried over anhydrous Na$_2$SO$_4$, filtered and concentrated under reduced pressure. The crude material was purified by silica gel column chromatography eluting with 30% EtOAc/n-hexanes to afford compound 4 (900 mg). This mixture was purified by normal phase preparative HPLC (Method S) to afford compound 4E (200 mg, 0.84 mmol, 27%) and corresponding cis-isomer 4Z (260 mg, 1.09 mmol, 34%) as an off white solids respectively.

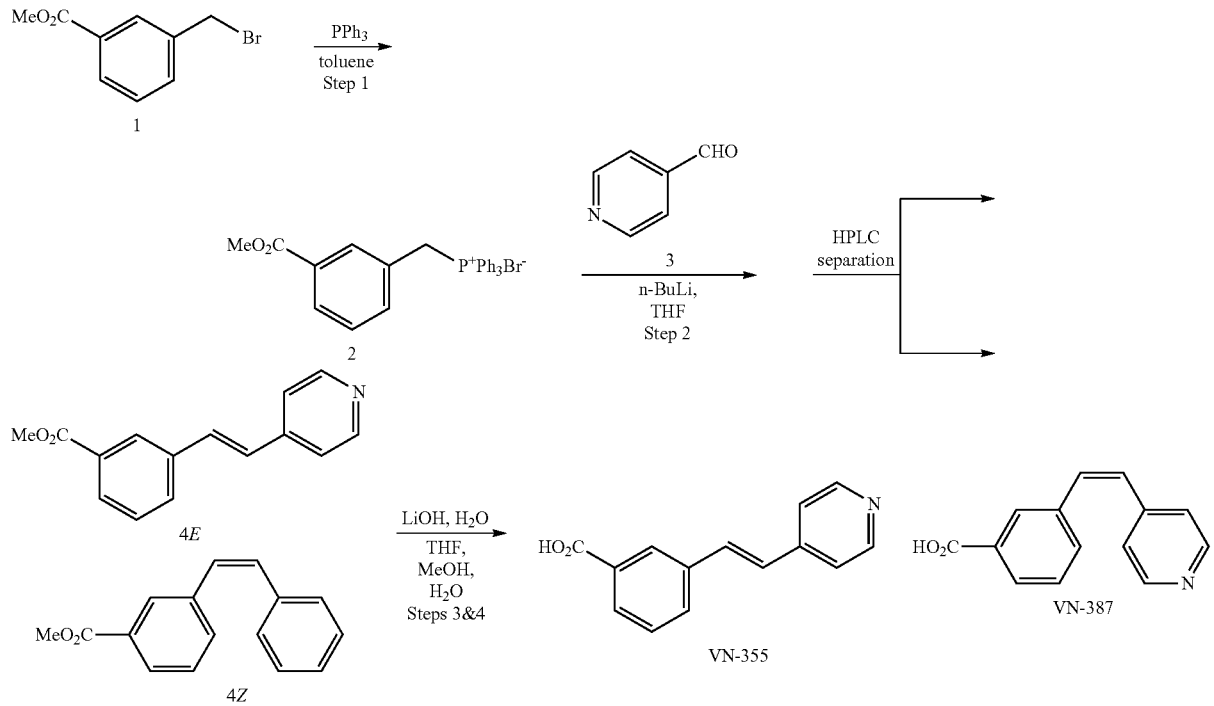

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-d$_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(pyridin-4-yl)vinyl) benzoate (4E) & methyl (Z)-3-(2-(pyridin-4-yl)vinyl)benzoate (4Z). To a stirred solution of compound 2 (1.5 g, 3.06 mmol) in THF (15 mL) was added n-BuLi (2.5 M in hexanes, 1.35 mL, 3.37 mmol) at −78° C. under inert atmosphere. The reaction mixture was gradually warmed to RT and stirred for 30 min. Then a solution of isonicotinaldehyde 3 (327 mg, 3.06 mmol) in THF (5 mL) was added at −78° C. The reaction mixture was gradually warmed to RT and stirred for 6 h. The progress of the reaction was monitored by TLC; after the completion, the reaction mixture was quenched with saturated NH$_4$Cl solution (30 mL)

Analytical data of compound 4E: $^1$H NMR (500 MHz, DMSO-d$_6$): δ 8.85-8.83 (m, 2H), 8.32 (s, 1H), 8.16 (br d, J=5.2 Hz, 2H), 8.08-7.97 (m, 3H), 7.68-7.58 (m, 2H), 3.90 (s, 3H). LC-MS: m/z 240.1 [M+H]$^+$ at 3.47 RT (99.90% purity).

Analytical data of compound 4Z: $^1$H NMR (500 MHz, DMSO-d$_6$): δ 8.66 (d, J=6.4 Hz, 2H), 7.92-7.88 (m, 1H), 7.84 (s, 1H), 7.56 (d, J=6.4 Hz, 2H), 7.52-7.45 (m, 2H), 7.17 (d, J=12.2 Hz, 1H), 6.86 (d, J=12.8 Hz, 1H), 3.83 (s, 3H). LC-MS: m/z 240.1 [M+H]$^+$ at 3.42 RT (98.47% purity).

Step-3: Synthesis of (E)-3-(2-(pyridin-4-yl)vinyl)benzoic acid (VN-355). To a stirred solution of compound 4E (200 mg, 0.84 mmol) in a mixture of THF/methanol (1:1, 6 mL) was added a solution of lithium hydroxide monohydride (105 mg, 2.51 mmol) in water (2 mL) at RT and stirred for 6 h. The progress of the reaction was monitored by TLC; after the completion, the reaction mixture was concentrated under reduced pressure. The residue was diluted with water (30 mL) and washed with Et$_2$O (2×10 mL). The organic layer was separated; the aqueous layer was acidified with 1N HCl solutions to pH ~4. The obtained solid was filtered, washed with water (5 mL), n-pentane (2×5 mL) and dried under vacuum to afford VN-355 (50 mg, 0.22 mmol, 28%) as an off white solid. $^1$H NMR (400 MHz, DMSO-d$_6$): δ 13.09 (br s, 1H), 8.56 (br d, J=4.9 Hz, 2H), 8.22 (t, J=1.5 Hz, 1H), 7.94-7.86 (m, 2H), 7.68-7.51 (m, 4H), 7.35 (d, J=16.6 Hz, 1H). LC-MS: m/z 226.1 [M+H]$^+$ at 1.51 RT (97.36% purity). HPLC: 99.26%.

Step-4: Synthesis of (Z)-3-(2-(pyridin-4-yl)vinyl)benzoic acid (VN-387). To a stirred solution of compound 4Z (250 mg, 1.05 mmol) in a mixture of THF/methanol (1:1, 3 mL) was added a solution of lithium hydroxide monohydride (132 mg, 3.14 mmol) in water (1 mL) at RT and stirred for 6 h. The progress of the reaction was monitored by TLC; after the completion, the reaction mixture was concentrated under reduced pressure. The residue was diluted with water (30 mL) and washed with Et$_2$O (2×10 mL). The organic layer was separated; the aqueous layer was acidified with 1N HCl solutions to pH ~4. The obtained solid was filtered, washed with water (5 mL), n-pentane (2×10 mL) and dried under vacuum to afford VN-387 (80 mg, 0.35 mmol, 34%) as an off white solid. $^1$H NMR (400 MHz, DMSO-d$_6$): δ 12.95 (br s, 1H), 8.49-8.43 (m, 2H), 7.85-7.76 (m, 2H), 7.45-7.41 (m, 2H), 7.17-7.12 (m, 2H), 6.92 (d, J=12.3 Hz, 1H), 6.70 (d, J=12.3 Hz, 1H); $^1$H NMR (400 MHz, DMSO-d$_6$, D$_2$O Exc.): δ 8.41 (d, J=5.5 Hz, 2H), 7.83-7.78 (m, 1H), 7.74 (s, 1H), 7.42 (d, J=4.9 Hz, 2H), 7.14 (d, J=5.8 Hz, 2H), 6.90 (d, J=12.3 Hz, 1H), 6.68 (d, J=12.3 Hz, 1H). LC-MS: m/z 226.2 [M+H]$^+$ at 1.43 RT (99.75% purity). HPLC: 99.47%.

Preparation of VN-359. The synthetic strategy for preparing VN-359 is detailed in the scheme below.

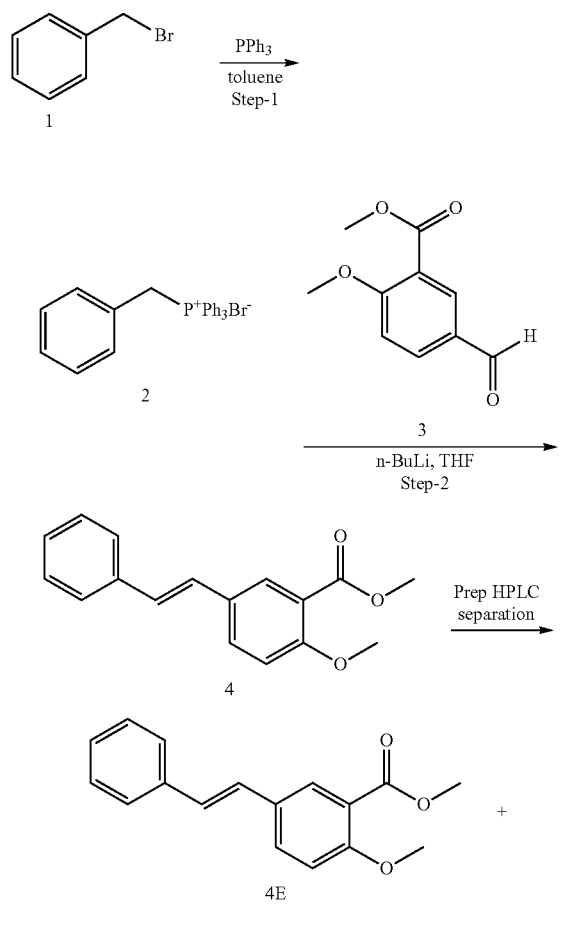

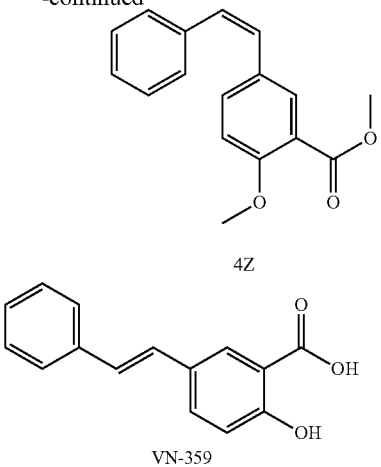

Step-1: Synthesis of Benzyltriphenylphosphonium bromide (2). To a stirred solution of (bromomethyl)benzene 1 (1.39 mL, 11.69 mmol) in toluene (20 mL) was added triphenylphosphine (3.06 g, 11.69 mmol) at RT under inert atmosphere. The reaction mixture was heated to reflux temperature and stirred for 16 h. Then the solid was filtered, washed with toluene (2×20 mL), n-hexanes (2×15 mL) and dried under vacuum to afford compound 2 (4.7 g, 10.85 mmol, 97%) as white solid. $^1$H NMR (400 MHz, DMSO-d$_6$): δ 7.95-7.86 (m, 3H), 7.79-7.63 (m, 12H), 7.33-7.26 (m, 1H), 7.26-7.20 (m, 2H), 7.00-6.96 (m, 2H), 5.22-5.16 (m, 2H).

Step-2: Synthesis of Methyl (E)-2-methoxy-5-styrylbenzoate (4E). To a stirred solution of compound 2 (1 g, 2.31 mmol) in THF (15 mL) was added n-BuLi (1.6 M in hexanes, 1.59 mL, 2.55 mmol) at –78° C. under inert atmosphere. The reaction mixture was gradually warmed to RT and stirred for 30 min. Then a solution of methyl 5-formyl-2-methoxybenzoate 3 (449 mg, 2.31 mmol) in THF (5 mL) was added at –78° C. The reaction mixture was gradually warmed to RT and stirred for 6 h. The progress of the reaction was monitored by TLC; after the completion, the reaction mixture was quenched with saturated NH$_4$Cl solution (20 mL) and extracted with EtOAc (2×30 mL). The combined organic extracts were washed with brine (20 mL), dried over anhydrous Na$_2$SO$_4$, filtered and concentrated under reduced pressure. The crude material was purified by silica gel column chromatography eluting with 10% EtOAc/n-hexanes to afford compound 4 (630 mg). This mixture was purified by normal phase preparative HPLC (Method S) to afford compound 4E (200 mg, 0.75 mmol, 32%) and corresponding cis-isomer 4Z (230 mg, 0.86 mmol, 37%) as off white solids respectively. The compound 4E (trans-isomer) was taken to next step.

Analytical data of compound 4E: $^1$H NMR (400 MHz, CDCl$_3$): δ 7.97 (d, J=2.5 Hz, 1H), 7.61 (dd, J=8.7, 2.4 Hz, 1H), 7.51-7.47 (m, 2H), 7.39-7.32 (m, 2H), 7.28-7.27 (m, 0.4H), 7.26-7.23 (m, 0.6H), 7.04 (d, J=2.3 Hz, 2H), 6.98 (d, J=8.7 Hz, 1H), 3.93 (s, 3H), 3.93 (s, 3H). LC-MS: m/z 269.1 [M+H]$^+$ at 4.12 RT (99.77% purity).

Analytical data of compound 4Z: $^1$H NMR (400 MHz, DMSO-d$_6$): δ 7.52 (d, J=2.3 Hz, 1H), 7.34 (dd, J=8.7, 2.3 Hz, 1H), 7.31-7.26 (m, 2H), 7.25-7.20 (m, 3H), 7.03 (d, J=8.7 Hz, 1H), 6.64-6.55 (m, 2H), 3.79 (s, 3H), 3.72 (s, 3H). LC-MS: m/z 269.2 [M+H]$^+$ at 4.36 RT (97.30% purity).

Step-3: Synthesis of (E)-2-hydroxy-5-styrylbenzoic acid (VN-359). To a stirred solution of compound 4E (150 mg, 0.56 mmol) in $CH_2Cl_2$ (7 mL) was added boron tribromide (1 M in $CH_2Cl_2$, 1.12 mL, 1.12 mmol) at −50° C. under inert atmosphere. The reaction mixture was gradually warmed to RT and stirred for 4 h. The progress of the reaction was monitored by TLC, after the completion, the reaction mixture was quenched with ice cold water (20 mL) and extracted with $CH_2Cl_2$ (2×20 mL). The combined organic extracts were washed with brine (10 mL), dried over anhydrous $Na_2SO_4$, filtered and concentrated under reduced pressure to obtain the crude (~120 mg).

This lot was combined with another lot (35 mg, crude) and was purified by triturations with $CH_2Cl_2$/n-pentane (1:4, 10 mL) and dried under vacuum to afford VN-359 (21 mg, 0.09 mmol, 16%) as an off white solid. $^1$H NMR (400 MHz, DMSO-$d_6$): δ 11.54 (br s, 1H), 7.97 (d, J=2.3 Hz, 1H), 7.80 (dd, J=8.7, 2.1 Hz, 1H), 7.58 (d, J=7.3 Hz, 2H), 7.36 (t, J=7.6 Hz, 2H), 7.27-7.21 (m, 2H), 7.15-7.09 (m, 1H), 6.97 (d, J=8.5 Hz, 1H); $^1$H NMR (400 MHz, DMSO-$d_6$, $D_2O$ Exc.): δ 7.94 (d, J=2.3 Hz, 1H), 7.78 (dd, J=8.7, 2.4 Hz, 1H), 7.56 (d, J=7.3 Hz, 2H), 7.34 (t, J=7.6 Hz, 2H), 7.27-7.16 (m, 2H), 7.11-7.04 (m, 1H), 6.95 (d, J=8.7 Hz, 1H). LC-MS: m/z 238.8 [M−H]$^-$ at 2.87 RT (98.04% purity). HPLC: 98.83%.

Preparation of VN-362. The synthetic strategy for preparing VN-362 is detailed in the scheme below.

mmol) in DMF (10 mL) were added 4-(2-chloroethyl) morpholine hydrochloride 2 (1.01 g, 5.45 mmol) and potassium carbonate (1.25 g, 9.09 mmol) at RT under inert atmosphere. The reaction mixture was heated to 80° C. and stirred for 16 h. The progress of the reaction was monitored by TLC; after the completion, the reaction mixture was cooled to RT; quenched with water (50 mL) and extracted with EtOAc (2×30 mL). The combined organic extracts were washed with water (30 mL) and brine (20 mL). The organic layer was separated, dried over anhydrous $Na_2SO_4$, filtered and concentrated under reduced pressure to afford compound 3 (1.1 g, 3.3 mmol, 73%) as colorless liquid. $^1$H NMR (400 MHz, CDCl$_3$): δ 7.31-7.27 (m, 2H), 7.02-6.96 (m, 1H), 6.89-6.85 (m, 1H), 4.08 (t, J=5.6 Hz, 2H), 3.75-3.71 (m, 4H), 2.78 (t, J=5.6 Hz, 2H), 2.59-2.54 (m, 4H). LC-MS: m/z 334.1 [M+H]$^+$ at 1.72 RT (66.36% purity).

Step-2: Synthesis of Methyl 3-vinylbenzoate (4). To a stirred solution of methyl 3-bromobenzoate 6 (3 g, 13.95 mmol) in 1,2-dimethoxyethane (40 mL) were added 4,4,5,5-tetramethyl-2-vinyl-1,3,2-dioxaborolane 7 (2.15 g, 13.95 mmol), potassium carbonate (1.92 g, 13.95 mmol) and water (20 mL) at RT. The reaction mixture was purged with argon for 5 min. Then Pd(PPh$_3$)$_4$ (1.61 g, 1.39 mmol) was added to the reaction mixture at RT; gradually heated to 80° C. and stirred for 16 h. The progress of the reaction was monitored by TLC; after the completion, the reaction mixture was

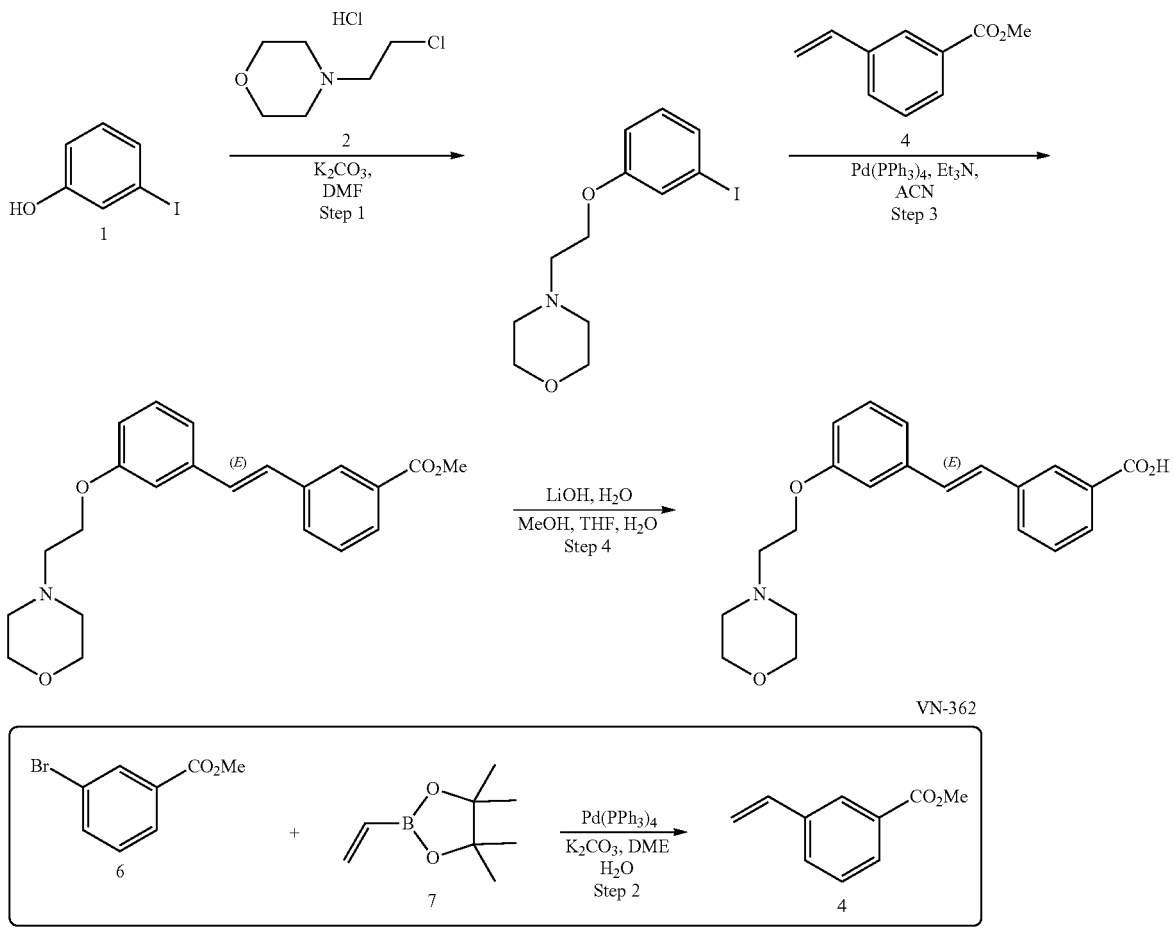

Step-1: Synthesis of 4-(2-(3-iodophenoxy)ethyl)morpholine (3). To a stirred solution of 3-iodophenol 1 (1 g, 4.54 cooled to RT, filtered through a pad of celite and the celite bed was washed with EtOAc (20 mL). The filtrate was concentrated under reduced pressure. The residue was diluted with water (50 mL) and extracted with EtOAc (2×60 mL). The combined organic extracts were washed with brine (30 mL), dried over anhydrous Na$_2$SO$_4$, filtered and concentrated under reduced pressure. The crude material was purified by silica gel column chromatography eluting with 5% EtOAc/n-hexanes to afford compound 4 (900 mg, 5.55 mmol, 40%) as colorless liquid. $^1$H NMR (400 MHz, CDCl$_3$): δ 8.08 (t, J=1.8 Hz, 1H), 7.92 (dt, J=7.7, 1.4 Hz, 1H), 7.59 (dt, J=7.7, 1.3 Hz, 1H), 7.40 (t, J=7.7 Hz, 1H), 6.75 (dd, J=17.6, 10.9 Hz, 1H), 5.83 (dd, J=17.6, 0.6 Hz, 1H), 5.33 (d, J=10.9 Hz, 1H), 3.93 (s, 3H).

Step-3: Synthesis of Methyl (E)-3-(3-(2-morpholinoethoxy)styryl)benzoate (5). To a stirred solution of compound 3 (500 mg, 1.5 mmol) in acetonitrile (7 mL) were added compound 4 (292 mg, 1.8 mmol) and triethylamine (0.42 mL, 3.0 mmol) in a sealed tube at RT under inert atmosphere. The reaction mixture was purged with argon for 5 min. Then Pd(PPh$_3$)$_4$ (260 mg, 0.22 mmol) was added to the reaction mixture at RT; the vessel was sealed, gradually heated to 80° C. and stirred for 16 h. The progress of the reaction was monitored by TLC; after the completion, the reaction mixture was cooled to RT; diluted with EtOAc (30 mL) and filtered through a pad of celite and the celite bed was washed with EtOAc (20 mL). The filtrate was concentrated under reduced pressure. The crude material was purified by silica gel column chromatography eluting with 40% EtOAc/n-hexanes to afford compound 5 (320 mg, 0.87 mmol, 58%) as pale yellow oily liquid. The compound was not pure even after column purification. This material was taken to next step without further purification. LC-MS: m/z 368.3 [M+H]$^+$ at 2.05 RT (34.03% purity).

Step-4: Synthesis of (E)-3-(3-(2-morpholinoethoxy)styryl)benzoic acid (VN-362). To a stirred solution of compound 5 (320 mg, impure) in a mixture of THF/methanol (1:1, 8 mL) was added a solution of lithium hydroxide monohydride (110 mg, 2.61 mmol) in water (4 mL) at RT and stirred for 16 h. The progress of the reaction was monitored by TLC; after the completion, the reaction mixture was concentrated under reduced pressure. The residue was diluted with water (20 mL) and washed with EtOAc (2×10 mL) to remove insoluble organic impurities. The organic layer was separated; the aqueous layer was neutralized with saturated aqueous citric acid solution and extracted with EtOAC (2×30 mL). The combined organic extracts were washed with brine (15 mL), dried over anhydrous Na$_2$SO$_4$, filtered and concentrated under reduced pressure. The crude material was purified by triturating with Et$_2$O (2×5 mL) and dried under vacuum to afford VN-362 (50 mg, 0.14 mmol, 16%) as an off white solid. $^1$H NMR (400 MHz, DMSO-d$_6$): δ 12.69 (br s, 1H), 8.15 (s, 1H), 7.89-7.80 (m, 2H), 7.51 (t, J=7.7 Hz, 1H), 7.43-7.35 (m, 1H), 7.33-7.24 (m, 3H), 7.23-7.17 (m, 1H), 6.87 (dd, J=8.0, 1.6 Hz, 1H), 4.14 (t, J=5.8 Hz, 2H), 3.62-3.56 (m, 4H), 2.72 (t, J=5.7 Hz, 2H), 2.56-2.51 (m, 4H); $^1$H NMR (400 MHz, DMSO-d$_6$, D$_2$O Exc.): δ 8.12 (s, 1H), 7.86-7.79 (m, 2H), 7.50 (t, J=7.7 Hz, 1H), 7.38-7.16 (m, 5H), 6.88-6.83 (m, 1H), 4.12 (t, J=5.7 Hz, 2H), 3.60-3.55 (m, 4H), 2.71 (t, J=5.6 Hz, 2H), 2.54-2.50 (m, 4H). LC-MS: m/z 354.3 [M+H]$^+$ at 1.87 RT (96.40% purity). HPLC: 96.72%.

Preparation of VN-363. The synthetic strategy for preparing VN-363 is detailed in the scheme below.

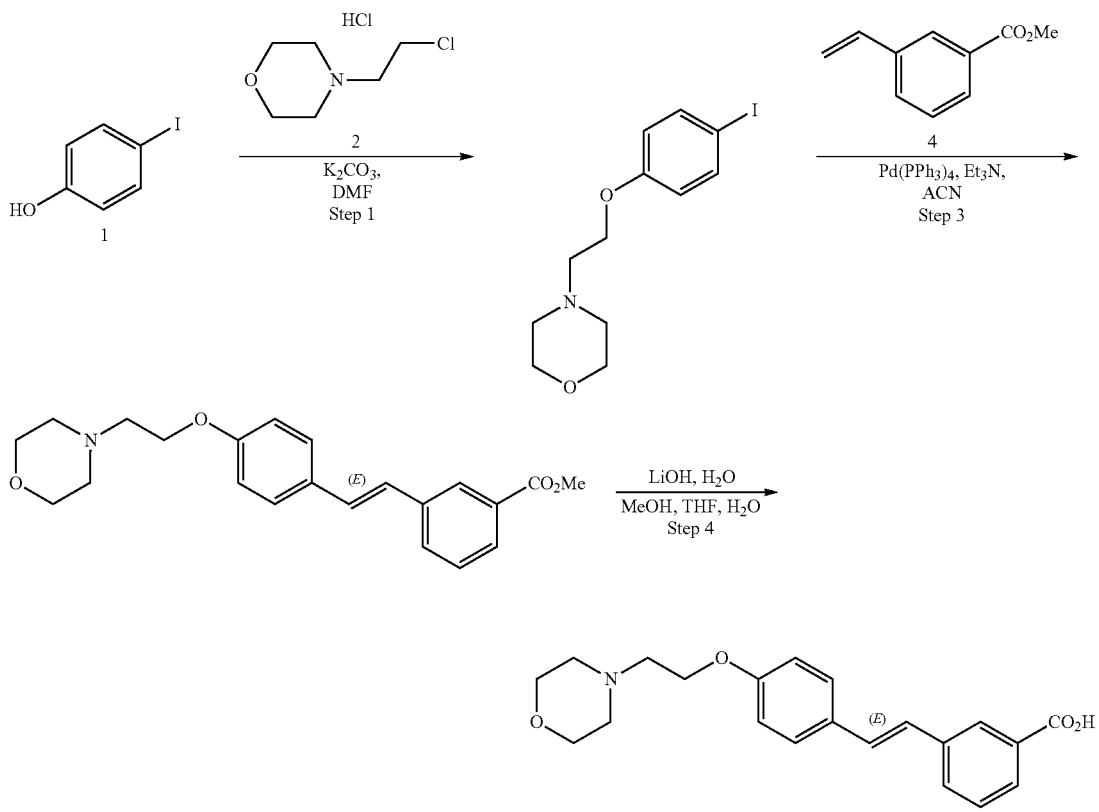

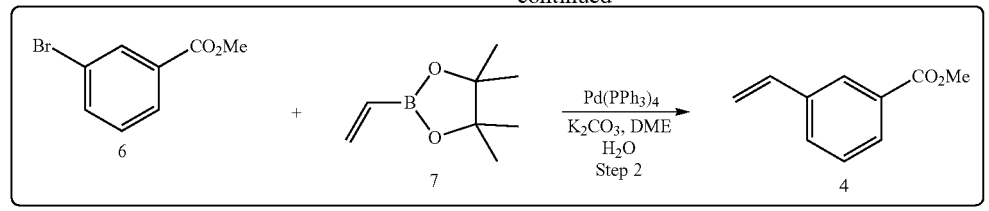

Step-1: Synthesis of 4-(2-(4-iodophenoxy)ethyl)morpholine (3). To a stirred solution of 4-iodophenol 1 (1 g, 4.54 mmol) in DMF (20 mL) were added 4-(2-chloroethyl) morpholine hydrochloride 2 (1.01 g, 5.45 mmol) and potassium carbonate (1.25 g, 9.09 mmol) at RT under inert atmosphere. The reaction mixture was heated to 80° C. and stirred for 16 h. The progress of the reaction was monitored by TLC; after the completion, the reaction mixture was cooled to RT; quenched with water (50 mL) and extracted with EtOAc (2×30 mL). The combined organic extracts were washed with water (30 mL) and brine (20 mL). The organic layer was separated, dried over anhydrous $Na_2SO_4$, filtered and concentrated under reduced pressure. The crude material was purified by silica gel column chromatography eluting with 10% EtOAc/n-hexanes to afford compound 3 (1.1 g, 3.3 mmol, 73%) as pink liquid. $^1$H NMR (500 MHz, $CDCl_3$): δ 7.56 (d, J=8.7 Hz, 2H), 6.69 (d, J=9.3 Hz, 2H), 4.08 (t, J=5.8 Hz, 2H), 3.76-3.71 (m, 4H), 2.79 (t, J=5.5 Hz, 2H), 2.59-2.55 (m, 4H). LC-MS: m/z 334.0 [M+H]$^+$ at 3.59 RT (98.67% purity).

Step-2: Synthesis of Methyl 3-vinylbenzoate (4). To a stirred solution of methyl 3-bromobenzoate 6 (3 g, 13.95 mmol) in 1,2-dimethoxyethane (40 mL) were added 4,4,5,5-tetramethyl-2-vinyl-1,3,2-dioxaborolane 7 (2.15 g, 13.95 mmol), potassium carbonate (1.92 g, 13.95 mmol) and water (20 mL) at RT. The reaction mixture was purged with argon for 5 min. Then Pd(PPh$_3$)$_4$ (1.61 g, 1.39 mmol) was added to the reaction mixture at RT; gradually heated to 80° C. and stirred for 16 h. The progress of the reaction was monitored by TLC; after the completion, the reaction mixture was cooled to RT, filtered through a pad of celite and the celite bed was washed with EtOAc (20 mL). The filtrate was concentrated under reduced pressure. The residue was diluted with water (50 mL) and extracted with EtOAc (2×60 mL). The combined organic extracts were washed with brine (30 mL), dried over anhydrous $Na_2SO_4$, filtered and concentrated under reduced pressure. The crude material was purified by silica gel column chromatography eluting with 5% EtOAc/n-hexanes to afford compound 4 (900 mg, 5.55 mmol, 40%) as colorless liquid. $^1$H NMR (400 MHz, $CDCl_3$): δ 8.08 (t, J=1.8 Hz, 1H), 7.92 (dt, J=7.7, 1.4 Hz, 1H), 7.59 (dt, J=7.7, 1.3 Hz, 1H), 7.40 (t, J=7.7 Hz, 1H), 6.75 (dd, J=17.6, 10.9 Hz, 1H), 5.83 (dd, J=17.6, 0.6 Hz, 1H), 5.33 (d, J=10.9 Hz, 1H), 3.93 (s, 3H).

Step-3: Synthesis of Methyl (E)-3-(4-(2-morpholinoethoxy)styryl)benzoate (5). To a stirred solution of compound 3 (500 mg, 1.5 mmol) in acetonitrile (7 mL) were added compound 4 (292 mg, 1.8 mmol) and triethylamine (0.42 mL, 3.0 mmol) in a sealed tube at RT under inert atmosphere. The reaction mixture was purged with argon for 5 min. Then Pd(PPh$_3$)$_4$ (260 mg, 0.22 mmol) was added to the reaction mixture at RT; the vessel was sealed and gradually heated to 80° C. and stirred for 16 h. The progress of the reaction was monitored by TLC; after the completion, the reaction mixture was cooled to RT; diluted with EtOAc (30 mL) and filtered through a pad of silica gel to remove the catalyst. The solvent was concentrated under reduced pressure to obtain the crude. The crude material was purified by silica gel column chromatography eluting with 30% EtOAc/n-hexanes to afford compound 5 (280 mg, 0.76 mmol, 51%) as pale yellow oily liquid. The compound was not pure even after column purification. This material was carried to next step without further purification. LC-MS: m/z 368.2 [M+H]$^+$ at 2.05 RT (38.01% purity).

Step-4: Synthesis of (E)-3-(4-(2-morpholinoethoxy)styryl)benzoic acid (VN-363). To a stirred solution of compound 5 (280 mg, impure) in a mixture of THF/methanol (1:1, 6 mL) was added a solution of lithium hydroxide monohydride (96 mg, 2.29 mmol) in water (3 mL) at RT and stirred for 16 h. The progress of the reaction was monitored by TLC; after the completion, the reaction mixture was concentrated under reduced pressure. The residue was diluted with water (20 mL) and washed with EtOAc (2×10 mL) to remove water insoluble organic impurities. The organic layer was separated; the aqueous layer was neutralized with saturated aqueous citric acid solution. The obtained solid was extracted into $CH_2Cl_2$ (30 mL). The solvent was concentrated under reduced pressure to obtain the crude. The crude material was purified by triturating with Et$_2$O (2×5 mL) followed by EtOH (2 mL) and dried under vacuum to afford VN-363 (50 mg, 0.14 mmol, 19%) as an off white solid. $^1$H NMR (400 MHz, DMSO-d$_6$): δ 12.99 (br s, 1H), 8.11 (s, 1H), 7.81 (br t, J=6.3 Hz, 2H), 7.57 (d, J=8.7 Hz, 2H), 7.48 (t, J=7.7 Hz, 1H), 7.32-7.15 (m, 2H), 6.97 (d, J=8.8 Hz, 2H), 4.11 (t, J=5.7 Hz, 2H), 3.61-3.54 (m, 4H), 2.70 (t, J=5.7 Hz, 2H), 2.48-2.44 (m, 4H); $^1$H NMR (400 MHz, DMSO-d$_6$, D$_2$O Exc.): δ 8.06 (s, 1H), 7.82-7.76 (m, 2H), 7.55 (d, J=8.8 Hz, 2H), 7.47 (t, J=7.7 Hz, 1H), 7.27-7.09 (m, 2H), 6.94 (d, J=8.7 Hz, 2H), 4.10 (t, J=5.6 Hz, 2H), 3.61-3.55 (m, 4H), 2.74 (t, J=5.5 Hz, 2H), 2.56-2.52 (m, 2H). LC-MS: m/z 354.3 [M+H]$^+$ at 1.82 RT (96.46% purity). HPLC: 97.08%.

Preparation of VN-384. The synthetic strategy for preparing VN-384 is detailed in the scheme below.

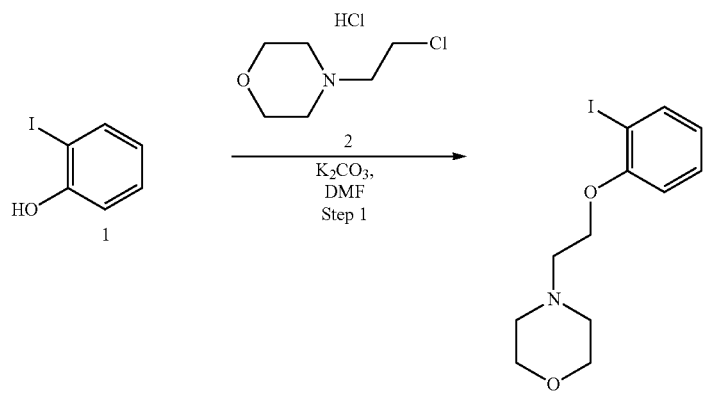
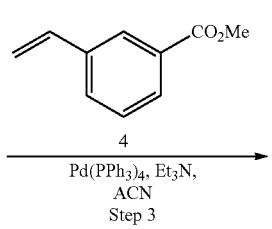
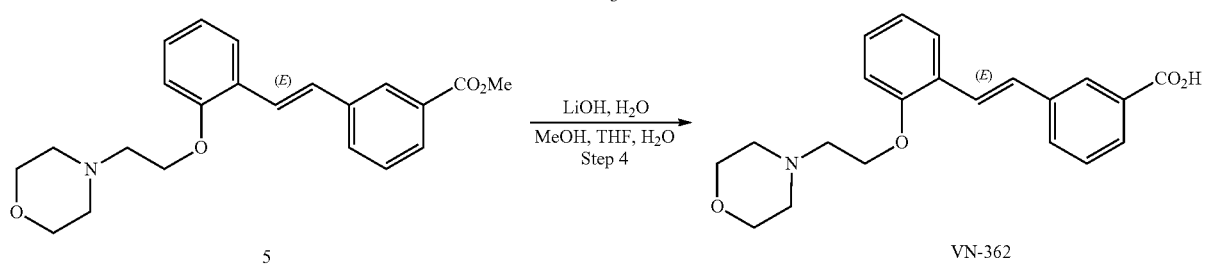
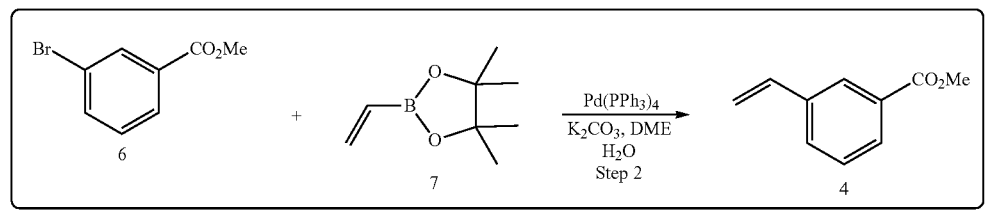

Step-1: Synthesis of 4-(2-(2-iodophenoxy)ethyl)morpholine (3). To a stirred solution of 2-iodophenol 1 (1 g, 4.54 mmol) in DMF (20 mL) were added 4-(2-chloroethyl) morpholine hydrochloride 2 (1.01 g, 5.45 mmol) and potassium carbonate (1.25 g, 9.09 mmol) at RT under inert atmosphere. The reaction mixture was heated to 80° C. and stirred for 16 h. The progress of the reaction was monitored by TLC; after the completion, the reaction mixture was cooled to RT; quenched with water (50 mL) and extracted with EtOAc (2×30 mL). The combined organic extracts were washed with water (30 mL) and brine (20 mL). The organic layer was separated, dried over anhydrous $Na_2SO_4$, filtered and concentrated under reduced pressure to afford compound 3 (1.2 g, 5.11 mmol, 79%) as colorless liquid. $^1$H NMR (400 MHz, $CDCl_3$): δ 7.77 (dd, J=7.8, 1.5 Hz, 1H), 7.31-7.26 (m, 1H), 6.81 (dd, J=8.2, 1.3 Hz, 1H), 6.71 (td, J=7.6, 1.4 Hz, 1H), 4.16 (t, J=5.6 Hz, 2H), 3.75-3.72 (m, 4H), 2.88 (t, J=5.6 Hz, 2H), 2.68-2.64 (m, 4H). LC-MS: m/z 334.1 $[M+H]^+$ at 1.64 RT (99.48% purity).

Step-2: Synthesis of Methyl 3-vinylbenzoate (4). To a stirred solution of methyl 3-bromobenzoate 6 (3 g, 13.95 mmol) in 1,2-dimethoxyethane (40 mL) were added 4,4,5,5-tetramethyl-2-vinyl-1,3,2-dioxaborolane 7 (2.15 g, 13.95 mmol), potassium carbonate (1.92 g, 13.95 mmol) and water (20 mL) at RT. The reaction mixture was purged with argon for 5 min. Then $Pd(PPh_3)_4$ (1.61 g, 1.39 mmol) was added to the reaction mixture at RT; gradually heated to 80° C. and stirred for 16 h. The progress of the reaction was monitored by TLC; after the completion, the reaction mixture was cooled to RT, filtered through a pad of celite and the celite bed was washed with EtOAc (20 mL). The filtrate was concentrated under reduced pressure. The residue was diluted with water (50 mL) and extracted with EtOAc (2×60 mL). The combined organic extracts were washed with brine (30 mL), dried over anhydrous $Na_2SO_4$, filtered and concentrated under reduced pressure. The crude material was purified by silica gel column chromatography eluting with 5% EtOAc/n-hexanes to afford compound 4 (900 mg, 5.55 mmol, 40%) as colorless liquid. $^1$H NMR (400 MHz, $CDCl_3$): δ 8.08 (t, J=1.8 Hz, 1H), 7.92 (dt, J=7.7, 1.4 Hz, 1H), 7.59 (dt, J=7.7, 1.3 Hz, 1H), 7.40 (t, J=7.7 Hz, 1H), 6.75 (dd, J=17.6, 10.9 Hz, 1H), 5.83 (dd, J=17.6, 0.6 Hz, 1H), 5.33 (d, J=10.9 Hz, 1H), 3.93 (s, 3H).

Step-3: Synthesis of Methyl (E)-3-(2-(2-morpholinoethoxy)styryl)benzoate (5). To a stirred solution of compound 3 (500 mg, 1.5 mmol) in acetonitrile (5 mL) were added compound 4 (292 mg, 1.8 mmol) and triethylamine (0.42 mL, 3.0 mmol) in a sealed tube at RT under inert atmosphere. The reaction mixture was purged with argon for 5 min. Then $Pd(PPh_3)_4$ (173 mg, 0.15 mmol) was added to the reaction mixture at RT; the vessel was sealed, gradually heated to 80° C. and stirred for 16 h. The progress of the reaction was monitored by TLC; the starting material was not consumed completely, then the reaction mixture was cooled to RT, another lot of $Pd(PPh_3)_4$ (87 mg, 0.07 mmol) was added; heated to 80° C. and stirred for 3 h. The progress of the reaction was monitored by TLC; after the completion, the reaction mixture was cooled to RT; diluted with EtOAc (30 mL), filtered through a pad of celite and the celite bed was washed with EtOAc (20 mL). The filtrate was concentrated under reduced pressure. The crude material was purified by silica gel column chromatography eluting with 5% MeOH/CH$_2$Cl$_2$ to afford compound 5 (300 mg, 0.82 mmol, 54%) as brown syrupy liquid. The compound was not pure even after column purification. This material was taken to next step without further purification. $^1$H NMR (400 MHz, CDCl$_3$): δ 8.18 (t, J=1.8 Hz, 1H), 7.91 (dt, J=7.8, 1.4 Hz, 1H), 7.71-7.66 (m, 2H), 7.59 (dd, J=7.7, 1.6 Hz, 1H), 7.55-7.45 (m, 2H), 7.45-7.40 (m, 1H), 7.25-7.22 (m, 1H), 7.18 (d, J=16.6 Hz, 1H), 7.02-6.96 (m, 1H), 6.91 (dd, J=8.3, 0.8 Hz, 1H), 4.20 (t, J=5.7 Hz, 2H), 3.95 (s, 3H), 3.77-3.71 (m, 4H), 2.89 (t, J=5.7 Hz, 2H), 2.67-2.62 (m, 4H). LC-MS: m/z 368.2 [M+H]$^+$ at 2.04 RT (82.65% purity).

(br d, J=7.5 Hz, 1H), 7.71-7.66 (m, 1H), 7.54-7.47 (m, 2H), 7.42-7.36 (m, 1H), 7.30-7.24 (m, 1H), 7.07 (d, J=8.1 Hz, 1H), 6.99 (t, J=7.2 Hz, 1H), 4.18 (t, J=5.5 Hz, 2H), 3.62-3.56 (m, 4H), 2.79 (t, J=5.5 Hz, 2H), 2.57-2.53 (m, 4H); $^1$H NMR (500 MHz, DMSO-d$_6$, D$_2$O Exc.): δ 8.08 (s, 1H), 7.82 (d, J=8.1 Hz, 1H), 7.77 (d, J=8.1 Hz, 1H), 7.66 (dd, J=7.5, 1.2 Hz, 1H), 7.53-7.46 (m, 2H), 7.37-7.31 (m, 1H), 7.29-7.22 (m, 1H), 7.04 (d, J=8.1 Hz, 1H), 6.98 (t, J=7.5 Hz, 1H), 4.16 (t, J=5.5 Hz, 2H), 3.60-3.54 (m, 4H), 2.79 (t, J=5.2 Hz, 2H), 2.56-2.54 (m, 4H). LC-MS: m/z 354.3 [M+H]$^+$ at 1.90 RT (99.24% purity). HPLC: 98.04%.

Preparation of VN-365 & VN-385. The synthetic strategy for preparing VN-365 and VN-385 is detailed in the scheme below.

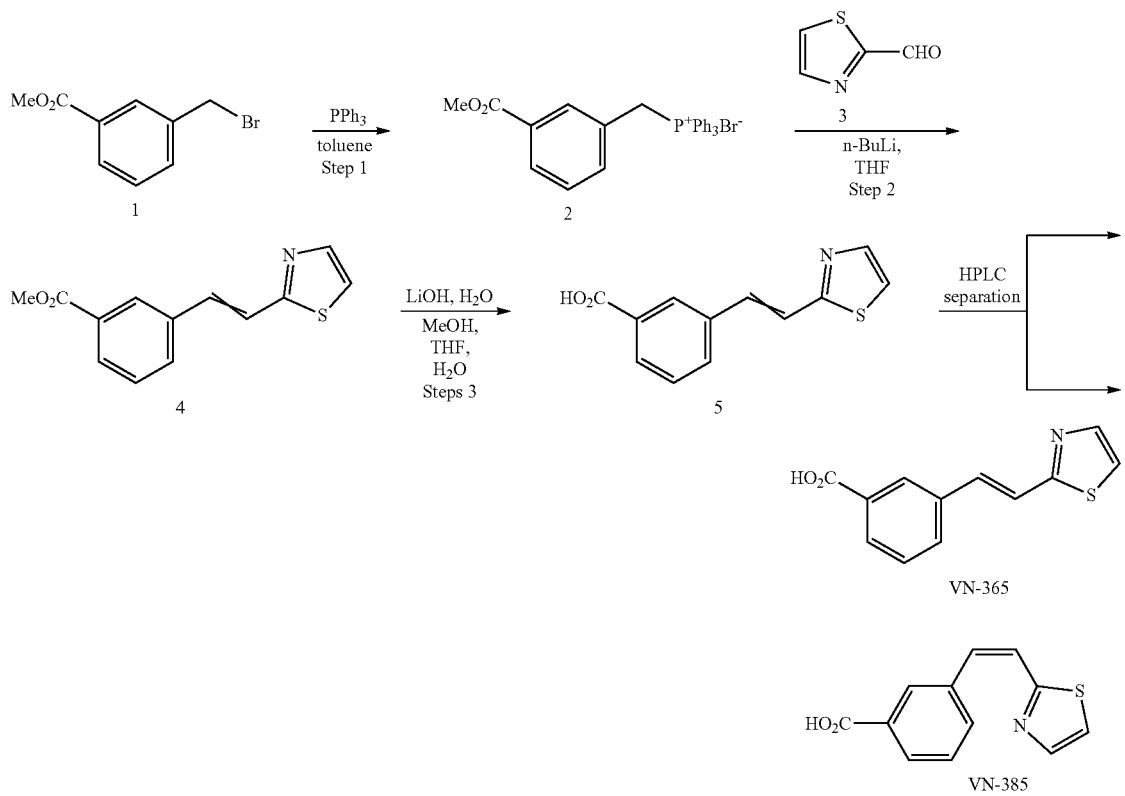

Step-4: Synthesis of (E)-3-(2-(2-morpholinoethoxy)styryl)benzoic acid (VN-384). To a stirred solution of compound 5 (250 mg, impure) in a mixture of THF/methanol (1:1, 8 mL) was added a solution of lithium hydroxide monohydride (86 mg, 2.04 mmol) in water (4 mL) at RT and stirred for 16 h. The progress of the reaction was monitored by TLC; after the completion, the reaction mixture was concentrated under reduced pressure.

The residue was diluted with water (20 mL) and washed with EtOAc (2×10 mL) to remove water insoluble organic impurities. The organic layer was separated; the aqueous layer was neutralized with saturated aqueous citric acid solution and extracted into CH$_2$Cl$_2$ (2×20 mL). The combined organic extracts were dried over anhydrous Na$_2$SO$_4$, filtered and concentrated under reduced pressure. The crude material was purified by triturating with Et$_2$O (2×3 mL) and dried under vacuum to afford VN-384 (80 mg, 0.23 mmol, 34%) as an off white solid. $^1$H NMR (500 MHz, DMSO-d$_6$): δ 13.03 (br s, 1H), 8.11 (s, 1H), 7.83 (d, J=7.5 Hz, 1H), 7.79

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-d$_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(thiazol-2-yl)vinyl)benzoate (4). To a stirred solution of compound 2 (1 g, 2.04 mmol) in THF (10 mL) was added n-BuLi (2.0 M in hexanes, 1.12 mL, 2.24 mmol) at −78° C. under inert atmosphere. The reaction mixture was gradually warmed to RT and stirred for 30 min. Then a solution of thiazole-2- carbaldehyde 3 (231 mg, 2.04 mmol) in THF (5 mL) was added at −78° C. The reaction mixture was gradually warmed to RT and stirred for 16 h. The progress of the reaction was monitored by TLC; after the completion, the reaction mixture was quenched with saturated NH₄Cl solution (20 mL) and extracted with EtOAc (2×30 mL). The combined organic extracts were washed with brine (20 mL), dried over anhydrous Na₂SO₄, filtered and concentrated under reduced pressure. The crude material was purified by silica gel column chromatography eluting with 20% EtOAc/ n-hexanes to afford compound 4 (380 mg, 1.55 mmol, 76%) as a mixture of cis and trans-isomers as colorless syrup. The mixture was taken to next step without further purification. LC-MS: m/z 246.0 [M+H]⁺ at 3.47 RT (68.38% purity) & m/z 246.3 [M+H]⁺ at 3.59 RT (19.02% purity).

Step-3: Synthesis of (E)-3-(2-(thiazol-2-yl)vinyl)benzoic acid (VN-365) & (Z)-3-(2-(thiazol-2-yl)vinyl)benzoic acid (VN-385). To a stirred solution of compound 4 (370 mg, mixture) in a mixture of THF/methanol (1:1, 4 mL) was added a solution of lithium hydroxide monohydride (190 mg, 4.53 mmol) in water (2 mL) at RT and stirred for 6 h. The progress of the reaction was monitored by TLC; after the completion, the reaction mixture was concentrated under reduced pressure. The residue was diluted with water (30 mL) and washed with Et₂O (2×10 mL). The organic layer was separated; the aqueous layer was acidified with 1N HCl solutions to pH ~3-4 and extracted with EtOAc (2×20 mL). The combined organic extracts were dried over anhydrous Na₂SO₄, filtered and concentrated under reduced pressure to obtain the desired compound 5 (280 mg). The crude material was purified by normal phase preparative HPLC (Method V) to afford VN-366 (35 mg, 0.15 mmol, 10%) & VN-393 (60 mg, 0.26 mmol, 17%) as off white solids respectively.

Analytical data of VN-365: ¹H NMR (400 MHz, DMSO-d₆): δ 13.07 (br s, 1H), 8.20 (t, J=1.6 Hz, 1H), 7.98 (dt, J=7.8, 1.3 Hz, 1H), 7.92-7.87 (m, 2H), 7.73 (d, J=3.3 Hz, 1H), 7.59 (d, J=1.1 Hz, 2H), 7.54 (t, J=7.8 Hz, 1H); ¹H NMR (400 MHz, DMSO-d₆, D₂O Exc.): δ 8.16 (t, J=1.6 Hz, 1H), 7.96-7.87 (m, 2H), 7.85 (d, J=3.3 Hz, 1H), 7.67 (d, J=3.3 Hz, 1H), 7.57-7.51 (m, 3H). LC-MS: m/z 232.1 [M+H]⁺ at 2.05 RT (98.56% purity). HPLC: 99.36%.

Analytical data of VN-385: ¹H NMR (400 MHz, DMSO-d₆): δ 12.99 (br s, 1H), 8.05 (t, J=1.6 Hz, 1H), 7.93 (dt, J=7.7, 1.2 Hz, 1H), 7.82 (d, J=3.3 Hz, 1H), 7.81-7.77 (m, 1H), 7.63 (d, J=3.3 Hz, 1H), 7.54 (t, J=7.7 Hz, 1H), 7.02 (d, J=12.3 Hz, 1H), 6.94 (d, J=12.7 Hz, 1H); ¹H NMR (400 MHz, DMSO-d₆, D₂O Exc.): δ 8.00 (s, 1H), 7.93-7.89 (m, 1H), 7.77 (d, J=3.3 Hz, 1H), 7.71-7.67 (m, 1H), 7.57-7.51 (m, 2H), 7.03 (d, J=12.2 Hz, 1H), 6.91 (d, J=12.2 Hz, 1H). LC-MS: m/z 232.1 [M+H]⁺ at 1.98 RT (99.82% purity). HPLC: 99.74%.

Preparation of VN-366 & VN-383. The synthetic strategy for preparing VN-367 and VN-394 is detailed in the scheme below.

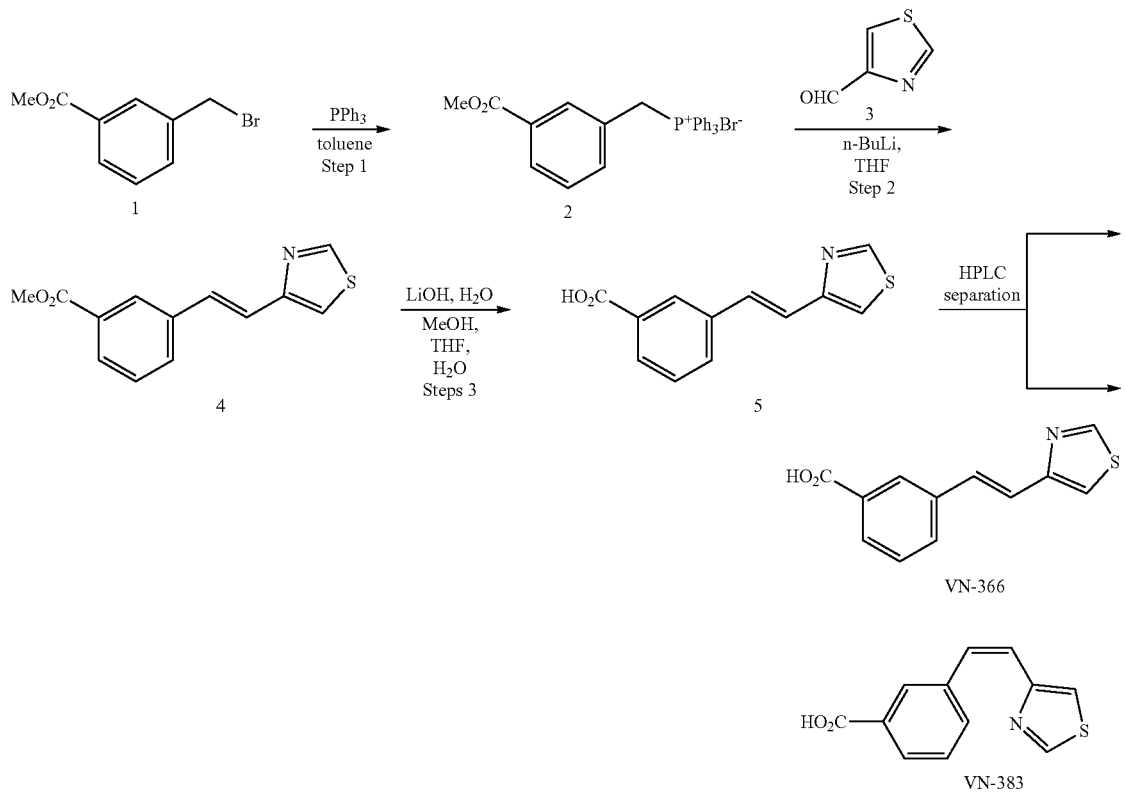

Step-1: Synthesis of (3-(methoxycarbonyl)benzyl)triphenylphosphonium bromide (2). To a stirred solution of methyl 3-(bromomethyl)benzoate 1 (1 g, 4.37 mmol) in toluene (10 mL) was added triphenylphosphine (1.14 g, 4.37 mmol) at RT under inert atmosphere. The reaction mixture was heated to reflux temperature and stirred for 16 h. Then the solid was filtered, washed with toluene (2×10 mL), n-hexanes (2×10 mL) and dried under vacuum to afford compound 2 (1.7 g, 3.47 mmol, 81%) as white solid. ¹H NMR (400 MHz, DMSO-d₆): δ 7.95-7.84 (m, 4H), 7.79-

7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(thiazol-4-yl)vinyl)benzoate (4). To a stirred solution of compound 2 (1.3 g, 2.65 mmol) in THF (10 mL) was added n-BuLi (1.6 M in hexanes, 1.8 mL, 2.88 mmol) at −78° C. under inert atmosphere and stirred at the same temperature for 30 min. The reaction mixture was gradually warmed to RT and stirred for further 30 min. Then a solution of thiazole-4-carbaldehyde 3 (271 mg, 2.4 mmol) in THF (5 mL) was added at −78° C. The reaction mixture was gradually warmed to RT and stirred for 4 h. The progress of the reaction was monitored by TLC; after the completion, the reaction mixture was quenched with saturated $NH_4Cl$ solution (20 mL) at −78° C. and gradually warmed to RT. Then the mixture was diluted with water (20 mL) and extracted with EtOAc (2×40 mL). The combined organic extracts were washed with brine (20 mL), dried over anhydrous $Na_2SO_4$, filtered and concentrated under reduced pressure. The crude material was purified by column purification eluting with 2% EtOAc/n-hexanes to afford compound 4 (438 mg, 1.79 mmol, 74%) as a mixture of cis and trans-isomers as pale yellow liquid. The mixture was taken to next step without further purification. LC-MS: m/z 246.0 [M+H]$^+$ at 3.56 RT (28.18% purity) & m/z 246.0 [M+H]$^+$ at 3.67 RT (27.18% purity).

Step-3: Synthesis of (E)-3-(2-(thiazol-4-yl)vinyl)benzoic acid (VN-366) & (Z)-3-(2-(thiazol-4-yl)vinyl)benzoic acid (VN-383). To a stirred solution of compound 4 (50 mg, mixture) in a mixture of THF/methanol (1:1, 4 mL) was added a solution of lithium hydroxide monohydride (26 mg, 0.61 mmol) in water (2 mL) at RT and stirred for 16 h. The progress of the reaction was monitored by TLC; after the completion, the reaction mixture was concentrated under reduced pressure. The residue was diluted with water (10 mL) and washed with EtOAC (2×5 mL) to remove water insoluble organic impurities. The organic layer was separated; the aqueous layer was neutralized with 1N HCl solutions. The obtained solid was extracted into EtOAc (20 mL). The solvent was removed under reduced pressure followed by triturations with n-pentane (2×5 mL) and dried under vacuum to afford the desired compound 5 (25 mg).

This lot was combined with another lot (SMB-MA1706-014, 200 mg) and was purified by preparative HPLC (Method W) to afford VN-366 (34 mg, 0.15 mmol) & VN-383 (15.5 mg, 0.07 mmol) as off white solids respectively.

Analytical data of VN-366: $^1$H NMR (400 MHz, DMSO-d$_6$): δ 13.03 (br s, 1H), 9.15 (d, J=1.6 Hz, 1H), 8.14 (t, J=1.5 Hz, 1H), 7.85 (dd, J=7.7, 1.7 Hz, 2H), 7.75 (d, J=1.9 Hz, 1H), 7.53-7.51 (m, 1H), 7.50-7.47 (m, 1H), 7.46-7.41 (m, 1H); $^1$H NMR (400 MHz, DMSO-d$_6$, D$_2$O Exc.): δ 9.08 (d, J=1.5 Hz, 1H), 8.09 (t, J=1.6 Hz, 1H), 7.85-7.81 (m, 2H), 7.72 (d, J=1.9 Hz, 1H), 7.53-7.47 (m, 1H), 7.44-7.35 (m, 2H). LC-MS: m/z 232.1 [M+H]$^+$ at 2.07 RT (98.45% purity). HPLC: 96.51%.

Analytical data of VN-383: $^1$H NMR (400 MHz, DMSO-d$_6$): δ 12.89 (br s, 1H), 9.04 (d, J=1.9 Hz, 1H), 7.97 (t, J=1.6 Hz, 1H), 7.82 (dt, J=7.8, 1.4 Hz, 1H), 7.67 (dt, J=7.7, 1.4 Hz, 1H), 7.51 (d, J=1.9 Hz, 1H), 7.43 (t, J=7.7 Hz, 1H), 6.73 (s, 2H); $^1$H NMR (400 MHz, DMSO-d$_6$, D$_2$O Exc.): δ 8.96 (d, J=2.0 Hz, 1H), 7.93 (t, J=1.6 Hz, 1H), 7.80 (dt, J=7.7, 1.4 Hz, 1H), 7.61 (dt, J=7.9, 1.4 Hz, 1H), 7.45-7.40 (m, 2H), 6.71 (s, 2H). LC-MS: m/z 232.1 [M+H]$^+$ at 2.01 RT (99.71% purity). HPLC: 99.75%.

Preparation of VN-367 & VN-386. The synthetic strategy for preparing VN-367 and VN-386 is detailed in the scheme below.

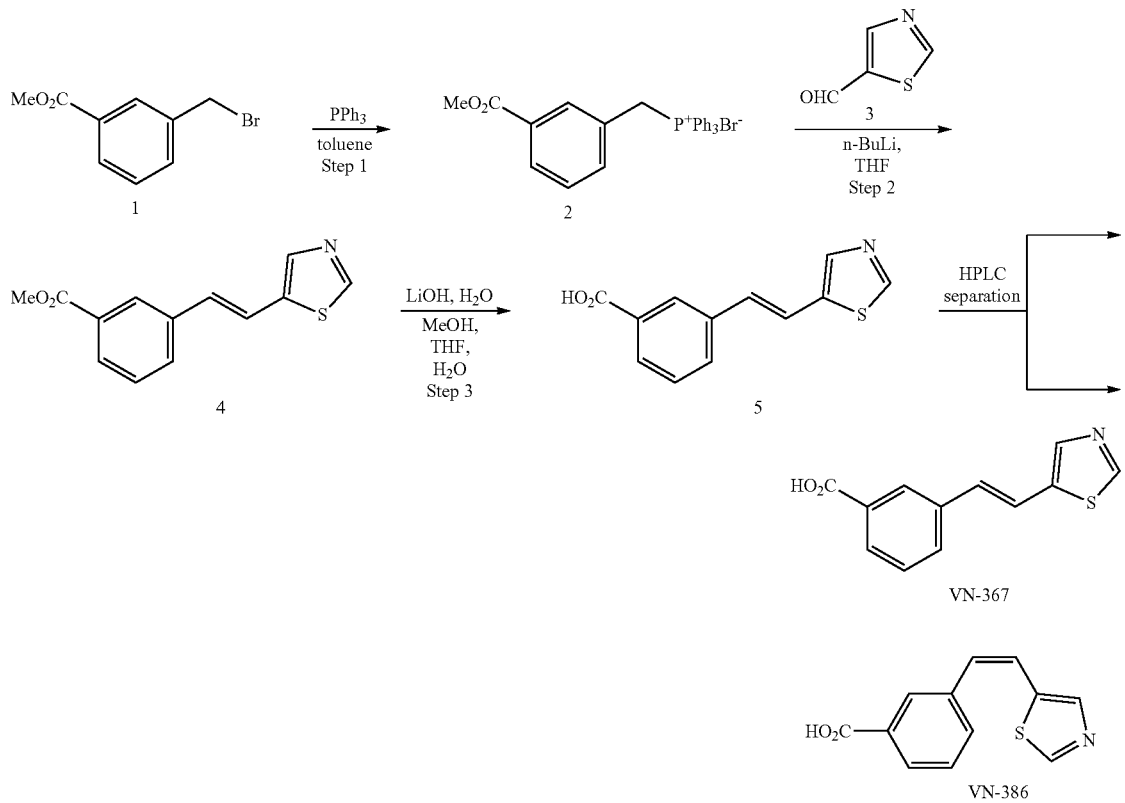

Step-1: Synthesis of (3-(methoxycarbonyl)benzyl)triphenylphosphonium bromide (2). To a stirred solution of methyl 3-(bromomethyl)benzoate 1 (1 g, 4.37 mmol) in toluene (10 mL) was added triphenylphosphine (1.14 g, 4.37 mmol) at RT under inert atmosphere. The reaction mixture was heated to reflux temperature and stirred for 16 h. Then the solid was filtered, washed with toluene (2×10 mL), n-hexanes (2×10 mL) and dried under vacuum to afford compound 2 (1.7 g, 3.47 mmol, 81%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(thiazol-5-yl)vinyl)benzoate (4). To a stirred solution of compound 2 (1.3 g, 2.65 mmol) in THF (10 mL) was added n-BuLi (1.6 M in hexanes, 1.8 mL, 2.89 mmol) at −78° C. under inert atmosphere and stirred at the same temperature for 30 min. The reaction mixture was gradually warmed to RT and stirred for further 30 min. Then a solution of thiazole-5-carbaldehyde 3 (0.2 mL, 2.41 mmol) in THF (5 mL) was added at −78° C. The reaction mixture was gradually warmed to RT and stirred for 16 h. The progress of the reaction was monitored by TLC; after the completion, the reaction mixture was quenched with saturated NH$_4$Cl solution (20 mL) at −78° C. and gradually warmed to RT. Then the mixture was diluted with water (20 mL) and extracted with EtOAc (2×40 mL). The combined organic extracts were washed with brine (20 mL), dried over anhydrous Na$_2$SO$_4$, filtered and concentrated under reduced pressure. The crude material was purified by silica gel column chromatography eluting with 2% EtOAc/n-hexanes to afford compound 4 (400 mg, 1.63 mmol, 62%) as a mixture of cis and trans-isomers as pale yellow liquid. The mixture was taken to next step without further purification. LC-MS: m/z 246.1 [M+H]$^+$ at 2.37 RT (29.67% purity) & m/z 246.1 [M+H]$^+$ at 2.44 RT (40.16% purity).

Step-3: Synthesis of (E)-3-(2-(thiazol-5-yl)vinyl)benzoic acid (VN-367) & (Z)-3-(2-(thiazol-5-yl)vinyl)benzoic acid (VN-386). To a stirred solution of compound 4 (50 mg, mixture) in a mixture of THF/methanol (1:1, 2 mL) was added a solution of lithium hydroxide monohydride (26 mg, 0.61 mmol) in water (1 mL) at RT and stirred for 16 h. The progress of the reaction was monitored by TLC; after the completion, the reaction mixture was concentrated under reduced pressure. The residue was diluted with water (10 mL) and washed with EtOAC (2×5 mL) to remove water insoluble organic impurities. The organic layer was separated; the aqueous layer was neutralized with 1N HCl solutions. The obtained solid was extracted into EtOAc (20 mL). The solvent was removed under reduced pressure followed by triturations with Et$_2$O (2×5 mL) and dried under vacuum to afford the desired compound 5 (35 mg).

This lot was combined with another lot (SMB-MA1706-015, 300 mg) and was purified by preparative HPLC (Method X) to afford VN-367 (46 mg, 0.2 mmol) & VN-386 (98 mg, 0.42 mmol) as off white solids respectively.

Analytical data of VN-367: $^1$H NMR (400 MHz, DMSO-$d_6$): δ 13.04 (br s, 1H), 9.02 (s, 1H), 8.15 (s, 1H), 8.03 (s, 1H), 7.87-7.82 (m, 2H), 7.64 (d, J=16.3 Hz, 1H), 7.51 (t, J=7.7 Hz, 1H), 7.11 (d, J=16.2 Hz, 1H); $^1$H NMR (400 MHz, DMSO-$d_6$, D$_2$O Exc.): δ 8.95 (s, 1H), 8.09 (s, 1H), 8.00 (s, 1H), 7.85-7.80 (m, 2H), 7.58 (d, J=16.2 Hz, 1H), 7.50 (t, J=7.7 Hz, 1H), 7.08 (d, J=16.2 Hz, 1H). LC-MS: m/z 232.1 [M+H]$^+$ at 2.02 RT (98.68% purity). HPLC: 99.64%.

Analytical data of VN-386: $^1$H NMR (400 MHz, DMSO-$d_6$): δ 13.02 (br s, 1H), 8.84 (s, 1H), 7.95-7.84 (m, 3H), 7.57-7.49 (m, 2H), 6.96 (d, J=11.9 Hz, 1H), 6.81 (d, J=11.9 Hz, 1H); $^1$H NMR (400 MHz, DMSO-$d_6$, D$_2$O Exc.): δ 8.76 (s, 1H), 7.92-7.79 (m, 3H), 7.57-7.47 (m, 2H), 6.93 (d, J=12.0 Hz, 1H), 6.79 (d, J=11.8 Hz, 1H). LC-MS: m/z 232.1 [M+H]$^+$ at 2.00 RT (98.25% purity). HPLC: 98.87%.

Preparation of VN-368 & VN-373. The synthetic strategy for preparing VN-369 and VN-374 is detailed in the scheme below.

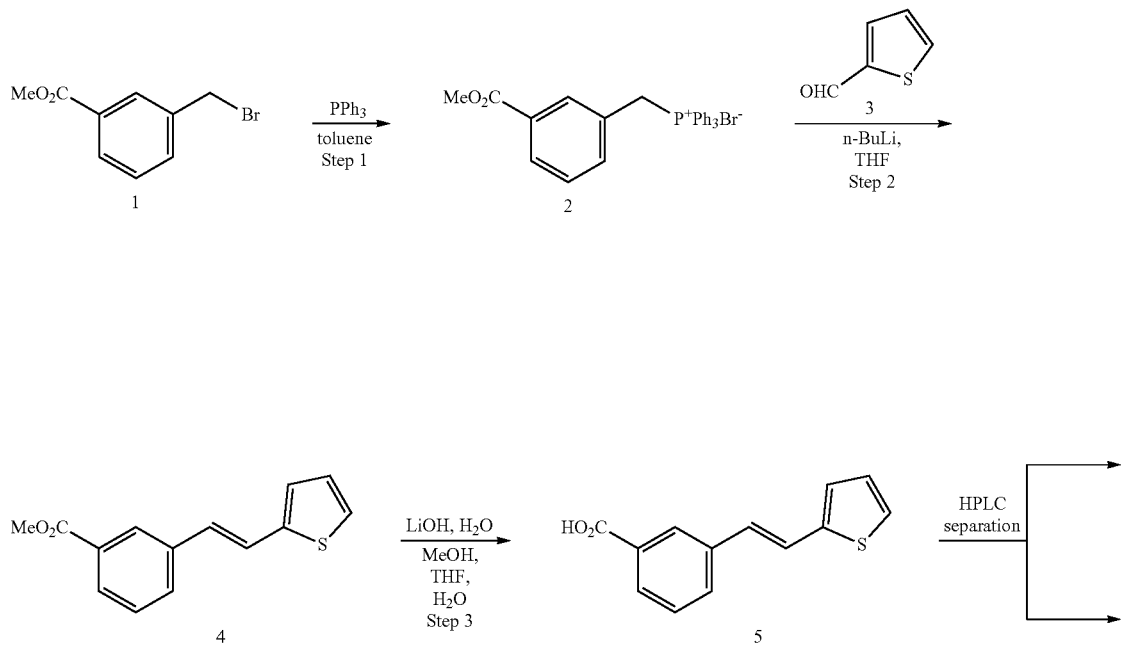

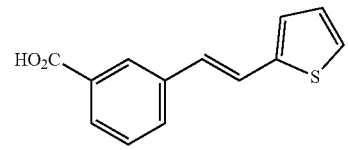

VN-368

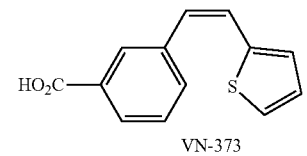

VN-373

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(thiophen-2-yl)vinyl)benzoate (4). To a stirred solution of compound 2 (400 mg, 0.82 mmol) in THF (10 mL) was added n-BuLi (2.5 M in hexanes, 0.36 mL, 0.9 mmol) at −78° C. under inert atmosphere. The reaction mixture was gradually warmed to RT and stirred for 30 min. Then a solution of thiophene-2-carbaldehyde 3 (91 mg, 0.82 mmol) in THF (2 mL) was added at −78° C. The reaction mixture was gradually warmed to RT and stirred for 16 h. The progress of the reaction was monitored by TLC, after the completion, the reaction mixture was quenched with saturated NH$_4$Cl solution (15 mL) and extracted with EtOAc (2×20 mL). The combined organic extracts were washed with brine (15 mL), dried over anhydrous Na$_2$SO$_4$, filtered and concentrated under reduced pressure. The crude material was purified by silica gel column chromatography (eluent: 10% EtOAc/n-hexanes) to afford compound 4 (90 mg, 0.37 mmol, 47%) as a mixture of cis and trans-isomers as colorless syrup. LC-MS: m/z 245.1 [M+H]$^+$ at 4.29 RT (44.77% purity) & m/z 245.4 [M+H]$^+$ at 4.39 RT (41.71% purity).

Step-3: Synthesis of (E)-3-(2-(thiophen-2-yl)vinyl)benzoic acid (VN-368) & (Z)-3-(2-(thiophen-2-yl)vinyl)benzoic acid (VN-373). To a stirred solution of compound 4 (210 mg, mixture) in a mixture of THF (0.5 mL) and methanol (0.7 mL) was added a solution of lithium hydroxide monohydride (108 mg, 2.58 mmol) in water (0.5 mL) at RT and stirred for 6 h. The progress of the reaction was monitored by TLC, after the completion, the reaction mixture was concentrated under reduced pressure. The residue was diluted with water (15 mL) and extracted with ether (2×10 mL). The organic layer was separated and the aqueous layer was acidified with 2 N HCl solutions to pH ~3-4 and extracted with EtOAc (2×20 mL). The combined organic extracts were dried over anhydrous Na$_2$SO$_4$, filtered and concentrated under reduced pressure. The crude material was purified by normal phase preparative HPLC (Method C) to afford VN-368 (45 mg, 0.19 mmol, 23%) & VN-373 (35 mg, 0.15 mmol, 18%) as off white solids respectively.

Analytical data of VN-368: $^1$H NMR (400 MHz, DMSO-$d_6$): δ 13.02 (br s, 1H), 8.11 (s, 1H), 7.82 (dd, J=7.8, 1.2 Hz, 2H), 7.58-7.45 (m, 3H), 7.29-7.26 (m, 1H), 7.08 (dd, J=5.0, 3.5 Hz, 1H), 7.03 (d, J=16.3 Hz, 1H); $^1$H NMR (400 MHz, DMSO-$d_6$, D$_2$O Exc.): δ 8.05 (s, 1H), 7.79 (br d, J=7.8 Hz, 2H), 7.52-7.41 (m, 3H), 7.25 (d, J=3.3 Hz, 1H), 7.05 (dd, J=5.0, 3.6 Hz, 1H), 6.99 (d, J=16.3 Hz, 1H). LC-MS: m/z 228.7 [M−H]$^−$ at 2.63 RT (99.01% purity). HPLC: 97.03%.

Analytical data of VN-373: $^1$H NMR (400 MHz, DMSO-$d_6$): δ 12.98 (br s, 1H), 7.93-7.86 (m, 2H), 7.60-7.48 (m, 2H), 7.35 (d, J=5.0 Hz, 1H), 7.09 (d, J=3.5 Hz, 1H), 6.96 (dd, J=5.1, 3.6 Hz, 1H), 6.86 (d, J=12.0 Hz, 1H), 6.63 (d, J=12.0 Hz, 1H); $^1$H NMR (400 MHz, DMSO-$d_6$, D$_2$O Exc.): δ 7.91-7.83 (m, 2H), 7.55-7.47 (m, 2H), 7.26 (d, J=5.0 Hz, 1H), 7.05 (d, J=3.4 Hz, 1H), 6.93 (dd, J=5.1, 3.6 Hz, 1H), 6.83 (d, J=11.9 Hz, 1H), 6.60 (d, J=11.9 Hz, 1H). LC-MS: m/z 228.7 [M−H]$^−$ at 2.59 RT (97.55% purity). HPLC: 98.26%.

Preparation of VN-369 & VN-374. The synthetic strategy for preparing VN-370 and VN-375 is detailed in the scheme below.

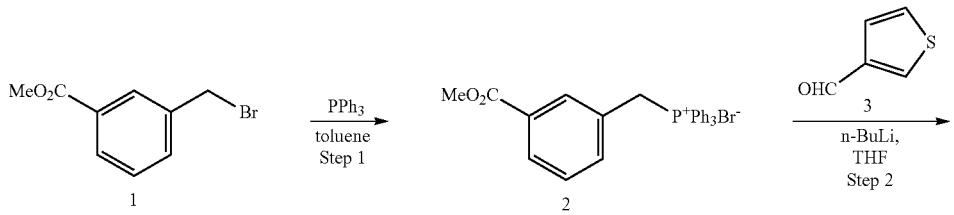

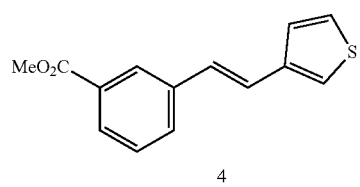 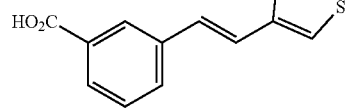 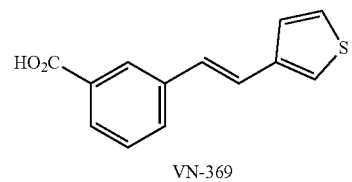

VN-369

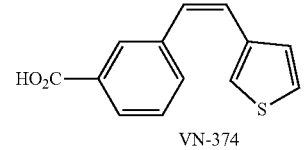

VN-374

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-d$_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(2-(thiophen-3-yl)vinyl)benzoate (4). To a stirred solution of compound 2 (500 mg, 1.02 mmol) in THF (10 mL) was added n-BuLi (2.5 M in hexanes, 0.82 mL, 2.04 mmol) at −78° C. under inert atmosphere. The reaction mixture was gradually warmed to RT and stirred for 1 h. Then a solution of thiophene-3-carbaldehyde 3 (137 mg, 1.22 mmol) in THF (5 mL) was added at −78° C. The reaction mixture was gradually warmed to RT and stirred for 16 h. The progress of the reaction was monitored by TLC, after the completion, the reaction mixture was quenched with saturated NH$_4$Cl solution (20 mL) and extracted with EtOAc (2×25 mL). The combined organic extracts were washed with brine (15 mL), dried over anhydrous Na$_2$SO$_4$, filtered and concentrated under reduced pressure. The crude material was purified by combi-flash column chromatography (eluent: 5% EtOAc/n-hexanes) to afford compound 4 (100 mg, 0.41 mmol, 40%) as a mixture of cis and trans-isomers as colorless syrup. LC-MS: m/z 245.1 [M+H]$^+$ at 4.46 RT (62.36% purity).

Step-3: Synthesis of (E)-3-(2-(thiophen-3-yl)vinyl)benzoic acid (VN-369) & (Z)-3-(2-(thiophen-3-yl)vinyl)benzoic acid (VN-374). To a stirred solution of compound 4 (100 mg, mixture) in a mixture of THF/methanol (1:1, 3 mL) was added a solution of lithium hydroxide monohydride (34 mg, 0.82 mmol) in water (1.5 mL) at 0° C. and stirred at RT for 16 h. The progress of the reaction was monitored by TLC, after the completion, the reaction mixture was concentrated under reduced pressure. The residue was diluted with water (20 mL) and extracted with ether (2×5 mL). The organic layer was separated and the aqueous layer was acidified with 5 N HCl solutions to pH ~3-2 and extracted with EtOAc (2×20 mL). The combined organic extracts were dried over anhydrous Na$_2$SO$_4$, filtered and concentrated under reduced pressure. The crude material was purified by combi-flash column chromatography followed by preparative HPLC purification (Method Q) to afford VN-369 (30 mg, 0.13 mmol, 32%) & VN-374 (38 mg, 0.16 mmol, 40%) as off white solids respectively.

Analytical data of VN-369: $^1$H NMR (400 MHz, DMSO-d$_6$): δ 13.03 (br s, 1H), 8.10 (s, 1H), 7.83-7.77 (m, 2H), 7.65-7.60 (m, 1H), 7.60-7.56 (m, 1H), 7.54-7.46 (m, 2H), 7.40-7.32 (m, 1H), 7.22-7.15 (m, 1H); $^1$H NMR (400 MHz, DMSO-d$_6$, D$_2$O Exc.): δ 8.03 (s, 1H), 7.81-7.75 (m, 2H), 7.57-7.53 (m, 1H), 7.51-7.43 (m, 3H), 7.32-7.25 (m, 1H), 7.12-7.06 (m, 1H). LC-MS: m/z 228.7 [M−H]$^−$ at 2.53 RT (99.11% purity). HPLC: 98.96%.

Analytical data of VN-374: $^1$H NMR (500 MHz, DMSO-d$_6$): δ 12.97 (br s, 1H), 7.88-7.80 (m, 2H), 7.52-7.37 (m, 4H), 6.77 (d, J=5.2 Hz, 1H), 6.70-6.59 (m, 2H); $^1$H NMR (500 MHz, DMSO-d$_6$, D$_2$O Exc.): δ 7.85-7.79 (m, 2H), 7.50-7.41 (m, 2H), 7.39-7.34 (m, 2H), 6.74 (d, J=4.6 Hz, 1H), 6.67-6.58 (m, 2H). LC-MS: m/z 228.7 [M−H]$^−$ at 2.50 RT (98.50% purity). HPLC: 99.66%.

Preparation of VN-390 & VN-372. The synthetic strategy for preparing VN-390 and VN-372 is detailed in the scheme below.

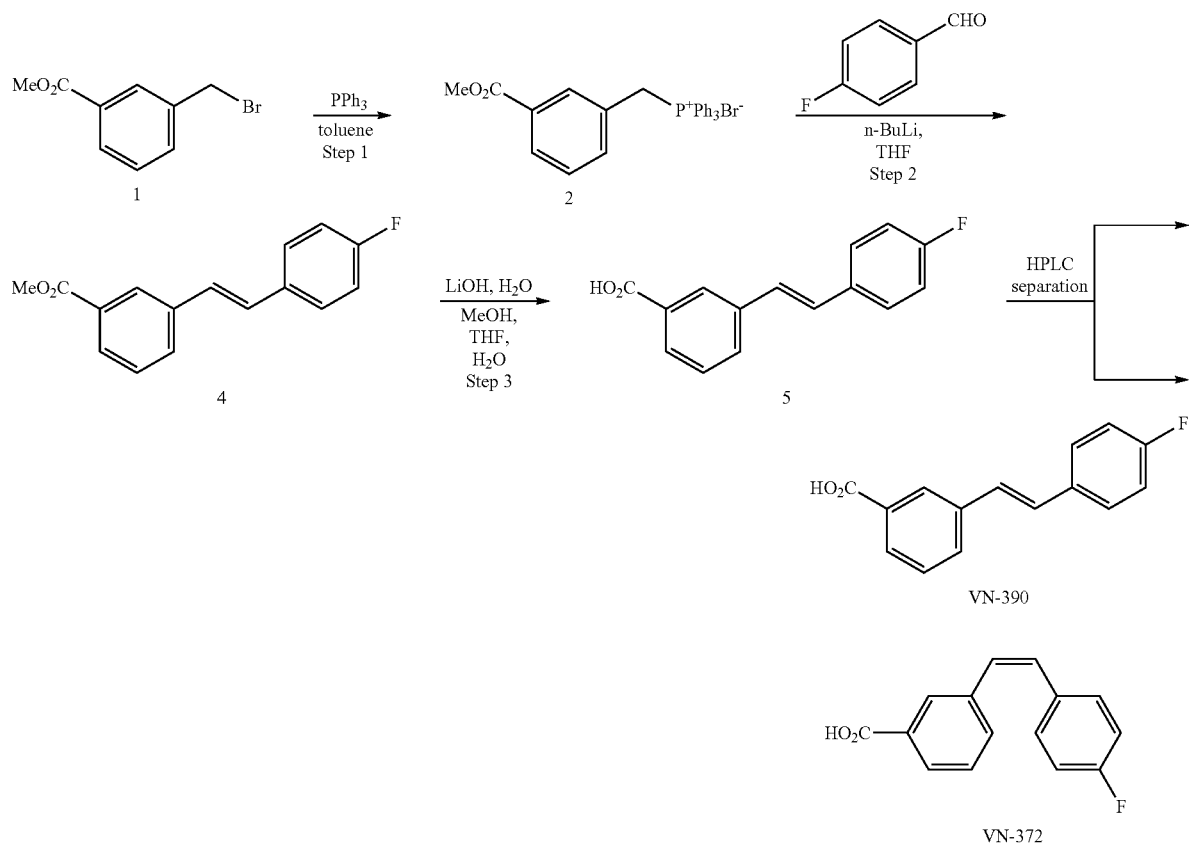

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(4-fluorostyryl)benzoate (4). To a stirred solution of compound 2 (200 mg, 0.41 mmol) in THF (10 mL) was added n-BuLi (2.5 M in hexanes, 0.18 mL, 0.45 mmol) at −78° C. under inert atmosphere. The reaction mixture was gradually warmed to RT and stirred for 20 min. Then a solution of 4-fluorobenzaldehyde 3 (51 mg, 0.41 mmol) in THF (2 mL) was added at −78° C. The reaction mixture was gradually warmed to RT and stirred for 16 h. The progress of the reaction was monitored by TLC, after the completion, the reaction mixture was quenched with saturated NH$_4$Cl solution (20 mL) and extracted with EtOAc (2×20 mL). The combined organic extracts were washed with brine (15 mL), dried over anhydrous Na$_2$SO$_4$, filtered and concentrated under reduced pressure to obtain the crude (~200 mg). This lot was combined with another lot (SMB-MA1704-068, 300 mg crude) and was purified by silica gel column chromatography (eluent: 5% EtOAc/n-hexanes) to afford compound 4 (210 mg, 0.82 mmol, 80%) as a mixture of cis and trans-isomers as colorless liquid. LC-MS: m/z 257.2 [M+H]$^+$ at 4.48 RT (95.93% purity).

Step-3: Synthesis of (E)-3-(4-fluorostyryl)benzoic acid (VN-390) & (Z)-3-(4-fluorostyryl)benzoic acid (VN-372). To a stirred solution of compound 4 (100 mg, mixture) in a mixture of THF/methanol (1:1, 1 mL) was added a solution of lithium hydroxide monohydride (25 mg, 0.58 mmol) in water (0.5 mL) at RT and stirred for 5 h. The progress of the reaction was monitored by TLC, after the completion, the reaction mixture was concentrated under reduced pressure. The residue was diluted with water (10 mL) and extracted with ether (2×10 mL). The organic layer was separated and the aqueous layer was acidified with 2 N HCl solutions to pH ~3-4 and extracted with EtOAc (2×20 mL). The combined organic extracts were dried over anhydrous Na$_2$SO$_4$, filtered and concentrated under reduced pressure to obtain the crude (~100 mg). This batch was repeated with 100 mg to obtain the crude (~100 mg).

These crude materials (~100 mg each) was combined and was purified by normal phase preparative HPLC (Method D) to afford VN-390 (40 mg, 0.16 mmol, 21%) & VN-372 (50 mg, 0.21 mmol, 26%) as off white solids respectively.

Analytical data of VN-390: $^1$H NMR (400 MHz, DMSO-$d_6$): δ 13.02 (br s, 1H), 8.14 (s, 1H), 7.86-7.81 (m, 2H), 7.73-7.67 (m, 2H), 7.51 (t, J=7.7 Hz, 1H), 7.38-7.27 (m, 2H), 7.23 (t, J=8.9 Hz, 2H); $^1$H NMR (400 MHz, DMSO-$d_6$, D$_2$O Exc.): δ 8.10 (s, 1H), 7.83 (t, J=7.2 Hz, 2H), 7.67 (dd, J=8.2, 5.8 Hz, 2H), 7.51 (t, J=7.7 Hz, 1H), 7.33-7.14 (m, 4H). LC-MS: m/z 240.7 [M−H]$^−$ at 2.80 RT (99.39% purity). HPLC: 99.22%.

Analytical data of VN-372: $^1$H NMR (400 MHz, DMSO-d$_6$): δ 12.94 (br s, 1H), 7.81-7.77 (m, 2H), 7.44-7.36 (m, 2H), 7.26-7.20 (m, 2H), 7.14-7.07 (m, 2H), 6.70 (s, 2H); $^1$H NMR (400 MHz, DMSO-d$_6$, D$_2$O Exc.): δ 7.78-7.70 (m, 2H), 7.43-7.35 (m, 2H), 7.20-7.14 (m, 2H), 7.07-6.99 (m, 2H), 6.66 (s, 2H). LC-MS: m/z 240.8 [M−H]$^−$ at 2.74 RT (99.18% purity). HPLC: 99.48%.

Preparation of VN-371 & VN-379. The synthetic strategy for preparing VN-371 and VN-379 is detailed in the scheme below.

stirred solution of compound 2 (800 mg, 1.63 mmol) in THF (15 mL) was added n-BuLi (2.5 M in hexanes, 1.31 mL, 3.26 mmol) at −78° C. under inert atmosphere. The reaction mixture was gradually warmed to RT and stirred for 1 h. Then a solution of 4-chlorobenzaldehyde 3 (228 mg, 1.63 mmol) in THF (5 mL) was added at −78° C. The reaction mixture was gradually warmed to RT and stirred for 16 h. The progress of the reaction was monitored by TLC, after the completion, the reaction mixture was quenched with saturated NH$_4$Cl solution (20 mL) at 0° C. and extracted

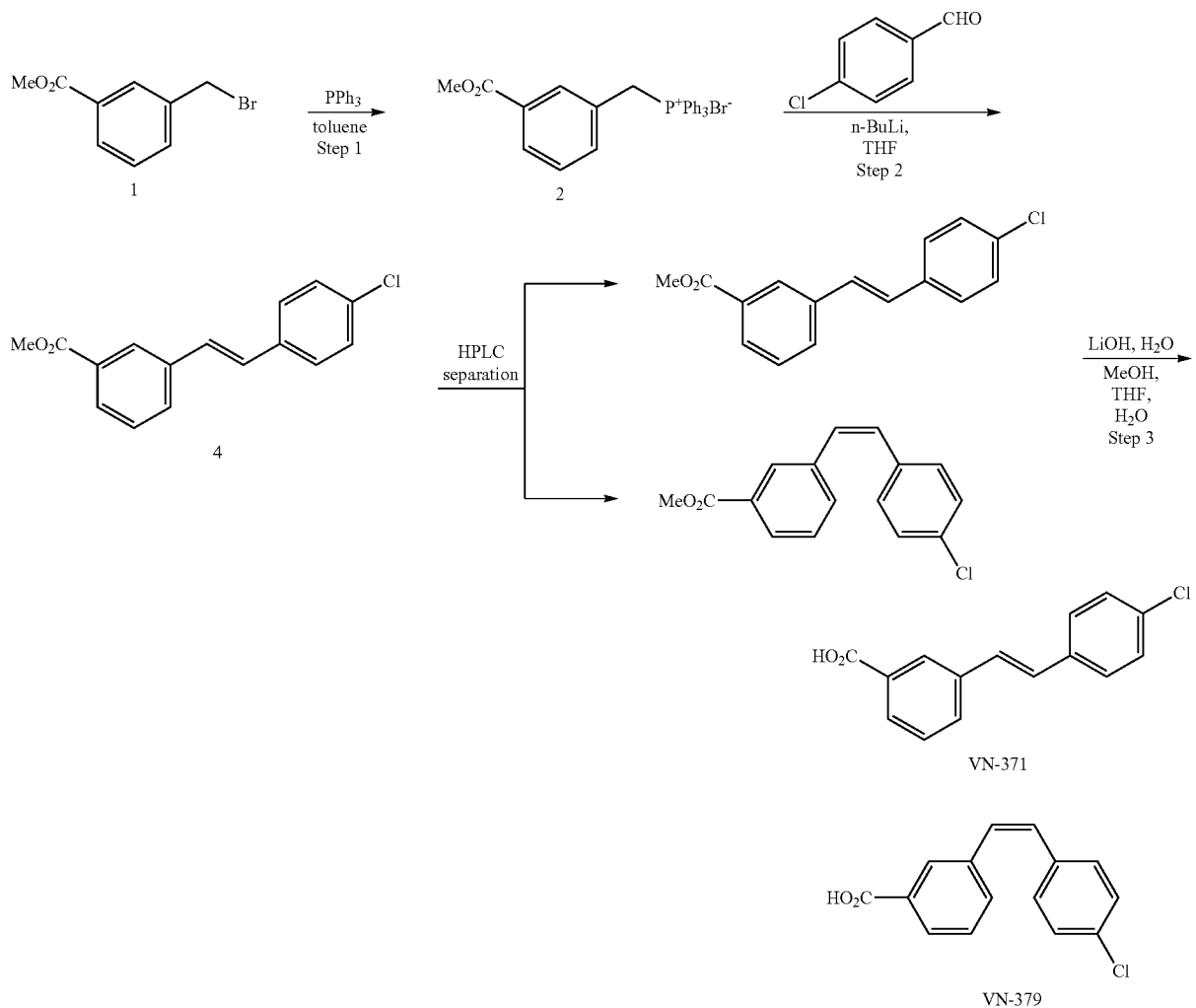

Step-1: Synthesis of (3-(methoxycarbonyl)benzyl)triphenylphosphonium bromide (2). To a stirred solution of methyl 3-(bromomethyl)benzoate 1 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (8.8 g, 17.91 mmol, 83%) as white solid. $^1$H NMR (400 MHz, DMSO-d$_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-2: Synthesis of Methyl (E)-3-(4-chlorostyryl)benzoate (4E) & methyl (Z)-3-(4-chlorostyryl)benzoate (4Z). To a with EtOAc (2×25 mL). The combined organic extracts were washed with brine (15 mL), dried over anhydrous Na$_2$SO$_4$, filtered and concentrated under reduced pressure. The crude material was purified by silica gel column chromatography (eluent: 10% EtOAc/n-hexanes) to afford a mixture of cis and trans-isomers as a pale yellow semi solid. This material was further purified by preparative HPLC (Method E) to afford compound 4E (80 mg, 0.29 mmol, 18%) & 4Z (90 mg, 0.33 mmol, 20%) as an off white solid and colorless liquid respectively.

Analytical data of 4E: $^1$H NMR (400 MHz, DMSO-d$_6$): δ8.16 (s, 1H), 7.94-7.84 (m, 2H), 7.68 (d, J=8.5 Hz, 2H), 7.54 (t, J=7.7 Hz, 1H), 7.48-7.31 (m, 4H), 3.88 (s, 3H). LC-MS: [M+H]$^+$ not observed; no ionisation at 4.82 RT (98.97% purity). HPLC: 100.00%.

Analytical data of 4Z: $^1$H NMR (400 MHz, DMSO-d6): δ 7.84-7.80 (m, 2H), 7.48-7.40 (m, 2H), 7.33 (d, J=8.5 Hz, 2H), 7.20 (d, J=8.4 Hz, 2H), 6.78-6.68 (m, 2H), 3.81 (s, 3H). LC-MS: m/z 273.2 [M+H]$^+$ at 4.79 RT (93.62% purity). HPLC: 100.00%.

Step-3: Synthesis of (E)-3-(4-chlorostyryl)benzoic acid (VN-371). To a stirred solution of compound 4E (80 mg, 0.29 mmol) in a mixture of THF/methanol (1:1, 1 mL) was added a solution of lithium hydroxide monohydride (37 mg, 0.88 mmol) in water (0.5 mL) at 0° C. and stirred at RT for 16 h. The progress of the reaction was monitored by TLC, after the completion, the reaction mixture was concentrated under reduced pressure. The residue was diluted with water (10 mL) and extracted with ether (2×5 mL). The organic layer was separated and the aqueous layer was acidified with 6 N HCl solutions to pH ~3-2 and extracted with 10% MeOH/CH$_2$Cl$_2$ (2×20 mL). The combined organic extracts were dried over anhydrous Na$_2$SO$_4$, filtered and concentrated under reduced pressure to afford VN-371 (20 mg, 0.08 mmol, 26%) as an off white solid. $^1$H NMR (400 MHz, DMSO-d$_6$): δ 8.15 (s, 1H), 7.87-7.80 (m, 2H), 7.67 (d, J=8.5 Hz, 2H), 7.52-7.42 (m, 3H), 7.41-7.29 (m, 2H); $^1$H NMR (400 MHz, DMSO-d$_6$, D$_2$O Exc.): δ 8.11 (s, 1H), 7.83 (dt, J=7.7, 1.7 Hz, 2H), 7.65 (d, J=8.5 Hz, 2H), 7.49 (t, J=7.7 Hz, 1H), 7.42 (d, J=8.5 Hz, 2H), 7.37-7.25 (m, 2H). LC-MS: m/z 257.0 [M−H]$^−$ at 2.65 RT (98.69% purity). HPLC: 99.36%.

Step-4: Synthesis of (Z)-3-(4-chlorostyryl)benzoic acid (VN-379). To a stirred solution of compound 4Z (80 mg, 0.29 mmol) in a mixture of THF/methanol (1:1, 1 mL) was added a solution of lithium hydroxide monohydride (37 mg, 0.88 mmol) in water (0.5 mL) at 0° C. and stirred at RT for 16 h. The progress of the reaction was monitored by TLC, after the completion, the reaction mixture was concentrated under reduced pressure. The residue was diluted with water (10 mL) and extracted with ether (2×5 mL). The organic layer was separated and the aqueous layer was acidified with 6 N HCl solutions to pH ~3-2 and extracted with 10% MeOH/CH$_2$Cl$_2$ (2×20 mL). The combined organic extracts were dried over anhydrous Na$_2$SO$_4$, filtered and concentrated under reduced pressure to afford VN-379 (70 mg, 0.27 mmol, 92%) as an off white solid. $^1$H NMR (400 MHz, DMSO-d$_6$): δ 7.82-7.77 (m, 2H), 7.42-7.37 (m, 2H), 7.35-7.30 (m, 2H), 7.21 (d, J=8.3 Hz, 2H), 6.77-6.72 (m, 1H), 6.71-6.65 (m, 1H); $^1$H NMR (400 MHz, DMSO-d$_6$, D$_2$O Exc.): δ 7.80-7.71 (m, 2H), 7.41-7.36 (m, 2H), 7.31-7.25 (m, 2H), 7.20-7.14 (m, 2H), 6.75-6.68 (m, 1H), 6.68-6.62 (m, 1H). LC-MS: m/z 256.8 [M−H]$^−$ at 2.57 RT (98.16% purity). HPLC: 98.11%.

Preparation of VN-375 & VN-378. The synthetic strategy for preparing VN-375 and VN-378 is detailed in the scheme below.

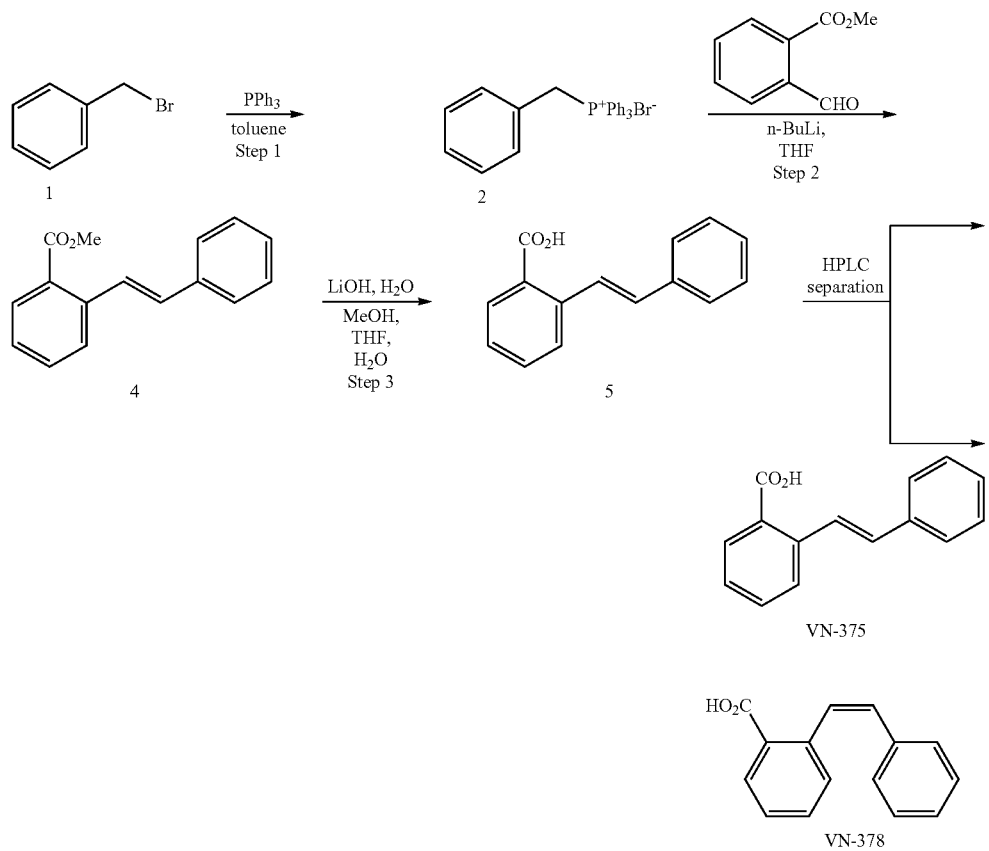

Step-1: Synthesis of Benzyltriphenylphosphonium bromide (2). To a stirred solution of (bromomethyl)benzene 1 (5 g, 29.07 mmol) in toluene (50 mL) was added triphenylphosphine (7.62 g, 29.07 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 2 (11 g, 25.38 mmol, 88%) as white solid. $^1$H NMR (400 MHz, DMSO-d$_6$): δ 7.95-7.86 (m, 3H), 7.79-7.63 (m, 12H), 7.33-7.26 (m, 1H), 7.26-7.20 (m, 2H), 7.00-6.96 (m, 2H), 5.22-5.16 (m, 2H).

Step-2: Synthesis of Methyl (E)-2-styrylbenzoate (4). To a stirred solution of compound 2 (700 mg, 1.62 mmol) in THF (10 mL) was added n-BuLi (2.0 M in hexanes, 0.89 mL, 1.78 mmol) at −78° C. under inert atmosphere. The reaction mixture was gradually warmed to RT and stirred for 30 min. Then a solution of methyl 2-formylbenzoate 3 (266 mg, 1.62 mmol) in THF (5 mL) was added at −78° C. The reaction mixture was gradually warmed to RT and stirred for 6 h. The progress of the reaction was monitored by TLC, after the completion, the reaction mixture was quenched with saturated NH$_4$Cl solution (20 mL) and extracted with EtOAc (2×20 mL). The combined organic extracts were washed with brine (15 mL), dried over anhydrous Na$_2$SO$_4$, filtered and concentrated under reduced pressure. The crude material was purified by silica gel column chromatography (eluent: 5% EtOAc/n-hexanes) to afford compound 4 (210 mg, 0.88 mmol, 52%) as a mixture of cis and trans-isomers as colorless syrup. LC-MS: m/z 239.2 [M+H]$^+$ at 4.40 RT (28.23% purity) & m/z 239.0 [M+H]$^+$ at 4.51 RT (69.37% purity).

Step-3: Synthesis of (E)-2-styrylbenzoic acid (VN-375) & (Z)-2-styrylbenzoic acid (VN-378). To a stirred solution of compound 4 (100 mg, mixture) in a mixture of THF/methanol (1:1, 3 mL) was added a solution of lithium hydroxide monohydride (53 mg, 1.26 mmol) in water (1.5 mL) at RT and stirred for 6 h. The progress of the reaction was monitored by TLC, after the completion, the reaction mixture was concentrated under reduced pressure. The residue was diluted with water (10 mL) and extracted with ether (2×7 mL). The organic layer was separated and the aqueous layer was acidified with 2 N HCl solutions to pH ~3-4 and extracted with EtOAc (2×20 mL). The combined organic extracts were dried over anhydrous Na$_2$SO$_4$, filtered and concentrated under reduced pressure to obtain the crude (~100 mg).

This crude material was combined with another lot (~100 mg crude) and was purified by normal phase preparative HPLC (Method F) to afford VN-375 (80 mg, 0.36 mmol, 42%) & VN-378 (30 mg, 0.13 mmol, 16%) as off white solids respectively.

Analytical data of VN-375: $^1$H NMR (400 MHz, DMSO-d$_6$): δ 13.03 (br s, 1H), 7.92 (d, J=16.3 Hz, 1H), 7.87-7.82 (m, 2H), 7.60-7.53 (m, 3H), 7.44-7.36 (m, 3H), 7.33-7.27 (m, 1H), 7.17 (d, J=16.3 Hz, 1H); $^1$H NMR (400 MHz, DMSO-d$_6$, D$_2$O Exc.): δ 7.85-7.76 (m, 3H), 7.57-7.48 (m, 3H), 7.40-7.34 (m, 3H), 7.30-7.24 (m, 1H), 7.11 (d, J=16.3 Hz, 1H). LC-MS: m/z 222.8 [M−H]$^−$ at 2.35 RT (99.16% purity). HPLC: 99.60%.

Analytical data of VN-378: $^1$H NMR (400 MHz, DMSO-d$_6$): δ 12.95 (br s, 1H), 7.96-7.90 (m, 1H), 7.40-7.34 (m, 2H), 7.20-7.09 (m, 4H), 7.05-6.99 (m, 3H), 6.61 (d, J=12.3 Hz, 1H); $^1$H NMR (400 MHz, DMSO-d$_6$, D$_2$O Exc.): δ 7.92-7.87 (m, 1H), 7.39-7.32 (m, 2H), 7.18-7.06 (m, 4H), 7.02-6.94 (m, 3H), 6.59 (d, J=12.3 Hz, 1H). LC-MS: m/z 222.8 [M−H]$^−$ at 2.39 RT (96.78% purity). HPLC: 99.33%.

Preparation of VN-384. The synthetic strategy for preparing VN-384 is detailed in the scheme below.

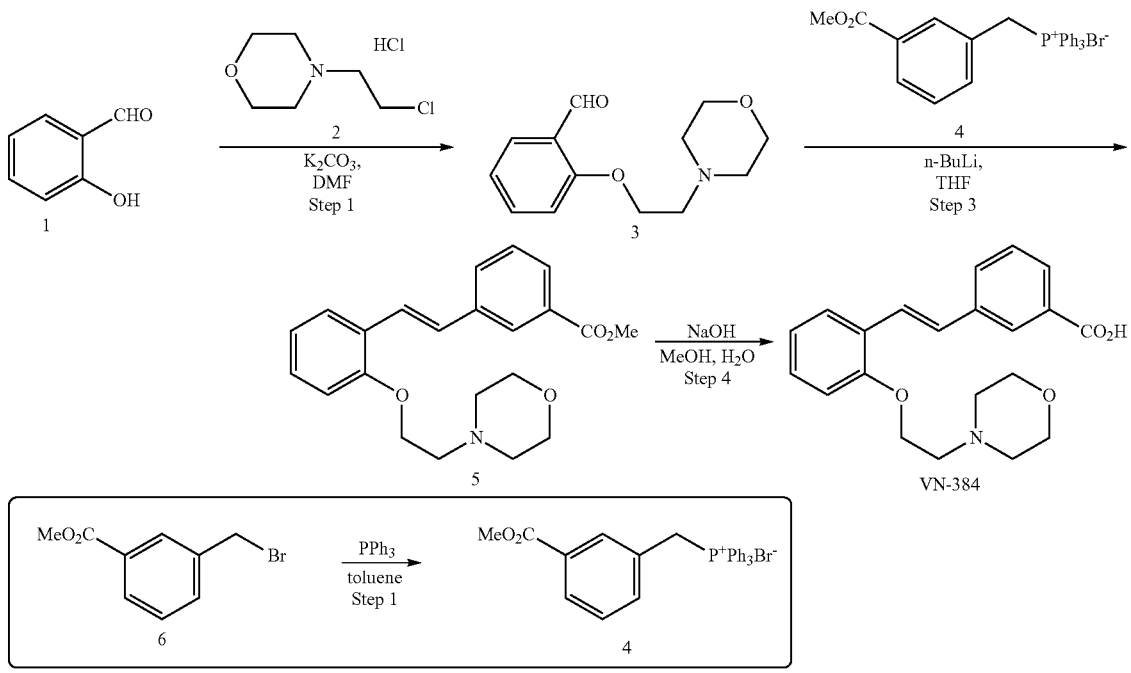

Step-1: Synthesis of 2-(2-morpholinoethoxy)benzaldehyde (3). To a stirred solution of 2-hydroxybenzaldehyde 1 (1 g, 8.2 mmol) in DMF (20 mL) were added 4-(2-chloroethyl)morpholine hydrochloride 2 (1.83 g, 9.84 mmol) and potassium carbonate (2.26 g, 16.39 mmol) at RT under inert atmosphere. The reaction mixture was heated to 80° C. and stirred for 16 h. The progress of the reaction was monitored by TLC; after the completion, the reaction mixture was cooled to RT; quenched with water (50 mL) and extracted with EtOAc (2×30 mL). The combined organic extracts were washed with water (30 mL) and brine (20 mL). The organic layer was separated and dried over anhydrous Na$_2$SO$_4$, filtered and concentrated under reduced pressure to afford compound 3 (1 g, 4.25 mmol, 52%) as brown liquid. $^1$H NMR (400 MHz, CDCl$_3$): δ 10.50 (d, J=0.9 Hz, 1H), 7.84 (dd, J=7.7, 1.8 Hz, 1H), 7.57-7.52 (m, 1H), 7.07-6.97 (m, 2H), 4.24 (t, J=5.6 Hz, 2H), 3.75-3.70 (m, 4H), 2.87 (t, J=5.6 Hz, 2H), 2.61-2.57 (m, 4H). LC-MS: m/z 236.0 [M+H]+ at 2.61 RT (93.48% purity).

Step-2: Synthesis of (3-(methoxycarbonyl)benzyl)triphenylphosphonium bromide (4). To a stirred solution of methyl 3-(bromomethyl)benzoate 6 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 4 (8.8 g, 17.91 mmol, 83%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-3: Synthesis of Methyl (E)-3-(2-(2-morpholinoethoxy)styryl)benzoate (5). To a stirred solution of compound 4 (800 mg, 1.63 mmol) in THF (20 mL) was added n-BuLi (2.5 M in hexanes, 1.63 mL, 4.08 mmol) at −78° C. under inert atmosphere. The reaction mixture was gradually warmed to RT and stirred for 1 h. Then a solution of compound 3 (384 mg, 1.63 mmol) in THF (5 mL) was added at −78° C. The reaction mixture was gradually warmed to RT and stirred for 16 h. The progress of the reaction was monitored by TLC; after the completion, the reaction mixture was quenched with saturated NH$_4$Cl solution (30 mL) and extracted with EtOAc (2×30 mL). The combined organic extracts were washed with brine (20 mL), dried over anhydrous Na$_2$SO$_4$, filtered and concentrated under reduced pressure. The crude material was purified by combi flash column chromatography to afford compound 5 (590 mg, 1.61 mmol, 98%) as a mixture of cis and trans-isomers as pale yellow semi solid. The mixture was taken to next step without further purification. LC-MS: m/z 368.2 [M+H]+ at 4.04 RT (27.29% purity) & m/z 368.2 [M+H]+ at 4.24 RT (26.32% purity).

Step-4: Synthesis of (E)-3-(2-(2-morpholinoethoxy)styryl)benzoic acid hydrochloride (VN-384). To a stirred solution of compound 5 (350 mg, mixture) in methanol (3 mL) was added a solution of sodium hydroxide (114 mg, 2.86 mmol) in water (1 mL) at RT. The reaction mixture was heated to reflux temperature and stirred for 3 h. The progress of the reaction was monitored by TLC; after the completion, the reaction mixture was concentrated under reduced pressure. The residue was acidified with saturated citric acid solutions to pH ~3-4 and extracted with 10% MeOH/CHCl$_3$ (2×20 mL). The combined organic extracts were dried over anhydrous Na$_2$SO$_4$, filtered and concentrated under reduced pressure. The obtained solid was diluted with water (5 mL), acidified with 6N HCl solution to pH~2 and extracted with 10% MeOH/CHCl$_3$ (2×20 mL). The combined organic extracts were dried over anhydrous Na$_2$SO$_4$, filtered and concentrated under reduced pressure. The solid was recrystallized with CH$_3$CN (2×5 mL), filtered and dried under vacuum to afford VN-384 (40 mg, 0.1 mmol, 11%) as an off white solid as HCl salt. $^1$H NMR (400 MHz, DMSO-$d_6$): δ 13.04 (br s, 1H), 10.88 (br s, 1H), 8.12 (s, 1H), 7.91-7.82 (m, 2H), 7.76 (br d, J=7.5 Hz, 1H), 7.57-7.49 (m, 2H), 7.37-7.27 (m, 2H), 7.12 (d, J=8.0 Hz, 1H), 7.05 (t, J=7.5 Hz, 1H), 4.50-4.48 (m, 2H), 4.01-3.96 (m, 2H), 3.81 (br t, J=11.7 Hz, 2H), 3.69-3.67 (m, 2H), 3.59-3.55 (m, 2H), 3.29-3.21 (m, 2H); $^1$H NMR (400 MHz, DMSO-$d_6$, D$_2$O Exc.): δ 8.11 (s, 1H), 7.85-7.80 (m, 2H), 7.73 (dd, J=7.7, 1.3 Hz, 1H), 7.55-7.49 (m, 2H), 7.33-7.24 (m, 2H), 7.10-7.02 (m, 2H), 4.38 (t, J=4.9 Hz, 2H), 3.95-3.88 (m, 2H), 3.81-3.74 (m, 2H), 3.62-3.55 (m, 2H), 3.35-3.33 (m, 4H). LC-MS: m/z 354.3 [M+H]+ at 1.85 RT (98.50% purity). HPLC: 97.70%.

Preparation of VN-388. The synthetic strategy for preparing VN-388 is detailed in the scheme below.

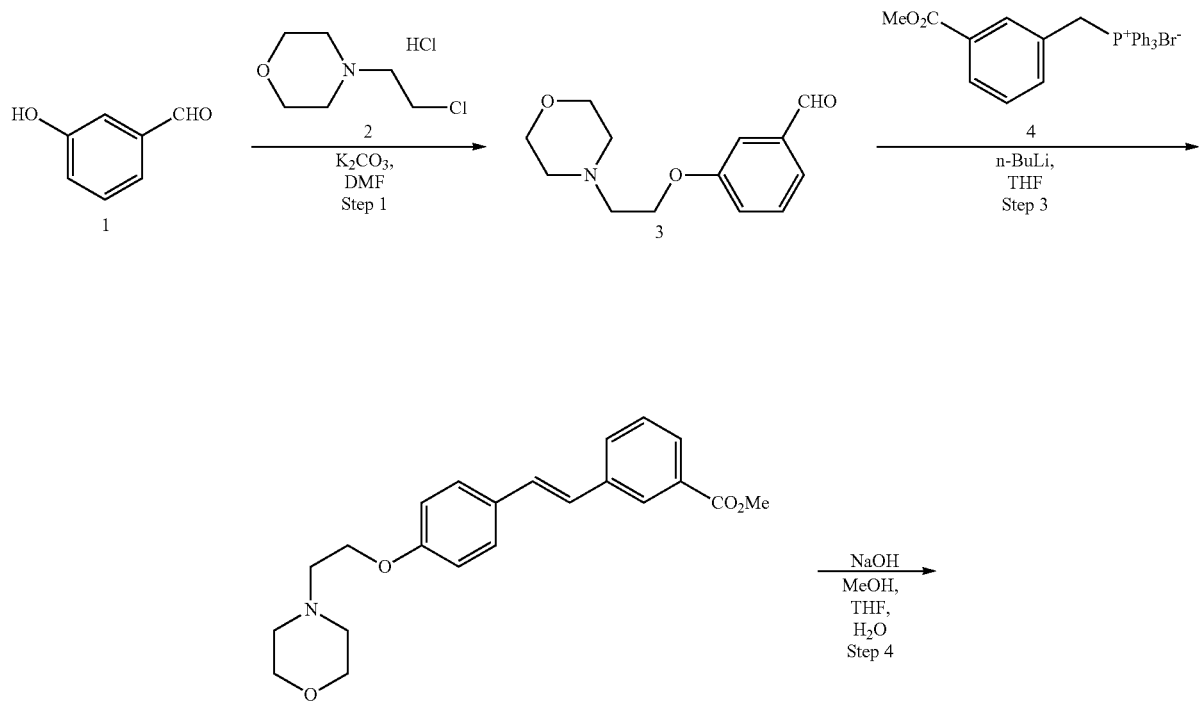

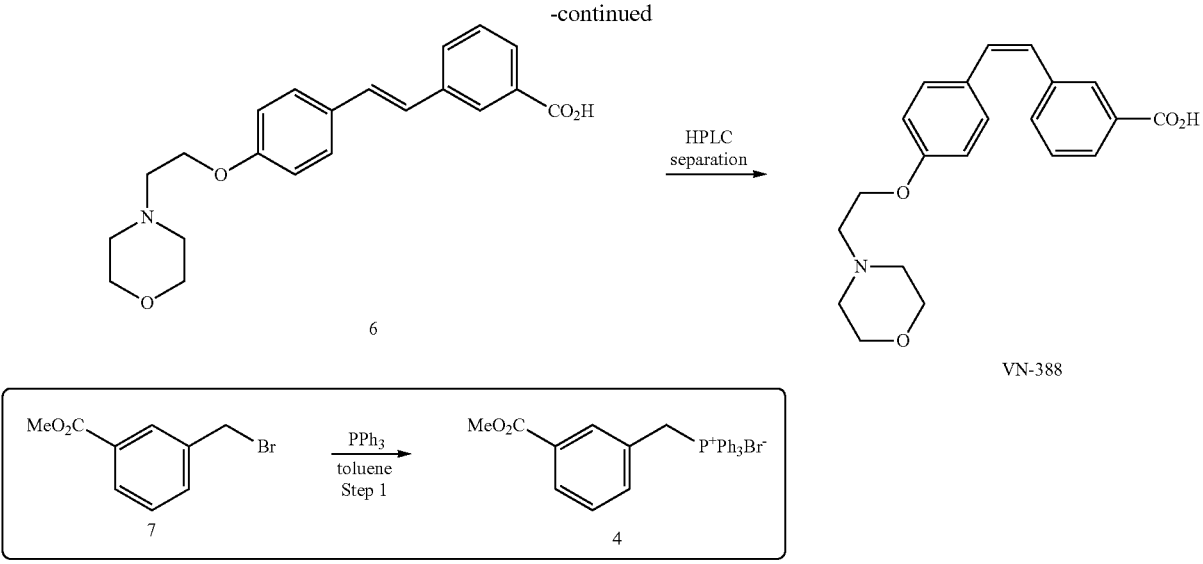

Step-1: Synthesis of 3-(2-morpholinoethoxy)benzaldehyde (3). To a stirred solution of 3-hydroxybenzaldehyde 1 (1 g, 8.2 mmol) in DMF (20 mL) were added 4-(2-chloroethyl)morpholine hydrochloride 2 (1.83 g, 9.84 mmol) and potassium carbonate (2.26 g, 16.39 mmol) at RT under inert atmosphere. The reaction mixture was heated to 80° C. and stirred for 16 h. The progress of the reaction was monitored by TLC; after the completion, the reaction mixture was cooled to RT; quenched with water (50 mL) and extracted with EtOAc (2×30 mL). The combined organic extracts were washed with water (2×30 mL) and brine (20 mL). The organic layer was separated and dried over anhydrous $Na_2SO_4$, filtered and concentrated under reduced pressure to afford compound 3 (1.4 g, 5.95 mmol, 73%) as colorless liquid. $^1$H NMR (400 MHz, $CDCl_3$): δ 9.97 (s, 1H), 7.48-7.39 (m, 3H), 7.21-7.18 (m, 1H), 4.17 (t, J=5.6 Hz, 2H), 3.76-3.72 (m, 4H), 2.83 (t, J=5.6 Hz, 2H), 2.61-2.57 (m, 4H). LC-MS: m/z 236.0 [M+H]$^+$ at 2.64 RT (96.90% purity).

Step-2: Synthesis of (3-(methoxycarbonyl)benzyl)triphenylphosphonium bromide (4). To a stirred solution of methyl 3-(bromomethyl)benzoate 7 (5 g, 21.83 mmol) in toluene (50 mL) was added triphenylphosphine (5.72 g, 21.83 mmol) at RT under inert atmosphere. The reaction mixture was heated to reflux temperature and stirred for 6 h. Then the solid was filtered, washed with toluene (2×20 mL), n-hexanes (2×20 mL) and dried under vacuum to afford compound 4 (8.8 g, 17.91 mmol, 83%) as white solid. $^1$H NMR (400 MHz, DMSO-$d_6$): δ 7.95-7.84 (m, 4H), 7.79-7.72 (m, 6H), 7.71-7.64 (m, 6H), 7.54-7.52 (m, 1H), 7.41 (t, J=7.8 Hz, 1H), 7.31-7.27 (m, 1H), 5.29-5.23 (m, 2H), 3.77 (s, 3H).

Step-3: Synthesis of Methyl (E)-3-(3-(2-morpholinoethoxy)styryl)benzoate (5). To a stirred solution of compound 4 (1.5 g, 3.06 mmol) in THF (25 mL) was added n-BuLi (2.5 M in hexanes, 3.06 mL, 7.65 mmol) at −78° C. under inert atmosphere. The reaction mixture was gradually warmed to RT and stirred for 1 h. Then a solution of compound 3 (863 mg, 3.67 mmol) in THF (5 mL) was added at −78° C. The reaction mixture was gradually warmed to RT and stirred for 16 h. The progress of the reaction was monitored by TLC; after the completion, the reaction mixture was quenched with saturated $NH_4Cl$ solution (30 mL) at 0° C. and extracted with EtOAc (2×40 mL). The combined organic extracts were washed with brine (20 mL), dried over anhydrous $Na_2SO_4$, filtered and concentrated under reduced pressure. The crude material was purified by combi-flash column chromatography eluting with 50% EtOAc/n-hexanes to afford compound 5 (900 mg, 2.45 mmol, 80%) as a mixture of cis and trans-isomers as colorless semi solid. The mixture was taken to next step without further purification. LC-MS: m/z 368.2 [M+H]$^+$ at 4.03 RT (24.78% purity) & m/z 368.2 [M+H]$^+$ at 4.08 RT (20.04% purity).

Step-4: Synthesis of (Z)-3-(3-(2-morpholinoethoxy)styryl)benzoic acid (VN-388). To a stirred solution of compound 5 (700 mg, mixture) in a mixture of THF/methanol (1:1, 6 mL) was added a solution of sodium hydroxide (229 mg, 5.72 mmol) in water (3 mL) at RT and stirred for 16 h. The progress of the reaction was monitored by TLC; after the completion, the reaction mixture was concentrated under reduced pressure. The residue was diluted with water (15 mL) and extracted with ether (2×10 mL). The organic layer was separated; the aqueous layer was acidified with 1 N HCl solutions to pH ~2 and extracted with 10% MeOH/$CH_2Cl_2$ (2×30 mL). The combined organic extracts were dried over anhydrous $Na_2SO_4$, filtered and concentrated under reduced pressure to afford the desired compound 6 (500 mg). The crude material was purified by normal phase preparative HPLC (Method T) to afford VN-388 (90 mg, 0.25 mmol, 13%) as an off white solid. $^1$H NMR (400 MHz, DMSO-$d_6$): δ 9.93 (br s, 1H), 7.86-7.77 (m, 2H), 7.48-7.37 (m, 2H), 7.22 (t, J=7.8 Hz, 1H), 6.91-6.81 (m, 3H), 6.76-6.66 (m, 2H), 4.22-4.20 (m, 2H), 4.00-3.62 (m, 4H), 3.56-3.43 (m, 2H), 3.22-3.08 (m, 2H); $^1$H NMR (400 MHz, DMSO-$d_6$, $D_2O$ Exc.): δ 7.80-7.75 (m, 2H), 7.46-7.36 (m, 2H), 7.19 (t, J=8.0 Hz, 1H), 6.89-6.78 (m, 3H), 6.72-6.64 (m, 2H), 4.16 (t, J=4.8 Hz, 2H), 3.81-3.72 (m, 4H), 3.43 (br t, J=4.7 Hz, 2H), 3.24-3.20 (m, 4H). LC-MS: m/z 354.2 [M+H]$^+$ at 2.63 RT (99.50% purity). HPLC: 99.74%.

Preparative HPLC Methods: Final compounds were purified by prep-HPLC, using different methods given below.

| S. No: | Target | Prep HPLC Method |
|---|---|---|
| 1 | VN-317 | N & J |
| 2 | VN-318 | J |
| 3 | VN-321 | G |

-continued

| S. No: | Target | Prep HPLC Method |
|---|---|---|
| 4 | VN-378 | H |
| 5 | VN-378 | I |
| 6 | VN-323 | P |
| 7 | VN-328 | K |
| 8 | VN-329 & VN-338 | N |
| 9 | VN-330 & VN-339 | F & M |
| 10 | VN-331 | D |
| 11 | VN-322 | J & N |
| 12 | VN-333 & VN-342 | F |
| 13 | VN-383 tetrazole | O |
| 14 | VN-335 | L |
| 15 | VN-336 | J |
| 16 | VN-341 | G |
| 17 | VN-343 | J |
| 18 | VN-344 | M |
| 19 | VN-347 & VN-377 | A |
| 20 | VN-348 & VN-377 | B |
| 21 | VN-351 & VN-380 | U |
| 22 | VN-353 | R |
| 23 | VN-354 & VN-380 | Y |
| 24 | VN-355 & VN-387 | S |
| 25 | VN-359 | S |
| 26 | VN-365 & VN-385 | V |
| 27 | VN-366 & VN-383 | W |
| 28 | VN-367 & VN-386 | X |
| 29 | VN-368 & VN-373 | C |
| 30 | VN-369 & VN-371 | Q |
| 31 | VN-371 & VN-372 | D |
| 32 | VN-371 & VN-396 | E |
| 33 | VN-375 & VN-378 | F |
| 34 | VN-376 | B |
| 35 | VN-388 | T |

Method-A
Column: Chiral pak IC (250×20 mm), 5u
Mobile phase A: 0.1% DEA in n-HEXANE; Mobile phase B: EtOH:MeOH (50:50)
Flow Rate: 20 ml/min; Programme: (95:05)
Method-B
Column: Chiral pak IC (250×20 mm), 5u
Mobile phase A: n-HEXANE, Mobile phase B: IPA
Flow Rate: 20 ml/min; Programme: (99:01)
Method-C
Column: Inertsil Diol (250×20 mm), 5u
Mobile phase A: 0.1% TFA in n-HEXANE, Mobile phase B: DCM:EtOH (90:10)
Flow Rate: 20 ml/min; Programme: (88:12)
Method-D
Column: YMC Diol (250×20 mm), 5u
Mobile phase A: n-HEXANE, Mobile phase B: DCM:MeOH (80:20)
Flow Rate: 20 ml/min; Programme: (75:25)
Method-E
Column: Inertsil Diol (250×20 mm), 5u
Mobile phase A: 0.1% TFA in n-HEXANE, Mobile phase B: DCM
Flow Rate: 20 ml/min; Programme: (99:01)
Method-F
Column: Inertsil Diol (250×20 mm), 5u
Mobile phase A: n-HEXANE, Mobile phase B: DCM:MeOH (50:50)
Flow Rate: 20 ml/min; Programme: A:B (95:05)
Method-G
Column: Chiral pak IC (250×20 mm), 5u
Mobile phase A: 0.1% TFA in n-HEXANE, Mobile phase B: THF, Mobile phase C: DCM:MeOH (80:20)
Flow Rate: 20 ml/min Programme: (90:05:05)
Method-H
Column: Chiral pak IC (250×20 mm), 5u
Mobile phase A: n-HEXANE, Mobile phase B: EtOH:MeOH (50:50)
Flow Rate: 20 ml/min Programme: (98:02)
Method-I
Column: X-Select CSH C-18 (250×20 mm), 5u
Mobile phase A: ACN, Mobile phase B: 5 Mm Ammonium bicarbonate.
Flow Rate: 15 ml/min Programme: B %-0.01-95%, 2-95%, 4-70%, 12-55%, 30-0%, 35-0%
Method-J
Column: X-Select CSH C-18 (250×20 mm), 5u
Mobile phase A: ACN, Mobile phase B: 0.05% TFA in water
Flow Rate: 15 ml/min Programme: B %-0.01-95%, 2-95%, 10-70%20-30%, 25-10%, 35-10%
Method-K
Column: X-Select CSH C-18 (250×19 mm), 5u
Mobile phase A: ACN, Mobile phase B: 0.05% Aq. TFA
Flow Rate: 15 ml/min Programme: B %-0.01-80%, 2-80%, 5-70%, 15-30%, 22-10%, 22.1-0%, 30-0%
Method-L
Column: X-Select CSH C-18 (250×19 mm), 5u
Mobile phase A: ACN, Mobile phase B: 0.05% Aq. TFA
Flow Rate: 15 ml/min Programme: B %-0.01-80%, 2-80%, 8-50%, 16-30%, 20-30%, 25-0%, 30-0%
Method-M
Column: X-Select CSH C-18 (250×20 mm), 5u
Mobile phase A: ACN, Mobile phase B: 5 Mm Ammonium acetate.
Flow Rate: 15 ml/min Programme: B %-0.01-95%, 3-95%, 10-70%, 20-10%, 25-10%
Method-N
Column: Inertsil Diol (250×20 mm), 5u
Mobile phase A: n-HEXANE, Mobile phase B: DCM:MeOH (50:50)
Flow Rate: 20 ml/min; Programme: A:B (99:01)
Method-O
Column: X-Select CSH C-18 (250×20 mm), 5u
Mobile phase A: ACN, Mobile phase B: 0.05% TFA in water
Flow Rate: 15 ml/min Programme: B %-0.01-80%, 2-80%, 8-60%, 20-30%, 28-10%, 35-10%
Method-P
Column: X-Select CSH C-18 (250×20 mm), 5u
Mobile phase A: ACN, Mobile phase B: 0.05% TFA in water.
Flow Rate: 15 ml/min Programme: B %-0.01/90, 2/90, 8/65/20/30, 27/10, 35/10
Method-Q
Column: Inertsil Diol (250×20 mm), 5u
Mobile phase A: n-HEXANE, Mobile phase B: EtOH:MeOH (50:50)
Flow Rate: 20 ml/min; Programme: A:B (95:05)
Method-R
Column: Inertsil Diol (250×20 mm), 5 um
Mobile phase A: 0.1% TFA in n-Hexane, Mobile phase B: EtOH:MeOH (50:50)
Flow Rate: 20 ml/min; Programme: A:B::(80:20)
Method-S
Column: Chiral pak IA (250×20 mm), 5 um
Mobile phase A: 0.1% TFA in n-Hexane, Mobile phase B: EtOH:MeOH (50:50)
Flow Rate: 20 ml/min Programme: A:B::(80:20)

Method-T
Column: Chiral pak IA (250×20 mm), 5 um
Mobile phase A: 0.1% TFA in n-Hexane, Mobile phase B: DCM:MeOH (50:50)
Flow Rate: 20 ml/min Programme: A:B::(75:25)
Method-U
Column: Chiral pak IC (250×20 mm), 5 um
Mobile phase A: 0.1% TFA in n-HEXANE, Mobile phase B: DCM:MeOH (50:50)
Flow Rate: 20 ml/min Programme: A:B::(75:25)
Method-V
Column: Chiral pak IA (250×20 mm), 5 um
Mobile phase A: 0.1% TFA in n-Hexane, Mobile phase B: DCM:MeOH (50:50)
Flow Rate: 20 ml/min Programme: A:B::(80:20)
Method-W
Column: Chiral pak IC (250×20 mm), 5 um
Mobile phase A: 0.1% DEA in n-HEXANE; Mobile phase B: DCM:MeOH (50:50)
Flow Rate: 20 ml/min; Programme: (75:25)
Method-X
Column: Chiral pak IA (250×20 mm), 5 um
Mobile phase A: 0.1% DEA in n-Hexane, Mobile phase B: DCM:MeOH (50:50)
Flow Rate: 20 ml/min Programme: A:B::(80:20)
Method-Y
Column: Chiral pak IA (250×20 mm), 5 um
Mobile phase A: n-Hexane, Mobile phase B: EtOH: MeOH (50:50)
Flow Rate: 20 ml/min Programme: A:B::(80:20)

Evaluation of the Activity of ADMA-Lowering Agents

The structure and activity of example ADMA-lowering agents are shown in Tables 1 and 2 below.

TABLE 1

Structure and Activity of Stilbene-Based ADMA-Modulating Agents

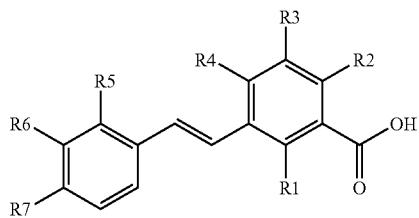

| Cmpd | $EC_{50}$ nM | R1 | R2 | R3 | R4 | R5 | R6 | R7 | Stereo |
|---|---|---|---|---|---|---|---|---|---|
| VN-330 | 53 | H | H | H | H | H | H | H | Trans |
| VN-339 | Ambiguous | H | H | H | H | H | H | H | Cis |
| VN-329 | 8.7 | H | H | H | H | CH3 | H | H | Trans |
| VN-359 | 0.16 | H | OH | H | H | H | H | H | Trans |
| VN-328 | 18.6 | H | H | H | H | H | H | OH | Trans |
| VN-338 | Ambiguous | H | H | H | H | H | H | OH | Cis |
| VN-200 | — | OH | H | H | H | H | H | H | Trans |
| VN-201 | — | H | H | OH | H | H | H | H | Trans |
| VN-202 | — | H | H | H | OH | H | H | H | Trans |
| VN-390 | 3.4 | H | H | H | H | H | H | F | Trans |
| VN-372 | 10.4 | H | H | H | H | H | H | F | Cis |
| VN-317 | 7 | H | H | H | H | CH3 | H | OH | Trans |
| VN-371 | 1.4 | H | H | H | H | H | H | Cl | Trans |
| VN-379 | 3.9 | H | H | H | H | H | H | Cl | Cis |
| VN-333 | 1.8 | H | H | H | H | CH3 | H | OCH3 | Trans |
| VN-342 | 81.5 | H | H | H | H | CH3 | H | OCH3 | Cis |
| VN-363 | 0.97 | H | H | H | H | H | H | Y | Trans |
| VN-362 | 1.3 | H | H | H | H | H | Y | H | Trans |
| VN-384 | 1.6 | H | H | H | H | Y | H | H | trans |
| VN-364 | 11.31 | H | H | H | H | Y | H | H | trans |
| VN-388 | Ambiguous | H | H | H | H | H | Y | H | cis |

Y = 2-(morpholin-4-yl)ethoxy-

TABLE 2

Structure and Activity of ADMA-Lowering Agents Including Heterocycles.

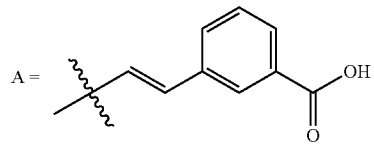 [SMILES: */C=C/c1cccc(C(=O)O)c1]

| Name | R | EC50 nM | Stereo |
|---|---|---|---|
| VN-380 | A, oxazol-4-yl | 0.17 | Cis |
| VN-381 | A, pyridin-3-yl | 0.73 | Cis |
| VN-387 | A, pyridin-4-yl | 1.7 | Cis |

TABLE 2-continued

Structure and Activity of ADMA-Lowering Agents Including Heterocycles.

A = [structure: substituted cinnamic acid with 3-carboxyphenyl group]

| Name | R | EC50 nM | Stereo |
|---|---|---|---|
| VN-373 | 2-thienyl (A) | 0.76 | Cis |
| VN-374 | 3-thienyl (A) | — | Cis |
| VN-386 | thiazolyl (A) | 2.8 | Cis |
| VN-385 | 2-thiazolyl (A) | — | Cis |
| VN-351 | oxazolyl (A) | 87 | Trans |
| not synth | 2-oxazolyl (A) | — | Trans |
| not synth | 5-oxazolyl (A) | — | Trans |
| VN-353 | 2-pyridyl (A) | 58 | Trans |
| VN-355 | 4-pyridyl (A) | 651 | Trans |
| VN-354 | 3-pyridyl (A) | 672 | Trans |
| VN-368 | 2-thienyl (A) | 0.79 | Trans |
| VN-369 | 3-thienyl (A) | 1.23 | Trans |
| VN-365 | 2-thiazolyl (A) | 180 | Trans |
| VN-367 | 5-thiazolyl (A) | 1056 | Trans |
| VN-366 | 4-thiazolyl (A) | 1366 | Trans |

TABLE 3

Structure and Activity of Other ADMA-Lowering Agents.

| Cmpd | Structure | EC50 nM |
|---|---|---|
| VN-347 | phenyl-cyclopropyl-benzoic acid | 3.3 |
| VN-322 | (2-methyl-4-hydroxyphenyl)-cyclopropyl-benzoic acid | 90 |

TABLE 3-continued

Structure and Activity of Other ADMA-Lowering Agents.

| Cmpd | Structure | EC50 nM |
|---|---|---|
| VN-376 | ![structure] | 527.1 |

In Vivo Activity of the ADMA-Lowering Compounds

A rat model of monocrotalin induced PAH was used for in vivo studies. Male Sprague Dawley rats about 250 g were purchased from Charles river. PAH was induced by a single s.c. injection of 60 mg/kg monocrotalin. VN-317 (1 mg/kg) or vehicle was administered subcutaneously on day one and once a day thereafter. After 6 weeks, the disease development was determined by pulmonary artery (PA) pressure measurements, echocardiography, and histology. PA pressure was determined by right heart catheterization using a 1.4-F micromanometer-tipped Millar catheter with fluoroscopy guidance. Transthoracic echocardiography was performed using a GE vivid i with 5.0-13.0 MHz i12L-RS linear array transducer. Pulmonary artery acceleration time (PAAT) was measured using pulse-wave Doppler echocardiography with the sample volume centrally positioned in the PA distal to the pulmonary valve. M-mode was applied to measure the right ventricular cavity thickness during end diastole using the parasternal long-axis view obtained from the right side of the rat. Tissue and blood samples were collected at termination. Tissues were fixed in 10% formalin, embedded in paraffin, and then processed for histomorphometry. Macrophage in lung tissues were determined by immunostaining using CD68 antibodies.

DDAH Modulating Activity of Compounds

Figure 1B:
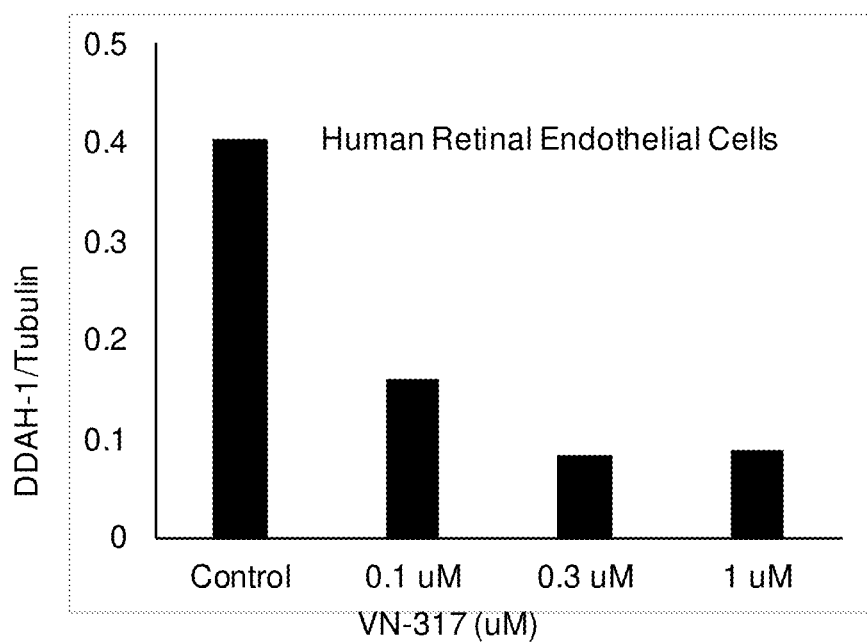

Expression of DDAH was determined in human pulmonary artery smooth muscle cells (FIG. 1A) and human retinal microvascular endothelial cells (FIG. 1B). Cells were treated with different concentrations of VN-317. After 24 hours, cells were extracted in lysis buffer as described under methods. Extracts were subjected to SDS gel electrophoresis. Proteins from SDS gel were transferred to PVDF membrane and for western blotting using DDAH-1 antibodies. As shown in FIG. 1A, VN-317 enhanced DDAH-1 protein in pulmonary artery smooth muscle cells whereas reduced DDAH-1 protein in human retinal microvascular cells. Therese data illustrate differential modulation of DDAH by VN-317 in different cell types.

Figure 2:
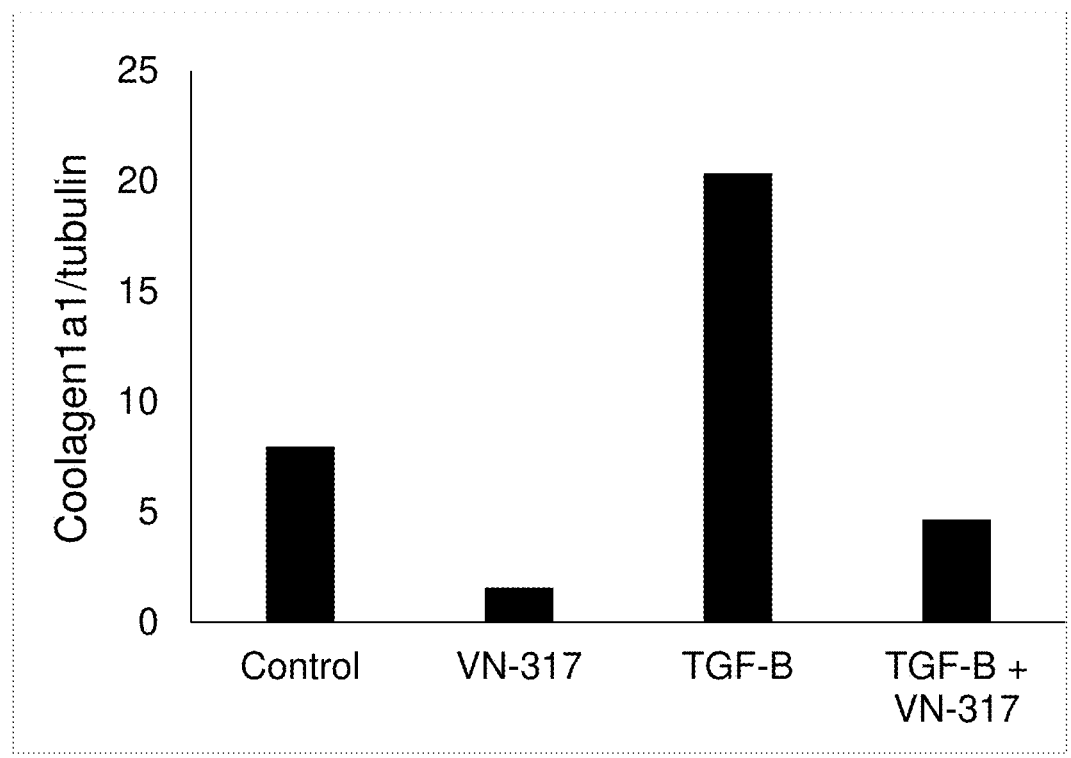
FIG. 2 shows the inhibition of collagen synthesis in smooth muscle cells, a key protein in fibrotic diseases.

FIG. 2 shows effect of the compounds on collagen synthesis in myofibroblast like smooth muscle cells. Cells were treated with VN-317 in the presence or absence of TGF-beta. After 48 hours, cells were extracted in 50 ul lysis buffer and cell extract was subjected to SDS gel electrophoresis. Proteins from the 12% polyacrylamide gels were transferred to PVDF membranes for westerns and blotted collagen 1a antibodies from Abcam. The results show that VN-317 reduced collagen production in response to TGF-beta, supporting the potential antifibrotic activity of the compounds.

Figure 3:
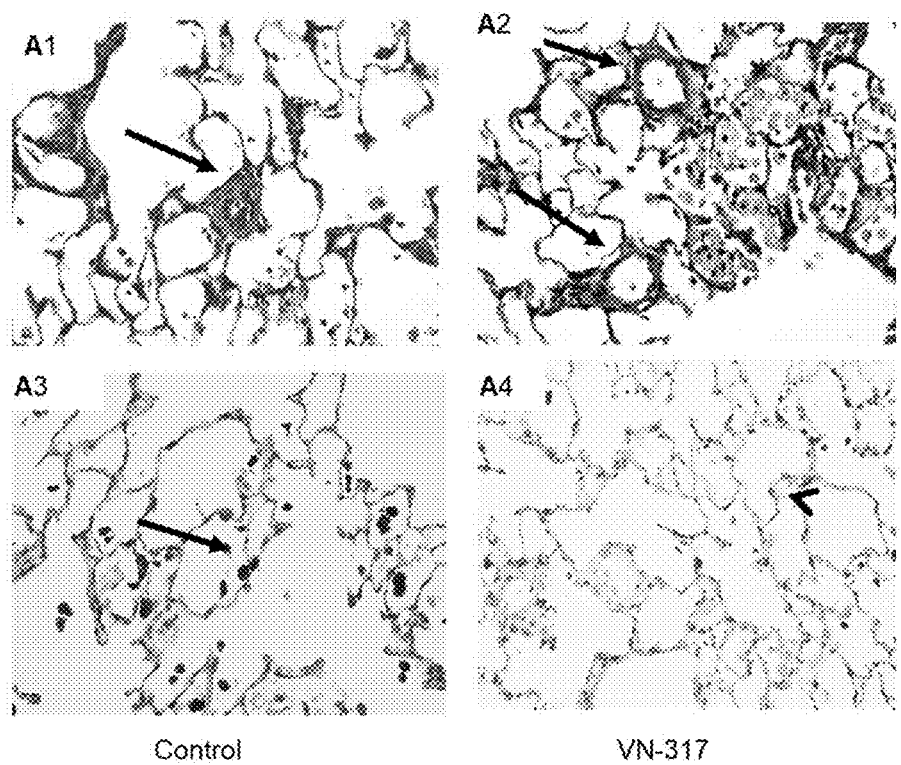
FIG. 3 shows histology finding demonstrating that VN-317 reduces pulmonary arteriole thickening and inflammation in the lung in a model of pulmonary arterial hypertension (PAH). Panel A1 shows hyperplasia of small arteries in the monocrotalin-induced pulmonary arterial hypertension (PAH) rat model, whereas open artery is observed in the VN-317 treated group (panel A2). Panel A3 shows inflammatory cell infiltration (CD68 immuno-staining) in the control group. A dramatic reduction in CD 68 stained cells was observed in the VN-317 treated group (panel A4).
Figure 4:
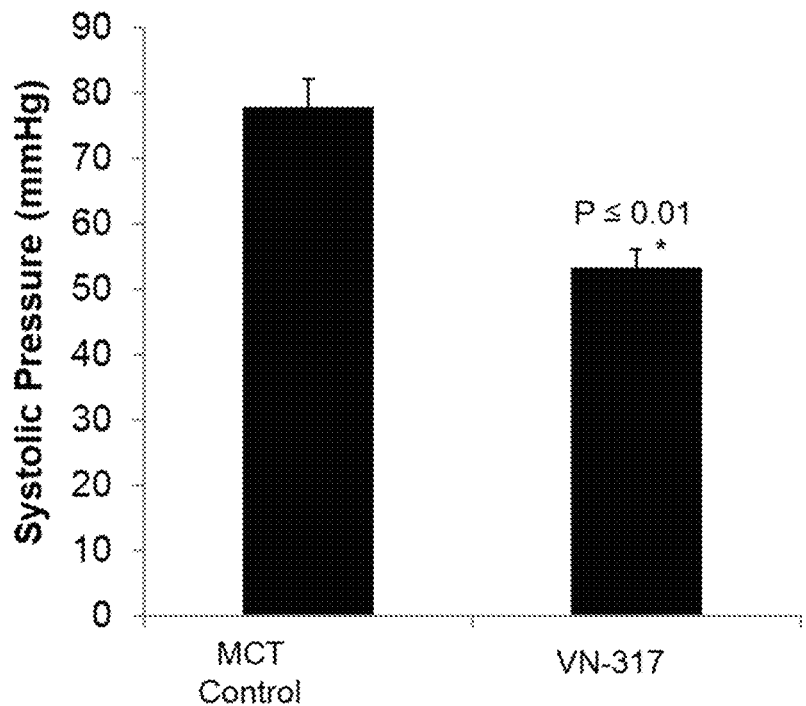
FIG. 4 is a plot showing reduction in pulmonary artery pressure (PAP) by VN-317 in a model of PAH. An elevated PAP is observed in an MCT model (control); however, the PAP was significantly reduced by treatment with VN-317
Figure 5A:
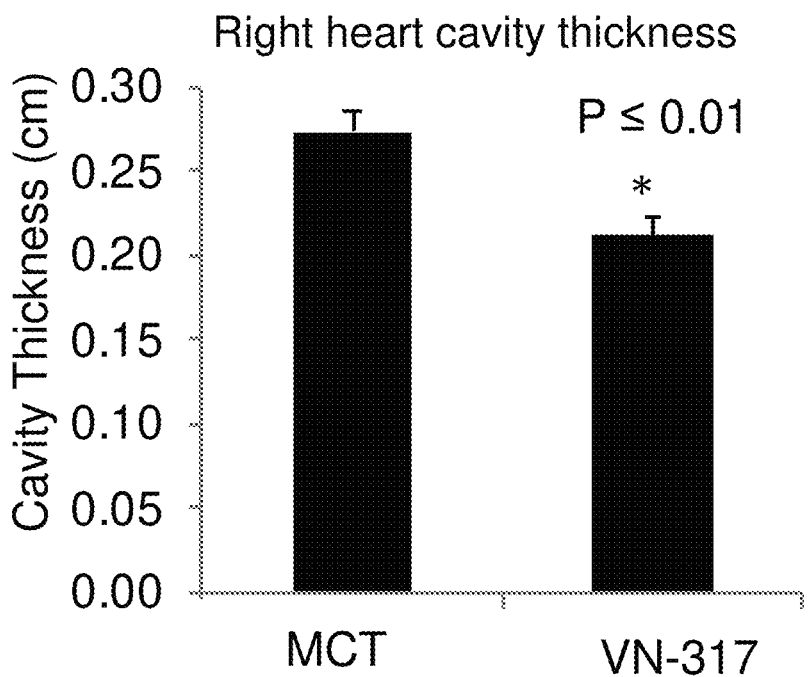
FIG. 5A-5B are plots showing the effect of VN-317 on right ventricle cavity thickness (FIG. 5A) pulmonary artery blood acceleration time (PAAT) (5B) in a model of PAH.
Figure 5B:
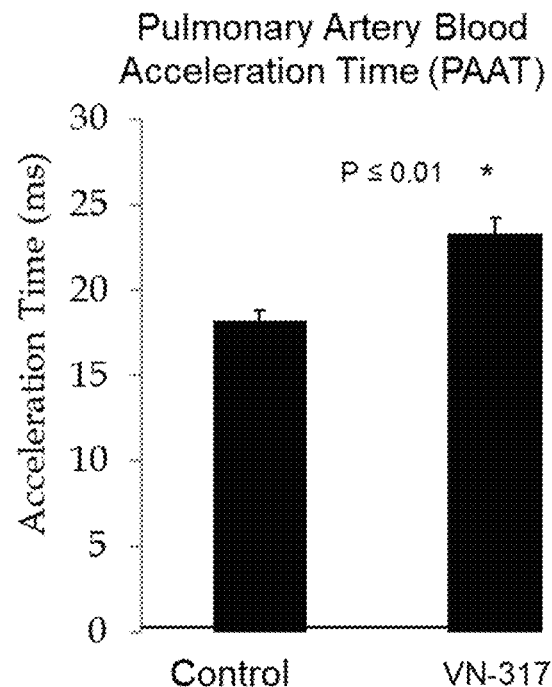
Figure 6A:
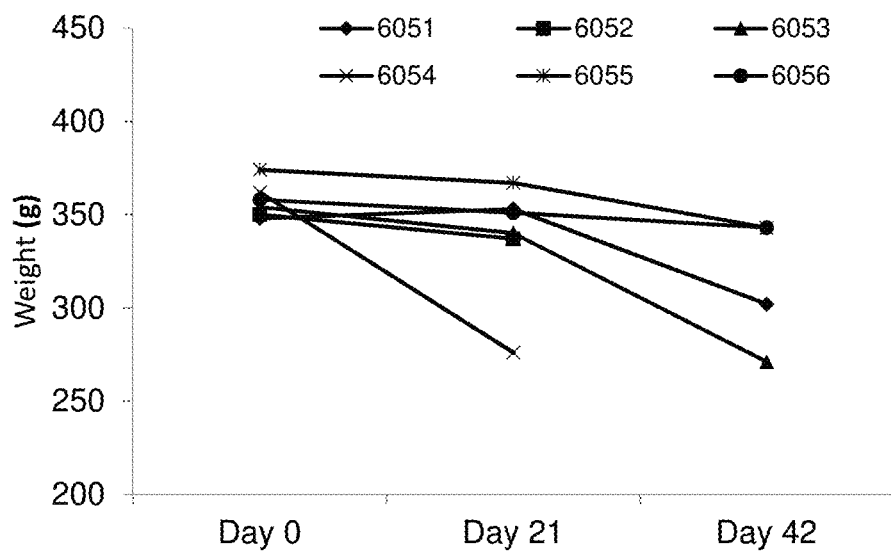
FIG. 6 shows the effect of VN-317 on body weight and mortality in a model of PAH (2 animal died before reaching week 6 in the MCT group and none in the VN-317 treated group (N=6 animals were enrolled is each group). * * indicate SD, p<0.05
Figure 6B:
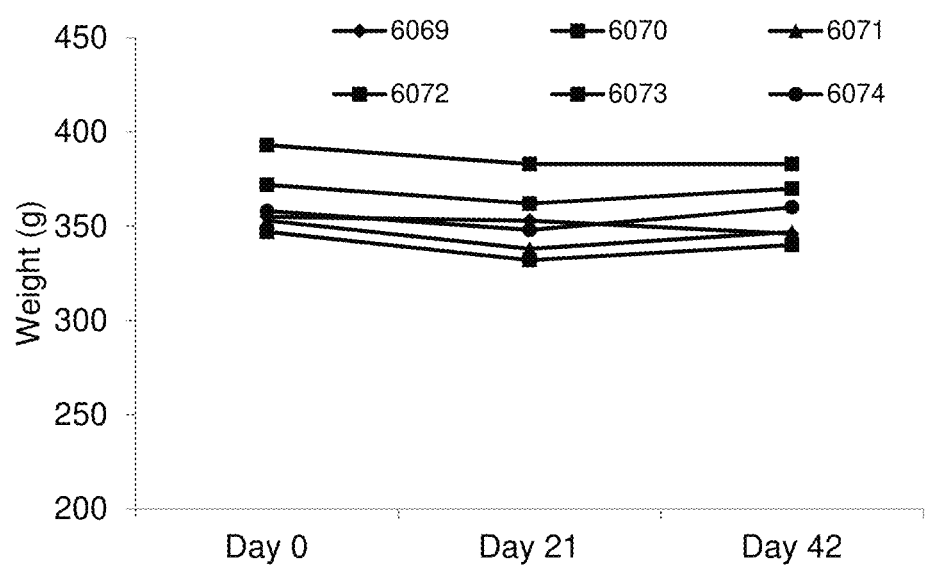

As shown in FIG. 3, VN-317 reduced pulmonary artery medial thickening, reduced vascular disease in the lung, and reduced inflammation in the lung in a model of PAH. As shown in FIG. 4, VN-317 reduced pulmonary artery pressure in a model of PAH. As shown in FIGS. 5A-5B, VN-317 also reduced right ventricle cavity thickness (FIG. 5A), increased pulmonary artery blood and acceleration time (PAAT, FIG. 5B), in a model of PAH. As shown in FIG. 6, VN-317 reduced mortality in a model of PAH. As shown in FIG. 6, VN-317 treatment prevented the body weight loss and mortality in a model of PAH. FIG. 6A shows MCT treated group over time (number indicate animal ID) and FIG. 6B shows MCT plus VN-317 treated animals.

The compounds, compositions, and methods of the appended claims are not limited in scope by the specific compounds, compositions, and methods described herein, which are intended as illustrations of a few aspects of the claims. Any compounds, compositions, and methods that are functionally equivalent are intended to fall within the scope of the claims. Various modifications of the compounds, compositions, and methods in addition to those shown and described herein are intended to fall within the scope of the appended claims. Further, while only certain representative compounds, compositions, and method steps disclosed herein are specifically described, other combinations of the compounds, compositions, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A compound defined by the formula:

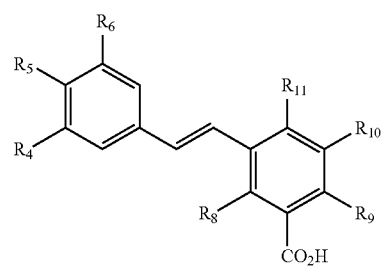

or a pharmaceutically acceptable salt, wherein
  i) $R_8$, $R_9$, $R_{10}$, $R_{11}$, $R_5$ and $R_4$ are hydrogen and $R_6$ is methyl; or ii) $R_8$, $R_9$, $R_{10}$, $R_{11}$, $R_6$, and $R_5$ are hydrogen and $R_4$ is methyl; or iii) $R_8$, $R_9$, $R_{10}$, $R_{11}$, $R_6$, and $R_5$ are hydrogen and $R_4$ is chloro or floro; or iv) $R_8$, $R_9$, $R_{10}$, $R_{11}$, and $R_6$ are hydrogen, $R_5$ is methyl and $R_4$ is methoxy; or v) $R_8$, $R_9$, $R_{10}$, $R_{11}$, and $R_5$ are hydrogen, $R_6$ is methyl and $R_4$ is hydroxy; or vi) $R_8$, $R_9$, $R_{10}$, $R_{11}$, $R_6$, and $R_5$ are hydrogen and $R_4$ is 2-(morpholin-4-yl)ethoxy; or vii) $R_8$, $R_9$, $R_{10}$, $R_{11}$, $R_6$, and $R_4$ are hydrogen and $R_5$ is 2-(morpholin-4-yl)ethoxy; or viii) $R_8$, $R_9$, $R_{10}$, $R_{11}$, $R_5$, and $R_4$ are hydrogen and $R_6$ is 2-(morpholin-4-yl)ethoxy.

2. The compound of claim 1, wherein $R_8$, $R_9$, $R_{10}$, $R_{11}$, $R_6$, and $R_4$ are hydrogen and $R_5$ is 2-(morpholin-4-yl)ethoxy.

3. A pharmaceutical composition comprising a compound of claim 1.

4. A pharmaceutical composition comprising a compound of claim of claim 2 or a pharmaceutically acceptable salt thereof.

* * * * *